US011230712B2

(12) United States Patent
Kordasiewicz et al.

(10) Patent No.: US 11,230,712 B2
(45) Date of Patent: Jan. 25, 2022

(54) COMPOUNDS AND METHODS FOR REDUCING SNCA EXPRESSION

(71) Applicant: Ionis Pharmaceuticals, Inc., Carlsbad, CA (US)

(72) Inventors: Holly Kordasiewicz, San Diego, CA (US); Tracy A. Cole, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/759,698

(22) PCT Filed: Nov. 9, 2018

(86) PCT No.: PCT/US2018/060097
§ 371 (c)(1),
(2) Date: Apr. 27, 2020

(87) PCT Pub. No.: WO2019/164562
PCT Pub. Date: Aug. 29, 2019

(65) Prior Publication Data
US 2020/0392494 A1 Dec. 17, 2020

Related U.S. Application Data

(60) Provisional application No. 62/584,009, filed on Nov. 9, 2017.

(51) Int. Cl.
*C12N 15/113* (2010.01)
*A61P 25/16* (2006.01)

(52) U.S. Cl.
CPC ............ *C12N 15/113* (2013.01); *A61P 25/16* (2018.01); *C12N 2310/11* (2013.01); *C12N 2310/31* (2013.01); *C12N 2310/315* (2013.01); *C12N 2310/322* (2013.01); *C12N 2310/341* (2013.01); *C12N 2310/351* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,102,785 A | 4/1992 | Livak et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |

(Continued)

FOREIGN PATENT DOCUMENTS

| | | |
|---|---|---|
| WO | WO 2017/119463 | 7/1917 |
| WO | WO 2019/140231 | 7/1919 |

(Continued)

OTHER PUBLICATIONS

Abeliovich et al., "Mice lacking alpha-synuclein display functional deficits in the nigrostriatal dopamine system." Neuron (2000) 25(1):239-252.

(Continued)

*Primary Examiner* — Tracy Vivlemore
(74) *Attorney, Agent, or Firm* — McNeill Baur PLLC

(57) ABSTRACT

Provided are compounds, methods, and pharmaceutical compositions for reducing the amount or activity of SNCA mRNA in a cell or animal, and in certain instances reducing the amount of alpha-synuclein protein in a cell or animal. Such compounds, methods, and pharmaceutical compositions are useful to ameliorate at least one symptom or hallmark of a neurodegenerative disease. Such symptoms and hallmarks include motor dysfunction, aggregation of alpha-synuclein, neurodegeneration, cognitive decline and dementia. Such neurodegenerative diseases include Parkinson's disease, dementia with Lewy bodies, diffuse Lewy body disease, pure autonomic failure, multiple system atrophy, neuronopathic Gaucher's disease and Alzheimer's disease.

25 Claims, No Drawings
Specification includes a Sequence Listing.

(56) References Cited

U.S. PATENT DOCUMENTS

| | | |
|---|---|---|
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Hamlambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistum et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,277,640 B1 | 8/2001 | Bennett et al. |
| 6,300,319 B1 | 10/2001 | Manoharan |
| 6,426,220 B1 | 7/2002 | Bennett et al. |
| 6,455,308 B1 | 9/2002 | Freier et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,833,361 B2 | 12/2004 | Hong et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,579,458 B2 | 8/2009 | Khvorova et al. |
| 7,595,306 B2 | 9/2009 | Bumcrot |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,750,141 B2 | 7/2010 | Crooke et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,389,487 B2 | 3/2013 | Bohn et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 9,663,783 B2 | 5/2017 | Freier |
| 10,815,480 B2 | 10/2020 | Freier |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2004/0219671 A1 | 11/2004 | McSwiggen |
| 2004/0226056 A1 | 11/2004 | Roch et al. |
| 2005/0064548 A1 | 3/2005 | Lindquist et al. |

(56) References Cited

U.S. PATENT DOCUMENTS

| | | |
|---|---|---|
| 2005/0130923 A1 | 6/2005 | Bhat et al. |
| 2005/0137155 A1 | 6/2005 | McSwiggen et al. |
| 2006/0148740 A1 | 7/2006 | Platenburg |
| 2007/0031844 A1 | 2/2007 | Khvorova et al. |
| 2007/0161595 A1 | 7/2007 | Bumcrot et al. |
| 2007/0192879 A1 | 8/2007 | Yoshimoto et al. |
| 2007/0225209 A1 | 9/2007 | Roch et al. |
| 2007/0287831 A1 | 12/2007 | Seth et al. |
| 2008/0003570 A1 | 1/2008 | Rogers et al. |
| 2008/0039418 A1 | 2/2008 | Freier |
| 2008/0039618 A1 | 2/2008 | Allerson et al. |
| 2009/0092981 A1 | 4/2009 | Swayze et al. |
| 2009/0176729 A1 | 7/2009 | Tan |
| 2010/0190837 A1 | 7/2010 | Migawa et al. |
| 2010/0197762 A1 | 8/2010 | Swayze et al. |
| 2010/0204306 A1 | 8/2010 | Tan |
| 2011/0054005 A1 | 3/2011 | Naito et al. |
| 2012/0129912 A1 | 5/2012 | Mouradian et al. |
| 2012/0322991 A1 | 12/2012 | Montefeltro et al. |
| 2013/0130378 A1 | 5/2013 | Manoharan et al. |
| 2014/0005252 A1 | 1/2014 | Bennett et al. |
| 2014/0107330 A1 | 4/2014 | Freier et al. |
| 2014/0120158 A1 | 5/2014 | Montefeltro et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2017/0044526 A1 | 2/2017 | Wan et al. |
| 2017/0275621 A1 | 9/2017 | Butler et al. |
| 2018/0073022 A1 | 3/2018 | Freier |
| 2020/0040061 A1* | 2/2020 | Lundberg ........... A61K 48/0075 |
| 2021/0087562 A1 | 3/2021 | Freier |

FOREIGN PATENT DOCUMENTS

| | | |
|---|---|---|
| WO | WO 2019/140236 | 7/1919 |
| WO | WO 2019/164562 | 8/1919 |
| WO | WO 2001/057277 | 8/2001 |
| WO | WO 2001/077384 | 10/2001 |
| WO | WO 2003/004602 | 1/2003 |
| WO | WO 2004/106356 | 12/2004 |
| WO | WO 2005/021570 | 3/2005 |
| WO | WO 2005/097817 | 10/2005 |
| WO | WO 2006/034348 | 3/2006 |
| WO | WO 2007/134181 | 11/2007 |
| WO | WO 2007/135426 | 11/2007 |
| WO | WO 2008/101157 | 8/2008 |
| WO | WO 2008/109509 | 9/2008 |
| WO | WO 2008/150729 | 12/2008 |
| WO | WO 2008/154401 | 12/2008 |
| WO | WO 2009/006478 | 1/2009 |
| WO | WO 2009/079399 | 6/2009 |
| WO | WO 2011/131693 | 10/2011 |
| WO | WO 2012/068405 | 5/2012 |
| WO | WO 2013/173637 | 11/2013 |
| WO | WO 2014/064257 | 5/2014 |

OTHER PUBLICATIONS

Alarcon-Aris et al., "Selective alpha-Synuclein Knockdown in Monoamine Neurons by Intranasal Oligonucleotide Delivery: Potential Therapy for Parkinison's Disease" Molecular Therapy (2018) 26(2): 1-18.

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.

Altmann et al., "Second-generation antisense oligonucleotides: structure-activity relationships and the design of improved signal-transduction inhibitors" Biochem. Soc. Trans. (1996) 24:630-637.

Altmann et al., "Second Generation of Antisense Oligonucleotides: From Nuclease Resistance to Biological Efficacy in Animals" Chimia (1996) 50(4):168-176.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16(7-9):917-926.

Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Burre et al., "Alpha-synuclein promotes SNARE-complex assembly in vivo and in vitro." Science (2010) 329(5999): 1663-1667.

Cabin et al., "Synaptic vesicle depletion correlates with attenuated synaptic responses to prolonged repetitive stimulation in mice lacking alpha-synuclein." J. Neurosci. (2002) 22(20):8797-8807.

Chan et al. "Antisense Oligonucleotides: from design to therapeutic application" Clinical and Experimental Pharmacology and Physiology (2006) 533-540.

Chen et al., "RNA interference targeting a-synuclein attenuates methamphetamine-induced neurotoxicity in SH-SY5Y cells" Brain Research (2013) 1521: 59-67.

Chiasson et al., "The application of antisense oligonucleotide technology to the brain: some pitfalls." Cellular and Molecular Neurobiology (1994) 14(5):507-521.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Clayton et al., "Synucleins in synaptic plasticity and neurodegenerative disorders" J. Neurosci. (1999) 58(1):120-129.

Cole et al., "Alpha-synuclein antisense oligonucleotides as a disease-modifying therapy for Parkinson's disease" bioRxiv preprint (2019) 1-42.

Conway et al., "Kinetic Stabilization of the α-Synuclein Protofibril by a Dopamine-α-Synuclein Adduct" Science (2001) 294(5545):1346-1349.

Crooke et al., "Basic Principles of Antisense Therapeutics" Antisense Research and Application (1998) Chapter 1:1-50.

Davidson et al., "Stabilization of alpha-synuclein secondary structure upon binding to synthetic membranes." J. Bioi. Chem. (1998) 273(16):9443-9449.

Elayadi et al., "Application of PNA and LNA oligomers to chemotherapy" Curr. Opinions Invens. Drugs (2001) 2:558-561.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

European Search Report for application EP 11840796.4 dated Dec. 4, 2014.

Fleming et al., "Early and Progressive Sensorimotor Anomalies in Mice Overexpressing Wild-Type Human α-Synuclein" J. Neurosci. (2004) 24(42):9434-9440.

Fleming et al., "Olfactory deficits in mice overexpressing human wildtype alpha-synuclein." Eur. J. Neurosci. (2008) 28(2):247-256.

Fountaine et al., "RNA Interference-Mediated Knockdown of a-Synuclein Protects Human Dopaminergic Neuroblastoma Cells From MPP+ Toxicity and Reduces Dopamine Transport" Journal of Neuroscience Research (2007) 85:351-363.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

(56) References Cited

OTHER PUBLICATIONS

Gautschi et al., "Activity of a Novel bcl-2/bcl-xL-Bispecific Antisense Oligonucleotide Against Tumors of Diverse Histologic Origins" Gautschi et al. (2001) 93(6):463-471.
GenBank Accession No. NM 000345.3.
Gorbatyuk et al., "In Vivo RNAi-Mediated α-Synuclein Silencing Induces Nigrostriatal Degeneration" Mol. Ther. (2010) 18(8): 1450-1457.
Henry et al., "Chemically Modified Oligonucleotides Exhibit Decreased Immune Stimulation in Mice" J Pharma Exp Ther (2000) 468-479.
International Search Report for application PCT/US11/61245 dated May 18, 2012.
International Search Report for application PCT/US18/60097 dated Sep. 30, 2019.
Iwai et al., "The precursor protein of non-A beta component of Alzheimer's disease amyloid is a presynaptic protein of the central nervous system." Neuron (1995) 14(2):467-475.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.
Kramer et al., "Presynaptic—Synuclein Aggregates, Not Lewy Bodies, Cause Neurodegenemtion in Dementia with Lewy Bodies" J. Neurosci. (2007) 27(6):1405-1410.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Lee et al., "Membrane-bound α-Synuclein Has a High Aggregation Propensity and the Ability to Seed the Aggregation of the Cytosolic Form" J. Biol. Chem. (2002) 277(1):671-678.
Leumann, "DNA Analogues: From Supramolecular Principles to Biological Properties" Bioorganic & Medicinal Chemistry (2002) 10:841-854.
Lewis et al., "In vivo silencing of alpha-synuclein using naked siRNA" Mol Neurodegener (2008) 3:19.
Liu et al., "a-Synuclein produces a long-lasting increase in neurotransmitter release" The EMBO Journal (2004) 23:4506-4516.
Luna et al., "Differential alpha-synuclein expression contributes to selective vulnerability of hippocampal neuron subpopulations to figril-induced toxicity" Acta Neuropathol (2018). Publised online Mar. 3, 2018 https://doi.org/10.1007/s00401-018-1829-8.
Maguire-Zeiss et al., "a-Synuclein: A therapeutic target for Parkinson's disease?" Pharmacol Res (2008) 58:271-280.
Maher et al., "Comparative hybrid arrest by tandem antisense oligodeoxyribonucleotides or oligodeoxyribonucleoside methylpbosphonates in a cell-free system" Nucl. Acids. Res. (1988) 16(8):3341-3358.
Marti et al., "Clinical Overview of the Synucleinopathies" Movement Disorders (2003) 18(6):S21-S27.
Martin, "Ein neuer Zugang zu 2'-O-Alkylribonucleosiden and Eigenschaften deren Oligonucleotide" Helv. Chim. Acta (1995) 78:486-504.
McCormack et al., "a-Synuclein Suppression by Targeted Small Interfering RNA in the Primate Substantia Nigro" PLoS One (2010) 5(8):e12122.
Monti et al., "Alpha-synuclein protects cerebellar granule neurons against 6-hydroxydopamine-induced death" J. of Neurochemistry (2007) 103:518-530.
Murphy et al., "Synucleins Are Developmentally Expressed, and a-Synuclein Regulates the Size of the Presynaptic Vesicular Pool in Primly Hippocampal Neurons" The Journal of Neuroscience (2000) 20(9):3214-3220.

New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3:239-243.
Reynolds et al., "Rational siRNA design for RNA interference" Nature Biotechnology (2004) 22(3):326-330.
Rockenstein et al., "Differential neuropathological alterations in transgenic mice expressing alpha-synuclein from the platelet-derived growth factor and Thy-1 promoters." J. Neurosci. Res. (2002) 68(5):568-578.
Sanghvi et al., "Heterocyclic Base Modifications in Nucleic Acids and Their Applications in Antisense Oligonucleotides" Antisense Research and Applications (1993) pp. 273-288.
Sapru et al., "Silencing of human α-synuclein in vitro and in rat brain using lentiviral-mediated RNAi" Exp. Neurol. (2006) 198:382-390.
Schulz-Schaeffer, "The synaptic pathology of α-synuclein aggregation in dementia with Lewy bodies, Parkinson's disease and Parkinson's disease dementia" Acta Neuropathologica (2010) 120(2):131-143.
Seema et al., "In-silico analysis for RNA-interference mechanism of α-synuclein to treat Parkinson's disease" Int. J. Bioinformatics Research and App (2013) 9(6) Abstract Only.
Sibley et al., "Identification of Allele-Specific RNAi Effectors Targeting Genetic Forms of Parkinson's Disease" PLOS One (2011) 6(10): e26194.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Souza et al., "Chaperone-like activity of synucleins." FEBS Lett. (2000) 474(1):116-119.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26): 8362-8379.
Uversky, "Neuropathology, biochemistry, and biophysics of alpha-synuclein aggregation." J. Neurochem. (2007) 103(1): 17-37.
Vickers et al., "Efficient reduction of target RNAs by small interfering RNA and RNase H-dependent antisense agents. A comparative analysis" J Biol Chem (2003) 278(9): 7108-7118.
Vickers et al., "Effects of RNA secondary stucture on cellular antisense activity" Nucleic Acids Res (2000) 1340-1347.
Volpicelli-Daley et al., "G2019S-LRRK2 Expression Augments alpha-Synuclein Sequestration into Inclusions in Neurons" J. Neuroscience (2016) 36(28):7415-7427.
Wahlestedt et al., "Potent and nontoxic antisense oligonucleotides containing locked nucleic acids" PNAS (2000) 97:5633-5638.
Woolf et al., "Specificity of antisense oligonucleotides in vivo" PNAS (1992) 89:7305-7309.
Xu et al., "Effective Small Interfering RNAs and Phosphorothioate Antisense DNAs have different preferences for Target Sites in the Luciferase mRNAs" Biochemical and Biophysical Research Communications (2003) 306:712-717.
Yoshida, "Multiple system atrophy: alpha-synuclein and neuronal degeneration." Neuropathology (2007) 27(5):484-493.
Zhang et al., "PowerBLAST: A New Network BLAST Application for Interactive or Automated Sequence Analysis and Annotation" Genome Res. (1997) 7:649-656.
Zhou e al., "Fine Tuning of Electrostatics around the Internucleotidic Phosphate through Incorporation of Modified 2',4'-Carhocyclic-LNAs and -ENAs Leads to Significant Modulation of Antisense Properties" J. Org. Chem. (2009) 74:118-134.

\* cited by examiner

COMPOUNDS AND METHODS FOR REDUCING SNCA EXPRESSION

SEQUENCE LISTING

The present application is being filed along with a Sequence Listing in electronic format. The Sequence Listing is provided as a file entitled BIOL0289USASEQ_ST25.txt, created on Apr. 27, 2020, which is 712 KB in size. The information in the electronic format of the sequence listing is incorporated herein by reference in its entirety.

FIELD

Provided are compounds, methods, and pharmaceutical compositions for reducing the amount or activity of alpha-synuclein (SNCA) mRNA in a cell or animal, and in certain instances reducing the amount of alpha-synuclein protein in a cell or animal. Such compounds, methods, and pharmaceutical compositions are useful to ameliorate at least one symptom or hallmark of a neurodegenerative disease. Such symptoms and hallmarks include motor dysfunction, aggregation of alpha-synuclein, neurodegeneration, cognitive decline and dementia. Such neurodegenerative diseases include Parkinson's disease, dementia with Lewy bodies, diffuse Lewy body disease, pure autonomic failure, multiple system atrophy, neuronopathic Gaucher's disease and Alzheimer's disease.

BACKGROUND

Alpha-synuclein is a small, highly charged 140-amino acid residue protein, predominantly expressed in central nervous system (CNS) neurons, where it is localized at presynaptic terminals in close proximity to synaptic vesicles (Iwai, et al., Neuron. 1995. 14: 467-475). Alpha-synuclein is encoded by the SNCA gene. Alpha-synuclein can associate with lipid membranes by forming amphipathic α-helices, as shown in vitro (Davidson, et al., J. Biol. Chem. 1998. 273: 9443-9449). Although the function of alpha-synuclein is still poorly understood, several studies suggest that it is involved in modulating synaptic transmission, the density of synaptic vesicles, and neuronal plasticity (Cabin et al., J. Neurosci. 2002. 22: 8797-8807). It has also been suggested that alpha-synuclein may have a chaperone function, as indicated by its effectiveness in preventing aggregation of proteins in in vitro assays (Souza et al., FEBS Lett. 2000. 474: 116-119). Moreover, in vivo assays demonstrate that alpha-synuclein chaperone activity is instrumental in promoting the assembly of the SNARE-complex, which is essential for neurotransmitter release in the presynaptic terminals of the brain (Burre et al., Science. 329: 1663-1667). Decreased SNARE-complex assembly is associated with neurological impairment, thus, indicating a link between presynaptic alpha-synuclein aggregates and neurodegeneration (Kramer and Schulz-Schaeffer, J.Neurosci. 2007. 27: 1405-1410). Knockout mouse models of alpha-synuclein are not lethal, and brain morphology is intact, suggesting that alpha-synuclein is not required for neuronal development and/or that compensatory pathways are present (Abeliovich et al., Neuron. 2000. 25: 239-252).

Misfolding, aggregation, and fibrillation of alpha-synuclein are implicated as critical factors in several neurodegenerative diseases, including, Parkinson's disease, Lewy body variant of Alzheimer's disease, diffuse Lewy body disease, dementia with Lewy bodies, and multiple system atrophy (Schulz-Schaeffer Acta Neuropathol. 2010. 120: 131-143; Yoshida. Neuropathology. 2007. 27: 484-493). In each of these cases, alpha-synuclein protein is misfolded and assembles in aggregates in Lewy bodies and Lewy neurites (Uversky. J. Neurochem. 2007. 103: 17-37). Several recent studies have shown that lipidic environments that promote alpha-synuclein folding also accelerate alpha-synuclein aggregation, suggesting that the lipid-associated conformation of alpha-synuclein may be relevant to alpha-synuclein misfolding in neurodegenerative diseases (Conway et al., Science. 2001. 294: 6-9; Lee et al., J. Biol. Chem. 2002. 277: 671-678). Mutations at position 53, where alanine is changed to threonine, and at position 30, where alanine is changed to proline, have been shown to cause alpha-synuclein to be in a random coil state, so that aggregation is more likely to occur (Clayton and George, J. Neurosci. 1999. 58: 120-129).

Currently there is a lack of acceptable options for treating neurodegenerative disease such as Parkinson's disease, dementia with Lewy bodies, diffuse Lewy body disease, pure autonomic failure, multiple system atrophy, neuronopathic Gaucher's disease and Alzheimer's disease. It is therefore an object herein to provide compounds, methods, and pharmaceutical compositions for the treatment of such diseases.

SUMMARY OF THE INVENTION

Provided herein are compounds, methods and pharmaceutical compositions for reducing the amount or activity of SNCA mRNA, and in certain embodiments reducing the amount of alpha-synuclein protein in a cell or animal. In certain embodiments, the animal has a neurodegenerative disease. In certain embodiments, the animal has Parkinson's disease, dementia with Lewy bodies, diffuse Lewy body disease, pure autonomic failure, multiple system atrophy, neuronopathic Gaucher's disease or Alzheimer's disease. In certain embodiments, compounds useful for reducing expression of SNCA mRNA are oligomeric compounds. In certain embodiments, compounds useful for reducing expression of SNCA mRNA are modified oligonucleotides.

Also provided are methods useful for ameliorating at least one symptom or hallmark of a neurodegenerative disease. In certain embodiments, the neurodegenerative disease is Parkinson's disease, dementia with Lewy bodies, diffuse Lewy body disease, pure autonomic failure, multiple system atrophy, neuronopathic Gaucher's disease and Alzheimer's disease. In certain embodiments, the symptom or hallmark includes motor dysfunction, aggregation of alpha-synuclein, neurodegeneration, cognitive decline and dementia. In certain embodiments, amelioration of these symptoms results in improved motor function, reduction of alpha-synuclein aggregates, reduced neurodegeneration and/or reduced dementia.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyribosy sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to an animal.

As used herein, "animal" means a human or non-human animal.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom or hallmark is motor dysfunction, aggregation of alpha-synuclein, neurodegeneration, cognitive decline and/or dementia. In certain embodiments, amelioration of these symptoms results in improved motor function, reduction of alpha-synuclein aggregates, reduced neurodegeneration and/or reduced dementia.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "constrained ethyl" or "cEt" or "cEt modified sugar" means a β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-CH(CH$_3$)—O-2', and wherein the methyl group of the bridge is in the S configuration.

As used herein, "cEt nucleoside" means a nucleoside comprising cEt modified sugar.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-deoxyribosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, the term "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "MOE" means methoxyethyl. "2'-MOE" or "2'-MOE modified sugar" means a 2'-OCH$_2$CH$_2$OCH$_3$ group in place of the 2'—OH group of a ribosyl sugar moiety.

As used herein, "2'-MOE nucleoside" means a nucleoside comprising a 2'-MOE modified sugar As used herein, "motif" means the pattern of unmodified and/or modified sugar moieties, nucleobases, and/or internucleoside linkages, in an oligonucleotide.

As used herein, "mRNA" means an RNA transcript that encodes a protein and includes pre-mRNA and mature mRNA unless otherwise specified.

As used herein, "neurodegenerative disease" means a condition marked by progressive loss of structure or function of neurons, including death of neurons. In certain embodiments, the neurodegenerative disease is Parkinson's disease, dementia with Lewy bodies, diffuse Lewy body disease, pure autonomic failure, multiple system atrophy, neuronopathic Gaucher's disease and Alzheimer's disease.

As used herein, "nucleobase" means an unmodified nucleobase or a modified nucleobase. As used herein an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein "prodrug" means a therapeutic agent in a form outside the body that is converted to a different form within an animal or cells thereof. Typically conversion of a prodrug within the animal is facilitated by the action of an enzymes (e.g., endogenous or viral enzyme) or chemicals present in cells or tissues and/or by physiologic conditions.

As used herein, "reducing or inhibiting the amount or activity" refers to a reduction or blockade of the transcriptional expression or activity relative to the transcriptional expression or activity in an untreated or control sample and does not necessarily indicate a total elimination of transcriptional expression or activity.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard cell assay" means the assay described in Example 10 and reasonable variations thereof.

As used herein, "standard in vivo assay" means the experiment described in Example 22 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the results of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to an animal. For example, a therapeutically effective amount improves a symptom of a disease.

The present disclosure provides the following non-limiting numbered embodiments:

Embodiment 1. An oligomeric compound comprising a modified oligonucleotide consisting of 10-30 linked nucleosides and having a nucleobase sequence comprising at least 12, 13, 14, 15, 16 or 17 nucleobases of any of SEQ ID NOS: 2193, 1703, 28-1702, 1704-2192, and 2194-2793.

Embodiment 2. An oligomeric compound comprising a modified oligonucleotide consisting of 10-30 linked nucleosides and having a nucleobase sequence complementary to at least 8, at least 9, at least 10, at least 11, at least 12, at least 13, at least 14, at least 15, at least 16, at least 17, at least 18, at least 19, or at least 20 contiguous nucleobases of: an equal length portion of nucleobases 50915-50943 of SEQ ID NO: 2;

an equal length portion of nucleobases 19630-19656 of SEQ ID NO: 2;
an equal length portion of nucleobases 28451-28491 of SEQ ID NO: 2;
an equal length portion of nucleobases 48712-48760 of SEQ ID NO: 2;
an equal length portion of nucleobases 23279-23315 of SEQ ID NO: 2;
an equal length portion of nucleobases 20964-21018 of SEQ ID NO: 2;
an equal length portion of nucleobases 22454-22477 of SEQ ID NO: 2;
an equal length portion of nucleobases 72294-72321 of SEQ ID NO: 2;
an equal length portion of nucleobases 20549-20581 of SEQ ID NO: 2; or
an equal length portion of nucleobases 27412-27432 of SEQ ID NO: 2.

Embodiment 3. The oligomeric compound of embodiment 1 or 2, wherein the modified oligonucleotide has a nucleobase sequence that is at least 80%, 85%, 90%, 95%, or 100% complementary to any of the nucleobase sequences of SEQ ID NO: 1-6, when measured across the entire nucleobase sequence of the modified oligonucleotide.

Embodiment 4. The oligomeric compound of any of embodiments 1-3, wherein the modified oligonucleotide comprises at least one modified nucleoside.

Embodiment 5. The oligomeric compound of embodiment 4, wherein the modified oligonucleotide comprises at least one modified nucleoside comprising a modified sugar moiety.

Embodiment 6. The oligomeric compound of embodiment 5, wherein the modified oligonucleotide comprises at least one modified nucleoside comprising a bicyclic sugar moiety.

Embodiment 7. The oligomeric compound of embodiment 6, wherein the modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 8. The oligomeric compound of any of embodiments 4-7, wherein the modified oligonucleotide comprises at least one modified nucleoside comprising a non-bicyclic modified sugar moiety.

Embodiment 9. The oligomeric compound of embodiment 8, wherein the modified oligonucleotide comprises at least one modified nucleoside comprising a non-bicyclic modified sugar moiety comprising a 2'-MOE modified sugar or 2'-OMe modified sugar.

Embodiment 10. The oligomeric compound of any of embodiments 4-9, wherein the modified oligonucleotide comprises at least one modified nucleoside comprising a sugar surrogate.

Embodiment 11. The oligomeric compound of embodiment 10, wherein the modified oligonucleotide comprises at least one modified nucleoside comprising a sugar surrogate selected from morpholino and PNA.

Embodiment 12. The oligomeric compound of any of embodiments 1-11, wherein the modified oligonucleotide has a sugar motif comprising:
a 5'-region consisting of 1-5 linked 5'-region nucleosides;
a central region consisting of 6-10 linked central region nucleosides; and
a 3'-region consisting of 1-5 linked 3'-region nucleosides;
wherein
each of the 5'-region nucleosides and each of the 3'-region nucleosides comprises a modified sugar moiety and each of the central region nucleosides comprises an unmodified 2'-deoxyribosyl sugar moiety.

Embodiment 13. The oligomeric compound of any of embodiments 1-12, wherein the modified oligonucleotide comprises at least one modified internucleoside linkage.

Embodiment 14. The oligomeric compound of embodiment 13, wherein each internucleoside linkage of the modified oligonucleotide is a modified internucleoside linkage.

Embodiment 15. The oligomeric compound of embodiment 13 or 14 wherein at least one internucleoside linkage is a phosphorothioate internucleoside linkage.

Embodiment 16. The oligomeric compound of embodiment 13 or 15 wherein the modified oligonucleotide comprises at least one phosphodiester internucleoside linkage.

Embodiment 17. The oligomeric compound of any of embodiments 13, 15, or 16, wherein each internucleoside linkage is either a phosphodiester internucleoside linkage or a phosphorothioate internucleoside linkage.

Embodiment 18. The oligomeric compound of any of embodiments 1-17, wherein the modified oligonucleotide comprises at least one modified nucleobase.

Embodiment 19. The oligomeric compound of embodiment 18, wherein the modified nucleobase is a 5-methyl cytosine.

Embodiment 20. The oligomeric compound of any of embodiments 1-19, wherein the modified oligonucleotide consists of 12-30, 12-22, 12-20, 14-20, 15-25, 16-20, 18-22 or 18-20 linked nucleosides.

Embodiment 21. The oligomeric compound of any of embodiments 1-20, wherein the modified oligonucleotide consists of 17 or 20 linked nucleosides.

Embodiment 22. The oligomeric compound of any of embodiments 1-21 consisting of the modified oligonucleotide.

Embodiment 23. The oligomeric compound of any of embodiments 1-21 comprising a conjugate group comprising a conjugate moiety and a conjugate linker.

Embodiment 24. The oligomeric compound of embodiment 23, wherein the conjugate group comprises a GalNAc cluster comprising 1-3 GalNAc ligands.

Embodiment 25. The oligomeric compound of embodiment 23 or 24, wherein the conjugate linker consists of a single bond.

Embodiment 26. The oligomeric compound of embodiment 24, wherein the conjugate linker is cleavable.

Embodiment 27. The oligomeric compound of embodiment 26, wherein the conjugate linker comprises 1-3 linker-nucleosides.

Embodiment 28. The oligomeric compound of any of embodiments 23-27, wherein the conjugate group is attached to the modified oligonucleotide at the 5'-end of the modified oligonucleotide.

Embodiment 29. The oligomeric compound of any of embodiments 23-27, wherein the conjugate group is attached to the modified oligonucleotide at the 3'-end of the modified oligonucleotide.

Embodiment 30. The oligomeric compound of any of embodiments 1-29 comprising a terminal group.

Embodiment 31. The oligomeric compound of any of embodiments 1-30 wherein the oligomeric compound is a singled-stranded oligomeric compound.

Embodiment 32. The oligomeric compound of any of embodiments 1-26 or 28-30, wherein the oligomeric compound does not comprise linker-nucleosides.

Embodiment 33. An oligomeric duplex comprising an oligomeric compound of any of embodiments 1-30 or 32.

Embodiment 34. An antisense compound comprising or consisting of an oligomeric compound of any of embodiments 1-32 or an oligomeric duplex of embodiment 33.

Embodiment 35. A pharmaceutical composition comprising an oligomeric compound of any of embodiments 1-32 or an oligomeric duplex of embodiment 33 and a pharmaceutically acceptable carrier or diluent.

Embodiment 36. A modified oligonucleotide according to the following formula:

(SEQ ID NO: 1887)
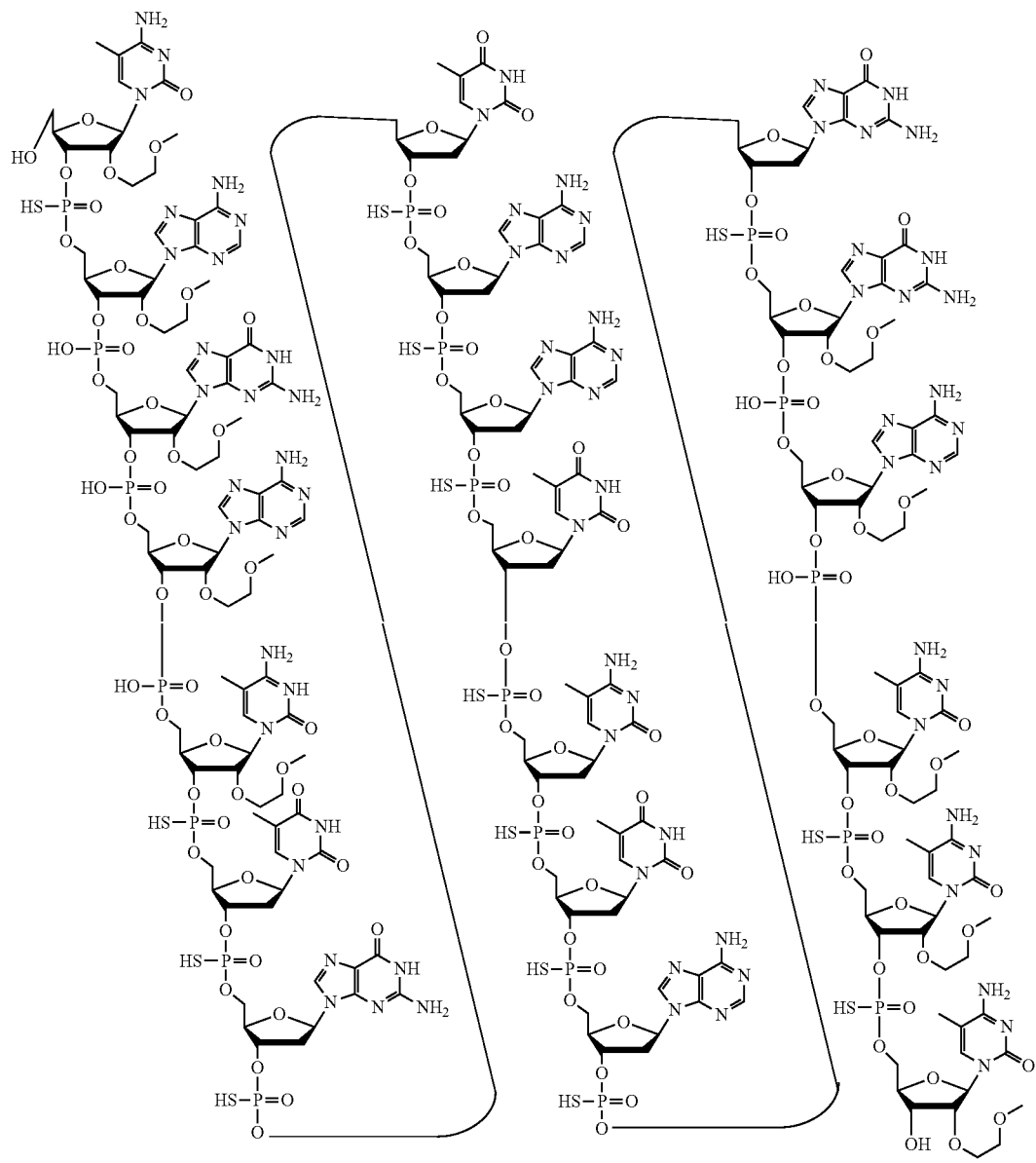
or a salt thereof.
Consistent with the definitions and disclosure herein, compound of Embodiment 36 may be made by deliberately controlling stereochemistry of any, all or none of the linkages.
Embodiment 37. A modified oligonucleotide according to the following formula:

(SEQ ID NO: 2166)
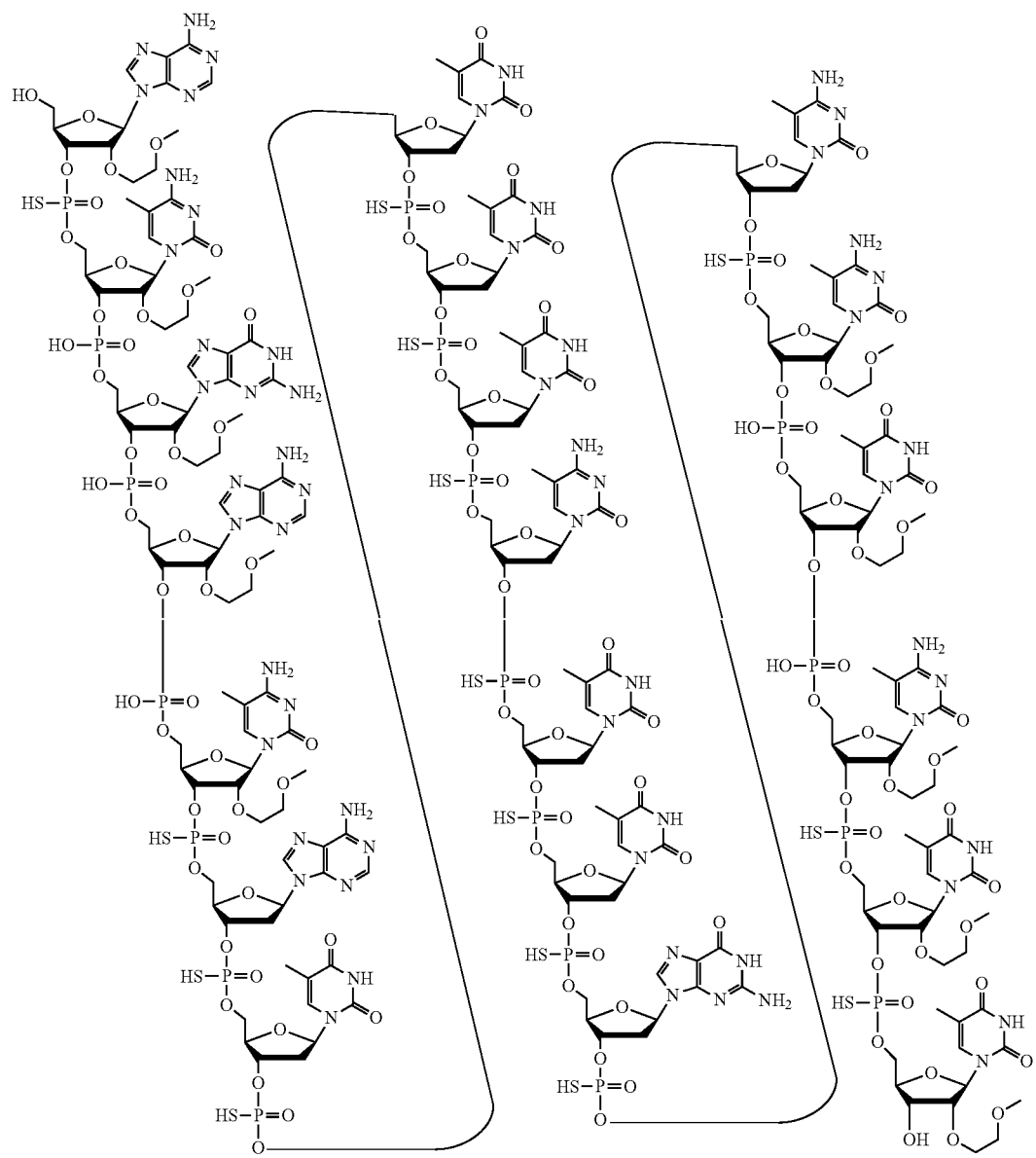
or a salt thereof.
Consistent with the definitions and disclosure herein, compound of Embodiment 37 may be made by deliberately controlling stereochemistry of any, all or none of the linkages.
Embodiment 38. A modified oligonucleotide according to the following formula:

(SEQ ID NO: 2193)
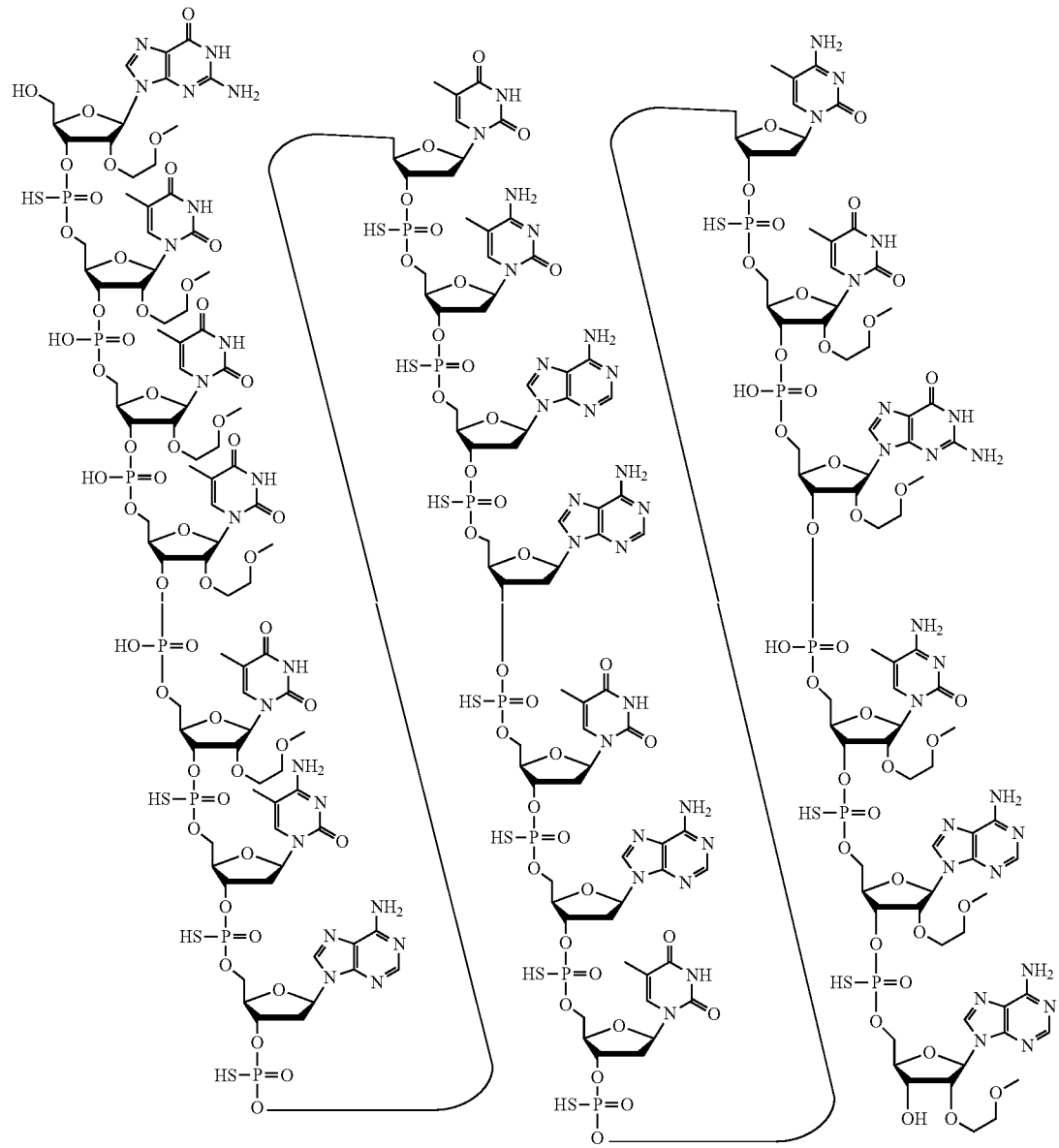
or a salt thereof.
Consistent with the definitions and disclosure herein, compound of Embodiment 38 may be made by deliberately controlly stereochemistry of any, all or none of the linkages.
Embodiment 39. A modified oligonucleotide according to the following formula:

(SEQ ID NO: 1639)
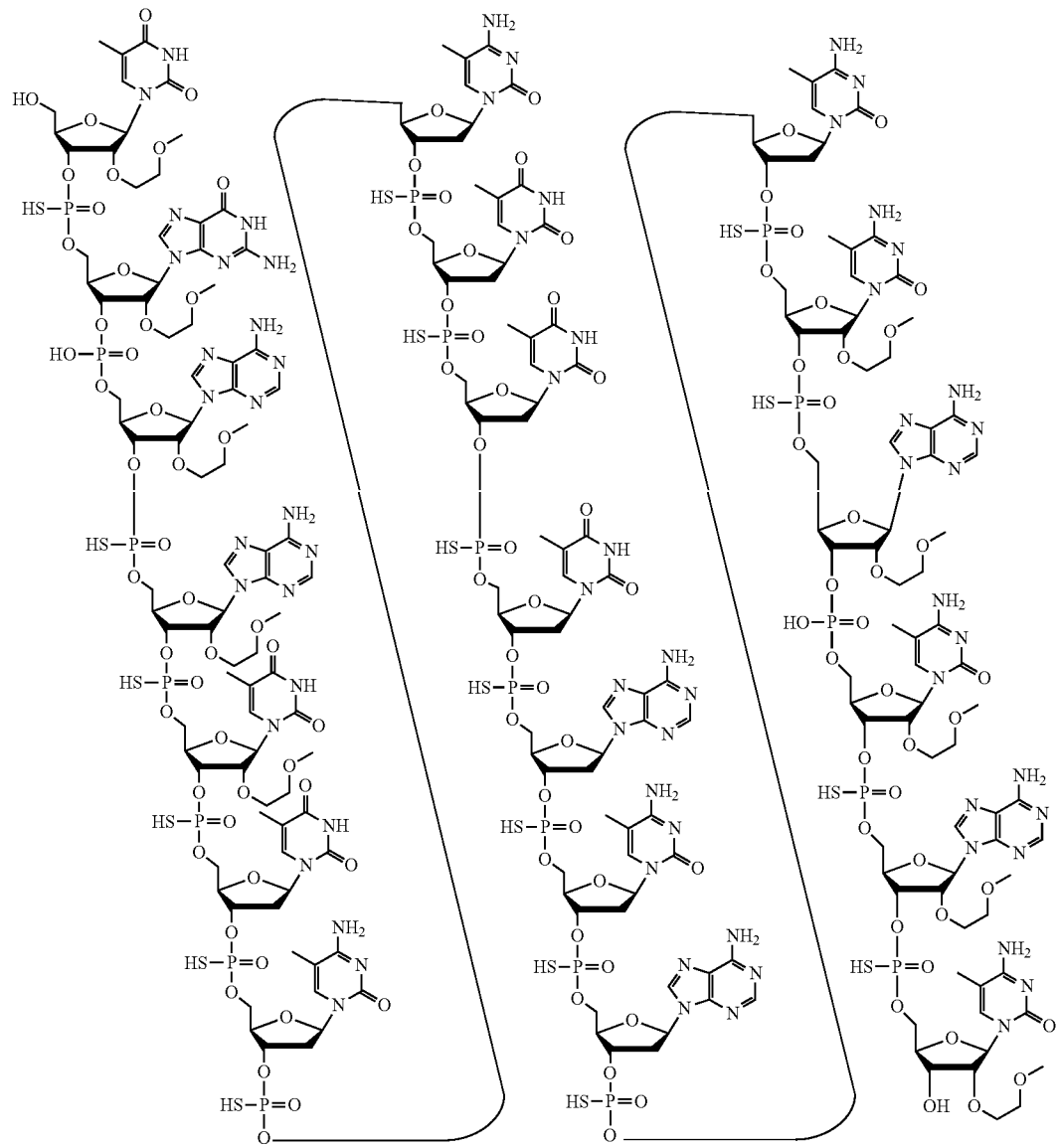
or a salt thereof.
Consistent with the definitions and disclosure herein, compound of Embodiment 39 may be made by deliberately controlling stereochemistry of any, all or none of the linkages.
Embodiment 40. A modified oligonucleotide according to the following formula:

(SEQ ID NO: 1703)
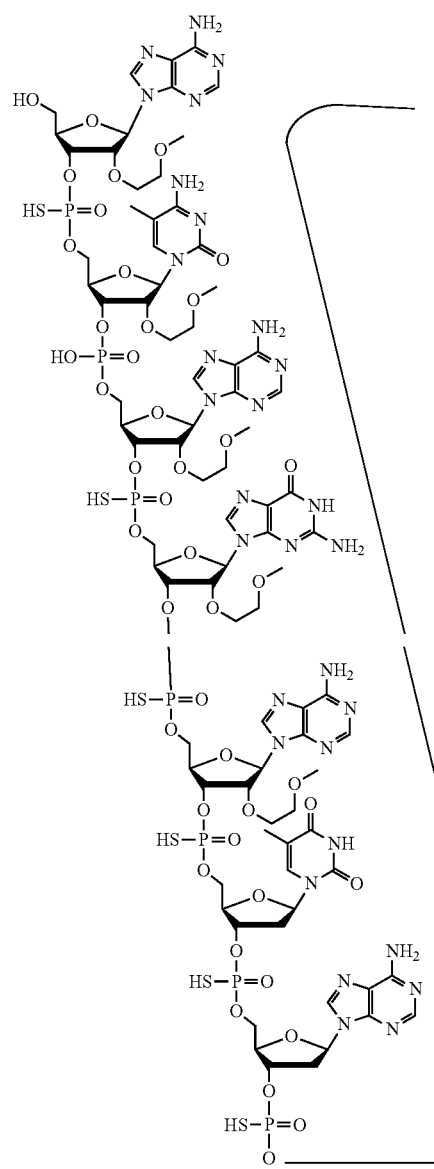
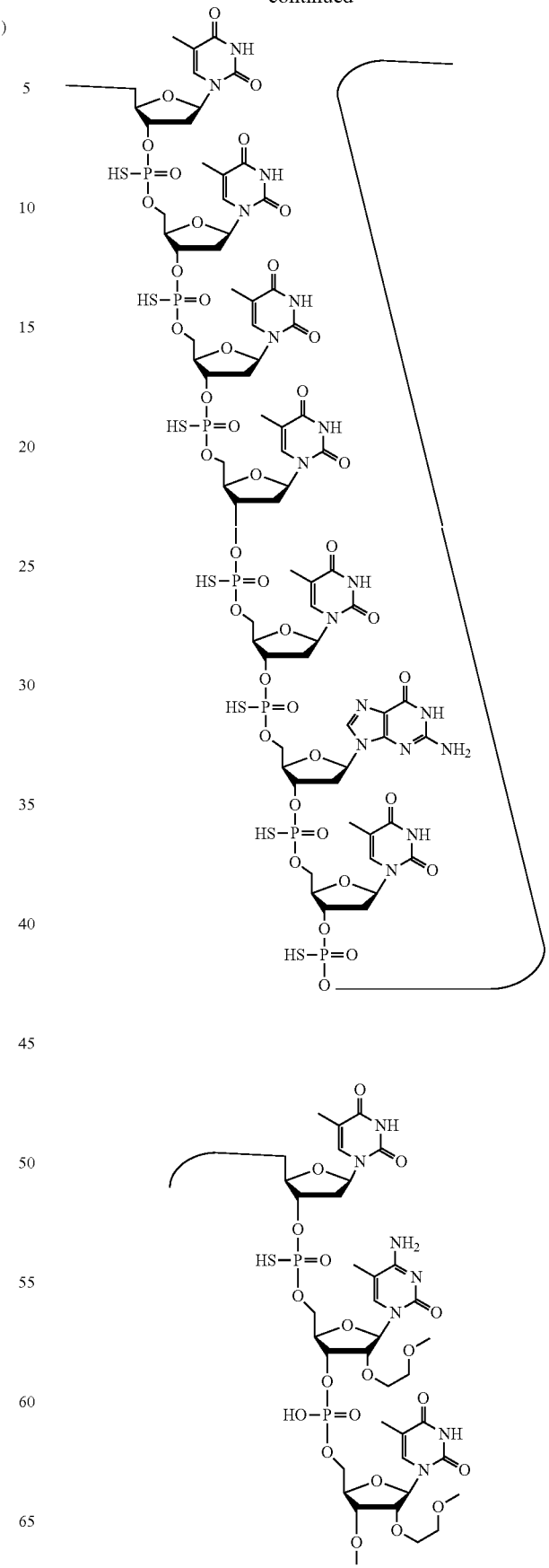

-continued

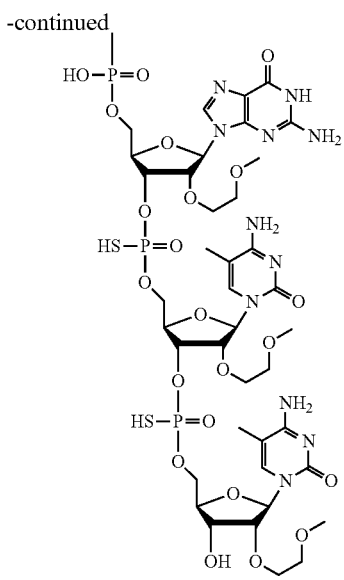

or a salt thereof.

Consistent with the definitions and disclosure herein, compound of Embodiment 40 may be made by deliberately controlling stereochemistry of any, all or none of the linkages.

Embodiment 41. The modified oligonucleotide of any of embodiments 36-40, which is a sodium salt of the formula.

Embodiment 42. A chirally enriched population of the modified oligonucleotide of any of embodiments 36-40 wherein the population is enriched for modified oligonucleotides comprising at least one particular phosphorothioate internucleoside linkage having a particular stereochemical configuration.

Embodiment 43. The chirally enriched population of embodiment 42, wherein the population is enriched for modified oligonucleotides comprising at least one particular phosphorothioate internucleoside linkage having the (Sp) configuration.

Embodiment 44. The chirally enriched population of embodiment 42, wherein the population is enriched for modified oligonucleotides comprising at least one particular phosphorothioate internucleoside linkage having the (Rp) configuration.

Embodiment 45. The chirally enriched population of embodiment 42, wherein the population is enriched for modified oligonucleotides having a particular, independently selected stereochemical configuration at each phosphorothioate internucleoside linkage Embodiment 46. The chirally enriched population of embodiment 45, wherein the population is enriched for modified oligonucleotides having the (Sp) configuration at each phosphorothioate internucleoside linkage.

Embodiment 47. The chirally enriched population of embodiment 45, wherein the population is enriched for modified oligonucleotides having the (Rp) configuration at each phosphorothioate internucleoside linkage.

Embodiment 48. The chirally enriched population of embodiment 45, wherein the population is enriched for modified oligonucleotides having the (Rp) configuration at one particular phosphorothioate internucleoside linkage and the (Sp) configuration at each of the remaining phosphorothioate internucleoside linkages.

Embodiment 48. The chirally enriched population of embodiment 42 or embodiment 45 wherein the population is enriched for modified oligonucleotides having at least 3 contiguous phosphorothioate internucleoside linkages in the Sp, Sp, and Rp configurations, in the 5' to 3' direction.

Embodiment 49. The chirally enriched population of embodiment 42 or embodiment 45 wherein the population is enriched for modified oligonucleotides having at least 3 contiguous phosphorothioate internucleoside linkages in the Sp, Sp, and Rp configurations, in the 5' to 3' direction.

Embodiment 50. A chirally enriched population of oligomeric compounds of any of embodiments 1-32, wherein all of the phosphorothioate internucleoside linkages of the modified oligonucleotide are stereorandom.

Embodiment 51. A pharmaceutical composition comprising the modified oligonucleotide of any of embodiments 36-40 and a pharmaceutically acceptable diluent or carrier.

Embodiment 52. The pharmaceutical composition of embodiment 51, wherein the pharmaceutically acceptable diluent is artificial cerebrospinal fluid.

Embodiment 53. The pharmaceutical composition of embodiment 50, wherein the pharmaceutical composition consists essentially of the modified oligonucleotide and artificial cerebrospinal fluid.

Embodiment 54. A method comprising administering to an animal a pharmaceutical composition of any of embodiments 35 or 51-53.

Embodiment 55. A method of treating a disease associated with SNCA comprising administering to an individual having or at risk for developing a disease associated with SNCA a therapeutically effective amount of a pharmaceutical composition according to any of embodiments 35 or 51-53; and thereby treating the disease associated with SNCA.

Embodiment 56. The method of embodiment 55, wherein the disease associated with SNCA is a neurodegenerative disease.

Embodiment 57. The method of embodiment 56, wherein the neurodegenerative disease is any of Parkinson's disease, dementia with Lewy bodies, diffuse Lewy body disease, pure autonomic failure, multiple system atrophy, neuronopathic Gaucher's disease and Alzheimer's disease.

Embodiment 58. The method of embodiment 56, wherein at least one symptom or hallmark of the neurodegenerative disease is ameliorated.

Embodiment 59. The method of embodiment 58, wherein the symptom or hallmark is any of motor dysfunction, aggregation of alpha-synuclein, neurodegeneration, cognitive decline and dementia.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modifed sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$O CH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)- alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$O N(R$_m$)(R$_n$), O(CH$_2$)$_2$O(CH$_2$)$_2$N(CH$_3$)$_2$, and N-substituted acetamide (OCH$_2$C(=O)—N(R.)(R.)), where each R$_m$ and R$_n$ is, independently, H, an amino protecting group, or substituted or unsubstituted C$_1$-C$_{10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$O N(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'—(CH$_2$)$_2$-2', 4'—(CH$_2$)$_3$-2', 4'—CH$_2$—O-2' ("LNA"), 4'-CH$_2$—S-2', 4'—(CH$_2$)$_2$—O-2' ("ENA"), 4'-CH(CH$_3$)—O-2' (referred to as "constrained ethyl" or "cEt"), 4'-CH$_2$—O—CH$_2$-2', 4'—CH$_2$—N(R)-2', 4'—CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'—C(R$_a$R$_b$)—O—N(R)-2', 4'—CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, [C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Wengel e a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794, 499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

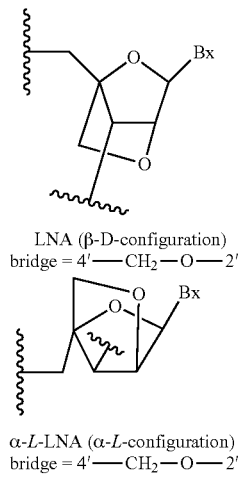

LNA (β-D-configuration)
bridge = 4'——CH$_2$—O——2'

α-L-LNA (α-L-configuration)
bridge = 4'——CH$_2$—O——2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

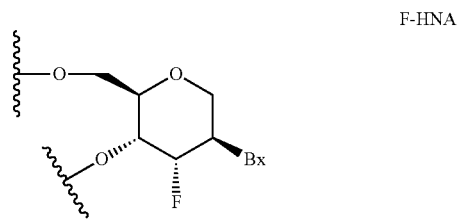

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

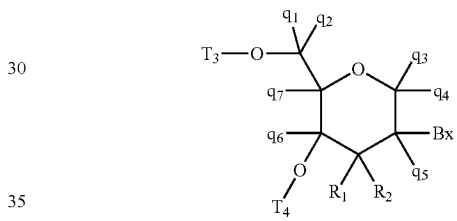

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom.

For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

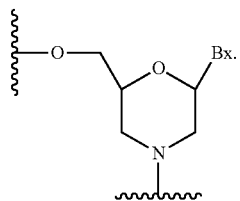

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp)

Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie, International Edition*, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

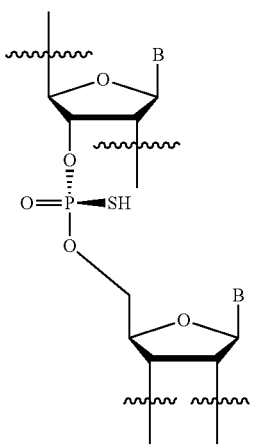

(Rp)

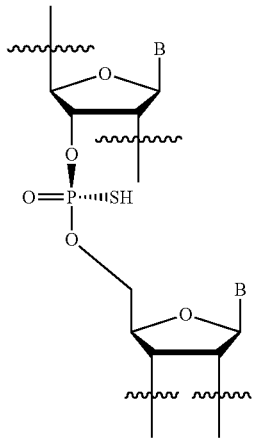

(Sp)

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside. In certain embodiments, at least one nucleoside of each wing of a gapmer is a modified nucleoside. In certain embodiments, at least two nucleosides of each wing of a gapmer are modified nucleosides. In certain embodiments, at least three nucleosides of each wing of a gapmer are modified nucleosides. In certain embodiments, at least four nucleosides of each wing of a gapmer are modified nucleosides.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]–[# of nucleosides in the gap]–[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprise unmodified deoxynucleosides sugars. Thus, a 5-10-5 MOE gapmer consists of 5 linked MOE modified nucleosides in the 5'-wing, 10 linked deoxynucleosides in the gap, and 5 linked MOE nucleosides in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phophate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. SNCA

In certain embodiments, oligomeric compounds comprise or consist of an oligonucleotide comprising a region that is complementary to a target nucleic acid, wherein the target nucleic acid is SNCA. In certain embodiments, SNCA nucleic acid has the sequence set forth in SEQ ID NO: 1 (GENBANK Accession No: NM_000345.3), SEQ ID NO: 2 (GENBANK Accession No: NT_016354.20 TRUNC 30800000-30919000), SEQ ID NO: 3 (GENBANK Accession No: JN709863.1), SEQ ID NO: 4 (GENBANK Accession No: BC013293.2), SEQ ID NO: 5 (GENBANK Accession No: NM_001146055.1), and SEQ ID NO: 6 (GENBANK Accession No: HQ830269.1).

In certain embodiments, contacting a cell with an oligomeric compound complementary to SEQ ID NO: 1, SEQ ID NO: 2, SEQ ID NO: 3, SEQ ID NO: 4, SEQ ID NO: 5, or SEQ ID NO: 6 reduces the amount of SNCA mRNA, and in certain embodiments reduces the amount of alpha-synuclein protein. In certain embodiments, the oligomeric compound consists of a modified oligonucleotide. In certain embodiments, contacting a cell in an animal with an oligomeric compound complementary to SEQ ID NO: 1, SEQ ID NO: 2, SEQ ID NO: 3, SEQ ID NO: 4, SEQ ID NO: 5, or SEQ ID NO: 6 ameliorates one or more symptom or hallmark of a neurodegenerative disease. In certain embodiments, the oligomeric compound consists of a modified oligonucleotide. In certain embodiments, the symptom or hallmark is motor dysfunction, aggregation of alpha-synuclein, neurodegeneration, cognitive decline and dementia. In certain embodiments, contacting a cell in an animal with an oligonucleotide complementary to SEQ ID NO: 1, SEQ ID NO: 2, SEQ ID NO: 3, SEQ ID NO: 4, SEQ ID NO: 5, or SEQ ID NO: 6 results in improved motor function, reduction of alpha-synuclein aggregates, reduced neurodegeneration and/or reduced dementia. In certain embodiments, the oligomeric compound consists of a modified oligonucleotide

C. Certain Tart et Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the cells and tissues that comprise the central nervous system (CNS). Such cells and tissues include motor cortex, frontal cortex, caudate, amygdala, pons, substantia nigra, putamen, cerebellar peduncle, corpus collosum, dorsal cochlear nucleus (DCN), entorhinal cortex (Ent Cortex), hippocampus, insular cortex, medulla oblongata, central gray matter, pulvinar, occipital cortex, cerebral cortex, temporal cortex, globus pallidus, superior colliculi, and basal forbrain nuclei.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

VII. Certain Compositions

1. Compound No: 763085

In certain embodiments, Compound No: 763085 is characterized as a 5-10-5 MOE gapmer, having a sequence of (from 5' to 3') CAGACTGTAATCTAGGACCC (incorporated herein as SEQ ID NO: 1887), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No: 763085 is characterized by the following chemical notation: mCes Aeo Geo Aeo mCes Tds Gds Tds Ads Ads Tds mCds Tds Ads Gds Geo Aeo mCes mCes mCe; wherein, A=an adenine nucleobase, mC=a 5-methyl cytosine nucleobase, G=a guanine nucleobase, T=a thymine nucleobase, e=a 2'-MOE modified sugar, d=a 2'-deoxyribose sugar, s=a phosphorothioate internucleoside linkage, and o=a phosphodiester internucleoside linkage.

In certain embodiments, Compound No: 763085 is represented by the following chemical structure:

Structure 1. Compound No. 763085

(SEQ ID NO: 1887)

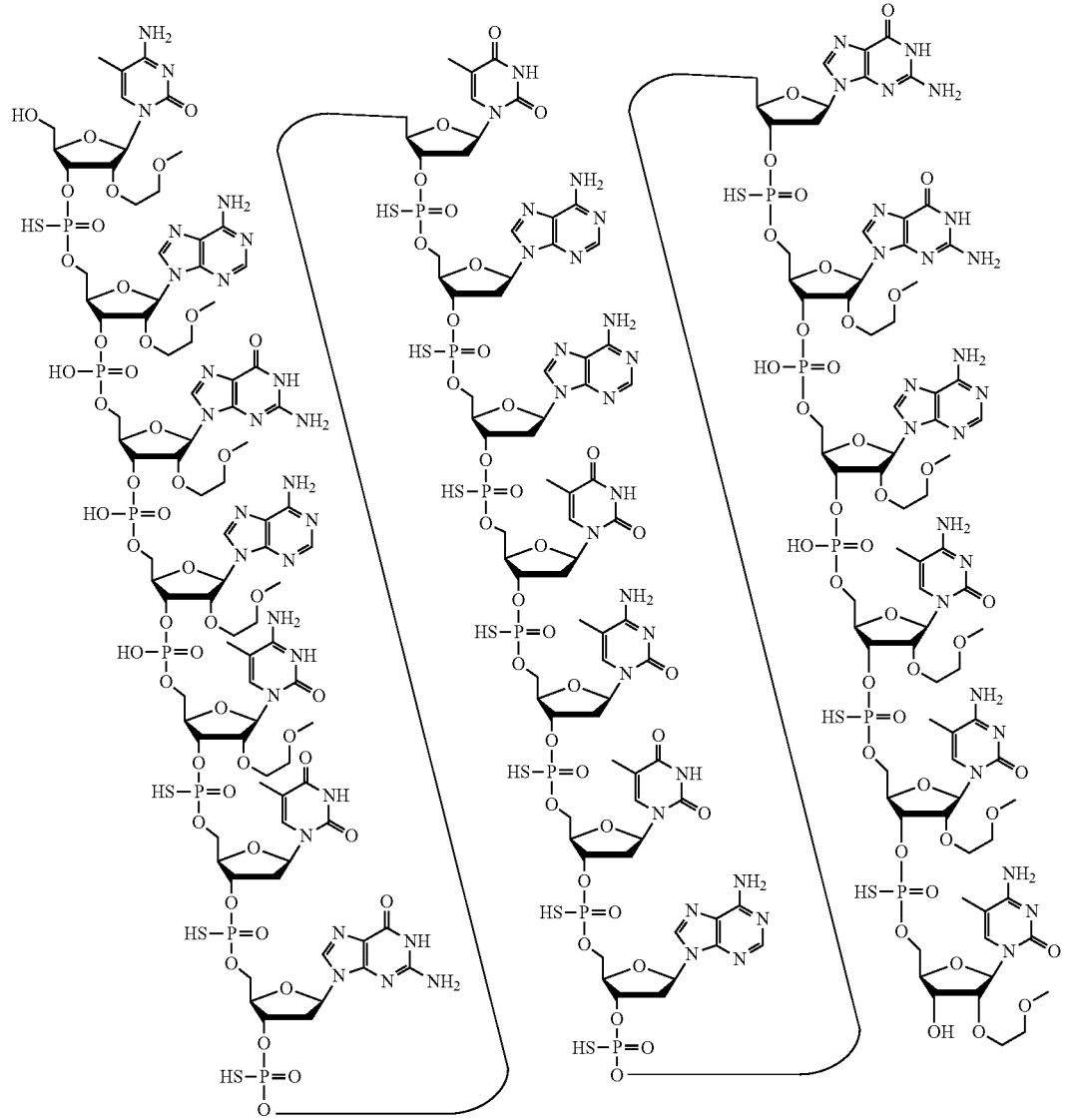

2. Compound No: 763364

In certain embodiments, Compound No: 763364 is characterized as a 5-10-5 MOE gapmer, having a sequence of (from 5' to 3') ACGACATTTTCTTGCCTCTT (incorporated herein as SEQ ID NO: 2166), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No: 763364 is characterized by the following chemical notation: Aes mCeo Geo Aeo mCes Ads Tds Tds Tds Tds mCds Tds Tds Gds mCds mCeo Teo mCes Tes Te; wherein, A=an adenine nucleobase, mC=a 5-methyl cytosine nucleobase, G=a guanine nucleobase, T=a thymine nucleobase, e=a 2'-MOE modified sugar, d=a 2'-deoxyribose sugar, s=a phosphorothioate internucleoside linkage, and o=a phosphodiester internucleoside linkage.

In certain embodiments, Compound No: 763364 is represented by the following chemical structure:

Structure 2. Compound No: 763364

(SEQ ID NO: 2166)

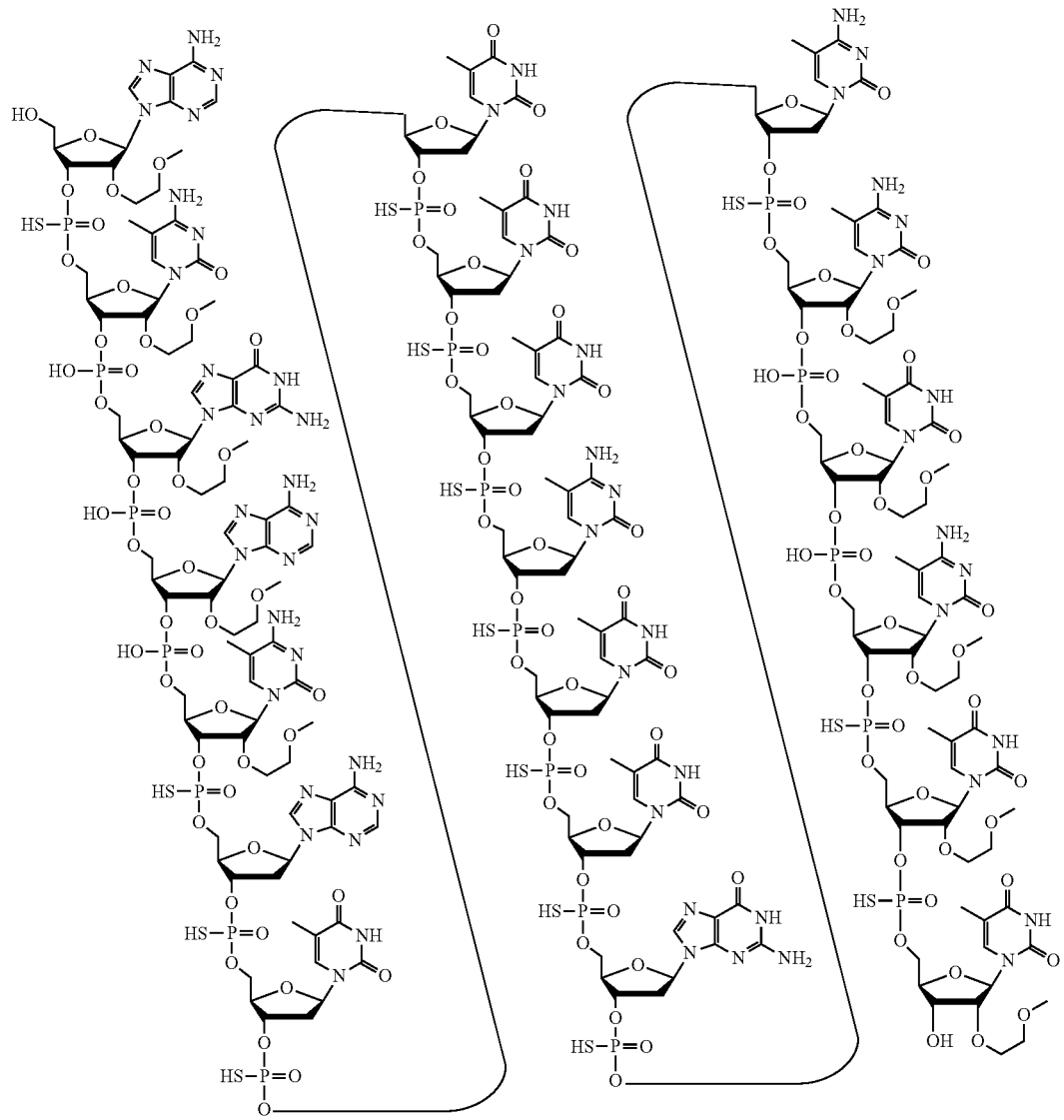

3. Compound No: 763391

In certain embodiments, Compound No: 763391 is characterized as a 5-10-5 MOE gapmer, having a sequence of (from 5' to 3') GTTTTCATCAATATCTGCAA (incorporated herein as SEQ ID NO: 2193), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No: 763391 is characterized by the following chemical notation: Ges Teo Teo Teo Tes mCds Ads Tds mCds Ads Ads Tds Ads Tds mCds Teo Geo mCes Aes Ae; wherein, A=an adenine nucleobase, mC=a 5-methyl cytosine nucleobase, G=a guanine nucleobase, T=a thymine nucleobase, e=a 2'-MOE modified sugar, d=a 2'-deoxyribose sugar, s=a phosphorothioate internucleoside linkage, and o=a phosphodiester internucleoside linkage.

In certain embodiments, Compound No: 763391 is represented by the following chemical structure:

Structure 3. Compound No: 763391

(SEQ ID NO: 2193)

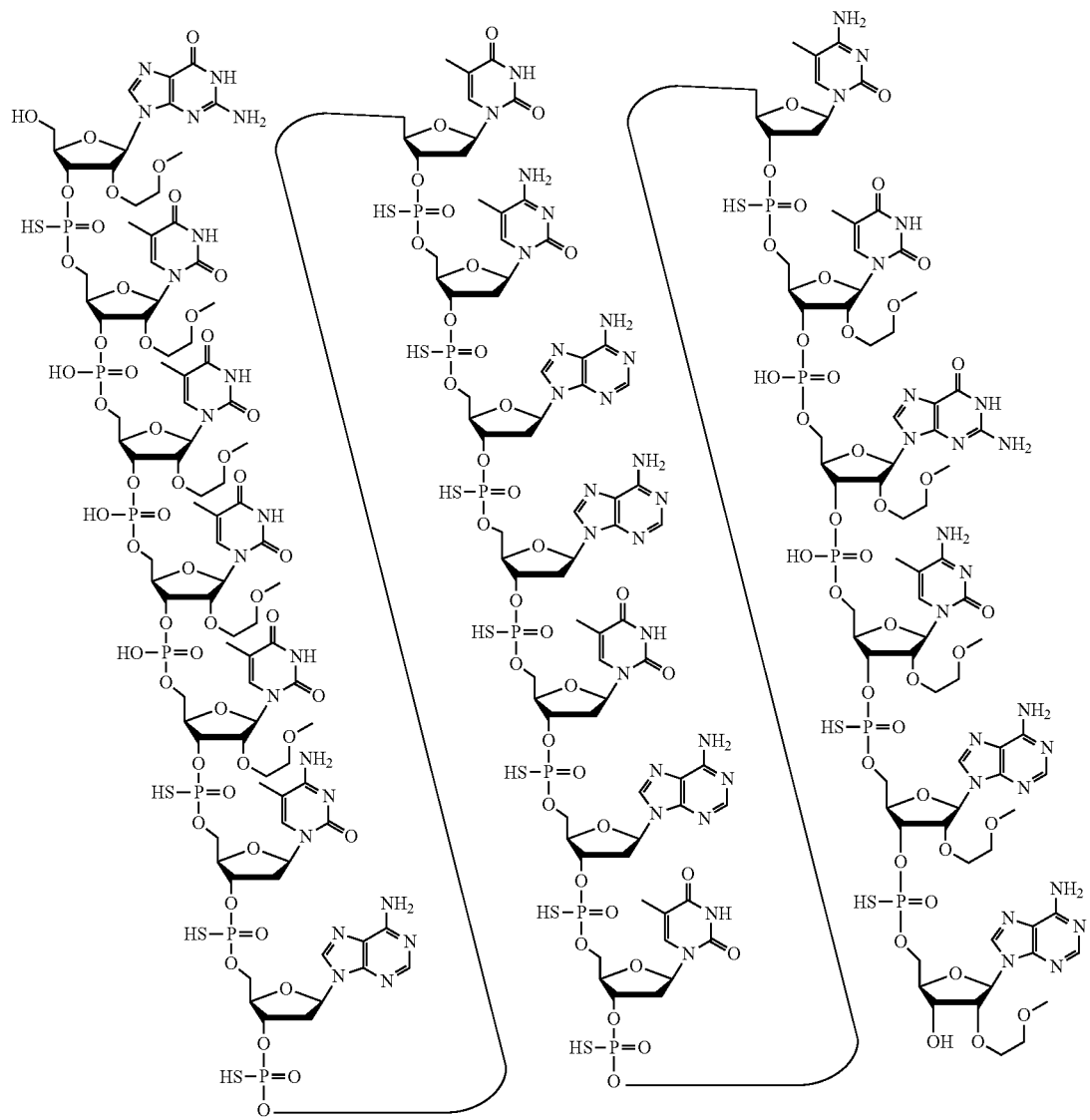

4. Compound No: 789243

In certain embodiments, Compound No: 789243 is characterized as a 5-10-5 MOE gapmer, having a sequence of (from 5' to 3') TGAATTCCTTTACACCACAC (incorporated herein as SEQ ID NO: 1639), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3 and 17 to 18 are phosphodiester internucleoside linkages and the internucleoside linkages between nucleosides 1 to 2, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No: 789243 is characterized by the following chemical notation: Tes Geo Aes Aes Tes Tds mCds mCds Tds Tds Tds Ads mCds Ads mCds mCes Aeo mCes Aes mCe; wherein, A=an adenine nucleobase, mC=a 5-methyl cytosine nucleobase, G=a guanine nucleobase, T=a thymine nucleobase, e=a 2'-MOE modified sugar, d=a 2'-deoxyribose sugar, s=a phosphorothioate internucleoside linkage, and o=a phosphodiester internucleoside linkage.

In certain embodiments, Compound No: 789243 is represented by the following chemical structure:

Structure 4. Compound No: 789243
(SEQ ID NO: 1639)

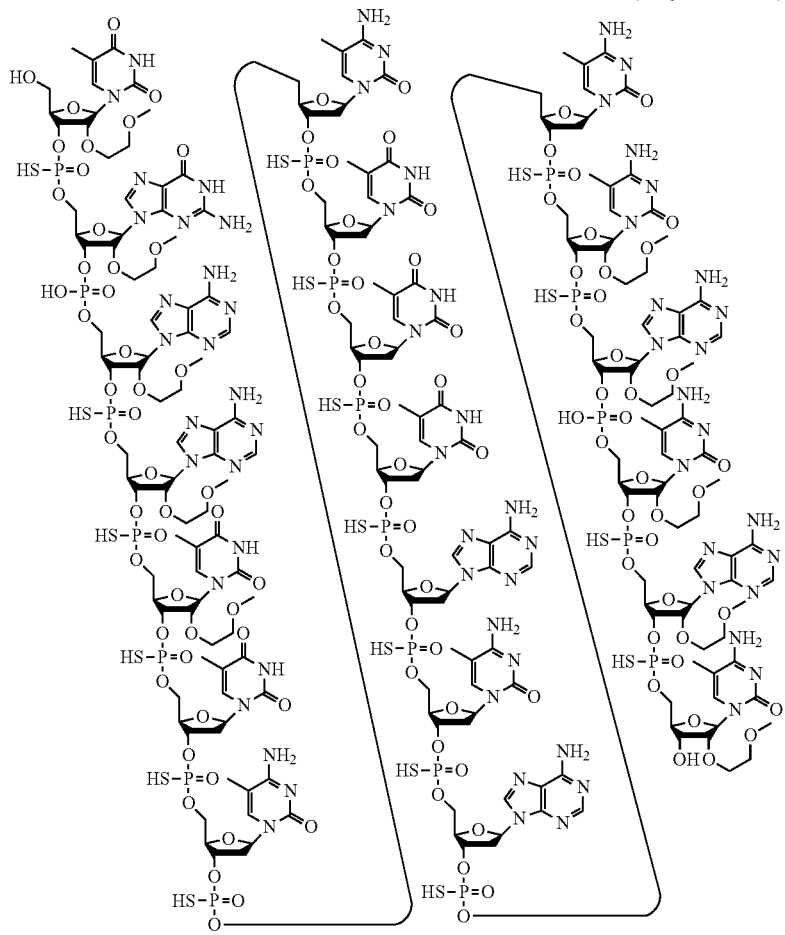

5. Compound No: 827599

In certain embodiments, Compound No: 827599 is characterized as a 5-10-5 MOE gapmer, having a sequence of (from 5' to 3') ACAGATATTTTTGTTCTGCC (incorporated herein as SEQ ID NO: 1703), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 16 to 17, and 17 to 18 are phosphodiester internucleoside linkages and the internucleoside linkages between nucleosides 1 to 2, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No: 827599 is characterized by the following chemical notation: Aes mCeo Aes Ges Aes Tds Ads Tds Tds Tds Tds Tds Gds Tds Tds mCeo Teo Ges mCes mCe; wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

In certain embodiments, Compound No: 827599 is represented by the following chemical structure:

Structure 5. Compound No: 827599

(SEQ ID NO: 1703)

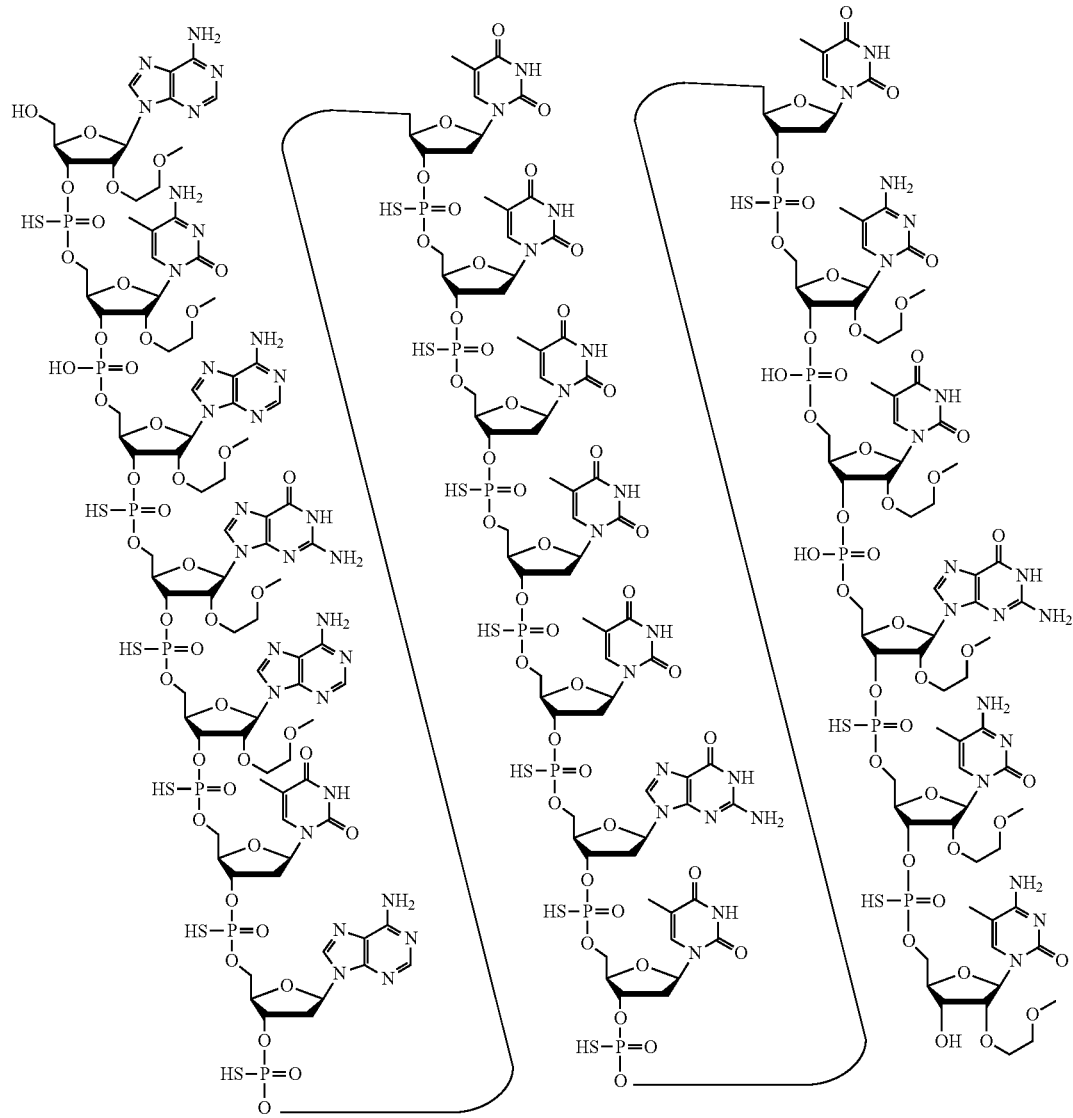

VIII. Certain Comparator Compositions

In certain embodiments, Compound No: 387978, a 5-10-5 MOE gapmer, having a sequence of (from 5' to 3') TCCTTGGCCTTTGAAAGTCC (incorporated herein as SEQ ID NO: 21), wherein each internucleoside linkage is a phorsphorothioate internucleoside linkage, each cytosine is a 5-methyl cytosine, and each of nucleosides 1-5 and 16-20 (from 5' to 3') comprise a 2'-MOE modified sugar, which was previously described in WO 2012/068405, incorporated herein by reference, is a comparator compound. Compound No. 387978 was selected as a comparator compound because it was potent in multiple dose studies of reducing human SNCA mRNA without overt toxicity in various studies as described in WO 2012/068405. Thus, based on the disclosure of WO 2012/068405, Compound No. 387978 was deemed potent with an acceptable tolerability profile.

In certain embodiments, Compound No: 387985, a 5-10-5 MOE gapmer, having a sequence of (from 5' to 3') CCAA-CATTTGTCACTTGCTC (incorporated herein as SEQ ID NO: 22), wherein each internucleoside linkage is a phorsphorothioate internucleoside linkage, each cytosine is a 5-methyl cytosine, and each of nucleosides 1-5 and 16-20 (from 5' to 3') comprise a 2'-MOE modified sugar, which was previously described in WO 2012/068405, incorporated herein by reference, is a comparator compound. Compound No. 387985 was selected as a comparator compound because it was potent in multiple dose studies of reducing human SNCA mRNA without overt toxicity in various studies as described in WO 2012/068405. Thus, based on the disclosure of WO 2012/068405, Compound No. 387985 was deemed potent with an acceptable tolerability profile.

In certain embodiments, compounds described herein are superior relative to the compounds described in WO 2012/

068405 because they demonstrate one or more improved properties, such as, potency and tolerability.

Compound 763085

For example, as provided in Example 10 (hereinbelow), Compound 763085 demonstrated an $IC_{50}$ of <0.44 µM in SHSH-SY5Y cells when tested at concentrations of 0.44 µM, 1.33 µM, 4.00 µM and 12.00 µM. Comparator Compound 387985 demonstrated an $IC_{50}$ of 5.00 µM in the same study. Therefore, Compound 763085 is demonstrably more potent than Comparator Compound 387985 in this assay.

For example, as provided in Example 11 (hereinbelow), Compound 763085 demonstrated an $IC_{50}$ of 0.47 µM in SHSH-SY5Y cells when tested at concentrations of 0.032 µM, 0.160 µM, 0.800 µM, 4.000 µM and 20.000 µM. Comparator Compound 387985 demonstrated an $IC_{50}$ of 4.20 µM in the same study. Therefore, Compound 763085 is demonstrably more potent than Comparator Compound 387985 in this assay.

For example, as provided in Example 17 (hereinbelow), Compound 763085 demonstrated functional observational battery (FOB) scores of 0.8 and 1.3 whereas Comparator Compound 387985 demonstrated a FOB score of 6.0 in wild-type C57/B16 mice after 3 hours when treated with 700 µg of oligonucleotide by ICV administration. Therefore, Compound 763085 is demonstrably more tolerable than Comparator Compound 387985 in this assay.

Compound 763364

For example, as provided in Example 10 (hereinbelow), Compound 763364 demonstrated an $IC_{50}$ of <0.44 µM in SHSH-SY5Y cells when tested at concentrations of 0.44 µM, 1.33 µM, 4.00 µM and 12.00 µM. Comparator Compound 387985 demonstrated an $IC_{50}$ of 5.00 µM in the same study. Therefore, Compound 763364 is demonstrably more potent than Comparator Compound 387985 in this assay.

For example, as provided in Example 11 (hereinbelow), Compound 763364 demonstrated an $IC_{50}$ of 0.86 µM in SHSH-SY5Y cells when tested at concentrations of 0.032 µM, 0.160 µM, 0.800 µM, 4.000 µM and 20.000 µM. Comparator Compound 387985 demonstrated an $IC_{50}$ of 4.20 µM in the same study. Therefore, Compound 763364 is demonstrably more potent than Comparator Compound 387985 in this assay.

Compound 763391

For example, as provided in Example 10 (hereinbelow), Compound 763391 demonstrated an $IC_{50}$ of 0.94 µM and 2.49 µM in SHSH-SY5Y cells when tested at concentrations of 0.44 µM, 1.33 µM, 4.00 µM and 12.00 µM. Comparator Compound 387985 demonstrated an $IC_{50}$ of 5.00 µM in the same study. Therefore, Compound 763391 is demonstrably more potent than Comparator Compound 387985 in this assay.

For example, as provided in Example 11 (hereinbelow), Compound 763391 demonstrated an $IC_{50}$ of 1.10 µM in SHSH-SY5Y cells when tested at concentrations of 0.032 µM, 0.160 µM, 0.800 µM, 4.000 µM and 20.000 µM. Comparator Compound 387985 demonstrated an $IC_{50}$ of 4.20 µM in the same study. Therefore, Compound 763391 is demonstrably more potent than Comparator Compound 387985 in this assay.

For example, as provided in Example 17 (hereinbelow), Compound 763391 demonstrated a FOB score of 0.0 and 2.3 whereas Comparator Compound 387985 demonstrated a FOB score of 6.0 in wild-type C57/B16 mice after 3 hours when treated with 700 µg of oligonucleotide by ICV administration. Therefore, Compound 763391 is demonstrably more tolerable than Comparator Compound 387985 in this assay.

For example, as provided in Example 18 (hereinbelow), Compound 763391 demonstrated FOB scores of 0.0 and 1.3 whereas Comparator Compound 387985 demonstrated a FOB score of 3.8 in Sprague Dawley rats after 3 hours when treated with 3 mg of oligonucleotide by IT administration. Therefore, Compound 763391 is demonstrably more tolerable than Comparator Compound 387985 in this assay.

Compound 789243

For example, as provided in Example 10 (hereinbelow), Compound 789243 demonstrated an $IC_{50}$ of 2.40 µM in SHSH-SY5Y cells when tested at concentrations of 0.44 µM, 1.33 µM, 4.00 µM and 12.00 µM. Comparator Compound 387985 demonstrated an $IC_{50}$ of 5.00 µM in the same study. Therefore, Compound 789243 is demonstrably more potent than Comparator Compound 387985 in this assay.

For example, as provided in Example 11 (hereinbelow), Compound 789243 demonstrated an $IC_{50}$ of 2.25 µM and 1.90 µM in SHSH-SY5Y cells when tested at concentrations of 0.032 µM, 0.160 µM, 0.800 µM, 4.000 µM and 20.000 µM. Comparator Compound 387985 demonstrated an $IC_{50}$ of 4.20 µM in the same study. Therefore, Compound 789243 is demonstrably more potent than Comparator Compound 387985 in this assay.

For example, as provided in Example 17 (hereinbelow), Compound 789243 demonstrated a FOB score of 0.3 and 0.0 whereas Comparator Compound 387985 demonstrated a FOB score of 6.0 in wild-type C57/B16 mice after 3 hours when treated with 700 µg of oligonucleotide by ICV administration. Therefore, Compound 789243 is demonstrably more tolerable than Comparator Compound 387985 in this assay.

For example, as provided in Example 18 (hereinbelow), Compound 789243 demonstrated FOB scores of 1.8 and 1.5 whereas Comparator Compound 387985 demonstrated a FOB score of 3.8 in Sprague Dawley rats after 3 hours when treated with 3 mg of oligonucleotide by IT administration. Therefore, Compound 789243 is demonstrably more tolerable than Comparator Compound 387985 in this assay.

Compound 827599

For example, as provided in Example 10 (hereinbelow), Compound 827599 demonstrated an $IC_{50}$ of 0.40 µM µM in SHSH-SY5Y cells when tested at concentrations of 0.44 µM, 1.33 µM, 4.00 µM and 12.00 µM. Comparator Compound 387985 demonstrated an $IC_{50}$ of 5.00 µM in the same study. Therefore, Compound 827599 is demonstrably more potent than Comparator Compound 387985 in this assay.

For example, as provided in Example 11 (hereinbelow), Compound 827599 demonstrated an $IC_{50}$ of 0.40 µM in SHSH-SY5Y cells when tested at concentrations of 0.032 µM, 0.160 µM, 0.800 µM, 4.000 µM and 20.000 µM. Comparator Compound 387985 demonstrated an $IC_{50}$ of 4.20 µM in the same study. Therefore, Compound 827599 is demonstrably more potent than Comparator Compound 387985 in this assay.

For example, as provided in Example 17 (hereinbelow), Compound 827599 demonstrated a FOB score of 0.0 whereas Comparator Compound 387985 demonstrated a FOB score of 6.0 in wild-type C57/B16 mice after 3 hours when treated with 700 µg of oligonucleotide by ICV administration. Therefore, Compound 827599 is demonstrably more tolerable than Comparator Compound 387985 in this assay.

For example, as provided in Example 18 (hereinbelow), Compound 827599 demonstrated a FOB score of 2.0 whereas Comparator Compound 387985 demonstrated a FOB score of 3.8 in Sprague Dawley rats after 3 hours when treated with 3 mg of oligonucleotide by IT administration. Therefore, Compound 827599 is demonstrably more tolerable than Comparator Compound 387985 in this assay.

IX. Certain Hotspot Regions

1. Nucleobases 50915-50943 of SEQ ID NO: 2

In certain embodiments, nucleobases 50915-50943 of SEQ ID NO: 2 comprise a hotspot region. In certain embodiments, modified oligonucleotides are complementary to nucleobases 50915-50943 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the internucleoside linkages of the modified oligonucleotides are phosphorothioate internucleoside linkages and phosphodiester internucleoside linkages.

The nucleobase sequences of SEQ ID Nos: 243, 1601-1603, and 2188, 2189, 2190, 2191, 2192, 2193, 2194, 2195, 2196 and 2197 are complementary to nucleobases 50915-50943 of SEQ ID NO: 2.

In certain embodiments, modified oligonucleotides complementary to nucleobases 50915-50943 of SEQ ID NO: 2 achieve at least 45% reduction of SNCA RNA in vitro in the standard cell assay.

2. Nucleobases 19630-19656 of SEQ ID NO: 2

In certain embodiments, nucleobases 19630-19656 of SEQ ID NO: 2 comprise a hotspot region. In certain embodiments, modified oligonucleotides are complementary to nucleobases 19630-19656 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 1103, 1700, 1701, 1702, 1703, 1704, 1705, 1706 and 1707 are complementary to nucleobases 19630-19656 of SEQ ID NO: 2.

In certain embodiments, modified oligonucleotides complementary to nucleobases 19630-19656 of SEQ ID NO: 2 achieve at least 48% reduction of SNCA RNA in vitro in the standard cell assay.

3. Nucleobases 28451-28491 of SEQ ID NO: 2

In certain embodiments, nucleobases 28451-28491 of SEQ ID NO: 2 comprise a hotspot region. In certain embodiments, modified oligonucleotides are complementary to nucleobases 28451-28491 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 1168, 1882, 1883, 1884, 1885, 1886, 1887, 1888, 1889, 1890, 1891, 1892 and 1893 are complementary to nucleobases 28451-28491 of SEQ ID NO: 2.

In certain embodiments, modified oligonucleotides complementary to nucleobases 28451-28491 of SEQ ID NO: 2 achieve at least 47% reduction of SNCA RNA in vitro in the standard cell assay.

4. Nucleobases 48712-48760 of SEQ ID NO:2

In certain embodiments, nucleobases 48712-48760 of SEQ ID NO: 2 comprise a hotspot region. In certain embodiments, modified oligonucleotides are complementary to nucleobases 48712-48760 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 471, 1585-1588, and 2157-2166 are complementary to nucleobases 48712-48760 of SEQ ID NO: 2.

In certain embodiments, modified oligonucleotides complementary to nucleobases 48712-48760 of SEQ ID NO: 2 achieve at least 40% reduction of SNCA RNA in vitro in the standard cell assay.

5. Nucleobases 23279-23315 of SEQ ID NO: 2

In certain embodiments, nucleobases 23279-23315 of SEQ ID NO: 2 comprise a hotspot region. In certain embodiments, modified oligonucleotides are complementary to nucleobases 23279-23315 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 164, 1130-1133, and 1797-1810 are complementary to nucleobases 23279-23315 of SEQ ID NO: 2.

In certain embodiments, modified oligonucleotides complementary to nucleobases 23279-23315 of SEQ ID NO: 2 achieve at least 57% reduction of SNCA RNA in vitro in the standard cell assay.

6. Nucleobases 20964-21018 of SEQ ID NO: 2

In certain embodiments, nucleobases 20964-21018 of SEQ ID NO: 2 comprise a hotspot region. In certain embodiments, modified oligonucleotides are complementary to nucleobases 20964-21018 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 391, 468, 1112-1116, and 1723-1741 are complementary to nucleobases 20964-21018 of SEQ ID NO: 2.

In certain embodiments, modified oligonucleotides complementary to nucleobases 20964-21018 of SEQ ID NO: 2 achieve at least 42% reduction of SNCA RNA in vitro in the standard cell assay.

7. Nucleobases 22454-22477 of SEQ ID NO: 2

In certain embodiments, nucleobases 22454-22477 of SEQ ID NO: 2 comprise a hotspot region. In certain embodiments, modified oligonucleotides are complementary to nucleobases 22454-22477 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 88, 1123-1126, and 1778-1782 are complementary to nucleobases 22454-22477 of SEQ ID NO: 2.

In certain embodiments, modified oligonucleotides complementary to nucleobases 22454-22477 of SEQ ID NO: 2 achieve at least 50% reduction of SNCA RNA in vitro in the standard cell assay.

8. Nucleobases 72294-72321 of SEQ ID NO: 2

In certain embodiments, nucleobases 72294-72321 of SEQ ID NO: 2 comprise a hotspot region. In certain embodiments, modified oligonucleotides are complementary to nucleobases 72294-72321 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 1323 and 2345-2353 are complementary to nucleobases 72294-72321 of SEQ ID NO: 2.

In certain embodiments, modified oligonucleotides complementary to nucleobases 72294-72321 of SEQ ID NO: 2 achieve at least 58% reduction of SNCA RNA in vitro in the standard cell assay.

9. Nucleobases 20549-20581 of SEQ ID NO: 2

In certain embodiments, nucleobases 20549-20581 of SEQ ID NO: 2 comprise a hotspot region. In certain embodiments, modified oligonucleotides are complementary to nucleobases 20549-20581 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 314 and 1107-1110 are complementary to nucleobases 20549-20581 of SEQ ID NO: 2.

In certain embodiments, modified oligonucleotides complementary to nucleobases 20549-20581 of SEQ ID NO: 2 achieve at least 58% reduction of SNCA RNA in vitro in the standard cell assay.

10. Nucleobases 27412-27432 of SEQ ID NO: 2

In certain embodiments, nucleobases 27412-27432 of SEQ ID NO: 2 comprise a hotspot region. In certain embodiments, modified oligonucleotides are complementary to nucleobases 27412-27432 of SEQ ID NO: 2. In certain embodiments, modified oligonucleotides are 17 or 20 nucleobases in length. In certain embodiments, modified oligonucleotides are gapmers. In certain embodiments, the gapmers are MOE gapmers or mixed cEt and MOE gapmers. In certain embodiments, the nucleosides of the modified oligonucleotides are linked by phosphorothioate internucleoside linkages and phosphodiester internucleoside linkages.

The nucleobase sequences of SEQ ID Nos: 468, 1113-1114, and 1163 are complementary to nucleobases 27412-27432 of SEQ ID NO: 2.

In certain embodiments, modified oligonucleotides complementary to nucleobases 27412-27432 of SEQ ID NO: 2 achieve at least 62% reduction of SNCA RNA in vitro in the standard cell assay.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "ATmCGAUCG," wherein mC indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (5), as a or such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of 5-8-4 MOE and cEt Gapmers with Mixed Internucleoside Linkages on Human SNCA In Vitro, Single Dose Modified oligonucleotides complementary to a human SNCA nucleic acid were designed and tested for their effect on SNCA mRNA in vitro. The modified oligonucleotides were tested in a series of experiments that had similar culture conditions.

Cultured SH-SY5Y cells at a density of 20,000 cells per well were transfected using electroporation with 7,000 nM concentration of modified oligonucleotide or no modified oligonucleotide for untreated controls. After approximately 24 hours, RNA was isolated from the cells and SNCA mRNA levels were measured by quantitative real-time PCR Human primer probe set RTS2621 (forward sequence ACGAACCTGAAGCCTAAGAAATATCT, designated herein as SEQ ID NO: 11; reverse sequence GAGCACTTGTACAGGATGGAACAT, designated herein as SEQ ID NO: 12; probe sequence TGCTCCCAAGTTTCTTGAGATCTGCTGACA, designated herein as SEQ ID: 13) was used to measure mRNA levels. SNCA mRNA levels were adjusted according to total RNA content, as measured by RIBOGREEN®. Results are presented in the tables below as percent reduction of the amount of SNCA mRNA, relative to untreated control cells (these conditions describe a "Standard Cell Assay"). The modified oligonucleotides marked with an asterisk (*) target the amplicon region of the primer probe set. Additional assays may be used to measure the potency and efficacy of oligonucleotides targeting the amplicon region. Compound No. 387978, previously disclosed in WO 2012/068405 was also tested and is a comparator oligonucleotide. Compound No. 387978 is a 5-10-5 MOE gapmer wherein each internucleoside linkage is a phosphorothioate internucleoside linkage and each cytosine residue is a 5-methyl cytosine.

The modified oligonucleotides in tables 1-7 are 5-8-4 mixed MOE and cEt gapmers. The gapmers are 17 nucleobases in length, wherein the central gap segment comprises eight 2'-deoxynucleosides and is flanked by a wing segment on the 5' end comprising five 2'-MOE nucleosides and a wing segment on the 3' end comprising two cEt nucleosides and two 2'-MOE nucleosides. The sugar motif for the gapmers is (from 5' to 3'): eeeeedddddddkkee; wherein 'd' represents a 2'-deoxyribose sugar; 'e' represents a 2'-MOE modified sugar; and represents a cEt modified sugar. All cytosine residues throughout each gapmer are 5-methyl cytosines. The internucleoside linkages are mixed phosphodiester and phosphorothioate linkages. The internucleoside linkage motif for the gapmers is (from 5' to 3'): sooossssssssssoss; wherein 'o' represents a phosphodiester internucleoside linkage and 's' represents a phosphorothioate internucleoside linkage. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the Tables below is complementary to human SNCA nucleic acid sequences SEQ ID NO: 1, SEQ ID NO: 2, SEQ ID NO: 3, SEQ ID NO: 4, SEQ ID NO: 5, or SEQ ID NO: 6, as indicated. 'N/A' indicates that the modified oligonucleotide is not complementary to that particular nucleic acid with 100% complementarity. A value of 0% reduction indicates that the compound had no effect or increased mRNA concentrations in the cell. As shown below, modified oligonucleotides complementary to human SNCA reduced the amount of human SNCA mRNA.

TABLE 1

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 64 | 21 |
| 709518 | 9 | 25 | 3191 | 3207 | TAGTCCTCCTCCTTCTC | 34 | 30 |
| 709524 | 102 | 118 | 3284 | 3300 | TGCAGCCCGCACGCACC | 33 | 31 |
| 709530 | 232 | 248 | N/A | N/A | TTACACCACACTGTCGT | 43 | 32 |
| 709536 | 240 | 256 | 4691 | 4707 | GAATTCCTTTACACCAC | 81 | 33 |
| 709542 | 256 | 272 | 4707 | 4723 | TACATCCATGGCTAATG | 53 | 34 |
| 709548 | 278 | 294 | 4729 | 4745 | CCTTTGAAAGTCCTTTC | 62 | 35 |
| 709554 | 288 | 304 | 4739 | 4755 | CCCTCCTTGGCCTTTGA | 54 | 36 |
| 709560 | 372 | 388 | N/A | N/A | GAGCCTACATAGAGAAC | 61 | 37 |
| 709566 | 385 | 401 | 12198 | 12214 | CTCCTTGGTTTTGGAGC | 22 | 38 |
| 709572 | 405 | 421 | 12218 | 12234 | GCCACACCATGCACCAC | 79 | 39 |
| 709578 | 440 | 456 | 18007 | 18023 | TTGTCACTTGCTCTTTG | 65 | 40 |
| 709584 | 450 | 466 | 18017 | 18033 | CCTCCAACATTTGTCAC | 23 | 41 |
| 709590 | 470 | 486 | 18037 | 18053 | TCACACCCGTCACCACT | 58 | 42 |
| 709596 | 512 | 528 | 18079 | 18095 | CAATGCTCCCTGCTCCC | 61 | 43 |
| 709602 | 584 | 600 | 111119 | 111135 | GAATTCCTTCCTGTGGG | 0 | 44 |
| 709608 | 650 | 666 | N/A | N/A | CTTGATACCCTTCCTCA | 0 | 45 |
| 709614* | 729 | 745 | 113797 | 113813 | CTTGTACAGGATGGAAC | 1 | 46 |
| 709620 | 789 | 805 | 113857 | 113873 | TTCGAGATACACTGTAA | 34 | 47 |
| 709626 | 798 | 814 | 113866 | 113882 | ATGGAAGACTTCGAGAT | 0 | 48 |
| 709632 | 866 | 882 | 113934 | 113950 | TCACTTCAGTGAAAGGG | 67 | 49 |
| 709638 | 892 | 908 | 113960 | 113976 | CACACAAAGACCCTGCT | 0 | 50 |
| 709644 | 906 | 922 | 113974 | 113990 | CACAAAATCCACAGCAC | 0 | 51 |
| 709650 | 934 | 950 | 114002 | 114018 | AATTTGTTTTAACATCG | 0 | 52 |
| 709656 | 956 | 972 | 114024 | 114040 | TGGTAGTCACTTAGGTG | 30 | 53 |
| 709662 | 1034 | 1050 | 114102 | 114118 | TCTTATAATATATGATA | 0 | 54 |
| 709668 | 1133 | 1149 | 114201 | 114217 | CATAGTTTCATGCTCAC | 66 | 55 |
| 709674 | 1213 | 1229 | 114281 | 114297 | TTCTCACCATTTATATA | 9 | 56 |
| 709680 | 1277 | 1293 | 114345 | 114361 | TATTATTAAAGTGAGAT | 13 | 57 |
| 709686 | 1327 | 1343 | 114395 | 114411 | TTTGTCCTTTGTGTCAG | 22 | 58 |
| 709692 | 1410 | 1426 | 114478 | 114494 | TCCGAGTGTAGGGTTAA | 12 | 59 |
| 709698 | 1476 | 1492 | 114544 | 114560 | AATCACAGCCACTTAAG | 11 | 60 |
| 709704 | 1590 | 1606 | 114658 | 114674 | ACATCAAACAACAGTTC | 0 | 61 |
| 709710 | 1716 | 1732 | 114784 | 114800 | AGGTACAGCATTCACAC | 14 | 62 |
| 709716 | 1744 | 1760 | 114812 | 114828 | CATGGTCGAATATTATT | 25 | 63 |
| 709722 | 1816 | 1832 | 114884 | 114900 | AAGGAGGGTGTAGTCAA | 40 | 64 |
| 709728 | 1882 | 1898 | 114950 | 114966 | AAGTTAACCACATTCTC | 5 | 65 |

TABLE 1-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709734 | 2013 | 2029 | 115081 | 115097 | GGTAGTTCCAACGATGT | 29 | 66 |
| 709740 | 2079 | 2095 | 115147 | 115163 | CAACATTTAAAGGAGGC | 35 | 67 |
| 709746 | 2165 | 2181 | 115233 | 115249 | TTTTCAGCACCCATGGG | 2 | 68 |
| 709752 | 2261 | 2277 | 115329 | 115345 | GTGACTTTTAGAAATGA | 43 | 69 |
| 709758 | 2327 | 2343 | 115395 | 115411 | CTCATGAATACATATAA | 11 | 70 |
| 709764 | 2400 | 2416 | 115468 | 115484 | TTCTATGGTAACCATCC | 37 | 71 |
| 709770 | 2469 | 2485 | 115537 | 115553 | TAGTGTAAGATGACACA | 11 | 72 |
| 709776 | 2540 | 2556 | 115608 | 115624 | ACTGTTCAATAACAAAT | 33 | 73 |
| 709782 | 2648 | 2664 | 115716 | 115732 | TCCTCTATTTCTTAATT | 1 | 74 |
| 709788 | 2714 | 2730 | 115782 | 115798 | TAAATTCATGGTCACAA | 68 | 75 |
| 709794 | 2783 | 2799 | 115851 | 115867 | AAAATTACCGTCAGATA | 36 | 76 |
| 709800 | 2867 | 2883 | 115935 | 115951 | AGGCTTATATGACTTAA | 12 | 77 |
| 709806 | 2933 | 2949 | 116001 | 116017 | GATTGATCCTCAGGCCA | 41 | 78 |
| 709812 | 2999 | 3015 | 116067 | 116083 | ACCGTGGAGTCATATGA | 0 | 79 |
| 709818 | 3065 | 3081 | 116133 | 116149 | ACACATTAGATTGTTCT | 16 | 80 |
| 709824 | 3131 | 3147 | 116199 | 116215 | GAAACATGTTTGCATCT | 47 | 81 |
| 709836 | N/A | N/A | 3445 | 3461 | GGCGACGCGAGGCTGGG | 22 | 82 |
| 709842 | N/A | N/A | 3553 | 3569 | ACAATTCCCAAATAATA | 6 | 83 |
| 709854 | N/A | N/A | 2097 | 2113 | GACAGCTGTTCCTGGAT | 32 | 84 |
| 709860 | N/A | N/A | 3957 | 3973 | ACCAAGAGAGCGGGCAG | 30 | 85 |
| 709866 | N/A | N/A | 8613 | 8629 | AAAGAATGCCACTAGGC | 23 | 86 |
| 709872 | N/A | N/A | 17660 | 17676 | TACAGGTGCAGTTATAT | 20 | 87 |
| 709878 | N/A | N/A | 22457 | 22473 | GCCTGTGACCTGTGCTT | 81 | 88 |
| 709884 | N/A | N/A | 27802 | 27818 | GACATCTCTAACATAAA | 56 | 89 |
| 709890 | N/A | N/A | 41133 | 41149 | AACAGATTCCAGCAGAG | 74 | 90 |
| 709896 | N/A | N/A | 48867 | 48883 | GATGGATATTGACTCCT | 53 | 91 |
| 709902 | N/A | N/A | 54583 | 54599 | TATATGCATTTTTCAGG | 48 | 92 |
| 709908 | N/A | N/A | 57557 | 57573 | AGACACTCTTACTTGAG | 0 | 93 |
| 709914 | N/A | N/A | 71391 | 71407 | TGAAGGACAACTGTGTA | 26 | 94 |
| 709922 | N/A | N/A | 75588 | 75604 | GACATCTGAAGTGTTCA | 59 | 95 |
| 709928 | N/A | N/A | 78911 | 78927 | ATAACCACCACTGAATT | 12 | 96 |
| 709934 | N/A | N/A | 80751 | 80767 | CCATGCTACATTGCTCA | 18 | 97 |
| 709940 | N/A | N/A | 83531 | 83547 | GAAAGAACAATGTCATC | 75 | 98 |
| 709946 | N/A | N/A | 89651 | 89667 | ACAAACCCAAAGAGATT | 51 | 99 |
|  | N/A | N/A | 88646 | 88662 |  |  |  |
| 709952 | N/A | N/A | 89681 | 89697 | GTCCCCAATCCCCACCC | 11 | 100 |
|  | N/A | N/A | 88676 | 88692 |  |  |  |

TABLE 1-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709958 | N/A | N/A | 89722 | 89738 | TCCTATAGAGATGAAGT | 40 | 101 |
|  | N/A | N/A | 88717 | 88733 |  |  |  |
| 709964 | N/A | N/A | 89731 | 89747 | TATCCACTCTCCTATAG | 0 | 102 |
|  | N/A | N/A | 88726 | 88742 |  |  |  |
| 709970 | N/A | N/A | 89191 | 89207 | TCCTTGAAAACTTCCAT | 48 | 103 |
| 709976 | N/A | N/A | 93421 | 93437 | GAGGTCAAATTTTCCAG | 30 | 104 |
| 709982 | N/A | N/A | 105440 | 105456 | GAGTGACAGTGGTGGGC | 28 | 105 |

TABLE 2

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 60 | 21 |
| 709519 | 22 | 38 | 3204 | 3220 | GTCCTCCTCCTCCTAGT | 32 | 106 |
| 709525 | 168 | 184 | 3350 | 3366 | GGCTTGAAGGCAAGGCG | 46 | 107 |
| 709531 | 233 | 249 | N/A | N/A | TTTACACCACACTGTCG | 33 | 108 |
| 709537 | 242 | 258 | 4693 | 4709 | ATGAATTCCTTTACACC | 46 | 109 |
| 709543 | 257 | 273 | 4708 | 4724 | ATACATCCATGGCTAAT | 62 | 110 |
| 709549 | 280 | 296 | 4731 | 4747 | GGCCTTTGAAAGTCCTT | 72 | 111 |
| 709555 | 301 | 317 | 4752 | 4768 | AGCAGCCACAACTCCCT | 75 | 112 |
| 709561 | 377 | 393 | N/A | N/A | TTTTGGAGCCTACATAG | 28 | 113 |
| 709567 | 387 | 403 | 12200 | 12216 | CCCTCCTTGGTTTTGGA | 46 | 114 |
| 709573 | 406 | 422 | 12219 | 12235 | TGCCACACCATGCACCA | 66 | 115 |
| 709579 | 442 | 458 | 18009 | 18025 | ATTTGTCACTTGCTCTT | 69 | 116 |
| 709585 | 453 | 469 | 18020 | 18036 | GCTCCTCCAACATTTGT | 57 | 117 |
| 709591 | 471 | 487 | 18038 | 18054 | GTCACACCCGTCACCAC | 71 | 118 |
| 709597 | 523 | 539 | 18090 | 18106 | AGTGGCTGCTGCAATGC | 68 | 119 |
| 709603 | 595 | 611 | 111130 | 111146 | CATATCTTCCAGAATTC | 9 | 120 |
| 709609* | 671 | 687 | 113739 | 113755 | CTTAGGCTTCAGGTTCG | 92 | 121 |
| 709615* | 740 | 756 | 113808 | 113824 | GGAACTGAGCACTTGTA | 67 | 122 |
| 709621 | 790 | 806 | 113858 | 113874 | CTTCGAGATACACTGTA | 31 | 123 |
| 709627 | 800 | 816 | 113868 | 113884 | TGATGGAAGACTTCGAG | 12 | 124 |
| 709633 | 877 | 893 | 113945 | 113961 | CTACCATGTATTCACTT | 53 | 125 |
| 709639 | 893 | 909 | 113961 | 113977 | GCACACAAAGACCCTGC | 33 | 126 |
| 709645 | 908 | 924 | 113976 | 113992 | GCCACAAAATCCACAGC | 56 | 127 |
| 709651 | 944 | 960 | 114012 | 114028 | AGGTGTTTTAATTTGT | 63 | 128 |

TABLE 2-continued

Percent reduction of human SNCA mRNA with 5-8-4 MOE
and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709657 | 967 | 983 | 114035 | 114051 | TTAGAAATAAGTGGTAG | 28 | 129 |
| 709663 | 1045 | 1061 | 114113 | 114129 | ACACCTAAAAATCTTAT | 26 | 130 |
| 709669 | 1144 | 1160 | 114212 | 114228 | ATTTATAGGTGCATAGT | 24 | 131 |
| 709675 | 1217 | 1233 | 114285 | 114301 | TTAATTCTCACCATTTA | 1 | 132 |
| 709681 | 1279 | 1295 | 114347 | 114363 | TTTATTATTAAAGTGAG | 4 | 133 |
| 709687 | 1347 | 1363 | 114415 | 114431 | GCTATTAATAACTTTAT | 6 | 134 |
| 709693 | 1421 | 1437 | 114489 | 114505 | CTTCAGGGAATTCCGAG | 35 | 135 |
| 709699 | 1487 | 1503 | 114555 | 114571 | TTTCAATAATTAATCAC | 16 | 136 |
| 709705 | 1628 | 1644 | 114696 | 114712 | GGCTCAATTAAAAATGT | 0 | 137 |
| 709711 | 1727 | 1743 | 114795 | 114811 | TATTGTCAGAAAGGTAC | 28 | 138 |
| 709717 | 1749 | 1765 | 114817 | 114833 | TTATTCATGGTCGAATA | 0 | 139 |
| 709723 | 1827 | 1843 | 114895 | 114911 | TATGGCTCTCTAAGGAG | 17 | 140 |
| 709729 | 1893 | 1909 | 114961 | 114977 | TGAGTTAAACAAAGTTA | 6 | 141 |
| 709735 | 2024 | 2040 | 115092 | 115108 | AAGGTGACTCTGGTAGT | 35 | 142 |
| 709741 | 2090 | 2106 | 115158 | 115174 | CATATATTTGGCAACAT | 27 | 143 |
| 709747 | 2177 | 2193 | 115245 | 115261 | CCATCAAGTTTATTTTC | 30 | 144 |
| 709753 | 2272 | 2288 | 115340 | 115356 | ACTTTCTACTAGTGACT | 16 | 145 |
| 709759 | 2338 | 2354 | 115406 | 115422 | ATATCACATTACTCATG | 22 | 146 |
| 709765 | 2414 | 2430 | 115482 | 115498 | GTAAAAAGGAAGTTTC | 11 | 147 |
| 709771 | 2480 | 2496 | 115548 | 115564 | CCATTTCTCTCTAGTGT | 16 | 148 |
| 709777 | 2551 | 2567 | 115619 | 115635 | TCCTGAAATATACTGTT | 5 | 149 |
| 709783 | 2659 | 2675 | 115727 | 115743 | GTCTAGTTCTGTCCTCT | 34 | 150 |
| 709789 | 2726 | 2742 | 115794 | 115810 | CACATAAATCCTTAAAT | 7 | 151 |
| 709795 | 2794 | 2810 | 115862 | 115878 | TTCACTGCTCAAAAATT | 8 | 152 |
| 709801 | 2878 | 2894 | 115946 | 115962 | GCTTCCTGAAAAGGCTT | 40 | 153 |
| 709807 | 2944 | 2960 | 116012 | 116028 | ACCTAGGACTGGATTGA | 1 | 154 |
| 709813 | 3010 | 3026 | 116078 | 116094 | TGGTAAAGCCGACCGTG | 29 | 155 |
| 709819 | 3076 | 3092 | 116144 | 116160 | AATACCAAACCACACAT | 4 | 156 |
| 709825 | 3145 | 3161 | 116213 | 116229 | GCCAGAAAGATGAGGAA | 13 | 157 |
| 709837 | N/A | N/A | 3456 | 3472 | CGCTGTGAGCCGGCGAC | 0 | 158 |
| 709843 | N/A | N/A | 3586 | 3602 | CCGCCTCTCTCTTTTTT | 26 | 159 |
| 709855 | N/A | N/A | 2112 | 2128 | CTTTCAGAGCTGGAAGA | 3 | 160 |
| 709861 | N/A | N/A | 4256 | 4272 | CAGAACTAACTGCTCAC | 28 | 161 |
| 709867 | N/A | N/A | 10668 | 10684 | AACATCACATGGGCTCA | 9 | 162 |
| 709873 | N/A | N/A | 18297 | 18313 | TCTGGGTTAATGCCTGA | 62 | 163 |
| 709879 | N/A | N/A | 23286 | 23302 | ATTGTTCTCAGAGACCA | 72 | 164 |

TABLE 2-continued

Percent reduction of human SNCA mRNA with 5-8-4 MOE
and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709885 | N/A | N/A | 31744 | 31760 | ACAGTAAAGATTTGCAT | 29 | 165 |
| 709891 | N/A | N/A | 42838 | 42854 | TGATGCCTCTACCTCCA | 70 | 166 |
| 709897 | N/A | N/A | 49481 | 49497 | TTGAAATTTTCCAGCTA | 69 | 167 |
|  | N/A | N/A | 80992 | 81008 |  |  |  |
| 709903 | N/A | N/A | 55047 | 55063 | TATACCTAATATGTTTG | 15 | 168 |
| 709909 | N/A | N/A | 58992 | 59008 | ATTTCATTAATCTGTGA | 63 | 169 |
| 709915 | N/A | N/A | 73191 | 73207 | CAGACTTTCTGTGTGGT | 77 | 170 |
| 709923 | N/A | N/A | 76780 | 76796 | AATTTGGAAGCTAATGT | 24 | 171 |
| 709929 | N/A | N/A | 79117 | 79133 | AGTTCCCATGAGACCAG | 56 | 172 |
| 709935 | N/A | N/A | 81199 | 81215 | TGGCTTGGAGCAAAAGG | 42 | 173 |
| 709941 | N/A | N/A | 85498 | 85514 | TTATGCAGTGGAACTAA | 20 | 174 |
| 709947 | N/A | N/A | 88649 | 88665 | CATACAAACCCAAAGAG | 0 | 175 |
|  | N/A | N/A | 89654 | 89670 |  |  |  |
| 709953 | N/A | N/A | 88708 | 88724 | GATGAAGTTAACTCCCT | 62 | 176 |
|  | N/A | N/A | 89713 | 89729 |  |  |  |
| 709959 | N/A | N/A | 88719 | 88735 | TCTCCTATAGAGATGAA | 0 | 177 |
|  | N/A | N/A | 89724 | 89740 |  |  |  |
| 709965 | N/A | N/A | 88728 | 88744 | TCTATCCACTCTCCTAT | 35 | 178 |
|  | N/A | N/A | 89733 | 89749 |  |  |  |
| 709971 | N/A | N/A | 89219 | 89235 | TCTGTTAACTGAGGTAG | 55 | 179 |
| 709977 | N/A | N/A | 93953 | 93969 | GGCTTCTGGCTGACTGA | 71 | 180 |
| 709983 | N/A | N/A | 106925 | 106941 | GAACATTAAAATTTGCA | 25 | 181 |

TABLE 3

Percent reduction of human SNCA mRNA with 5-8-4 MOE and cEt gapmers
with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 72 | 21 |
| 709520 | 44 | 60 | 3226 | 3242 | TGGGCCCCTTCTGGTCG | 14 | 182 |
| 709526 | 179 | 195 | 3361 | 3377 | GAAAGGCAGAAGGCTTG | 27 | 183 |
| 709532 | 234 | 250 | N/A | N/A | CTTTACACCACACTGTC | 45 | 184 |
| 709538 | 244 | 260 | 4695 | 4711 | TAATGAATTCCTTTACA | 35 | 185 |
| 709544 | 258 | 274 | 4709 | 4725 | AATACATCCATGGCTAA | 75 | 186 |
| 709550 | 282 | 298 | 4733 | 4749 | TTGGCCTTTGAAAGTCC | 77 | 187 |
| 709556 | 312 | 328 | 4763 | 4779 | GTTTTCTCAGCAGCAGC | 72 | 188 |
| 709562 | 379 | 395 | N/A | N/A | GGTTTTGGAGCCTACAT | 63 | 189 |
| 709568 | 395 | 411 | 12208 | 12224 | GCACCACTCCCTCCTTG | 55 | 190 |
| 709574 | 408 | 424 | 12221 | 12237 | GTTGCCACACCATGCAC | 49 | 191 |

TABLE 3-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709580 | 444 | 460 | 18011 | 18027 | ACATTTGTCACTTGCTC | 77 | 192 |
| 709586 | 464 | 480 | 18031 | 18047 | CCGTCACCACTGCTCCT | 83 | 193 |
| 709592 | 473 | 489 | 18040 | 18056 | CTGTCACACCCGTCACC | 78 | 194 |
| 709598 | 534 | 550 | 18101 | 18117 | TTGACAAAGCCAGTGGC | 31 | 195 |
| 709604 | 606 | 622 | 111141 | 111157 | GGATCCACAGGCATATC | 29 | 196 |
| 709610* | 682 | 698 | 113750 | 113766 | CAAAGATATTTCTTAGG | 23 | 197 |
| 709616* | 751 | 767 | 113819 | 113835 | CTGGGCACATTGGAACT | 4 | 198 |
| 709622 | 792 | 808 | 113860 | 113876 | GACTTCGAGATACACTG | 57 | 199 |
| 709628 | 811 | 827 | 113879 | 113895 | TCAATCACTGCTGATGG | 45 | 200 |
| 709634 | 887 | 903 | 113955 | 113971 | AAAGACCCTGCTACCAT | 52 | 201 |
| 709640 | 895 | 911 | 113963 | 113979 | CAGCACACAAAGACCCT | 65 | 202 |
| 709646 | 909 | 925 | 113977 | 113993 | AGCCACAAAATCCACAG | 56 | 203 |
| 709652 | 945 | 961 | 114013 | 114029 | TAGGTGTTTTAATTTG | 52 | 204 |
| 709658 | 978 | 994 | 114046 | 114062 | ATAGTGAGGATTTAGAA | 19 | 205 |
| 709664 | 1056 | 1072 | 114124 | 114140 | ATCATTAAAAGACACCT | 37 | 206 |
| 709670 | 1172 | 1188 | 114240 | 114256 | CGCAAAATGGTAAAATT | 25 | 207 |
| 709676 | 1226 | 1242 | 114294 | 114310 | CGTTTTATTTTAATTCT | 27 | 208 |
| 709682 | 1294 | 1310 | 114362 | 114378 | CTTATAAGCATGATTTT | 10 | 209 |
| 709688 | 1359 | 1375 | 114427 | 114443 | CTTCTTCAAATGGCTAT | 37 | 210 |
| 709694 | 1432 | 1448 | 114500 | 114516 | TGGCAGTGTTGCTTCAG | 63 | 211 |
| 709700 | 1520 | 1536 | 114588 | 114604 | CTACAATAGTAGTTGGG | 24 | 212 |
| 709706 | 1639 | 1655 | 114707 | 114723 | TGTTAATAAAAGGCTCA | 46 | 213 |
| 709712 | 1730 | 1746 | 114798 | 114814 | ATTTATTGTCAGAAAGG | 62 | 214 |
| 709718 | 1772 | 1788 | 114840 | 114856 | GGGAACCCACTTTTTTT | 17 | 215 |
| 709724 | 1838 | 1854 | 114906 | 114922 | CTAATGTGTCTTATGGC | 39 | 216 |
| 709730 | 1904 | 1920 | 114972 | 114988 | GTGAGGAATGCTGAGTT | 25 | 217 |
| 709736 | 2035 | 2051 | 115103 | 115119 | TGATCTCCTTTAAGGTG | 10 | 218 |
| 709742 | 2107 | 2123 | 115175 | 115191 | GGAAAAATCCTAGAATT | 6 | 219 |
| 709748 | 2188 | 2204 | 115256 | 115272 | AGAGTTTTTCACCATCA | 37 | 220 |
| 709754 | 2283 | 2299 | 115351 | 115367 | CTTGAAATTATACTTTC | 37 | 221 |
| 709760 | 2349 | 2365 | 115417 | 115433 | GCGCCCAATATATATCA | 30 | 222 |
| 709766 | 2425 | 2441 | 115493 | 115509 | TCTTCAATTAGGTAAAA | 17 | 223 |
| 709772 | 2491 | 2507 | 115559 | 115575 | CAAGAAACTTACCATTT | 11 | 224 |
| 709778 | 2562 | 2578 | 115630 | 115646 | CTTTCTAACCTTCCTGA | 21 | 225 |
| 709784 | 2670 | 2686 | 115738 | 115754 | CACTGCTATCAGTCTAG | 39 | 226 |
| 709790 | 2737 | 2753 | 115805 | 115821 | GAATTTGTATCCACATA | 53 | 227 |

TABLE 3-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709796 | 2806 | 2822 | 115874 | 115890 | TATATAAAGTAATTCAC | 12 | 228 |
| 709802 | 2889 | 2905 | 115957 | 115973 | ATATGAGACAAGCTTCC | 18 | 229 |
| 709808 | 2955 | 2971 | 116023 | 116039 | CTGCAAAATAAACCTAG | 41 | 230 |
| 709814 | 3021 | 3037 | 116089 | 116105 | CTGAACTGTTTTGGTAA | 30 | 231 |
| 709820 | 3087 | 3103 | 116155 | 116171 | ACCCCACTTGGAATACC | 37 | 232 |
| 709826 | 3156 | 3172 | 116224 | 116240 | ATACTGGATAAGCCAGA | 22 | 233 |
| 709832 | N/A | N/A | 18121 | 18137 | CCTTGCCCAACTGGTCC | 42 | 234 |
| 709838 | N/A | N/A | 3467 | 3483 | CCAGAGGAGGCCGCTGT | 15 | 235 |
| 709844 | N/A | N/A | 3597 | 3613 | CCGACTCCTCCCCGCCT | 24 | 236 |
| 709862 | N/A | N/A | 7047 | 7063 | TCTTTCCACTCTATCAG | 19 | 237 |
| 709868 | N/A | N/A | 10846 | 10862 | ACTGCATATTTAGAGTC | 13 | 238 |
| 709874 | N/A | N/A | 18424 | 18440 | ACATGAAAGCCCTCATT | 37 | 239 |
| 709880 | N/A | N/A | 25537 | 25553 | ATGAATTGCCACTATAA | 56 | 240 |
| 709886 | N/A | N/A | 32984 | 33000 | TGGATAAAAGAAGTTAC | 61 | 241 |
| 709892 | N/A | N/A | 43821 | 43837 | TACTTCTCTGGACCTCT | 74 | 242 |
| 709898 | N/A | N/A | 50921 | 50937 | TTTCATCAATATCTGCA | 90 | 243 |
| 709904 | N/A | N/A | 55614 | 55630 | AATTTAACCTTAAAGTA | 20 | 244 |
| 709910 | N/A | N/A | 59199 | 59215 | GTAGAGGCCCAATAAGT | 37 | 245 |
| 709916 | N/A | N/A | 74075 | 74091 | AGTTATTGCTATCAAGA | 57 | 246 |
| 709924 | N/A | N/A | 77666 | 77682 | GACTCTAGAAAAGCTCT | 70 | 247 |
| 709930 | N/A | N/A | 79403 | 79419 | CTTTTTCACTTGTCTCA | 48 | 248 |
| 709936 | N/A | N/A | 81475 | 81491 | AGAGCTGTTTGAAGTGA | 71 | 249 |
| 709942 | N/A | N/A | 85512 | 85528 | ACCTATGTTGAAACTTA | 48 | 250 |
| 709948 | N/A N/A | N/A N/A | 88651 89656 | 88667 89672 | GACATACAAACCCAAAG | 46 | 251 |
| 709954 | N/A N/A | N/A N/A | 88711 89716 | 88727 89732 | AGAGATGAAGTTAACTC | 61 | 252 |
| 709960 | N/A N/A | N/A N/A | 88720 89725 | 88736 89741 | CTCTCCTATAGAGATGA | 44 | 253 |
| 709966 | N/A N/A | N/A N/A | 88757 89762 | 88773 89778 | CCCTTTTCAAGAGCTTT | 82 | 254 |
| 709972 | N/A | N/A | 89254 | 89270 | TAAGCTCATATTTATAG | 23 | 255 |
| 709978 | N/A | N/A | 94005 | 94021 | TAAAAGATCATGAGGGC | 47 | 256 |
| 709984 | N/A | N/A | 107602 | 107618 | GAAACATGAGTTTAATA | 9 | 257 |

TABLE 4

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 71 | 21 |
| 709521 | 55 | 71 | 3237 | 3253 | GCCCCCTCTCTTGGGCC | 8 | 258 |
| 709527 | 190 | 206 | 3372 | 3388 | TCACGAGGGTGGAAAGG | 0 | 259 |
| 709533 | 236 | 252 | 4687 | 4703 | TCCTTTACACCACACTG | 63 | 260 |
| 709539 | 252 | 268 | 4703 | 4719 | TCCATGGCTAATGAATT | 24 | 261 |
| 709545 | 260 | 276 | 4711 | 4727 | TGAATACATCCATGGCT | 46 | 262 |
| 709551 | 283 | 299 | 4734 | 4750 | CTTGGCCTTTGAAAGTC | 72 | 263 |
| 709557 | 325 | 341 | 4776 | 4792 | CACACCCTGTTTGGTTT | 45 | 264 |
| 709563 | 381 | 397 | 12194 | 12210 | TTGGTTTTGGAGCCTAC | 69 | 265 |
| 709569 | 400 | 416 | 12213 | 12229 | ACCATGCACCACTCCCT | 41 | 266 |
| 709575 | 410 | 426 | 12223 | 12239 | CTGTTGCCACACCATGC | 45 | 267 |
| 709581 | 445 | 461 | 18012 | 18028 | AACATTTGTCACTTGCT | 65 | 268 |
| 709587 | 465 | 481 | 18032 | 18048 | CCCGTCACCACTGCTCC | 24 | 269 |
| 709593 | 475 | 491 | 18042 | 18058 | TGCTGTCACACCCGTCA | 55 | 270 |
| 709599 | 545 | 561 | 18112 | 18128 | ACTGGTCCTTTTTGACA | 15 | 271 |
| 709605 | 617 | 633 | 111152 | 111168 | CCTCATTGTCAGGATCC | 42 | 272 |
| 709611 | 693 | 709 | 113761 | 113777 | GAAACTGGGAGCAAAGA | 23 | 273 |
| 709617 | 762 | 778 | 113830 | 113846 | AAATGTCATGACTGGGC | 37 | 274 |
| 709623 | 793 | 809 | 113861 | 113877 | AGACTTCGAGATACACT | 36 | 275 |
| 709629 | 822 | 838 | 113890 | 113906 | GTACAGATACTTCAATC | 34 | 276 |
| 709635 | 888 | 904 | 113956 | 113972 | CAAAGACCCTGCTACCA | 8 | 277 |
| 709641 | 897 | 913 | 113965 | 113981 | CACAGCACACAAAGACC | 22 | 278 |
| 709647 | 910 | 926 | 113978 | 113994 | AAGCCACAAAATCCACA | 41 | 279 |
| 709653 | 947 | 963 | 114015 | 114031 | CTTAGGTGTTTTTAATT | 19 | 280 |
| 709659 | 1001 | 1017 | 114069 | 114085 | TTCTGAACAACAGCAAC | 41 | 281 |
| 709665 | 1067 | 1083 | 114135 | 114151 | TCTTAGACAGTATCATT | 38 | 282 |
| 709671 | 1183 | 1199 | 114251 | 114267 | ATAAAACACATCGCAAA | 13 | 283 |
| 709677 | 1241 | 1257 | 114309 | 114325 | TTTGCAATGAGATAACG | 8 | 284 |
| 709683 | 1295 | 1311 | 114363 | 114379 | GCTTATAAGCATGATTT | 22 | 285 |
| 709689 | 1370 | 1386 | 114438 | 114454 | TAAAATTCCTCCTTCTT | 4 | 286 |
| 709695 | 1443 | 1459 | 114511 | 114527 | AAACACACTTCTGGCAG | 19 | 287 |
| 709701 | 1531 | 1547 | 114599 | 114615 | AATAGACCACTCTACAA | 16 | 288 |
| 709707 | 1660 | 1676 | 114728 | 114744 | CGAGACAAAAATAACAA | 0 | 289 |
| 709713 | 1735 | 1751 | 114803 | 114819 | ATATTATTTATTGTCAG | 0 | 290 |
| 709719 | 1783 | 1799 | 114851 | 114867 | GCTTAGTTCCCGGGAAC | 5 | 291 |
| 709725 | 1849 | 1865 | 114917 | 114933 | GCTAATATGTGCTAATG | 29 | 292 |
| 709731 | 1930 | 1946 | 114998 | 115014 | GAATTTCTGATGATTAA | 9 | 293 |

TABLE 4-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709737 | 2046 | 2062 | 115114 | 115130 | GTCTAGAGAATTGATCT | 23 | 294 |
| 709743 | 2118 | 2134 | 115186 | 115202 | ACCTTTCCTAAGGAAAA | 0 | 295 |
| 709749 | 2200 | 2216 | 115268 | 115284 | ATTAATTTATACAGAGT | 5 | 296 |
| 709755 | 2294 | 2310 | 115362 | 115378 | GAATATTCTGTCTTGAA | 30 | 297 |
| 709761 | 2362 | 2378 | 115430 | 115446 | TCCTTCCTCACCAGCGC | 31 | 298 |
| 709767 | 2436 | 2452 | 115504 | 115520 | GTAGTAGTCTCTCTTCA | 26 | 299 |
| 709773 | 2507 | 2523 | 115575 | 115591 | CATAACTTAAATAAAAC | 0 | 300 |
| 709779 | 2573 | 2589 | 115641 | 115657 | CCTAACCGCCACTTTCT | 19 | 301 |
| 709785 | 2681 | 2697 | 115749 | 115765 | TTGTTCTAGGTCACTGC | 27 | 302 |
| 709791 | 2749 | 2765 | 115817 | 115833 | CACTTTAAAGGAGAATT | 0 | 303 |
| 709797 | 2827 | 2843 | 115895 | 115911 | GTCCCAAATAAACTATT | 0 | 304 |
| 709803 | 2900 | 2916 | 115968 | 115984 | CTCGGGAGTGAATATGA | 12 | 305 |
| 709809 | 2966 | 2982 | 116034 | 116050 | AGAATGTAAGTCTGCAA | 24 | 306 |
| 709815 | 3032 | 3048 | 116100 | 116116 | CAAAGTGCACTCTGAAC | 23 | 307 |
| 709821 | 3098 | 3114 | 116166 | 116182 | TTCTGAAAAAGACCCCA | 0 | 308 |
| 709827 | 3167 | 3183 | 116235 | 116251 | CAAATAGCTACATACTG | 2 | 309 |
| 709839 | N/A | N/A | 3495 | 3511 | CGGAGGCGGCACCCGGG | 8 | 310 |
| 709845 | N/A | N/A | 3608 | 3624 | TCTCCACAACTCCGACT | 18 | 311 |
| 709863 | N/A | N/A | 7156 | 7172 | TAATCAGGGAAGTGATG | 0 | 312 |
| 709869 | N/A | N/A | 14963 | 14979 | CTTCAGAAAATCTCCAG | 33 | 313 |
| 709875 | N/A | N/A | 20562 | 20578 | CACAACTATGCTGCAAT | 58 | 314 |
| 709881 | N/A | N/A | 25804 | 25820 | ATCATCCAGTAGAGTGA | 66 | 315 |
| 709887 | N/A | N/A | 33591 | 33607 | GAGAACACTTAAGTGAA | 44 | 316 |
| 709893 | N/A<br>N/A | N/A<br>N/A | 46160<br>53645 | 46176<br>53661 | ATTTCCATGAAGCCAAG | 88 | 317 |
| 709899 | N/A | N/A | 51477 | 51493 | CTAGAGACCACCTGAGA | 27 | 318 |
| 709905 | N/A | N/A | 56363 | 56379 | CTAATGAACAGAGAAAG | 2 | 319 |
| 709911 | N/A | N/A | 68799 | 68815 | CCAAAGTAAGAGGAGAT | 37 | 320 |
| 709917 | N/A | N/A | 74219 | 74235 | TGTTGCTAAGCACAAAC | 44 | 321 |
| 709925 | N/A | N/A | 78068 | 78084 | TCAAGGTGCCATATCTG | 51 | 322 |
| 709931 | N/A | N/A | 80286 | 80302 | AAAGAAAGGCAGTGTTG | 1 | 323 |
| 709937 | N/A | N/A | 82460 | 82476 | CCAATATGGATTCAGCA | 46 | 324 |
| 709943 | N/A | N/A | 86783 | 86799 | CAATTATTAGCAGTTAC | 55 | 325 |
| 709949 | N/A<br>N/A | N/A<br>N/A | 88653<br>89658 | 88669<br>89674 | TTGACATACAAACCCAA | 60 | 326 |
| 709955 | N/A<br>N/A | N/A<br>N/A | 88713<br>89718 | 88729<br>89734 | ATAGAGATGAAGTTAAC | 49 | 327 |

TABLE 4-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709961 | N/A | N/A | 88722 | 88738 | CACTCTCCTATAGAGAT | 0 | 328 |
|  | N/A | N/A | 89727 | 89743 |  |  |  |
| 709967 | N/A | N/A | 88759 | 88775 | TTCCCTTTTCAAGAGCT | 77 | 329 |
|  | N/A | N/A | 89764 | 89780 |  |  |  |
| 709973 | N/A | N/A | 91417 | 91433 | AGAAGGAATGCACAATA | 37 | 330 |
| 709979 | N/A | N/A | 94055 | 94071 | GCCATAATTCAAGTCAG | 63 | 331 |
| 709985 | N/A | N/A | 108049 | 108065 | ACTGACAACTTACAGCA | 30 | 332 |

TABLE 5

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 58 | 21 |
| 709522 | 66 | 82 | 3248 | 3264 | CTCGGTCGCTCGCCCCC | 36 | 333 |
| 709528 | 201 | 217 | 3383 | 3399 | CAGTTCTCCGCTCACGA | 26 | 334 |
| 709534 | 237 | 253 | 4688 | 4704 | TTCCTTTACACCACACT | 60 | 335 |
| 709540 | 254 | 270 | 4705 | 4721 | CATCCATGGCTAATGAA | 47 | 336 |
| 709546 | 262 | 278 | 4713 | 4729 | CATGAATACATCCATGG | 31 | 337 |
| 709552 | 284 | 300 | 4735 | 4751 | CCTTGGCCTTTGAAAGT | 41 | 338 |
| 709558 | 336 | 352 | 4787 | 4803 | GCTGCTTCTGCCACACC | 61 | 339 |
| 709564 | 382 | 398 | 12195 | 12211 | CTTGGTTTTGGAGCCTA | 63 | 340 |
| 709570 | 402 | 418 | 12215 | 12231 | ACACCATGCACCACTCC | 56 | 341 |
| 709576 | 418 | 434 | N/A | N/A | CTCAGCCACTGTTGCCA | 57 | 342 |
| 709582 | 446 | 462 | 18013 | 18029 | CAACATTTGTCACTTGC | 72 | 343 |
| 709588 | 467 | 483 | 18034 | 18050 | CACCCGTCACCACTGCT | 56 | 344 |
| 709594 | 486 | 502 | 18053 | 18069 | TTCTGGGCTACTGCTGT | 11 | 345 |
| 709600 | 556 | 572 | N/A | N/A | ATTCTTGCCCAACTGGT | 7 | 346 |
| 709606 | 628 | 644 | 111163 | 111179 | CATTTCATAAGCCTCAT | 12 | 347 |
| 709612* | 704 | 720 | 113772 | 113788 | GCAGATCTCAAGAAACT | 45 | 348 |
| 709618 | 778 | 794 | 113846 | 113862 | CTGTAAAAACTTTGAGA | 27 | 349 |
| 709624 | 794 | 810 | 113862 | 113878 | AAGACTTCGAGATACAC | 43 | 350 |
| 709630 | 844 | 860 | 113912 | 113928 | CCGAAATGCTGAGTGGG | 29 | 351 |
| 709636 | 889 | 905 | 113957 | 113973 | ACAAAGACCCTGCTACC | 14 | 352 |
| 709642 | 899 | 915 | 113967 | 113983 | TCCACAGCACACAAAGA | 30 | 353 |
| 709648 | 912 | 928 | 113980 | 113996 | TGAAGCCACAAAATCCA | 28 | 354 |
| 709654 | 949 | 965 | 114017 | 114033 | CACTTAGGTGTTTTTAA | 26 | 355 |
| 709660 | 1012 | 1028 | 114080 | 114096 | TCACTAACAACTTCTGA | 34 | 356 |

TABLE 5-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709666 | 1091 | 1107 | 114159 | 114175 | ACAAATTTCACAATACG | 32 | 357 |
| 709672 | 1198 | 1214 | 114266 | 114282 | TACAAACACAAGTGAAT | 14 | 358 |
| 709678 | 1266 | 1282 | 114334 | 114350 | TGAGATGGGATAAAAAT | 9 | 359 |
| 709684 | 1305 | 1321 | 114373 | 114389 | AATTCATGTTGCTTATA | 0 | 360 |
| 709690 | 1383 | 1399 | 114451 | 114467 | TCTCTACCTCTTCTAAA | 0 | 361 |
| 709696 | 1454 | 1470 | 114522 | 114538 | AGTGCATACCAAAACAC | 9 | 362 |
| 709702 | 1549 | 1565 | 114617 | 114633 | GACAGGATTGAAGGGAG | 26 | 363 |
| 709708 | 1671 | 1687 | 114739 | 114755 | AAAAATTATTTCGAGAC | 0 | 364 |
| 709714 | 1738 | 1754 | 114806 | 114822 | CGAATATTATTTATTGT | 0 | 365 |
| 709720 | 1794 | 1810 | 114862 | 114878 | TCTTCTACACTGCTTAG | 14 | 366 |
| 709726 | 1860 | 1876 | 114928 | 114944 | GCCTTGAATGTGCTAAT | 38 | 367 |
| 709732 | 1991 | 2007 | 115059 | 115075 | GGCATTTCCTGTAAAAA | 21 | 368 |
| 709738 | 2057 | 2073 | 115125 | 115141 | AATTTTTATCAGTCTAG | 45 | 369 |
| 709744 | 2137 | 2153 | 115205 | 115221 | TCTTCCCTGAAAGAGAA | 6 | 370 |
| 709750 | 2239 | 2255 | 115307 | 115323 | CCCCAGAATAATTAAAA | 1 | 371 |
| 709756 | 2305 | 2321 | 115373 | 115389 | TAGCATGTCTAGAATAT | 23 | 372 |
| 709762 | 2378 | 2394 | 115446 | 115462 | GTCACTCATTCCTCCTT | 24 | 373 |
| 709768 | 2447 | 2463 | 115515 | 115531 | CTTAGCACTCTGTAGTA | 9 | 374 |
| 709774 | 2518 | 2534 | 115586 | 115602 | CCTTGCTTAAACATAAC | 16 | 375 |
| 709780 | 2596 | 2612 | 115664 | 115680 | CTTTAGGTAGATTTAAA | 0 | 376 |
| 709786 | 2692 | 2708 | 115760 | 115776 | CTAATCTCAAATTGTTC | 12 | 377 |
| 709792 | 2761 | 2777 | 115829 | 115845 | TAAGGGAAGAAACACTT | 11 | 378 |
| 709798 | 2838 | 2854 | 115906 | 115922 | TTAAGTGTTTGGTCCCA | 53 | 379 |
| 709804 | 2911 | 2927 | 115979 | 115995 | CAGGTGAATGTCTCGGG | 29 | 380 |
| 709810 | 2977 | 2993 | 116045 | 116061 | AATAACTTGGGAGAATG | 6 | 381 |
| 709816 | 3043 | 3059 | 116111 | 116127 | CAATTGTGTGCCAAAGT | 15 | 382 |
| 709822 | 3109 | 3125 | 116177 | 116193 | TAGTGCAGAGATTCTGA | 38 | 383 |
| 709828 | 3174 | 3190 | 116242 | 116258 | TATGTCACAAATAGCTA | 3 | 384 |
| 709834 | N/A | N/A | 3415 | 3431 | AACCCGCTAACCTGTCG | 16 | 385 |
| 709840 | N/A | N/A | 3506 | 3522 | CACAGGAAGGGCGGAGG | 10 | 386 |
| 709846 | N/A | N/A | 3619 | 3635 | GTCCCTCTGCTTCTCCA | 4 | 387 |
| 709858 | N/A | N/A | 2166 | 2182 | CATACACACGCGAACTT | 4 | 388 |
| 709864 | N/A | N/A | 7240 | 7256 | TCAATTATTCATATGTC | 18 | 389 |
| 709870 | N/A | N/A | 15701 | 15717 | CTGCACAGTAAAATGTA | 8 | 390 |
| 709876 | N/A | N/A | 20986 | 21002 | AGTGTGAGCAAACATTC | 50 | 391 |
| 709876 | N/A | N/A | 27411 | 27427 | AGTGTGAGCAAACATTC | 50 | 391 |

TABLE 5-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709882 | N/A | N/A | 25926 | 25942 | AATTGAATACATTGTCT | 63 | 392 |
| 709888 | N/A | N/A | 39106 | 39122 | TCCTAAAGTATTGCACT | 31 | 393 |
| 709894 | N/A | N/A | 48228 | 48244 | CCTGGTCATGACTCTGA | 62 | 394 |
| 709900 | N/A | N/A | 52420 | 52436 | GATCAAATGTATAGAGA | 62 | 395 |
| 709906 | N/A | N/A | 56773 | 56789 | AGAGGCAGGGCTAGACA | 13 | 396 |
| 709912 | N/A | N/A | 68801 | 68817 | TGCCAAAGTAAGAGGAG | 56 | 397 |
| 709919 | N/A | N/A | 74295 | 74311 | ATAGAACTCTGTAGTCA | 72 | 398 |
| 709926 | N/A | N/A | 78080 | 78096 | CAAATGAACTTCTCAAG | 7 | 399 |
| 709932 | N/A | N/A | 80397 | 80413 | AAATTACACTGTTGAAT | 32 | 400 |
| 709938 | N/A | N/A | 82770 | 82786 | GGCAAAGGGCTCTGGTG | 34 | 401 |
| 709944 | N/A | N/A | 87946 | 87962 | GTAAGTTGTGACCATGC | 76 | 402 |
| 709950 | N/A | N/A | 88655 | 88671 | ACTTGACATACAAACCC | 45 | 403 |
| 709950 | N/A | N/A | 89660 | 89676 | ACTTGACATACAAACCC | 45 | 403 |
| 709956 | N/A | N/A | 88714 | 88730 | TATAGAGATGAAGTTAA | 26 | 404 |
|  | N/A | N/A | 89719 | 89735 |  |  |  |
| 709962 | N/A | N/A | 88723 | 88739 | CCACTCTCCTATAGAGA | 18 | 405 |
|  | N/A | N/A | 89728 | 89744 |  |  |  |
| 709968 | N/A | N/A | 88761 | 88777 | ATTTCCCTTTTCAAGAG | 19 | 406 |
|  | N/A | N/A | 89766 | 89782 |  | 19 | 406 |
| 709974 | N/A | N/A | 92159 | 92175 | TAACTCCATTTAATTGT | 17 | 407 |
| 709980 | N/A | N/A | 99285 | 99301 | ACAGTACACTATTTGTT | 25 | 408 |
| 709986 | N/A | N/A | 109588 | 109604 | ACCACCCCAAACTACCT | 0 | 409 |

TABLE 6

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 64 | 21 |
| 709523 | 91 | 107 | 3273 | 3289 | CGCACCTCACTTCCGCG | 20 | 410 |
| 709529 | 212 | 228 | 3394 | 3410 | ATGGCCACTCCCAGTTC | 21 | 411 |
| 709535 | 238 | 254 | 4689 | 4705 | ATTCCTTTACACCACAC | 84 | 412 |
| 709541 | 255 | 271 | 4706 | 4722 | ACATCCATGGCTAATGA | 43 | 413 |
| 709547 | 266 | 282 | 4717 | 4733 | CTTTCATGAATACATCC | 81 | 414 |
| 709553 | 286 | 302 | 4737 | 4753 | CTCCTTGGCCTTTGAAA | 31 | 415 |
| 709559 | 361 | 377 | 4812 | 4828 | GAGAACACCCTCTTTTG | 15 | 416 |
| 709565 | 383 | 399 | 12196 | 12212 | CCTGGTTTTGGAGCCT | 63 | 417 |
| 709571 | 404 | 420 | 12217 | 12233 | CCACACCATGCACCACT | 63 | 418 |

TABLE 6-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709577 | 431 | 447 | 17998 | 18014 | GCTCTTTGGTCTTCTCA | 45 | 419 |
| 709583 | 448 | 464 | 18015 | 18031 | TCCAACATTTGTCACTT | 22 | 420 |
| 709589 | 469 | 485 | 18036 | 18052 | CACACCCGTCACCACTG | 48 | 421 |
| 709595 | 501 | 517 | 18068 | 18084 | GCTCCCTCCACTGTCTT | 28 | 422 |
| 709601 | 567 | 583 | N/A | N/A | GCTCCTTCTTCATTCTT | 5 | 423 |
| 709607 | 639 | 655 | N/A | N/A | TCCTCAGAAGGCATTTC | 0 | 424 |
| 709613* | 715 | 731 | 113783 | 113799 | AACATCTGTCAGCAGAT | 56 | 425 |
| 709619 | 788 | 804 | 113856 | 113872 | TCGAGATACACTGTAAA | 18 | 426 |
| 709625 | 796 | 812 | 113864 | 113880 | GGAAGACTTCGAGATAC | 64 | 427 |
| 709631 | 855 | 871 | 113923 | 113939 | AAAGGGAAGCACCGAAA | 25 | 428 |
| 709637 | 891 | 907 | 113959 | 113975 | ACACAAAGACCCTGCTA | 12 | 429 |
| 709643 | 904 | 920 | 113972 | 113988 | CAAAATCCACAGCACAC | 50 | 430 |
| 709649 | 914 | 930 | 113982 | 113998 | ATTGAAGCCACAAAATC | 13 | 431 |
| 709655 | 952 | 968 | 114020 | 114036 | AGTCACTTAGGTGTTTT | 32 | 432 |
| 709661 | 1023 | 1039 | 114091 | 114107 | ATGATAGCAAATCACTA | 22 | 433 |
| 709667 | 1122 | 1138 | 114190 | 114206 | GCTCACATATTTTTAAG | 18 | 434 |
| 709673 | 1209 | 1225 | 114277 | 114293 | CACCATTTATATACAAA | 20 | 435 |
| 709679 | 1274 | 1290 | 114342 | 114358 | TATTAAAGTGAGATGGG | 28 | 436 |
| 709685 | 1316 | 1332 | 114384 | 114400 | TGTCAGTTCTTAATTCA | 17 | 437 |
| 709691 | 1399 | 1415 | 114467 | 114483 | GGTTAATGTTCCATTTT | 29 | 438 |
| 709697 | 1465 | 1481 | 114533 | 114549 | CTTAAGGAACCAGTGCA | 30 | 439 |
| 709703 | 1579 | 1595 | 114647 | 114663 | CAGTTCCCCAAAATACG | 0 | 440 |
| 709709 | 1705 | 1721 | 114773 | 114789 | TCACACCAATATCAGAC | 36 | 441 |
| 709715 | 1740 | 1756 | 114808 | 114824 | GTCGAATATTATTTATT | 11 | 442 |
| 709721 | 1805 | 1821 | 114873 | 114889 | AGTCAAATCATCTTCT | 17 | 443 |
| 709727 | 1871 | 1887 | 114939 | 114955 | ATTCTCTCAGAGCCTTG | 72 | 444 |
| 709733 | 2002 | 2018 | 115070 | 115086 | CGATGTTTAAAGGCATT | 0 | 445 |
| 709739 | 2068 | 2084 | 115136 | 115152 | GGAGGCCATGAAATTTT | 39 | 446 |
| 709745 | 2148 | 2164 | 115216 | 115232 | GAGTTAATAGATCTTCC | 36 | 447 |
| 709751 | 2250 | 2266 | 115318 | 115334 | AAATGACTATGCCCCAG | 44 | 448 |
| 709757 | 2316 | 2332 | 115384 | 115400 | ATATAAACTGCTAGCAT | 23 | 449 |
| 709763 | 2389 | 2405 | 115457 | 115473 | CCATCCTTATAGTCACT | 48 | 450 |
| 709769 | 2458 | 2474 | 115526 | 115542 | GACACATGCAGCTTAGC | 42 | 451 |
| 709775 | 2529 | 2545 | 115597 | 115613 | ACAAATCCTTTCCTTGC | 12 | 452 |
| 709781 | 2631 | 2647 | 115699 | 115715 | TAATACCAATACTTTTA | 21 | 453 |
| 709787 | 2703 | 2719 | 115771 | 115787 | TCAACTTTCCTAATC | 0 | 454 |
| 709793 | 2772 | 2788 | 115840 | 115856 | CAGATAAATATTAAGGG | 0 | 455 |

TABLE 6-continued

Percent reduction of human SNCA mRNA with 5-8-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 709799 | 2856 | 2872 | 115924 | 115940 | ACTTAAAGAACTTTTTG | 11 | 456 |
| 709805 | 2922 | 2938 | 115990 | 116006 | AGGCCACTTGGCAGGTG | 16 | 457 |
| 709811 | 2988 | 3004 | 116056 | 116072 | ATATGAGGCTGAATAAC | 16 | 458 |
| 709817 | 3054 | 3070 | 116122 | 116138 | TGTTCTGTTCCCAATTG | 48 | 459 |
| 709823 | 3120 | 3136 | 116188 | 116204 | GCATCTCACACTAGTGC | 30 | 460 |
| 709829 | 3180 | 3196 | 116248 | 116264 | ATTTATTATGTCACAAA | 0 | 461 |
| 709835 | N/A | N/A | 3426 | 3442 | AGTGGGAGGCAAACCCG | 8 | 462 |
| 709841 | N/A | N/A | 3517 | 3533 | GAAAGGAGCGCACAGG | 32 | 463 |
| 709853 | N/A | N/A | 2086 | 2102 | CTGGATCACACCAGAAT | 16 | 464 |
| 709859 | N/A<br>N/A | N/A<br>N/A | 2500<br>112970 | 2516<br>112986 | CTATCACCATTTTCCTT | 13 | 465 |
| 709865 | N/A | N/A | 7406 | 7422 | AGCCATAAGTGAAATTA | 48 | 466 |
| 709871 | N/A | N/A | 15993 | 16009 | AGTTCGATTTAAATGCC | 27 | 467 |
| 709877 | N/A<br>N/A | N/A<br>N/A | 20988<br>27413 | 21004<br>27429 | ACAGTGTGAGCAAACAT | 62 | 468 |
| 709883 | N/A | N/A | 26205 | 26221 | CCCTCTTTGTGTTATAC | 74 | 469 |
| 709889 | N/A | N/A | 40203 | 40219 | GAAAGTTTTTATGGAGA | 22 | 470 |
| 709895 | N/A | N/A | 48716 | 48732 | TGTATTTTGGATGCTTC | 85 | 471 |
| 709901 | N/A | N/A | 52979 | 52995 | GAAGTGACTATGTCTTC | 46 | 472 |
| 709907 | N/A | N/A | 57491 | 57507 | GCCAAATGAATGGGCCA | 59 | 473 |
| 709913 | N/A | N/A | 68942 | 68958 | ATCAAAAGGAACATCAA | 35 | 474 |
| 709921 | N/A | N/A | 75328 | 75344 | TATTCTTCTCCTCCATG | 34 | 475 |
| 709927 | N/A | N/A | 78404 | 78420 | AATGTTGGCAAGCTTGA | 48 | 476 |
| 709933 | N/A | N/A | 80489 | 80505 | ACTCACACTGCCTAGCT | 36 | 477 |
| 709939 | N/A | N/A | 83333 | 83349 | CCTATATATTCAAGATG | 22 | 478 |
| 709945 | N/A | N/A | 88047 | 88063 | AGAAGCTATCAAGACAT | 60 | 479 |
| 709951 | N/A<br>N/A | N/A<br>N/A | 88657<br>89662 | 88673<br>89678 | CCACTTGACATACAAAC | 24 | 480 |
| 709957<br>709957 | N/A<br>N/A | N/A<br>N/A | 88715<br>89720 | 88731<br>89736 | CTATAGAGATGAAGTTA | 39 | 481 |
| 709963<br>709963 | N/A<br>N/A | N/A<br>N/A | 88725<br>89730 | 88741<br>89746 | ATCCACTCTCCTATAGA | 6 | 482 |
| 709969 | N/A | N/A | 89098 | 89114 | AATAGGAGTTCAATGAA | 33 | 483 |
| 709975 | N/A | N/A | 93354 | 93370 | GTTAGATAATTATTGAG | 20 | 484 |
| 709981 | N/A | N/A | 100015 | 100031 | CTTCAAACCTTTTGACC | 15 | 485 |
| 709987 | N/A | N/A | 110359 | 110375 | CCTATTTATGGTATAAT | 0 | 486 |

TABLE 7

Percent reduction of human SNCA mRNA with 5-8-4 MOE and cEt gapmers with mixed internucleoside linkages

| Compound No | SEQ ID NO: 3 start | SEQ ID NO: 3 stop | SEQ ID NO: 4 start | SEQ ID NO: 4 stop | SEQ ID NO: 5 start | SEQ ID NO: 5 stop | SEQ ID NO: 6 start | SEQ ID NO: 6 stop | Sequence (5' to 3') | % Reduction | SEQ ID NO |
|---|---|---|---|---|---|---|---|---|---|---|---|
| 709830 | 369 | 385 | N/A | N/A | N/A | N/A | N/A | N/A | ACTACATAGAGAACACC | 60 | 487 |
| 709831 | 380 | 396 | N/A | N/A | N/A | N/A | N/A | N/A | TCTTCTCAGCCACTACA | 23 | 488 |
| 709833 | 523 | 539 | N/A | N/A | N/A | N/A | N/A | N/A | TTGATACCCTTCCTTGC | 0 | 489 |
| 709847 | N/A | N/A | 388 | 404 | N/A | N/A | N/A | N/A | ACCACACTGAGTCCCTC | 0 | 490 |
| 709848 | N/A | N/A | 389 | 405 | N/A | N/A | N/A | N/A | CACCACACTGAGTCCCT | 22 | 491 |
| 709849 | N/A | N/A | 390 | 406 | N/A | N/A | N/A | N/A | ACACCACACTGAGTCCC | 11 | 492 |
| 709850 | N/A | N/A | 392 | 408 | N/A | N/A | N/A | N/A | TTACACCACACTGAGTC | 26 | 493 |
| 709851 | N/A | N/A | 393 | 409 | N/A | N/A | N/A | N/A | TTTACACCACACTGAGT | 23 | 494 |
| 709852 | N/A | N/A | 394 | 410 | N/A | N/A | N/A | N/A | CTTTACACCACACTGAG | 24 | 495 |
| 709856 | N/A | N/A | N/A | N/A | 38 | 54 | N/A | N/A | TACACCACACTCTTTCA | 22 | 496 |
| 709857 | N/A | N/A | N/A | N/A | N/A | N/A | 89 | 105 | CCACACTCACTTCCGCG | 15 | 497 |

Example 2: Effect of 4-9-4 MOE and cEt Gapmers with Mixed Internucleoside Linkages on Human SNCA In Vitro, Single Dose Modified oligonucleotides complementary to a human SNCA nucleic acid were designed and tested as described in Example 1 for their effect on SNCA mRNA in vitro. The modified oligonucleotides were tested in a series of experiments that had similar culture conditions.

The modified oligonucleotides marked with an asterisk (*) target the amplicon region of the primer probe set. Additional assays may be used to measure the potency and efficacy of oligonucleotides targeting the amplicon region. Compound No. 387978, previously disclosed in WO 2012/068405 was also tested and is a comparator oligonucleotide. Compound No. 387978 is a 5-10-5 MOE gapmer wherein each internucleoside linkage is a phosphorothioate internucleoside linkage and each cytosine residue is a 5-methyl cytosine.

The modified oligonucleotides in tables 7-13 are 4-9-4 MOE and cEt gapmers. The gapmers are 17 nucleobases in length, wherein the central gap segment comprises nine 2'-deoxynucleosides and is flanked by wing segments on both the 5' end on the 3' end comprising two 2'-MOE nucleosides and two cEt nucleosides. The sugar motif for the gapmers is (from 5' to 3'): eekkddddddddkkee; wherein 'd' represents a 2'-deoxyribose sugar; 'e' represents a 2'-MOE modified sugar; and 'k' represents a cEt modified sugar. All cytosine residues throughout each gapmer are 5-methyl cytosines. The internucleoside linkages are mixed phosphodiester and phosphorothioate linkages. The internucleoside linkage motif for the gapmers is (from 5' to 3'): sooossssssssssoss; wherein 'o' represents a phosphodiester internucleoside linkage and 's' represents a phosphorothioate internucleoside linkage. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the Tables below is complementary to human SNCA nucleic acid sequences SEQ ID NO: 1 or SEQ ID NO: 2, as indicated. 'N/A' indicates that the modified oligonucleotide is not complementary to that particular nucleic acid with 100% complementarity. A value of 0% reduction indicates that the compound had no effect or increased mRNA concentrations in the cell. As shown below, modified oligonucleotides complementary to human SNCA reduced the amount of human SNCA mRNA.

TABLE 8

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 9 | 21 |
| 740410 | 240 | 256 | 4691 | 4707 | GAATTCCTTTACACCAC | 92 | 33 |
| 740316 | N/A | N/A | 3416 | 3432 | AAACCCGCTAACCTGTC | 16 | 498 |
| 740317 | N/A | N/A | 3419 | 3435 | GGCAAACCCGCTAACCT | 47 | 499 |

TABLE 8-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740318 | N/A | N/A | 3422 | 3438 | GGAGGCAAACCCGCTAA | 13 | 500 |
| 740319 | N/A | N/A | 3425 | 3441 | GTGGGAGGCAAACCCGC | 2 | 501 |
| 740320 | N/A | N/A | 3428 | 3444 | GGAGTGGGAGGCAAACC | 18 | 502 |
| 740321 | N/A | N/A | 3446 | 3462 | CGGCGACGCGAGGCTGG | 16 | 503 |
| 740322 | N/A | N/A | 3449 | 3465 | AGCCGGCGACGCGAGGC | 25 | 504 |
| 740323 | N/A | N/A | 3452 | 3468 | GTGAGCCGGCGACGCGA | 51 | 505 |
| 740324 | N/A | N/A | 3455 | 3471 | GCTGTGAGCCGGCGACG | 66 | 506 |
| 740325 | N/A | N/A | 3458 | 3474 | GCCGCTGTGAGCCGGCG | 5 | 507 |
| 740326 | N/A | N/A | 3463 | 3479 | AGGAGGCCGCTGTGAGC | 45 | 508 |
| 740327 | N/A | N/A | 3466 | 3482 | CAGAGGAGGCCGCTGTG | 21 | 509 |
| 740328 | N/A | N/A | 3469 | 3485 | CCCCAGAGGAGGCCGCT | 23 | 510 |
| 740329 | N/A | N/A | 3472 | 3488 | TGTCCCCAGAGGAGGCC | 0 | 511 |
| 740330 | N/A | N/A | 3475 | 3491 | GACTGTCCCCAGAGGAG | 24 | 512 |
| 740331 | N/A | N/A | 3496 | 3512 | GCGGAGGCGGCACCCGG | 13 | 513 |
| 740332 | N/A | N/A | 3499 | 3515 | AGGGCGGAGGCGGCACC | 25 | 514 |
| 740333 | N/A | N/A | 3502 | 3518 | GGAAGGGCGGAGGCGGC | 28 | 515 |
| 740334 | N/A | N/A | 3505 | 3521 | ACAGGAAGGGCGGAGGC | 1 | 516 |
| 740335 | N/A | N/A | 3508 | 3524 | CGCACAGGAAGGGCGGA | 19 | 517 |
| 740336 | N/A | N/A | 3511 | 3527 | GAGCGCACAGGAAGGGC | 33 | 518 |
| 740337 | N/A | N/A | 3514 | 3530 | AAGGAGCGCACAGGAAG | 64 | 519 |
| 740338 | N/A | N/A | 3518 | 3534 | GGAAAAGGAGCGCACAG | 40 | 520 |
| 740339 | N/A | N/A | 3521 | 3537 | GAAGGAAAAGGAGCGCA | 36 | 521 |
| 740340 | N/A | N/A | 3532 | 3548 | ATAGGAAAGAAGAAGGA | 42 | 522 |
| 740341 | N/A | N/A | 3536 | 3552 | TTTAATAGGAAAGAAGA | 3 | 523 |
| 740342 | N/A | N/A | 3540 | 3556 | AATATTTAATAGGAAAG | 0 | 524 |
| 740343 | N/A | N/A | 3548 | 3564 | TCCCAAATAATATTTAA | 42 | 525 |
| 740344 | N/A | N/A | 3551 | 3567 | AATTCCCAAATAATATT | 28 | 526 |
| 740345 | N/A | N/A | 3554 | 3570 | AACAATTCCCAAATAAT | 33 | 527 |
| 740346 | N/A | N/A | 3558 | 3574 | TTTAAACAATTCCCAAA | 15 | 528 |
| 740347 | N/A | N/A | 3561 | 3577 | AAATTTAAACAATTCCC | 48 | 529 |
| 740348 | N/A | N/A | 3587 | 3603 | CCCGCCTCTCTCTTTTT | 20 | 530 |
| 740349 | N/A | N/A | 3590 | 3606 | CTCCCCGCCTCTCTCTT | 0 | 531 |
| 740350 | N/A | N/A | 3594 | 3610 | ACTCCTCCCCGCCTCTC | 2 | 532 |
| 740351 | N/A | N/A | 3598 | 3614 | TCCGACTCCTCCCCGCC | 40 | 533 |
| 740352 | N/A | N/A | 3601 | 3617 | AACTCCGACTCCTCCCC | 55 | 534 |
| 740353 | N/A | N/A | 3604 | 3620 | CACAACTCCGACTCCTC | 56 | 535 |

TABLE 8-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740354 | N/A | N/A | 3607 | 3623 | CTCCACAACTCCGACTC | 31 | 536 |
| 740355 | N/A | N/A | 3610 | 3626 | CTTCTCCACAACTCCGA | 41 | 537 |
| 740356 | N/A | N/A | 3613 | 3629 | CTGCTTCTCCACAACTC | 27 | 538 |
| 740357 | N/A | N/A | 3616 | 3632 | CCTCTGCTTCTCCACAA | 30 | 539 |
| 740358 | N/A | N/A | 3620 | 3636 | AGTCCCTCTGCTTCTCC | 0 | 540 |
| 740359 | N/A | N/A | 3623 | 3639 | CTGAGTCCCTCTGCTTC | 26 | 541 |
| 740369 | 10 | 26 | 3192 | 3208 | CTAGTCCTCCTCCTTCT | 14 | 542 |
| 740370 | 23 | 39 | 3205 | 3221 | CGTCCTCCTCCTCCTAG | 27 | 543 |
| 740371 | 28 | 44 | 3210 | 3226 | GTCGCCGTCCTCCTCCT | 0 | 544 |
| 740372 | 45 | 61 | 3227 | 3243 | TTGGGCCCTTCTGGTC | 0 | 545 |
| 740373 | 48 | 64 | 3230 | 3246 | CTCTTGGGCCCCTTCTG | 42 | 546 |
| 740374 | 51 | 67 | 3233 | 3249 | CCTCTCTTGGGCCCCTT | 43 | 547 |
| 740375 | 54 | 70 | 3236 | 3252 | CCCCCTCTCTTGGGCCC | 31 | 548 |
| 740376 | 57 | 73 | 3239 | 3255 | TCGCCCCTCTCTTGGG | 0 | 549 |
| 740377 | 60 | 76 | 3242 | 3258 | CGCTCGCCCCTCTCTT | 23 | 550 |
| 740378 | 63 | 79 | 3245 | 3261 | GGTCGCTCGCCCCTCT | 35 | 551 |
| 740379 | 67 | 83 | 3249 | 3265 | GCTCGGTCGCTCGCCCC | 53 | 552 |
| 740380 | 92 | 108 | 3274 | 3290 | ACGCACCTCACTTCCGC | 58 | 553 |
| 740381 | 95 | 111 | 3277 | 3293 | CGCACGCACCTCACTTC | 43 | 554 |
| 740382 | 98 | 114 | 3280 | 3296 | GCCCGCACGCACCTCAC | 42 | 555 |
| 740383 | 101 | 117 | 3283 | 3299 | GCAGCCCGCACGCACCT | 44 | 556 |
| 740384 | 104 | 120 | 3286 | 3302 | GCTGCAGCCCGCACGCA | 19 | 557 |
| 740385 | 107 | 123 | 3289 | 3305 | TGCGCTGCAGCCCGCAC | 4 | 558 |
| 740386 | 110 | 126 | 3292 | 3308 | GTCTGCGCTGCAGCCCG | 59 | 559 |
| 740387 | 169 | 185 | 3351 | 3367 | AGGCTTGAAGGCAAGGC | 69 | 560 |
| 740388 | 172 | 188 | 3354 | 3370 | AGAAGGCTTGAAGGCAA | 66 | 561 |
| 740389 | 175 | 191 | 3357 | 3373 | GGCAGAAGGCTTGAAGG | 44 | 562 |
| 740390 | 178 | 194 | 3360 | 3376 | AAAGGCAGAAGGCTTGA | 44 | 563 |
| 740391 | 181 | 197 | 3363 | 3379 | TGGAAAGGCAGAAGGCT | 59 | 564 |
| 740392 | 184 | 200 | 3366 | 3382 | GGGTGGAAAGGCAGAAG | 32 | 565 |

TABLE 9

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 9 | 21 |
| 740410 | 240 | 256 | 4691 | 4707 | GAATTCCTTTACACCAC | 86 | 33 |
| 740393 | 187 | 203 | 3369 | 3385 | CGAGGGTGGAAAGGCAG | 56 | 566 |
| 740394 | 191 | 207 | 3373 | 3389 | CTCACGAGGGTGGAAAG | 30 | 567 |
| 740395 | 194 | 210 | 3376 | 3392 | CCGCTCACGAGGGTGGA | 57 | 568 |
| 740396 | 197 | 213 | 3379 | 3395 | TCTCCGCTCACGAGGGT | 40 | 569 |
| 740397 | 200 | 216 | 3382 | 3398 | AGTTCTCCGCTCACGAG | 52 | 570 |
| 740398 | 203 | 219 | 3385 | 3401 | CCCAGTTCTCCGCTCAC | 43 | 571 |
| 740399 | 206 | 222 | 3388 | 3404 | ACTCCCAGTTCTCCGCT | 33 | 572 |
| 740400 | 209 | 225 | 3391 | 3407 | GCCACTCCCAGTTCTCC | 44 | 573 |
| 740401 | 213 | 229 | 3395 | 3411 | AATGGCCACTCCCAGTT | 38 | 574 |
| 740402 | 216 | 232 | 3398 | 3414 | TCGAATGGCCACTCCCA | 45 | 575 |
| 740403 | 233 | 249 | N/A | N/A | TTTACACCACACTGTCG | 50 | 108 |
| 740404 | 234 | 250 | N/A | N/A | CTTTACACCACACTGTC | 62 | 577 |
| 740405 | 235 | 251 | N/A | N/A | CCTTTACACCACACTGT | 77 | 576 |
| 740406 | 236 | 252 | 4687 | 4703 | TCCTTTACACCACACTG | 85 | 260 |
| 740407 | 237 | 253 | 4688 | 4704 | TTCCTTTACACCACACT | 88 | 335 |
| 740408* | 238 | 254 | 4689 | 4705 | ATTCCTTTACACCACAC | 83 | 412 |
| 740409* | 239 | 255 | 4690 | 4706 | AATTCCTTTACACCACA | 89 | 577 |
| 740411 | 241 | 257 | 4692 | 4708 | TGAATTCCTTTACACCA | 83 | 578 |
| 740412 | 242 | 258 | 4693 | 4709 | ATGAATTCCTTTACACC | 87 | 584 |
| 740413 | 243 | 259 | 4694 | 4710 | AATGAATTCCTTTACAC | 78 | 579 |
| 740414 | 245 | 261 | 4696 | 4712 | CTAATGAATTCCTTTAC | 82 | 580 |
| 740415 | 246 | 262 | 4697 | 4713 | GCTAATGAATTCCTTTA | 80 | 581 |
| 740416 | 249 | 265 | 4700 | 4716 | ATGGCTAATGAATTCCT | 89 | 582 |
| 740417 | 253 | 269 | 4704 | 4720 | ATCCATGGCTAATGAAT | 64 | 583 |
| 740418 | 254 | 270 | 4705 | 4721 | CATCCATGGCTAATGAA | 69 | 336 |
| 740419 | 255 | 271 | 4706 | 4722 | ACATCCATGGCTAATGA | 76 | 413 |
| 740420 | 256 | 272 | 4707 | 4723 | TACATCCATGGCTAATG | 73 | 34 |
| 740421 | 257 | 273 | 4708 | 4724 | ATACATCCATGGCTAAT | 74 | 593 |
| 740422 | 258 | 274 | 4709 | 4725 | AATACATCCATGGCTAA | 85 | 186 |
| 740423 | 259 | 275 | 4710 | 4726 | GAATACATCCATGGCTA | 76 | 584 |
| 740424 | 260 | 276 | 4711 | 4727 | TGAATACATCCATGGCT | 77 | 262 |
| 740425 | 261 | 277 | 4712 | 4728 | ATGAATACATCCATGGC | 83 | 585 |
| 740426 | 263 | 279 | 4714 | 4730 | TCATGAATACATCCATG | 55 | 586 |
| 740427 | 265 | 281 | 4716 | 4732 | TTTCATGAATACATCCA | 88 | 587 |
| 740428 | 266 | 282 | 4717 | 4733 | CTTTCATGAATACATCC | 76 | 414 |

TABLE 9-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740429 | 267 | 283 | 4718 | 4734 | CCTTTCATGAATACATC | 86 | 588 |
| 740430 | 268 | 284 | 4719 | 4735 | TCCTTTCATGAATACAT | 91 | 589 |
| 740431 | 269 | 285 | 4720 | 4736 | GTCCTTTCATGAATACA | 82 | 590 |
| 740432 | 270 | 286 | 4721 | 4737 | AGTCCTTTCATGAATAC | 92 | 591 |
| 740433 | 271 | 287 | 4722 | 4738 | AAGTCCTTTCATGAATA | 68 | 592 |
| 740434 | 273 | 289 | 4724 | 4740 | GAAAGTCCTTTCATGAA | 67 | 593 |
| 740435 | 275 | 291 | 4726 | 4742 | TTGAAAGTCCTTTCATG | 25 | 594 |
| 740436 | 276 | 292 | 4727 | 4743 | TTTGAAAGTCCTTTCAT | 8 | 595 |
| 740437 | 277 | 293 | 4728 | 4744 | CTTTGAAAGTCCTTTCA | 66 | 596 |
| 740438 | 278 | 294 | 4729 | 4745 | CCTTTGAAAGTCCTTTC | 86 | 35 |
| 740439 | 279 | 295 | 4730 | 4746 | GCCTTTGAAAGTCCTTT | 88 | 597 |
| 740440 | 280 | 296 | 4731 | 4747 | GGCCTTTGAAAGTCCTT | 88 | 111 |
| 740441 | 281 | 297 | 4732 | 4748 | TGGCCTTTGAAAGTCCT | 58 | 598 |
| 740442 | 282 | 298 | 4733 | 4749 | TTGGCCTTTGAAAGTCC | 68 | 187 |
| 740443 | 283 | 299 | 4734 | 4750 | CTTGGCCTTTGAAAGTC | 75 | 263 |
| 740444 | 285 | 301 | 4736 | 4752 | TCCTTGGCCTTTGAAAG | 47 | 599 |
| 740445 | 286 | 302 | 4737 | 4753 | CTCCTTGGCCTTTGAAA | 57 | 415 |
| 740446 | 301 | 317 | 4752 | 4768 | AGCAGCCACAACTCCCT | 62 | 112 |
| 740447 | 302 | 318 | 4753 | 4769 | CAGCAGCCACAACTCCC | 65 | 600 |
| 740448 | 304 | 320 | 4755 | 4771 | AGCAGCAGCCACAACTC | 63 | 601 |
| 740449 | 305 | 321 | 4756 | 4772 | CAGCAGCAGCCACAACT | 52 | 602 |
| 740450 | 308 | 324 | 4759 | 4775 | TCTCAGCAGCAGCCACA | 63 | 603 |
| 740451 | 309 | 325 | 4760 | 4776 | TTCTCAGCAGCAGCCAC | 69 | 604 |
| 740452 | 311 | 327 | 4762 | 4778 | TTTTCTCAGCAGCAGCC | 75 | 605 |
| 740453 | 312 | 328 | 4763 | 4779 | GTTTTCTCAGCAGCAGC | 66 | 188 |
| 740454 | 313 | 329 | 4764 | 4780 | GGTTTTCTCAGCAGCAG | 79 | 606 |
| 740455 | 314 | 330 | 4765 | 4781 | TGGTTTTCTCAGCAGCA | 78 | 607 |
| 740456 | 317 | 333 | 4768 | 4784 | GTTTGGTTTTCTCAGCA | 82 | 608 |
| 740457 | 326 | 342 | 4777 | 4793 | CCACACCCTGTTTGGTT | 71 | 609 |
| 740458 | 329 | 345 | 4780 | 4796 | CTGCCACACCCTGTTTG | 54 | 610 |
| 740459 | 332 | 348 | 4783 | 4799 | CTTCTGCCACACCCTGT | 74 | 611 |
| 740460 | 333 | 349 | 4784 | 4800 | GCTTCTGCCACACCCTG | 73 | 612 |
| 740461 | 335 | 351 | 4786 | 4802 | CTGCTTCTGCCACACCC | 80 | 613 |
| 740462 | 336 | 352 | 4787 | 4803 | GCTGCTTCTGCCACACC | 77 | 339 |
| 740463 | 338 | 354 | 4789 | 4805 | CTGCTGCTTCTGCCACA | 64 | 614 |
| 740464 | 339 | 355 | 4790 | 4806 | CCTGCTGCTTCTGCCAC | 52 | 615 |

TABLE 9-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
| --- | --- | --- | --- | --- | --- | --- | --- |
| 740465 | 342 | 358 | 4793 | 4809 | TTTCCTGCTGCTTCTGC | 63 | 616 |
| 740466 | 345 | 361 | 4796 | 4812 | GTCTTTCCTGCTGCTTC | 69 | 617 |
| 740467 | 348 | 364 | 4799 | 4815 | TTTGTCTTTCCTGCTGC | 56 | 618 |
| 740468 | 362 | 378 | 4813 | 4829 | AGAGAACACCCTCTTTT | 47 | 619 |
| 740469 | 365 | 381 | 4816 | 4832 | CATAGAGAACACCCTCT | 71 | 620 |
| 740470 | 368 | 384 | 4819 | 4835 | CTACATAGAGAACACCC | 81 | 621 |

TABLE 10

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
| --- | --- | --- | --- | --- | --- | --- | --- |
| 387978 | 282 | 301 | 4733 | 4752 | TCCTTGGCCTTTGAAAGTCC | 32 | 21 |
| 740410 | 240 | 256 | 4691 | 4707 | GAATTCCTTTACACCAC | 90 | 33 |
| 740471 | 369 | 385 | 4820 | 4836 | CCTACATAGAGAACACC | 76 | 622 |
| 740472 | 371 | 387 | N/A | N/A | AGCCTACATAGAGAACA | 51 | 623 |
| 740473 | 372 | 388 | N/A | N/A | GAGCCTACATAGAGAAC | 74 | 37 |
| 740474 | 373 | 389 | N/A | N/A | GGAGCCTACATAGAGAA | 65 | 624 |
| 740475 | 374 | 390 | N/A | N/A | TGGAGCCTACATAGAGA | 46 | 625 |
| 740476 | 375 | 391 | N/A | N/A | TTGGAGCCTACATAGAG | 61 | 626 |
| 740477 | 378 | 394 | N/A | N/A | GTTTTGGAGCCTACATA | 56 | 627 |
| 740478 | 379 | 395 | N/A | N/A | GGTTTTGGAGCCTACAT | 72 | 189 |
| 740479 | 380 | 396 | 12193 | 12209 | TGGTTTTGGAGCCTACA | 78 | 628 |
| 740480 | 381 | 397 | 12194 | 12210 | TTGGTTTTGGAGCCTAC | 64 | 265 |
| 740481 | 382 | 398 | 12195 | 12211 | CTTGGTTTTGGAGCCTA | 43 | 340 |
| 740482 | 383 | 399 | 12196 | 12212 | CCTTGGTTTTGGAGCCT | 81 | 417 |
| 740483 | 384 | 400 | 12197 | 12213 | TCCTTGGTTTTGGAGCC | 79 | 629 |
| 740484 | 385 | 401 | 12198 | 12214 | CTCCTTGGTTTTGGAGC | 21 | 38 |
| 740485 | 386 | 402 | 12199 | 12215 | CCTCCTTGGTTTTGGAG | 19 | 630 |
| 740486 | 388 | 404 | 12201 | 12217 | TCCCTCCTTGGTTTTGG | 63 | 631 |
| 740487 | 391 | 407 | 12204 | 12220 | CACTCCCTCCTTGGTTT | 71 | 632 |
| 740488 | 396 | 412 | 12209 | 12225 | TGCACCACTCCCTCCTT | 62 | 633 |
| 740489 | 399 | 415 | 12212 | 12228 | CCATGCACCACTCCCTC | 51 | 634 |
| 740490 | 400 | 416 | 12213 | 12229 | ACCATGCACCACTCCCT | 61 | 266 |
| 740491 | 401 | 417 | 12214 | 12230 | CACCATGCACCACTCCC | 80 | 635 |
| 740492 | 402 | 418 | 12215 | 12231 | ACACCATGCACCACTCC | 69 | 341 |
| 740493 | 403 | 419 | 12216 | 12232 | CACACCATGCACCACTC | 69 | 636 |

TABLE 10-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740494 | 404 | 420 | 12217 | 12233 | CCACACCATGCACCACT | 78 | 418 |
| 740495 | 406 | 422 | 12219 | 12235 | TGCCACACCATGCACCA | 75 | 646 |
| 740496 | 407 | 423 | 12220 | 12236 | TTGCCACACCATGCACC | 68 | 637 |
| 740497 | 408 | 424 | 12221 | 12237 | GTTGCCACACCATGCAC | 50 | 191 |
| 740498 | 409 | 425 | 12222 | 12238 | TGTTGCCACACCATGCA | 81 | 638 |
| 740499 | 410 | 426 | 12223 | 12239 | CTGTTGCCACACCATGC | 79 | 267 |
| 740500 | 411 | 427 | N/A | N/A | ACTGTTGCCACACCATG | 88 | 639 |
| 740501 | 418 | 434 | N/A | N/A | CTCAGCCACTGTTGCCA | 68 | 342 |
| 740502 | 419 | 435 | N/A | N/A | TCTCAGCCACTGTTGCC | 66 | 640 |
| 740503 | 421 | 437 | N/A | N/A | CTTCTCAGCCACTGTTG | 57 | 641 |
| 740504 | 422 | 438 | N/A | N/A | TCTTCTCAGCCACTGTT | 59 | 642 |
| 740505 | 427 | 443 | 17994 | 18010 | TTTGGTCTTCTCAGCCA | 41 | 643 |
| 740506 | 432 | 448 | 17999 | 18015 | TGCTCTTTGGTCTTCTC | 27 | 644 |
| 740507 | 435 | 451 | 18002 | 18018 | ACTTGCTCTTTGGTCTT | 66 | 645 |
| 740508 | 437 | 453 | 18004 | 18020 | TCACTTGCTCTTTGGTC | 83 | 646 |
| 740509 | 438 | 454 | 18005 | 18021 | GTCACTTGCTCTTTGGT | 89 | 647 |
| 740510 | 439 | 455 | 18006 | 18022 | TGTCACTTGCTCTTTGG | 87 | 648 |
| 740511 | 440 | 456 | 18007 | 18023 | TTGTCACTTGCTCTTTG | 79 | 40 |
| 740512 | 441 | 457 | 18008 | 18024 | TTTGTCACTTGCTCTTT | 72 | 649 |
| 740513 | 442 | 458 | 18009 | 18025 | ATTTGTCACTTGCTCTT | 82 | 116 |
| 740514 | 443 | 459 | 18010 | 18026 | CATTTGTCACTTGCTCT | 76 | 650 |
| 740515 | 444 | 460 | 18011 | 18027 | ACATTTGTCACTTGCTC | 80 | 192 |
| 740516 | 445 | 461 | 18012 | 18028 | AACATTTGTCACTTGCT | 80 | 268 |
| 740517 | 446 | 462 | 18013 | 18029 | CAACATTTGTCACTTGC | 86 | 343 |
| 740518 | 447 | 463 | 18014 | 18030 | CCAACATTTGTCACTTG | 48 | 651 |
| 740519 | 448 | 464 | 18015 | 18031 | TCCAACATTTGTCACTT | 40 | 420 |
| 740520 | 449 | 465 | 18016 | 18032 | CTCCAACATTTGTCACT | 56 | 652 |
| 740521 | 451 | 467 | 18018 | 18034 | TCCTCCAACATTTGTCA | 17 | 653 |
| 740522 | 454 | 470 | 18021 | 18037 | TGCTCCTCCAACATTTG | 49 | 654 |
| 740523 | 457 | 473 | 18024 | 18040 | CACTGCTCCTCCAACAT | 60 | 655 |
| 740524 | 460 | 476 | 18027 | 18043 | CACCACTGCTCCTCCAA | 81 | 656 |
| 740525 | 463 | 479 | 18030 | 18046 | CGTCACCACTGCTCCTC | 55 | 657 |
| 740526 | 464 | 480 | 18031 | 18047 | CCGTCACCACTGCTCCT | 69 | 193 |
| 740527 | 466 | 482 | 18033 | 18049 | ACCCGTCACCACTGCTC | 87 | 658 |
| 740528 | 467 | 483 | 18034 | 18050 | CACCCGTCACCACTGCT | 82 | 344 |
| 740529 | 468 | 484 | 18035 | 18051 | ACACCCGTCACCACTGC | 76 | 659 |

TABLE 10-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740530 | 470 | 486 | 18037 | 18053 | TCACACCCGTCACCACT | 77 | 681 |
| 740531 | 471 | 487 | 18038 | 18054 | GTCACACCCGTCACCAC | 79 | 118 |
| 740532 | 472 | 488 | 18039 | 18055 | TGTCACACCCGTCACCA | 72 | 660 |
| 740533 | 473 | 489 | 18040 | 18056 | CTGTCACACCCGTCACC | 88 | 194 |
| 740534 | 474 | 490 | 18041 | 18057 | GCTGTCACACCCGTCAC | 84 | 661 |
| 740535 | 476 | 492 | 18043 | 18059 | CTGCTGTCACACCCGTC | 85 | 662 |
| 740536 | 479 | 495 | 18046 | 18062 | CTACTGCTGTCACACCC | 75 | 663 |
| 740537 | 482 | 498 | 18049 | 18065 | GGGCTACTGCTGTCACA | 59 | 664 |
| 740538 | 485 | 501 | 18052 | 18068 | TCTGGGCTACTGCTGTC | 54 | 665 |
| 740539 | 488 | 504 | 18055 | 18071 | TCTTCTGGGCTACTGCT | 48 | 666 |
| 740540 | 491 | 507 | 18058 | 18074 | CTGTCTTCTGGGCTACT | 61 | 667 |
| 740541 | 494 | 510 | 18061 | 18077 | CCACTGTCTTCTGGGCT | 61 | 668 |
| 740542 | 498 | 514 | 18065 | 18081 | CCCTCCACTGTCTTCTG | 26 | 669 |
| 740543 | 502 | 518 | 18069 | 18085 | TGCTCCCTCCACTGTCT | 62 | 670 |
| 740544 | 510 | 526 | 18077 | 18093 | ATGCTCCCTGCTCCCTC | 70 | 671 |
| 740545 | 513 | 529 | 18080 | 18096 | GCAATGCTCCCTGCTCC | 88 | 672 |
| 740546 | 523 | 539 | 18090 | 18106 | AGTGGCTGCTGCAATGC | 61 | 119 |
| 740547 | 526 | 542 | 18093 | 18109 | GCCAGTGGCTGCTGCAA | 58 | 673 |

TABLE 11

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 11 | 21 |
| 740410 | 240 | 256 | 4691 | 4707 | GAATTCCTTTACACCAC | 89 | 33 |
| 740548 | 529 | 545 | 18096 | 18112 | AAAGCCAGTGGCTGCTG | 76 | 674 |
| 740549 | 532 | 548 | 18099 | 18115 | GACAAAGCCAGTGGCTG | 72 | 675 |
| 740550 | 535 | 551 | 18102 | 18118 | TTTGACAAAGCCAGTGG | 63 | 676 |
| 740551 | 538 | 554 | 18105 | 18121 | CTTTTTGACAAAGCCAG | 71 | 677 |
| 740552 | 541 | 557 | 18108 | 18124 | GTCCTTTTGACAAAGC | 31 | 678 |
| 740553 | 544 | 560 | 18111 | 18127 | CTGGTCCTTTTTGACAA | 50 | 679 |
| 740554 | 547 | 563 | 18114 | 18130 | CAACTGGTCCTTTTTGA | 67 | 680 |
| 740555 | 550 | 566 | 18117 | 18133 | GCCCAACTGGTCCTTTT | 73 | 681 |
| 740556 | 553 | 569 | 18120 | 18136 | CTTGCCCAACTGGTCCT | 55 | 682 |
| 740557 | 557 | 573 | N/A | N/A | CATTCTTGCCCAACTGG | 15 | 683 |
| 740558 | 560 | 576 | N/A | N/A | CTTCATTCTTGCCCAAC | 60 | 684 |

TABLE 11-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740559 | 563 | 579 | N/A | N/A | CTTCTTCATTCTTGCCC | 72 | 685 |
| 740560 | 566 | 582 | N/A | N/A | CTCCTTCTTCATTCTTG | 48 | 686 |
| 740561 | 569 | 585 | 111104 | 111120 | GGGCTCCTTCTTCATTC | 60 | 687 |
| 740562 | 585 | 601 | 111120 | 111136 | AGAATTCCTTCCTGTGG | 38 | 688 |
| 740563 | 588 | 604 | 111123 | 111139 | TCCAGAATTCCTTCCTG | 63 | 689 |
| 740564 | 591 | 607 | 111126 | 111142 | TCTTCCAGAATTCCTTC | 45 | 690 |
| 740565 | 594 | 610 | 111129 | 111145 | ATATCTTCCAGAATTCC | 63 | 691 |
| 740566 | 597 | 613 | 111132 | 111148 | GGCATATCTTCCAGAAT | 73 | 692 |
| 740567 | 600 | 616 | 111135 | 111151 | ACAGGCATATCTTCCAG | 48 | 693 |
| 740568 | 603 | 619 | 111138 | 111154 | TCCACAGGCATATCTTC | 46 | 694 |
| 740569 | 607 | 623 | 111142 | 111158 | AGGATCCACAGGCATAT | 34 | 695 |
| 740570 | 610 | 626 | 111145 | 111161 | GTCAGGATCCACAGGCA | 72 | 696 |
| 740571 | 613 | 629 | 111148 | 111164 | ATTGTCAGGATCCACAG | 21 | 697 |
| 740572 | 616 | 632 | 111151 | 111167 | CTCATTGTCAGGATCCA | 75 | 698 |
| 740573 | 619 | 635 | 111154 | 111170 | AGCCTCATTGTCAGGAT | 79 | 699 |
| 740574 | 622 | 638 | 111157 | 111173 | ATAAGCCTCATTGTCAG | 31 | 700 |
| 740575 | 625 | 641 | 111160 | 111176 | TTCATAAGCCTCATTGT | 0 | 701 |
| 740576 | 627 | 643 | 111162 | 111178 | ATTTCATAAGCCTCATT | 35 | 702 |
| 740577 | 629 | 645 | 111164 | 111180 | GCATTTCATAAGCCTCA | 78 | 703 |
| 740578 | 632 | 648 | 111167 | 111183 | AAGGCATTTCATAAGCC | 67 | 704 |
| 740579 | 635 | 651 | 111170 | 111186 | CAGAAGGCATTTCATAA | 70 | 705 |
| 740580 | 638 | 654 | 111173 | 111189 | CCTCAGAAGGCATTTCA | 31 | 706 |
| 740581 | 641 | 657 | N/A | N/A | CTTCCTCAGAAGGCATT | 62 | 707 |
| 740582 | 644 | 660 | N/A | N/A | ACCCTTCCTCAGAAGGC | 60 | 708 |
| 740583 | 647 | 663 | N/A | N/A | GATACCCTTCCTCAGAA | 4 | 709 |
| 740584 | 651 | 667 | N/A | N/A | TCTTGATACCCTTCCTC | 29 | 710 |
| 740585 | 654 | 670 | 113722 | 113738 | TAGTCTTGATACCCTTC | 70 | 711 |
| 740586 | 672 | 688 | 113740 | 113756 | TCTTAGGCTTCAGGTTC | 66 | 712 |
| 740587 | 675 | 691 | 113743 | 113759 | ATTTCTTAGGCTTCAGG | 47 | 713 |
| 740588 | 678 | 694 | 113746 | 113762 | GATATTTCTTAGGCTTC | 61 | 714 |
| 740589 | 681 | 697 | 113749 | 113765 | AAAGATATTTCTTAGGC | 43 | 715 |
| 740590 | 684 | 700 | 113752 | 113768 | AGCAAAGATATTTCTTA | 49 | 716 |
| 740591 | 687 | 703 | 113755 | 113771 | GGGAGCAAAGATATTTC | 80 | 717 |
| 740592 | 690 | 706 | 113758 | 113774 | ACTGGGAGCAAAGATAT | 55 | 718 |
| 740593 | 694 | 710 | 113762 | 113778 | AGAAACTGGGAGCAAAG | 86 | 719 |
| 740594 | 697 | 713 | 113765 | 113781 | TCAAGAAACTGGGAGCA | 49 | 720 |

TABLE 11-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740595 | 700 | 716 | 113768 | 113784 | ATCTCAAGAAACTGGGA | 69 | 721 |
| 740596 | 703 | 719 | 113771 | 113787 | CAGATCTCAAGAAACTG | 72 | 722 |
| 740597 | 706 | 722 | 113774 | 113790 | CAGCAGATCTCAAGAAA | 72 | 723 |
| 740598 | 709 | 725 | 113777 | 113793 | TGTCAGCAGATCTCAAG | 47 | 724 |
| 740599 | 712 | 728 | 113780 | 113796 | ATCTGTCAGCAGATCTC | 32 | 725 |
| 740600 | 716 | 732 | 113784 | 113800 | GAACATCTGTCAGCAGA | 0 | 726 |
| 740601 | 719 | 735 | 113787 | 113803 | ATGGAACATCTGTCAGC | 9 | 727 |
| 740602 | 722 | 738 | 113790 | 113806 | AGGATGGAACATCTGTC | 19 | 728 |
| 740603 | 725 | 741 | 113793 | 113809 | TACAGGATGGAACATCT | 0 | 729 |
| 740604 | 730 | 746 | 113798 | 113814 | ACTTGTACAGGATGGAA | 55 | 730 |
| 740605 | 733 | 749 | 113801 | 113817 | AGCACTTGTACAGGATG | 61 | 731 |
| 740606 | 736 | 752 | 113804 | 113820 | CTGAGCACTTGTACAGG | 66 | 732 |
| 740607 | 739 | 755 | 113807 | 113823 | GAACTGAGCACTTGTAC | 49 | 733 |
| 740608 | 742 | 758 | 113810 | 113826 | TTGGAACTGAGCACTTG | 41 | 734 |
| 740609 | 745 | 761 | 113813 | 113829 | ACATTGGAACTGAGCAC | 36 | 735 |
| 740610 | 748 | 764 | 113816 | 113832 | GGCACATTGGAACTGAG | 47 | 736 |
| 740611 | 752 | 768 | 113820 | 113836 | ACTGGGCACATTGGAAC | 51 | 737 |
| 740612 | 755 | 771 | 113823 | 113839 | ATGACTGGGCACATTGG | 44 | 738 |
| 740613 | 758 | 774 | 113826 | 113842 | GTCATGACTGGGCACAT | 38 | 739 |
| 740614 | 761 | 777 | 113829 | 113845 | AATGTCATGACTGGGCA | 32 | 740 |
| 740615 | 764 | 780 | 113832 | 113848 | AGAAATGTCATGACTGG | 76 | 741 |
| 740616 | 767 | 783 | 113835 | 113851 | TTGAGAAATGTCATGAC | 54 | 742 |
| 740617 | 770 | 786 | 113838 | 113854 | ACTTTGAGAAATGTCAT | 34 | 743 |
| 740618 | 773 | 789 | 113841 | 113857 | AAAACTTTGAGAAATGT | 30 | 744 |
| 740619 | 776 | 792 | 113844 | 113860 | GTAAAACTTTGAGAAA | 69 | 745 |
| 740620 | 779 | 795 | 113847 | 113863 | ACTGTAAAACTTTGAG | 64 | 746 |
| 740621 | 782 | 798 | 113850 | 113866 | TACACTGTAAAACTTT | 39 | 747 |
| 740622 | 785 | 801 | 113853 | 113869 | AGATACACTGTAAAAC | 27 | 748 |
| 740623 | 786 | 802 | 113854 | 113870 | GAGATACACTGTAAAAA | 36 | 749 |
| 740624 | 787 | 803 | 113855 | 113871 | CGAGATACACTGTAAAA | 56 | 750 |

TABLE 12

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 11 | 21 |
| 740410 | 240 | 256 | 4691 | 4707 | GAATTCCTTTACACCAC | 89 | 33 |
| 740625 | 791 | 807 | 113859 | 113875 | ACTTCGAGATACACTGT | 76 | 751 |
| 740626 | 793 | 809 | 113861 | 113877 | AGACTTCGAGATACACT | 72 | 275 |
| 740627 | 795 | 811 | 113863 | 113879 | GAAGACTTCGAGATACA | 63 | 752 |
| 740628 | 796 | 812 | 113864 | 113880 | GGAAGACTTCGAGATAC | 71 | 427 |
| 740629 | 797 | 813 | 113865 | 113881 | TGGAAGACTTCGAGATA | 31 | 753 |
| 740630 | 799 | 815 | 113867 | 113883 | GATGGAAGACTTCGAGA | 50 | 754 |
| 740631 | 802 | 818 | 113870 | 113886 | GCTGATGGAAGACTTCG | 67 | 755 |
| 740632 | 805 | 821 | 113873 | 113889 | ACTGCTGATGGAAGACT | 73 | 756 |
| 740633 | 808 | 824 | 113876 | 113892 | ATCACTGCTGATGGAAG | 55 | 757 |
| 740634 | 812 | 828 | 113880 | 113896 | TTCAATCACTGCTGATG | 15 | 758 |
| 740635 | 815 | 831 | 113883 | 113899 | TACTTCAATCACTGCTG | 60 | 759 |
| 740636 | 818 | 834 | 113886 | 113902 | AGATACTTCAATCACTG | 72 | 760 |
| 740637 | 819 | 835 | 113887 | 113903 | CAGATACTTCAATCACT | 48 | 761 |
| 740638 | 820 | 836 | 113888 | 113904 | ACAGATACTTCAATCAC | 60 | 762 |
| 740639 | 821 | 837 | 113889 | 113905 | TACAGATACTTCAATCA | 38 | 763 |
| 740640 | 824 | 840 | 113892 | 113908 | AGGTACAGATACTTCAA | 63 | 764 |
| 740641 | 827 | 843 | 113895 | 113911 | GGCAGGTACAGATACTT | 45 | 765 |
| 740642 | 845 | 861 | 113913 | 113929 | ACCGAAATGCTGAGTGG | 63 | 766 |
| 740643 | 848 | 864 | 113916 | 113932 | AGCACCGAAATGCTGAG | 73 | 767 |
| 740644 | 851 | 867 | 113919 | 113935 | GGAAGCACCGAAATGCT | 48 | 768 |
| 740645 | 854 | 870 | 113922 | 113938 | AAGGGAAGCACCGAAAT | 46 | 769 |
| 740646 | 857 | 873 | 113925 | 113941 | TGAAAGGGAAGCACCGA | 34 | 770 |
| 740647 | 860 | 876 | 113928 | 113944 | CAGTGAAAGGGAAGCAC | 72 | 771 |
| 740648 | 863 | 879 | 113931 | 113947 | CTTCAGTGAAAGGGAAG | 21 | 772 |
| 740649 | 865 | 881 | 113933 | 113949 | CACTTCAGTGAAAGGGA | 75 | 773 |
| 740650 | 866 | 882 | 113934 | 113950 | TCACTTCAGTGAAAGGG | 79 | 49 |
| 740651 | 867 | 883 | 113935 | 113951 | TTCACTTCAGTGAAAGG | 31 | 774 |
| 740652 | 869 | 885 | 113937 | 113953 | TATTCACTTCAGTGAAA | 0 | 775 |
| 740653 | 870 | 886 | 113938 | 113954 | GTATTCACTTCAGTGAA | 35 | 776 |
| 740654 | 873 | 889 | 113941 | 113957 | CATGTATTCACTTCAGT | 78 | 777 |
| 740655 | 876 | 892 | 113944 | 113960 | TACCATGTATTCACTTC | 67 | 778 |
| 740656 | 879 | 895 | 113947 | 113963 | TGCTACCATGTATTCAC | 70 | 779 |
| 740657 | 882 | 898 | 113950 | 113966 | CCCTGCTACCATGTATT | 31 | 780 |
| 740658 | 885 | 901 | 113953 | 113969 | AGACCCTGCTACCATGT | 62 | 781 |
| 740659 | 886 | 902 | 113954 | 113970 | AAGACCCTGCTACCATG | 60 | 782 |

TABLE 12 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740660 | 890 | 906 | 113958 | 113974 | CACAAAGACCCTGCTAC | 4 | 783 |
| 740661 | 892 | 908 | 113960 | 113976 | CACACAAAGACCCTGCT | 29 | 50 |
| 740662 | 894 | 910 | 113962 | 113978 | AGCACACAAAGACCCTG | 70 | 784 |
| 740663 | 895 | 911 | 113963 | 113979 | CAGCACACAAAGACCCT | 66 | 202 |
| 740664 | 896 | 912 | 113964 | 113980 | ACAGCACACAAAGACCC | 47 | 785 |
| 740665 | 898 | 914 | 113966 | 113982 | CCACAGCACACAAAGAC | 61 | 786 |
| 740666 | 901 | 917 | 113969 | 113985 | AATCCACAGCACACAAA | 43 | 787 |
| 740667 | 905 | 921 | 113973 | 113989 | ACAAAATCCACAGCACA | 49 | 788 |
| 740668 | 911 | 927 | 113979 | 113995 | GAAGCCACAAAATCCAC | 80 | 789 |
| 740669 | 915 | 931 | 113983 | 113999 | GATTGAAGCCACAAAAT | 55 | 790 |
| 740670 | 918 | 934 | 113986 | 114002 | GTAGATTGAAGCCACAA | 86 | 791 |
| 740671 | 935 | 951 | 114003 | 114019 | TAATTTGTTTTAACATC | 49 | 792 |
| 740672 | 943 | 959 | 114011 | 114027 | GGTGTTTTAATTTGTT | 69 | 793 |
| 740673 | 944 | 960 | 114012 | 114028 | AGGTGTTTTAATTTGT | 72 | 128 |
| 740674 | 945 | 961 | 114013 | 114029 | TAGGTGTTTTAATTTG | 72 | 204 |
| 740675 | 946 | 962 | 114014 | 114030 | TTAGGTGTTTTAATTT | 47 | 794 |
| 740676 | 947 | 963 | 114015 | 114031 | CTTAGGTGTTTTAATT | 32 | 280 |
| 740677 | 950 | 966 | 114018 | 114034 | TCACTTAGGTGTTTTA | 0 | 795 |
| 740678 | 953 | 969 | 114021 | 114037 | TAGTCACTTAGGTGTTT | 9 | 796 |
| 740679 | 957 | 973 | 114025 | 114041 | GTGGTAGTCACTTAGGT | 19 | 797 |
| 740680 | 960 | 976 | 114028 | 114044 | TAAGTGGTAGTCACTTA | 0 | 798 |
| 740681 | 963 | 979 | 114031 | 114047 | AAATAAGTGGTAGTCAC | 55 | 799 |
| 740682 | 966 | 982 | 114034 | 114050 | TAGAAATAAGTGGTAGT | 61 | 800 |
| 740683 | 969 | 985 | 114037 | 114053 | ATTTAGAAATAAGTGGT | 66 | 801 |
| 740684 | 972 | 988 | 114040 | 114056 | AGGATTTAGAAATAAGT | 49 | 802 |
| 740685 | 975 | 991 | 114043 | 114059 | GTGAGGATTTAGAAATA | 41 | 803 |
| 740686 | 976 | 992 | 114044 | 114060 | AGTGAGGATTTAGAAAT | 36 | 804 |
| 740687 | 977 | 993 | 114045 | 114061 | TAGTGAGGATTTAGAAA | 47 | 805 |
| 740688 | 979 | 995 | 114047 | 114063 | AATAGTGAGGATTTAGA | 51 | 806 |
| 740689 | 982 | 998 | 114050 | 114066 | AAAATAGTGAGGATTT | 44 | 807 |
| 740690 | 985 | 1001 | 114053 | 114069 | CAAAAAATAGTGAGGA | 38 | 808 |
| 740691 | 989 | 1005 | 114057 | 114073 | GCAACAAAAAATAGTG | 32 | 809 |
| 740692 | 1002 | 1018 | 114070 | 114086 | CTTCTGAACAACAGCAA | 76 | 810 |
| 740693 | 1005 | 1021 | 114073 | 114089 | CAACTTCTGAACAACAG | 54 | 811 |
| 740694 | 1008 | 1024 | 114076 | 114092 | TAACAACTTCTGAACAA | 34 | 812 |
| 740695 | 1011 | 1027 | 114079 | 114095 | CACTAACAACTTCTGAA | 30 | 813 |

TABLE 12 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740696 | 1014 | 1030 | 114082 | 114098 | AATCACTAACAACTTCT | 69 | 814 |
| 740697 | 1017 | 1033 | 114085 | 114101 | GCAAATCACTAACAACT | 64 | 815 |
| 740698 | 1020 | 1036 | 114088 | 114104 | ATAGCAAATCACTAACA | 39 | 816 |
| 740699 | 1024 | 1040 | 114092 | 114108 | TATGATAGCAAATCACT | 27 | 817 |
| 740700 | 1027 | 1043 | 114095 | 114111 | ATATATGATAGCAAATC | 36 | 818 |
| 740701 | 1030 | 1046 | 114098 | 114114 | ATAATATATGATAGCAA | 56 | 819 |
| 740470 | 368 | 384 | 4819 | 4835 | CTACATAGAGAACACCC | 81 | 621 |

TABLE 13

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 387978 | 282 | 301 | 4733 | 4752 | TCCTTGGCCTTTGAAAGTCC | 18 | 21 |
| 740410 | 240 | 256 | 4691 | 4707 | GAATTCCTTTACACCAC | 84 | 33 |
| 740702 | 1033 | 1049 | 114101 | 114117 | CTTATAATATATGATAG | 16 | 820 |
| 740703 | 1036 | 1052 | 114104 | 114120 | AATCTTATAATATATGA | 27 | 821 |
| 740704 | 1041 | 1057 | 114109 | 114125 | CTAAAAATCTTATAATA | 0 | 822 |
| 740705 | 1044 | 1060 | 114112 | 114128 | CACCTAAAAATCTTATA | 11 | 823 |
| 740706 | 1047 | 1063 | 114115 | 114131 | AGACACCTAAAAATCTT | 49 | 824 |
| 740707 | 1048 | 1064 | 114116 | 114132 | AAGACACCTAAAAATCT | 25 | 825 |
| 740708 | 1049 | 1065 | 114117 | 114133 | AAAGACACCTAAAAATC | 27 | 826 |
| 740709 | 1052 | 1068 | 114120 | 114136 | TTAAAGACACCTAAAA | 6 | 827 |
| 740710 | 1055 | 1071 | 114123 | 114139 | TCATTAAAGACACCTA | 30 | 828 |
| 740711 | 1058 | 1074 | 114126 | 114142 | GTATCATTAAAAGACAC | 30 | 829 |
| 740712 | 1061 | 1077 | 114129 | 114145 | ACAGTATCATTAAAGA | 35 | 830 |
| 740713 | 1064 | 1080 | 114132 | 114148 | TAGACAGTATCATTAAA | 54 | 831 |
| 740714 | 1068 | 1084 | 114136 | 114152 | TTCTTAGACAGTATCAT | 57 | 832 |
| 740715 | 1071 | 1087 | 114139 | 114155 | TTATTCTTAGACAGTAT | 64 | 833 |
| 740716 | 1074 | 1090 | 114142 | 114158 | TCATTATTCTTAGACAG | 47 | 834 |
| 740717 | 1092 | 1108 | 114160 | 114176 | AACAAATTTCACAATAC | 60 | 835 |
| 740718 | 1095 | 1111 | 114163 | 114179 | ATTAACAAATTTCACAA | 34 | 836 |
| 740719 | 1106 | 1122 | 114174 | 114190 | GTATTATATATATTAAC | 32 | 837 |
| 740720 | 1121 | 1137 | 114189 | 114205 | CTCACATATTTTTAAGT | 44 | 838 |
| 740721 | 1124 | 1140 | 114192 | 114208 | ATGCTCACATATTTTTA | 45 | 839 |
| 740722 | 1127 | 1143 | 114195 | 114211 | TTCATGCTCACATATTT | 40 | 840 |
| 740723 | 1130 | 1146 | 114198 | 114214 | AGTTTCATGCTCACATA | 67 | 841 |

TABLE 13 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740724 | 1134 | 1150 | 114202 | 114218 | GCATAGTTTCATGCTCA | 51 | 842 |
| 740725 | 1137 | 1153 | 114205 | 114221 | GGTGCATAGTTTCATGC | 46 | 843 |
| 740726 | 1138 | 1154 | 114206 | 114222 | AGGTGCATAGTTTCATG | 54 | 844 |
| 740727 | 1140 | 1156 | 114208 | 114224 | ATAGGTGCATAGTTTCA | 63 | 845 |
| 740728 | 1143 | 1159 | 114211 | 114227 | TTTATAGGTGCATAGTT | 62 | 846 |
| 740729 | 1146 | 1162 | 114214 | 114230 | GTATTTATAGGTGCATA | 67 | 847 |
| 740730 | 1149 | 1165 | 114217 | 114233 | TTAGTATTTATAGGTGC | 72 | 848 |
| 740731 | 1152 | 1168 | 114220 | 114236 | TATTTAGTATTTATAGG | 32 | 849 |
| 740732 | 1164 | 1180 | 114232 | 114248 | GGTAAAATTTCATATTT | 33 | 850 |
| 740733 | 1173 | 1189 | 114241 | 114257 | TCGCAAAATGGTAAAAT | 49 | 851 |
| 740734 | 1176 | 1192 | 114244 | 114260 | ACATCGCAAAATGGTAA | 62 | 852 |
| 740735 | 1179 | 1195 | 114247 | 114263 | AACACATCGCAAAATGG | 42 | 853 |
| 740736 | 1182 | 1198 | 114250 | 114266 | TAAAACACATCGCAAAA | 28 | 854 |
| 740737 | 1185 | 1201 | 114253 | 114269 | GAATAAAACACATCGCA | 62 | 855 |
| 740738 | 1188 | 1204 | 114256 | 114272 | AGTGAATAAAACACATC | 16 | 856 |
| 740739 | 1191 | 1207 | 114259 | 114275 | ACAAGTGAATAAAACAC | 64 | 857 |
| 740740 | 1196 | 1212 | 114264 | 114280 | CAAACACAAGTGAATAA | 16 | 858 |
| 740741 | 1199 | 1215 | 114267 | 114283 | ATACAAACACAAGTGAA | 33 | 859 |
| 740742 | 1203 | 1219 | 114271 | 114287 | TTATATACAAACACAAG | 31 | 860 |
| 740743 | 1207 | 1223 | 114275 | 114291 | CCATTTATATACAAACA | 28 | 861 |
| 740744 | 1210 | 1226 | 114278 | 114294 | TCACCATTTATATACAA | 53 | 862 |
| 740745 | 1214 | 1230 | 114282 | 114298 | ATTCTCACCATTTATAT | 40 | 863 |
| 740746 | 1222 | 1238 | 114290 | 114306 | TTATTTTAATTCTCACC | 46 | 864 |
| 740747 | 1242 | 1258 | 114310 | 114326 | TTTTGCAATGAGATAAC | 0 | 865 |
| 740748 | 1245 | 1261 | 114313 | 114329 | TATTTTTGCAATGAGAT | 42 | 866 |
| 740749 | 1265 | 1281 | 114333 | 114349 | GAGATGGGATAAAAATA | 38 | 867 |
| 740750 | 1268 | 1284 | 114336 | 114352 | AGTGAGATGGGATAAAA | 32 | 868 |
| 740751 | 1271 | 1287 | 114339 | 114355 | TAAAGTGAGATGGGATA | 30 | 869 |
| 740752 | 1275 | 1291 | 114343 | 114359 | TTATTAAAGTGAGATGG | 24 | 870 |
| 740753 | 1278 | 1294 | 114346 | 114362 | TTATTATTAAAGTGAGA | 9 | 871 |
| 740754 | 1288 | 1304 | 114356 | 114372 | AGCATGATTTTTATTAT | 36 | 872 |

TABLE 13 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740755 | 1291 | 1307 | 114359 | 114375 | ATAAGCATGATTTTTAT | 2 | 873 |
| 740756 | 1292 | 1308 | 114360 | 114376 | TATAAGCATGATTTTTA | 25 | 874 |
| 740757 | 1296 | 1312 | 114364 | 114380 | TGCTTATAAGCATGATT | 20 | 875 |
| 740758 | 1299 | 1315 | 114367 | 114383 | TGTTGCTTATAAGCATG | 0 | 876 |
| 740759 | 1302 | 1318 | 114370 | 114386 | TCATGTTGCTTATAAGC | 27 | 877 |
| 740760 | 1306 | 1322 | 114374 | 114390 | TAATTCATGTTGCTTAT | 55 | 878 |
| 740761 | 1309 | 1325 | 114377 | 114393 | TCTTAATTCATGTTGCT | 35 | 879 |
| 740762 | 1312 | 1328 | 114380 | 114396 | AGTTCTTAATTCATGTT | 41 | 880 |
| 740763 | 1315 | 1331 | 114383 | 114399 | GTCAGTTCTTAATTCAT | 54 | 881 |
| 740764 | 1318 | 1334 | 114386 | 114402 | TGTGTCAGTTCTTAATT | 61 | 882 |
| 740765 | 1321 | 1337 | 114389 | 114405 | CTTTGTGTCAGTTCTTA | 68 | 883 |
| 740766 | 1324 | 1340 | 114392 | 114408 | GTCCTTTGTGTCAGTTC | 64 | 884 |
| 740767 | 1328 | 1344 | 114396 | 114412 | TTTTGTCCTTTGTGTCA | 30 | 885 |
| 740768 | 1331 | 1347 | 114399 | 114415 | TATTTTTGTCCTTTGTG | 36 | 886 |
| 740769 | 1336 | 1352 | 114404 | 114420 | CTTTATATTTTTGTCCT | 13 | 887 |
| 740770 | 1346 | 1362 | 114414 | 114430 | CTATTAATAACTTTATA | 15 | 888 |
| 740771 | 1349 | 1365 | 114417 | 114433 | TGGCTATTAATAACTTT | 43 | 889 |
| 740772 | 1352 | 1368 | 114420 | 114436 | AAATGGCTATTAATAAC | 36 | 890 |
| 740773 | 1355 | 1371 | 114423 | 114439 | TTCAAATGGCTATTAAT | 35 | 891 |
| 740774 | 1358 | 1374 | 114426 | 114442 | TTCTTCAAATGGCTATT | 40 | 892 |
| 740775 | 1361 | 1377 | 114429 | 114445 | TCCTTCTTCAAATGGCT | 45 | 893 |
| 740776 | 1364 | 1380 | 114432 | 114448 | TCCTCCTTCTTCAAATG | 8 | 894 |
| 740777 | 1369 | 1385 | 114437 | 114453 | AAAATTCCTCCTTCTTC | 39 | 895 |
| 740778 | 1372 | 1388 | 114440 | 114456 | TCTAAAATTCCTCCTTC | 33 | 896 |

Example 3: Effect of 4-9-4 MOE and cEt Gapmers with Mixed Internucleoside Linkages on Human SNCA In Vitro, Single Dose Modified oligonucleotides complementary to a human SNCA nucleic acid were designed and tested as described in Example 1 for their effect on SNCA mRNA in vitro. The modified oligonucleotides were tested in a series of experiments that had similar culture conditions.

The modified oligonucleotides in tables 14-23 are 4-9-4 MOE and cEt gapmers. The gapmers are 17 nucleobases in length, wherein the central gap segment comprises nine 2'-deoxynucleosides and is flanked by wing segments on both the 5' end on the 3' end comprising two 2'-MOE nucleosides and two cEt nucleosides. The sugar motif for the gapmers is (from 5' to 3'): eekkddddddddkkee; wherein 'd' represents a 2'-deoxyribose sugar; 'e' represents a 2'-MOE modified sugar; and 'k' represents a cEt modified sugar. All cytosine residues throughout each gapmer are 5-methyl cytosines. The internucleoside linkages are mixed phosphodiester and phosphorothioate linkages. The internucleoside linkage motif for the gapmers is (from 5' to 3'): sooosssssssssoss; wherein 'o' represents a phosphodiester internucleoside linkage and 's' represents a phosphorothioate internucleoside linkage. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the Tables below is complementary to human SNCA nucleic acid sequences SEQ ID NO: 1, SEQ ID NO: 2, SEQ ID NO: 3, SEQ ID NO: 4, SEQ ID NO: 5, or SEQ ID NO: 6, as indicated. 'N/A' indicates that the modified oligonucleotide is not complementary to that particular nucleic acid with 100% complementarity. A value of 0% reduction indicates that the compound had no effect or increased mRNA concentrations in the cell. As shown below, modified oligonucleotides complementary to human SNCA reduced the amount of human SNCA mRNA.

TABLE 14

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 97 | 33 |
| 740432 | 270 | 286 | 4721 | 4737 | AGTCCTTTCATGAATAC | 95 | 591 |
| 740779 | 1375 | 1391 | 114443 | 114459 | TCTTCTAAAATTCCTCC | 51 | 897 |
| 740780 | 1378 | 1394 | 114446 | 114462 | ACCTCTTCTAAAATTCC | 45 | 898 |
| 740781 | 1381 | 1397 | 114449 | 114465 | TCTACCTCTTCTAAAAT | 7 | 899 |
| 740782 | 1384 | 1400 | 114452 | 114468 | TTCTCTACCTCTTCTAA | 41 | 900 |
| 740783 | 1389 | 1405 | 114457 | 114473 | CCATTTTCTCTACCTCT | 90 | 901 |
| 740784 | 1392 | 1408 | 114460 | 114476 | GTTCCATTTTCTCTACC | 78 | 902 |
| 740785 | 1396 | 1412 | 114464 | 114480 | TAATGTTCCATTTTCTC | 62 | 903 |
| 740786 | 1400 | 1416 | 114468 | 114484 | GGGTTAATGTTCCATTT | 65 | 904 |
| 740787 | 1403 | 1419 | 114471 | 114487 | GTAGGGTTAATGTTCCA | 74 | 905 |
| 740788 | 1406 | 1422 | 114474 | 114490 | AGTGTAGGGTTAATGTT | 44 | 906 |
| 740789 | 1409 | 1425 | 114477 | 114493 | CCGAGTGTAGGGTTAAT | 70 | 907 |
| 740790 | 1412 | 1428 | 114480 | 114496 | ATTCCGAGTGTAGGGTT | 76 | 908 |
| 740791 | 1415 | 1431 | 114483 | 114499 | GGAATTCCGAGTGTAGG | 22 | 909 |
| 740792 | 1418 | 1434 | 114486 | 114502 | CAGGGAATTCCGAGTGT | 75 | 910 |
| 740793 | 1422 | 1438 | 114490 | 114506 | GCTTCAGGGAATTCCGA | 68 | 911 |
| 740794 | 1425 | 1441 | 114493 | 114509 | GTTGCTTCAGGGAATTC | 84 | 912 |
| 740795 | 1428 | 1444 | 114496 | 114512 | AGTGTTGCTTCAGGGAA | 76 | 913 |
| 740796 | 1431 | 1447 | 114499 | 114515 | GGCAGTGTTGCTTCAGG | 82 | 914 |
| 740797 | 1434 | 1450 | 114502 | 114518 | TCTGGCAGTGTTGCTTC | 55 | 915 |
| 740798 | 1437 | 1453 | 114505 | 114521 | ACTTCTGGCAGTGTTGC | 63 | 916 |
| 740799 | 1440 | 1456 | 114508 | 114524 | CACACTTCTGGCAGTGT | 19 | 917 |
| 740800 | 1444 | 1460 | 114512 | 114528 | AAAACACACTTCTGGCA | 50 | 918 |
| 740801 | 1447 | 1463 | 114515 | 114531 | ACCAAAACACACTTCTG | 87 | 919 |
| 740802 | 1450 | 1466 | 114518 | 114534 | CATACCAAAACACACTT | 87 | 920 |
| 740803 | 1453 | 1469 | 114521 | 114537 | GTGCATACCAAAACACA | 31 | 921 |
| 740804 | 1456 | 1472 | 114524 | 114540 | CCAGTGCATACCAAAAC | 77 | 922 |
| 740805 | 1459 | 1475 | 114527 | 114543 | GAACCAGTGCATACCAA | 67 | 923 |
| 740806 | 1462 | 1478 | 114530 | 114546 | AAGGAACCAGTGCATAC | 69 | 924 |
| 740807 | 1466 | 1482 | 114534 | 114550 | ACTTAAGGAACCAGTGC | 49 | 925 |
| 740808 | 1469 | 1485 | 114537 | 114553 | GCCACTTAAGGAACCAG | 82 | 926 |
| 740809 | 1472 | 1488 | 114540 | 114556 | ACAGCCACTTAAGGAAC | 64 | 927 |
| 740810 | 1475 | 1491 | 114543 | 114559 | ATCACAGCCACTTAAGG | 28 | 928 |
| 740811 | 1478 | 1494 | 114546 | 114562 | TTAATCACAGCCACTTA | 62 | 929 |
| 740812 | 1481 | 1497 | 114549 | 114565 | TAATTAATCACAGCCAC | 67 | 930 |
| 740813 | 1484 | 1500 | 114552 | 114568 | CAATAATTAATCACAGC | 74 | 931 |

TABLE 14 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740814 | 1488 | 1504 | 114556 | 114572 | CTTTCAATAATTAATCA | 22 | 932 |
| 740815 | 1492 | 1508 | 114560 | 114576 | CCCACTTTCAATAATTA | 20 | 933 |
| 740816 | 1521 | 1537 | 114589 | 114605 | TCTACAATAGTAGTTGG | 23 | 934 |
| 740817 | 1524 | 1540 | 114592 | 114608 | CACTCTACAATAGTAGT | 37 | 935 |
| 740818 | 1527 | 1543 | 114595 | 114611 | GACCACTCTACAATAGT | 62 | 936 |
| 740819 | 1530 | 1546 | 114598 | 114614 | ATAGACCACTCTACAAT | 55 | 937 |
| 740820 | 1533 | 1549 | 114601 | 114617 | GAAATAGACCACTCTAC | 50 | 938 |
| 740821 | 1536 | 1552 | 114604 | 114620 | GGAGAAATAGACCACTC | 64 | 939 |
| 740822 | 1545 | 1561 | 114613 | 114629 | GGATTGAAGGGAGAAAT | 49 | 940 |
| 740823 | 1548 | 1564 | 114616 | 114632 | ACAGGATTGAAGGGAGA | 71 | 941 |
| 740824 | 1551 | 1567 | 114619 | 114635 | TTGACAGGATTGAAGGG | 57 | 942 |
| 740825 | 1554 | 1570 | 114622 | 114638 | ACATTGACAGGATTGAA | 58 | 943 |
| 740826 | 1557 | 1573 | 114625 | 114641 | CAAACATTGACAGGATT | 62 | 944 |
| 740827 | 1580 | 1596 | 114648 | 114664 | ACAGTTCCCCAAAATAC | 50 | 945 |
| 740828 | 1583 | 1599 | 114651 | 114667 | ACAACAGTTCCCCAAAA | 6 | 946 |
| 740829 | 1586 | 1602 | 114654 | 114670 | CAAACAACAGTTCCCCA | 43 | 947 |
| 740830 | 1589 | 1605 | 114657 | 114673 | CATCAAACAACAGTTCC | 48 | 948 |
| 740831 | 1592 | 1608 | 114660 | 114676 | ACACATCAAACAACAGT | 68 | 949 |
| 740832 | 1595 | 1611 | 114663 | 114679 | CATACACATCAAACAAC | 24 | 950 |
| 740833 | 1627 | 1643 | 114695 | 114711 | GCTCAATTAAAAATGTA | 31 | 951 |
| 740834 | 1630 | 1646 | 114698 | 114714 | AAGGCTCAATTAAAAAT | 26 | 952 |
| 740835 | 1637 | 1653 | 114705 | 114721 | TTAATAAAAGGCTCAAT | 28 | 953 |
| 740836 | 1640 | 1656 | 114708 | 114724 | ATGTTAATAAAAGGCTC | 57 | 954 |
| 740837 | 1647 | 1663 | 114715 | 114731 | ACAATATATGTTAATAA | 3 | 955 |
| 740838 | 1661 | 1677 | 114729 | 114745 | TCGAGACAAAATAACA | 29 | 956 |
| 740839 | 1664 | 1680 | 114732 | 114748 | ATTTCGAGACAAAATA | 33 | 957 |
| 740840 | 1667 | 1683 | 114735 | 114751 | ATTATTTCGAGACAAAA | 34 | 958 |
| 740841 | 1670 | 1686 | 114738 | 114754 | AAAATTATTTCGAGACA | 47 | 959 |
| 740842 | 1673 | 1689 | 114741 | 114757 | TAAAAATTATTTCGAG | 11 | 960 |
| 740843 | 1685 | 1701 | 114753 | 114769 | ATAGATTTTAACTAAAA | 0 | 961 |
| 740844 | 1706 | 1722 | 114774 | 114790 | TTCACACCAATATCAGA | 64 | 962 |
| 740845 | 1709 | 1725 | 114777 | 114793 | GCATTCACACCAATATC | 55 | 963 |
| 740846 | 1712 | 1728 | 114780 | 114796 | ACAGCATTCACACCAAT | 73 | 964 |
| 740847 | 1715 | 1731 | 114783 | 114799 | GGTACAGCATTCACACC | 46 | 965 |
| 740848 | 1718 | 1734 | 114786 | 114802 | AAAGGTACAGCATTCAC | 65 | 966 |
| 740849 | 1721 | 1737 | 114789 | 114805 | CAGAAAGGTACAGCATT | 56 | 967 |

TABLE 14 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740850 | 1724 | 1740 | 114792 | 114808 | TGTCAGAAAGGTACAGC | 49 | 968 |
| 740851 | 1728 | 1744 | 114796 | 114812 | TTATTGTCAGAAAGGTA | 79 | 969 |
| 740852 | 1731 | 1747 | 114799 | 114815 | TATTTATTGTCAGAAAG | 52 | 970 |
| 740853 | 1734 | 1750 | 114802 | 114818 | TATTATTTATTGTCAGA | 79 | 971 |
| 740854 | 1737 | 1753 | 114805 | 114821 | GAATATTATTTATTGTC | 54 | 972 |
| 740855 | 1741 | 1757 | 114809 | 114825 | GGTCGAATATTATTTAT | 51 | 973 |

TABLE 15

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 91 | 33 |
| 740432 | 270 | 286 | 4721 | 4737 | AGTCCTTTCATGAATAC | 79 | 591 |
| 740856 | 1745 | 1761 | 114813 | 114829 | TCATGGTCGAATATTAT | 31 | 974 |
| 740857 | 1748 | 1764 | 114816 | 114832 | TATTCATGGTCGAATAT | 24 | 975 |
| 740858 | 1751 | 1767 | 114819 | 114835 | TTTTATTCATGGTCGAA | 62 | 976 |
| 740859 | 1754 | 1770 | 114822 | 114838 | TTTTTTTATTCATGGTC | 77 | 977 |
| 740860 | 1771 | 1787 | 114839 | 114855 | GGAACCCACTTTTTTT | 14 | 978 |
| 740861 | 1774 | 1790 | 114842 | 114858 | CCGGGAACCCACTTTTT | 25 | 979 |
| 740862 | 1777 | 1793 | 114845 | 114861 | TTCCCGGGAACCCACTT | 20 | 980 |
| 740863 | 1780 | 1796 | 114848 | 114864 | TAGTTCCCGGGAACCCA | 25 | 981 |
| 740864 | 1784 | 1800 | 114852 | 114868 | TGCTTAGTTCCCGGGAA | 25 | 982 |
| 740865 | 1787 | 1803 | 114855 | 114871 | CACTGCTTAGTTCCCGG | 51 | 983 |
| 740866 | 1790 | 1806 | 114858 | 114874 | CTACACTGCTTAGTTCC | 76 | 984 |
| 740867 | 1793 | 1809 | 114861 | 114877 | CTTCTACACTGCTTAGT | 37 | 985 |
| 740868 | 1796 | 1812 | 114864 | 114880 | CATCTTCTACACTGCTT | 54 | 986 |
| 740869 | 1799 | 1815 | 114867 | 114883 | AATCATCTTCTACACTG | 38 | 987 |
| 740870 | 1802 | 1818 | 114870 | 114886 | CAAAATCATCTTCTACA | 17 | 988 |
| 740871 | 1806 | 1822 | 114874 | 114890 | TAGTCAAAATCATCTTC | 40 | 989 |
| 740872 | 1809 | 1825 | 114877 | 114893 | GTGTAGTCAAAATCATC | 58 | 990 |
| 740873 | 1812 | 1828 | 114880 | 114896 | AGGGTGTAGTCAAAATC | 61 | 991 |
| 740874 | 1815 | 1831 | 114883 | 114899 | AGGAGGGTGTAGTCAAA | 43 | 992 |
| 740875 | 1818 | 1834 | 114886 | 114902 | CTAAGGAGGGTGTAGTC | 41 | 993 |
| 740876 | 1821 | 1837 | 114889 | 114905 | TCTCTAAGGAGGGTGTA | 43 | 994 |
| 740877 | 1824 | 1840 | 114892 | 114908 | GGCTCTCTAAGGAGGGT | 38 | 995 |
| 740878 | 1828 | 1844 | 114896 | 114912 | TTATGGCTCTCTAAGGA | 37 | 996 |

TABLE 15 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740879 | 1831 | 1847 | 114899 | 114915 | GTCTTATGGCTCTCTAA | 66 | 997 |
| 740880 | 1834 | 1850 | 114902 | 114918 | TGTGTCTTATGGCTCTC | 72 | 998 |
| 740881 | 1837 | 1853 | 114905 | 114921 | TAATGTGTCTTATGGCT | 67 | 999 |
| 740882 | 1840 | 1856 | 114908 | 114924 | TGCTAATGTGTCTTATG | 59 | 1000 |
| 740883 | 1843 | 1859 | 114911 | 114927 | ATGTGCTAATGTGTCTT | 66 | 1001 |
| 740884 | 1846 | 1862 | 114914 | 114930 | AATATGTGCTAATGTGT | 74 | 1002 |
| 740885 | 1850 | 1866 | 114918 | 114934 | TGCTAATATGTGCTAAT | 33 | 1003 |
| 740886 | 1853 | 1869 | 114921 | 114937 | ATGTGCTAATATGTGCT | 34 | 1004 |
| 740887 | 1856 | 1872 | 114924 | 114940 | TGAATGTGCTAATATGT | 52 | 1005 |
| 740888 | 1859 | 1875 | 114927 | 114943 | CCTTGAATGTGCTAATA | 59 | 1006 |
| 740889 | 1862 | 1878 | 114930 | 114946 | GAGCCTTGAATGTGCTA | 28 | 1007 |
| 740890 | 1865 | 1881 | 114933 | 114949 | TCAGAGCCTTGAATGTG | 52 | 1008 |
| 740891 | 1868 | 1884 | 114936 | 114952 | CTCTCAGAGCCTTGAAT | 48 | 1009 |
| 740892 | 1870 | 1886 | 114938 | 114954 | TTCTCTCAGAGCCTTGA | 74 | 1010 |
| 740893 | 1871 | 1887 | 114939 | 114955 | ATTCTCTCAGAGCCTTG | 83 | 444 |
| 740894 | 1872 | 1888 | 114940 | 114956 | CATTCTCTCAGAGCCTT | 80 | 1011 |
| 740895 | 1874 | 1890 | 114942 | 114958 | CACATTCTCTCAGAGCC | 57 | 1012 |
| 740896 | 1875 | 1891 | 114943 | 114959 | CCACATTCTCTCAGAGC | 57 | 1013 |
| 740897 | 1995 | 2011 | 115063 | 115079 | TAAAGGCATTTCCTGTA | 50 | 1014 |
| 740898 | 2081 | 2097 | 115149 | 115165 | GGCAACATTTAAAGGAG | 46 | 1015 |
| 740899 | 2251 | 2267 | 115319 | 115335 | GAAATGACTATGCCCCA | 61 | 1016 |
| 740900 | 2312 | 2328 | 115380 | 115396 | AAACTGCTAGCATGTCT | 62 | 1017 |
| 740901 | 2437 | 2453 | 115505 | 115521 | TGTAGTAGTCTCTCTTC | 77 | 1018 |
| 740902 | 2841 | 2857 | 115909 | 115925 | TGTTTAAGTGTTTGGTC | 79 | 1019 |
| 740903 | 2939 | 2955 | 116007 | 116023 | GGACTGGATTGATCCTC | 48 | 1020 |
| 740904 | 3158 | 3174 | 116226 | 116242 | ACATACTGGATAAGCCA | 83 | 1021 |
| 740905 | N/A | N/A | 2087 | 2103 | CCTGGATCACACCAGAA | 28 | 1022 |
| 740906 | N/A | N/A | 2090 | 2106 | GTTCCTGGATCACACCA | 45 | 1023 |
| 740907 | N/A | N/A | 2093 | 2109 | GCTGTTCCTGGATCACA | 41 | 1024 |
| 740908 | N/A | N/A | 2096 | 2112 | ACAGCTGTTCCTGGATC | 2 | 1025 |
| 740909 | N/A | N/A | 2099 | 2115 | AAGACAGCTGTTCCTGG | 19 | 1026 |
| 740910 | N/A | N/A | 2102 | 2118 | TGGAAGACAGCTGTTCC | 7 | 1027 |
| 740911 | N/A | N/A | 2105 | 2121 | AGCTGGAAGACAGCTGT | 13 | 1028 |
| 740912 | N/A | N/A | 2108 | 2124 | CAGAGCTGGAAGACAGC | 26 | 1029 |
| 740913 | N/A | N/A | 2113 | 2129 | TCTTTCAGAGCTGGAAG | 16 | 1030 |

TABLE 16

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 97 | 33 |
| 740432 | 270 | 286 | 4721 | 4737 | AGTCCTTTCATGAATAC | 92 | 591 |
| 740933 | N/A | N/A | 3624 | 3640 | CCTGAGTCCCTCTGCTT | 27 | 1031 |
| 740934 | N/A | N/A | 3849 | 3865 | TAATCTCTCAGCCCTTG | 55 | 1032 |
| 740935 | N/A | N/A | 4074 | 4090 | CCACCCTAGCGGACCCC | 35 | 1033 |
| 740936 | N/A | N/A | 4299 | 4315 | CCAGAAGAAGGCTAACA | 35 | 1034 |
| 740937 | N/A | N/A | 4524 | 4540 | GGCATTAAAAATTTAGC | 68 | 1035 |
| 740938 | N/A | N/A | 4684 | 4700 | TTTACACCACACTGGAA | 65 | 1036 |
| 740939 | N/A | N/A | 4685 | 4701 | CTTTACACCACACTGGA | 82 | 1037 |
| 740940 | N/A | N/A | 4686 | 4702 | CCTTTACACCACACTGG | 68 | 1038 |
| 740941 | N/A | N/A | 4821 | 4837 | ACCTACATAGAGAACAC | 83 | 1039 |
| 740942 | N/A | N/A | 5046 | 5062 | GGCAAAATTAAAAATCT | 38 | 1040 |
| 740943 | N/A | N/A | 5275 | 5291 | TTATACACATCACAGGG | 59 | 1041 |
| 740944 | N/A | N/A | 5500 | 5516 | AAGGTGGAACTTTAGGA | 73 | 1042 |
| 740945 | N/A | N/A | 5725 | 5741 | GACTCTTACTGCTATAG | 47 | 1043 |
| 740946 | N/A | N/A | 5984 | 6000 | TGATAGCATCACTGCAG | 13 | 1044 |
| 740947 | N/A | N/A | 6209 | 6225 | AACTCATCAATTTTTTC | 67 | 1045 |
| 740948 | N/A | N/A | 6439 | 6455 | GTAACCAATAAAAAATT | 24 | 1046 |
| 740949 | N/A | N/A | 6715 | 6731 | GTTGTTTGTAGACACAG | 54 | 1047 |
| 740950 | N/A | N/A | 6940 | 6956 | TGTTTATGACTACCTTC | 62 | 1048 |
| 740951 | N/A | N/A | 7165 | 7181 | ATTTTTTACTAATCAGG | 38 | 1049 |
| 740952 | N/A | N/A | 7615 | 7631 | GTCATTTGAAGAAATTT | 60 | 1050 |
| 740953 | N/A | N/A | 7840 | 7856 | GTGCATGTTATGTTGAC | 36 | 1051 |
| 740954 | N/A | N/A | 8065 | 8081 | TTATGAGTAATCTGTAA | 30 | 1052 |
| 740955 | N/A | N/A | 8290 | 8306 | GCCACTAAACCACACCA | 65 | 1053 |
| 740956 | N/A | N/A | 8544 | 8560 | GGGATGATGAGATCAGG | 40 | 1054 |
| 740957 | N/A | N/A | 8769 | 8785 | TTTTAGCTGCCCTTGCC | 25 | 1055 |
| 740958 | N/A | N/A | 8995 | 9011 | TTATCTCACATATATGT | 30 | 1056 |
| 740959 | N/A | N/A | 9240 | 9256 | ACACCACTCCATTGCAG | 46 | 1057 |
| 740960 | N/A | N/A | 9465 | 9481 | GGAGTGGACATGTTTTT | 43 | 1058 |
| 740961 | N/A | N/A | 9691 | 9707 | CAACACAGTGGCTCTTG | 24 | 1059 |
| 740962 | N/A | N/A | 9920 | 9936 | GAATGATAAATGTTTCA | 32 | 1060 |
| 740963 | N/A | N/A | 10146 | 10162 | AGATAGAAGTAGAGAGT | 14 | 1061 |
| 740964 | N/A | N/A | 10371 | 10387 | TTGTTTGTGCTGGAACT | 16 | 1062 |
| 740965 | N/A | N/A | 10596 | 10612 | CATAACAGATGTGAAGC | 45 | 1063 |
| 740966 | N/A | N/A | 10821 | 10837 | TGCAGCAGTGACAACAT | 73 | 1064 |
| 740967 | N/A | N/A | 11046 | 11062 | TTTACAGAATTATCATA | 37 | 1065 |

TABLE 16 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740968 | N/A | N/A | 11271 | 11287 | CATTACACATGTAATAA | 6 | 1066 |
| 740969 | N/A | N/A | 11729 | 11745 | CATTATGTAAAAAAAC | 0 | 1067 |
| 740970 | N/A | N/A | 11954 | 11970 | TACGATTTTAGCACAAA | 68 | 1068 |
| 740971 | N/A | N/A | 12182 | 12198 | CCTACAAAAACAAATTC | 0 | 1069 |
| 740972 | N/A | N/A | 12192 | 12208 | GGTTTTGGAGCCTACAA | 83 | 1070 |
| 740973 | N/A | N/A | 12421 | 12437 | GCAAGTATATTTTTAT | 62 | 1071 |
| 740974 | N/A | N/A | 12646 | 12662 | CCTGAAATGCACTCTGA | 54 | 1072 |
| 740975 | N/A | N/A | 12871 | 12887 | CTCATCTTCCTCAACAT | 56 | 1073 |
| 740976 | N/A | N/A | 13098 | 13114 | TCCATTTTAGAAGTCAG | 87 | 1074 |
| 740977 | N/A | N/A | 13331 | 13347 | TAACACTTATAAAATAC | 44 | 1075 |
| 740978 | N/A | N/A | 13556 | 13572 | GAGGTCCCTAGAAGGCA | 38 | 1076 |
| 740979 | N/A | N/A | 13781 | 13797 | TCTCCATTAGATCATCA | 43 | 1077 |
| 740980 | N/A | N/A | 14011 | 14027 | GAGAAAATAAAGTATAC | 41 | 1078 |
| 740981 | N/A | N/A | 14236 | 14252 | TGGTCCATGGGTGCAAT | 52 | 1079 |
| 740982 | N/A | N/A | 14461 | 14477 | ATATGCAAATTATTCTC | 40 | 1080 |
| 740983 | N/A | N/A | 14686 | 14702 | TTCCCAGCCCAAGTTTA | 1 | 1081 |
| 740984 | N/A | N/A | 14911 | 14927 | AATAGGTAACTTTATAT | 19 | 1082 |
| 740985 | N/A | N/A | 15136 | 15152 | TAATATATGGTTTTGAA | 28 | 1083 |
| 740986 | N/A | N/A | 15365 | 15381 | GGATTCTGCTTTATTTT | 51 | 1084 |
| 740987 | N/A | N/A | 15590 | 15606 | CGACACATTTAAAAACA | 36 | 1085 |
| 740988 | N/A | N/A | 15815 | 15831 | AAAGCGAGATTAAAAAT | 0 | 1086 |
| 740989 | N/A | N/A | 16040 | 16056 | GGATATGGCTGATGTCT | 13 | 1087 |
| 740990 | N/A | N/A | 16265 | 16281 | CCAATATTTAAATGGTG | 34 | 1088 |
| 740991 | N/A | N/A | 16591 | 16607 | GCCAATATTTACTTATT | 61 | 1089 |
| 740992 | N/A | N/A | 16818 | 16834 | TCATGTGGAATCTAAAG | 6 | 1090 |
| 740993 | N/A | N/A | 17043 | 17059 | AGTATGAAAATGAAGAG | 38 | 1091 |
| 740994 | N/A | N/A | 17501 | 17517 | ATTCTTGTTGTTCAGGC | 73 | 1092 |
| 740995 | N/A | N/A | 17726 | 17742 | GGAATGTAAAGCCATGA | 78 | 1093 |
| 740996 | N/A | N/A | 17951 | 17967 | ATTAAAGGGTGGTAGAA | 26 | 1094 |
| 740997 | N/A | N/A | 18176 | 18192 | AATGAACCGTAATCTCA | 87 | 1095 |
| 740998 | N/A | N/A | 18296 | 18312 | CTGGGTTAATGCCTGAA | 60 | 1096 |
| 740999 | N/A | N/A | 18297 | 18313 | TCTGGGTTAATGCCTGA | 67 | 163 |
| 741000 | N/A | N/A | 18298 | 18314 | ATCTGGGTTAATGCCTG | 86 | 1097 |
| 741001 | N/A | N/A | 18401 | 18417 | GAAATGTCACTGTTCCT | 97 | 1098 |
| 741002 | N/A | N/A | 18626 | 18642 | GGTTGGTATGTATTTTA | 92 | 1099 |
| 741003 | N/A | N/A | 18851 | 18867 | CAAGGAGGTCATTGTGG | 75 | 1100 |

TABLE 16 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741004 | N/A | N/A | 19183 | 19199 | CTTTGGCAAAGAAAGGA | 45 | 1101 |
| 741005 | N/A | N/A | 19408 | 19424 | AAATGAAAGTTGTTGTG | 85 | 1102 |
| 741006 | N/A | N/A | 19633 | 19649 | GATATTTTGTTCTGCC | 95 | 1103 |
| 741007 | N/A | N/A | 19868 | 19884 | GCTATAAATAGAATTAA | 42 | 1104 |
| 741008 | N/A | N/A | 20099 | 20115 | TAGATTTCTGTTTCCTC | 94 | 1105 |
| 741009 | N/A | N/A | 20324 | 20340 | AATGCAGGTGAATAAAA | 81 | 1106 |

TABLE 17

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 92 | 33 |
| 740432 | 270 | 286 | 4721 | 4737 | AGTCCTTTCATGAATAC | 87 | 591 |
| 741010 | N/A | N/A | 20549 | 20565 | CAATTTCTAGGTTCTAT | 86 | 1107 |
| 741011 | N/A | N/A | 20559 | 20575 | AACTATGCTGCAATTTC | 74 | 1108 |
| 741012 | N/A | N/A | 20561 | 20577 | ACAACTATGCTGCAATT | 86 | 1109 |
| 741013 | N/A | N/A | 20562 | 20578 | CACAACTATGCTGCAAT | 88 | 314 |
| 741014 | N/A | N/A | 20565 | 20581 | TTCCACAACTATGCTGC | 90 | 1110 |
| 741015 | N/A | N/A | 20774 | 20790 | GACCACAATTGCAGACA | 86 | 1111 |
| 741016 | N/A | N/A | 20985 | 21001 | GTGTGAGCAAACATTCT | 94 | 1112 |
| 741017 | N/A N/A | N/A N/A | 27412 20987 | 27428 21003 | CAGTGTGAGCAAACATT | 90 | 1113 |
| 741018 | N/A N/A | N/A N/A | 27413 20988 | 27429 21004 | ACAGTGTGAGCAAACAT | 85 | 468 |
| 741019 | N/A N/A | N/A N/A | 27414 20989 | 27430 21005 | CACAGTGTGAGCAAACA | 91 | 1114 |
| 741020 | N/A | N/A | 20991 | 21007 | GGCACAGTGTGAGCAAA | 89 | 1115 |
| 741021 | N/A | N/A | 20999 | 21015 | AAGTTTCTGGCACAGTG | 89 | 1116 |
| 741022 | N/A | N/A | 21224 | 21240 | GTTCAGAATTATGTCAT | 95 | 1117 |
| 741023 | N/A | N/A | 21449 | 21465 | TCTTATGTGCACATGAG | 63 | 1118 |
| 741024 | N/A | N/A | 21674 | 21690 | CATAGTAGCATTACAGA | 83 | 1119 |
| 741025 | N/A | N/A | 21899 | 21915 | TCAGGCAGTGGCTTCAC | 66 | 1120 |
| 741026 | N/A | N/A | 22129 | 22145 | TAAAAAAGTTGTTCAT | 32 | 1121 |
| 741027 | N/A | N/A | 22360 | 22376 | CACTCAAGTGTTTAAAA | 87 | 1122 |
| 741028 | N/A | N/A | 22454 | 22470 | TGTGACCTGTGCTTGTT | 91 | 1123 |
| 741029 | N/A | N/A | 22456 | 22472 | CCTGTGACCTGTGCTTG | 87 | 1124 |
| 741030 | N/A | N/A | 22457 | 22473 | GCCTGTGACCTGTGCTT | 86 | 88 |

TABLE 17 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741031 | N/A | N/A | 22458 | 22474 | TGCCTGTGACCTGTGCT | 87 | 1125 |
| 741032 | N/A | N/A | 22460 | 22476 | GTTGCCTGTGACCTGTG | 82 | 1126 |
| 741033 | N/A | N/A | 22599 | 22615 | TATTAGACACTTAAGGG | 82 | 1127 |
| 741034 | N/A | N/A | 22831 | 22847 | TCAATCTTAAATTTTTC | 85 | 1128 |
| 741035 | N/A | N/A | 23056 | 23072 | GTACTTTCCCACCTAGA | 88 | 1129 |
| 741036 | N/A | N/A | 23281 | 23297 | TCTCAGAGACCACAGCT | 88 | 1130 |
| 741037 | N/A | N/A | 23285 | 23301 | TTGTTCTCAGAGACCAC | 92 | 1131 |
| 741038 | N/A | N/A | 23286 | 23302 | ATTGTTCTCAGAGACCA | 86 | 164 |
| 741039 | N/A | N/A | 23287 | 23303 | TATTGTTCTCAGAGACC | 94 | 1132 |
| 741040 | N/A | N/A | 23289 | 23305 | CATATTGTTCTCAGAGA | 89 | 1133 |
| 741041 | N/A | N/A | 23506 | 23522 | ACTATTAACCACTGATC | 84 | 1134 |
| 741042 | N/A | N/A | 23731 | 23747 | GTTGCAGTCCACAGAAT | 79 | 1135 |
| 741043 | N/A | N/A | 23956 | 23972 | TAAAGATAAGTATCTCA | 91 | 1136 |
| 741044 | N/A | N/A | 24181 | 24197 | AAAACAAACCTAAGTCA | 43 | 1137 |
| 741045 | N/A | N/A | 24406 | 24422 | AAAAGCTAACAGCCTAT | 73 | 1138 |
| 741046 | N/A | N/A | 24631 | 24647 | TTAAATTGATGAGATGT | 88 | 1139 |
| 741047 | N/A | N/A | 24856 | 24872 | GTATTCTTTGCATTAGT | 89 | 1140 |
| 741048 | N/A | N/A | 25081 | 25097 | TAAAAGTGTACATTATT | 77 | 1141 |
| 741049 | N/A | N/A | 25306 | 25322 | CTCAAGGCAAAGCTGTA | 88 | 1142 |
| 741050 | N/A | N/A | 25531 | 25547 | TGCCACTATAAGCAGTC | 94 | 1143 |
| 741051 | N/A | N/A | 25756 | 25772 | TTCAAGCCCATGCCCTC | 84 | 1144 |
| 741052 | N/A | N/A | 25801 | 25817 | ATCCAGTAGAGTGAGAG | 79 | 1145 |
| 741053 | N/A | N/A | 25803 | 25819 | TCATCCAGTAGAGTGAG | 89 | 1146 |
| 741054 | N/A | N/A | 25804 | 25820 | ATCATCCAGTAGAGTGA | 85 | 315 |
| 741055 | N/A | N/A | 25807 | 25823 | GACATCATCCAGTAGAG | 92 | 1147 |
| 741056 | N/A | N/A | 25923 | 25939 | TGAATACATTGTCTTAA | 81 | 1148 |
| 741057 | N/A | N/A | 25925 | 25941 | ATTGAATACATTGTCTT | 90 | 1149 |
| 741058 | N/A | N/A | 25926 | 25942 | AATTGAATACATTGTCT | 94 | 392 |
| 741059 | N/A | N/A | 25927 | 25943 | TAATTGAATACATTGTC | 84 | 1150 |
| 741060 | N/A | N/A | 25929 | 25945 | CATAATTGAATACATTG | 80 | 1151 |
| 741061 | N/A | N/A | 25981 | 25997 | TGAGTAGCTATGGTTTA | 91 | 1152 |
| 741062 | N/A | N/A | 26202 | 26218 | TCTTTGTGTTATACAAT | 58 | 1153 |
| 741063 | N/A | N/A | 26204 | 26220 | CCTCTTTGTGTTATACA | 83 | 1154 |
| 741064 | N/A | N/A | 26205 | 26221 | CCCTCTTTGTGTTATAC | 87 | 469 |
| 741065 | N/A | N/A | 26206 | 26222 | TCCCTCTTTGTGTTATA | 77 | 1155 |
| 741066 | N/A | N/A | 26208 | 26224 | TTTCCCTCTTTGTGTTA | 78 | 1156 |
| 741067 | N/A | N/A | 26431 | 26447 | TACATACAATATTAAGG | 78 | 1157 |

TABLE 17 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741068 | N/A | N/A | 26656 | 26672 | AAAAGAATGGATTCTGA | 75 | 1158 |
| 741069 | N/A | N/A | 26881 | 26897 | AAGGAAAAACTCTGCCC | 73 | 1159 |
| 741070 | N/A | N/A | 27106 | 27122 | TCACCCCAAGGCATTTG | 56 | 1160 |
| 741071 | N/A | N/A | 27331 | 27347 | ACACCCTGATTCCCAAG | 82 | 1161 |
| 741072 | N/A | N/A | 27410 | 27426 | GTGTGAGCAAACATTCA | 89 | 1162 |
| 741073 | N/A | N/A | 27416 | 27432 | GTCACAGTGTGAGCAAA | 91 | 1163 |
| 741074 | N/A | N/A | 27556 | 27572 | GGGAAGTATTAGTGGAA | 86 | 1164 |
| 741075 | N/A | N/A | 27782 | 27798 | GCTGAAAATATGAAACA | 76 | 1165 |
| 741076 | N/A | N/A | 28007 | 28023 | ACTTCTAGCACTATTTT | 71 | 1166 |
| 741077 | N/A | N/A | 28232 | 28248 | TTGTGCATTTATTCCAC | 93 | 1167 |
| 741078 | N/A | N/A | 28457 | 28473 | GACTGTAATCTAGGACC | 90 | 1168 |
| 741079 | N/A | N/A | 28682 | 28698 | TGACTTTTGAATCAGTC | 59 | 1169 |
| 741080 | N/A | N/A | 29010 | 29026 | GAGCGATTCTCCTGGTT | 76 | 1170 |
| 741081 | N/A | N/A | 29235 | 29251 | CACAGTCCATAATATTG | 79 | 1171 |
| 741082 | N/A | N/A | 29460 | 29476 | TTTTTGTTAATAGTTCT | 80 | 1172 |
| 741083 | N/A | N/A | 29685 | 29701 | GCTTTCTCAGAGCCCAA | 89 | 1173 |
| 741084 | N/A | N/A | 29912 | 29928 | ATCTCTCTACCATGTGA | 79 | 1174 |
| 741085 | N/A | N/A | 30137 | 30153 | GTGGATAAAGTACATTA | 77 | 1175 |
| 741086 | N/A | N/A | 30362 | 30378 | AAATGGTATTCAGAGAT | 76 | 1176 |

TABLE 18

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 91 | 33 |
| 740432 | 270 | 286 | 4721 | 4737 | AGTCCTTTCATGAATAC | 94 | 591 |
| 741087 | N/A | N/A | 30587 | 30603 | TTTTCTCCTAAAGCCTT | 85 | 1177 |
| 741088 | N/A | N/A | 31037 | 31053 | CAGATTTCCAGCACACT | 81 | 1178 |
| 741089 | N/A | N/A | 31262 | 31278 | CCTTCTTAGTGGTAAGA | 64 | 1179 |
| 741090 | N/A | N/A | 31487 | 31503 | AATTACAGTGTAGGTAA | 52 | 1180 |
| 741091 | N/A | N/A | 31712 | 31728 | ATAAGAGGTCACTGGAT | 91 | 1181 |
| 741092 | N/A | N/A | 31937 | 31953 | AAGGAAACAGTCTACAT | 85 | 1182 |
| 741093 | N/A | N/A | 32162 | 32178 | CTATCATGATAAGTATA | 84 | 1183 |
| 741094 | N/A | N/A | 32387 | 32403 | TGTGGTTCTGCCCATCT | 88 | 1184 |
| 741095 | N/A | N/A | 32624 | 32640 | GCCTAAACATTTTACTT | 34 | 1185 |

TABLE 18 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741096 | N/A | N/A | 32858 | 32874 | GAAGTTTCTGAAGAAAT | 89 | 1186 |
| 741097 | N/A | N/A | 33083 | 33099 | TTTTCAGTAGATTTGAC | 86 | 1187 |
| 741098 | N/A | N/A | 33308 | 33324 | GCTATGACCCTCAAGCC | 68 | 1188 |
| 741099 | N/A | N/A | 33533 | 33549 | AATAGAGCAAAATTTCG | 87 | 1189 |
| 741100 | N/A | N/A | 33762 | 33778 | ATAATCAAACAAAGGG | 73 | 1190 |
| 741101 | N/A | N/A | 33987 | 34003 | AAAGTTCAATGCTGTGT | 94 | 1191 |
| 741102 | N/A | N/A | 34212 | 34228 | GAAATGGGCATGTAAAC | 72 | 1192 |
| 741103 | N/A | N/A | 34443 | 34459 | CAAAATACAATGTTCAA | 40 | 1193 |
| 741104 | N/A | N/A | 34668 | 34684 | ATTCTTCTATCCTAGAA | 12 | 1194 |
| 741105 | N/A | N/A | 34893 | 34909 | ATTATCATGGTTGCCCA | 91 | 1195 |
| 741106 | N/A | N/A | 35118 | 35134 | ATGAGATCTTTTTGCAT | 87 | 1196 |
| 741107 | N/A | N/A | 35343 | 35359 | AAGCAAGTTGTCCATGG | 90 | 1197 |
| 741108 | N/A | N/A | 35568 | 35584 | TGTTGGAGTTTACAATT | 76 | 1198 |
| 741109 | N/A | N/A | 35793 | 35809 | CTCACTAGCCCTGTGAC | 14 | 1199 |
| 741110 | N/A | N/A | 36018 | 36034 | TCTCTTTCATGGGTATT | 92 | 1200 |
| 741111 | N/A | N/A | 36252 | 36268 | GTCATTTTAATAAGTGT | 92 | 1201 |
| 741112 | N/A | N/A | 36484 | 36500 | CAATTAAATAAACCTCT | 65 | 1202 |
| 741113 | N/A | N/A | 36790 | 36806 | TATGGTGATATGGTTAG | 91 | 1203 |
| 741114 | N/A | N/A | 37018 | 37034 | CCATGTGTTTTGTGGC | 84 | 1204 |
| 741115 | N/A | N/A | 37243 | 37259 | CAAAGGTATAAGGTCAT | 94 | 1205 |
| 741116 | N/A | N/A | 37468 | 37484 | AGCTTGTATTTTTGAAA | 86 | 1206 |
| 741117 | N/A | N/A | 37788 | 37804 | CGCATCTGTCTTTCTTT | 78 | 1207 |
| 741118 | N/A | N/A | 38013 | 38029 | TAGGACAGGTGAAATAA | 72 | 1208 |
| 741119 | N/A | N/A | 38238 | 38254 | AGTTATTAGAATAACAC | 0 | 1209 |
| 741120 | N/A | N/A | 38464 | 38480 | AATAAAATGTCTTAATC | 25 | 1210 |
| 741121 | N/A | N/A | 38691 | 38707 | ACTCAAAAAAGAAGAAT | 44 | 1211 |
| 741122 | N/A | N/A | 38916 | 38932 | GTTTTCTCTGTATTGGC | 93 | 1212 |
| 741123 | N/A | N/A | 39141 | 39157 | TGGCCTAGTGGTTATAA | 19 | 1213 |
| 741124 | N/A | N/A | 39366 | 39382 | CACAAAGAGGAAACAGG | 80 | 1214 |
| 741125 | N/A | N/A | 39591 | 39607 | ACATTTTTTAACTGGAT | 92 | 1215 |
| 741126 | N/A | N/A | 39816 | 39832 | AGGCTAAATTTTAATAA | 6 | 1216 |
| 741127 | N/A | N/A | 40041 | 40057 | TAGCCTTTCATAGTACG | 90 | 1217 |
| 741128 | N/A | N/A | 40266 | 40282 | AAGAGGAAAAGCTTGGA | 43 | 1218 |
| 741129 | N/A | N/A | 40491 | 40507 | AAAAATTCTGGTGCCAA | 94 | 1219 |
| 741130 | N/A | N/A | 40716 | 40732 | AAGCTAAACTACCGCTG | 58 | 1220 |
| 741131 | N/A | N/A | 40941 | 40957 | GAATTTCCTGGATGCTC | 92 | 1221 |
| 741132 | N/A | N/A | 41130 | 41146 | AGATTCCAGCAGAGATT | 74 | 1222 |

TABLE 18 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741133 | N/A | N/A | 41132 | 41148 | ACAGATTCCAGCAGAGA | 89 | 1223 |
| 741134 | N/A | N/A | 41133 | 41149 | AACAGATTCCAGCAGAG | 87 | 90 |
| 741135 | N/A | N/A | 41134 | 41150 | GAACAGATTCCAGCAGA | 85 | 1224 |
| 741136 | N/A | N/A | 41136 | 41152 | GTGAACAGATTCCAGCA | 86 | 1225 |
| 741137 | N/A | N/A | 41166 | 41182 | ATCTGTAAGAAGTTTAG | 52 | 1226 |
| 741138 | N/A | N/A | 41391 | 41407 | TGAGAAATTTTATGGGT | 86 | 1227 |
| 741139 | N/A | N/A | 41620 | 41636 | TCATTCAAAACCATCCT | 78 | 1228 |
| 741140 | N/A | N/A | 41845 | 41861 | GATCACACTGCTTATAG | 84 | 1229 |
| 741141 | N/A | N/A | 42070 | 42086 | CAAGTTGATGGCATATA | 89 | 1230 |
| 741142 | N/A | N/A | 42295 | 42311 | GTGTACCAACCTCAAGT | 71 | 1231 |
| 741143 | N/A | N/A | 42532 | 42548 | TAAGTAAATACCTAGGG | 83 | 1232 |
| 741144 | N/A | N/A | 42757 | 42773 | GATTTGTGCCTGGCATC | 91 | 1233 |
| 741145 | N/A | N/A | 42835 | 42851 | TGCCTCTACCTCCAGCA | 89 | 1234 |
| 741146 | N/A | N/A | 42837 | 42853 | GATGCCTCTACCTCCAG | 87 | 1235 |
| 741147 | N/A | N/A | 42838 | 42854 | TGATGCCTCTACCTCCA | 85 | 166 |
| 741148 | N/A | N/A | 42839 | 42855 | CTGATGCCTCTACCTCC | 87 | 1236 |
| 741149 | N/A | N/A | 42982 | 42998 | TATCACAACTACATTGT | 40 | 1237 |
| 741150 | N/A | N/A | 43208 | 43224 | GGCCTCCTGCTGCAGCA | 31 | 1238 |
| 741151 | N/A | N/A | 43440 | 43456 | GCACTCATTTTAAATGT | 72 | 1239 |
| 741152 | N/A | N/A | 43665 | 43681 | TGGTAACTTAGGACAAG | 93 | 1240 |
| 741153 | N/A | N/A | 43818 | 43834 | TTCTCTGGACCTCTTAA | 67 | 1241 |
| 741154 | N/A | N/A | 43820 | 43836 | ACTTCTCTGGACCTCTT | 85 | 1242 |
| 741155 | N/A | N/A | 43821 | 43837 | TACTTCTCTGGACCTCT | 92 | 242 |
| 741156 | N/A | N/A | 43822 | 43838 | TTACTTCTCTGGACCTC | 90 | 1243 |
| 741157 | N/A | N/A | 43890 | 43906 | TCAATACAACTTAATTC | 48 | 1244 |
| 741158 | N/A | N/A | 44376 | 44392 | TTGGGCTGGAAGCAGTG | 43 | 1245 |
| 741159 | N/A | N/A | 44601 | 44617 | AAGATATGCAGAGGGTT | 92 | 1246 |
| 741160 | N/A | N/A | 44828 | 44844 | TGGTCTAACTGTGTTGC | 85 | 1247 |
| 741161 | N/A | N/A | 45053 | 45069 | GTTTATGGACTTTTAA | 87 | 1248 |
| 741162 | N/A | N/A | 45278 | 45294 | TTTTGTACTTTATGGAA | 89 | 1249 |
| 741163 | N/A | N/A | 45503 | 45519 | ACTTCTCCTTCAATTAA | 72 | 1250 |

TABLE 19

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 90 | 33 |
| 740432 | 270 | 286 | 4721 | 4737 | AGTCCTTTCATGAATAC | 90 | 591 |
| 741241 | N/A | N/A | 56397 | 56413 | AAAATTTTTGCACACTT | 94 | 1251 |
| 741242 | N/A | N/A | 56622 | 56638 | GCCAAATCAATGGATGA | 90 | 1252 |
| 741243 | N/A | N/A | 56847 | 56863 | AGTGACCAAGAGAATGA | 53 | 1253 |
| 741244 | N/A | N/A | 57072 | 57088 | TTTTAAAACACTGGCCT | 41 | 1254 |
| 741245 | N/A | N/A | 57297 | 57313 | TAGGATTAAACAGTCCA | 48 | 1255 |
| 741246 | N/A | N/A | 57522 | 57538 | TTATCTGTTGCTATGTG | 91 | 1256 |
| 741247 | N/A | N/A | 57747 | 57763 | AAGAAGGAGAATAGCAG | 86 | 1257 |
| 741248 | N/A | N/A | 57981 | 57997 | CGGGCAAACATGTTTTG | 47 | 1258 |
| 741249 | N/A | N/A | 58206 | 58222 | ATGACCTACATGCTAAA | 73 | 1259 |
| 741250 | N/A | N/A | 58431 | 58447 | AGAAGCAAAATGTCAGT | 88 | 1260 |
| 741251 | N/A | N/A | 58656 | 58672 | CCTAACAGCTTTACTTT | 50 | 1261 |
| 741252 | N/A | N/A | 58881 | 58897 | CTTTCACACATCTCTAA | 64 | 1262 |
| 741253 | N/A | N/A | 58991 | 59007 | TTTCATTAATCTGTGAA | 34 | 1263 |
| 741254 | N/A | N/A | 58992 | 59008 | ATTTCATTAATCTGTGA | 86 | 169 |
| 741255 | N/A | N/A | 58993 | 59009 | TATTTCATTAATCTGTG | 93 | 1264 |
| 741256 | N/A | N/A | 58995 | 59011 | TATATTTCATTAATCTG | 87 | 1265 |
| 741257 | N/A | N/A | 59106 | 59122 | CCTTACACAAAATATAA | 38 | 1266 |
| 741258 | N/A | N/A | 59354 | 59370 | ACACCAATATATTATTT | 67 | 1267 |
| 741259 | N/A | N/A | 59594 | 59610 | TAAAGGATGCAAAGGCA | 55 | 1268 |
| 741260 | N/A | N/A | 59948 | 59964 | TTCCAGCGATCCCACTC | 80 | 1269 |
| 741261 | N/A | N/A | 60173 | 60189 | CTCAACATCTTTAATGA | 35 | 1270 |
| 741262 | N/A | N/A | 60421 | 60437 | GGGACCTAAAACTATAA | 25 | 1271 |
| 741263 | N/A | N/A | 60758 | 60774 | AGCAGAATAGAAAATCC | 49 | 1272 |
| 741264 | N/A | N/A | 60983 | 60999 | TTCAATGCGACTCCCAT | 81 | 1273 |
| 741265 | N/A | N/A | 61216 | 61232 | CAACAAAACTGAGAATC | 24 | 1274 |
| 741266 | N/A | N/A | 61474 | 61490 | AATGCCTGCTTTCACCA | 76 | 1275 |
| 741267 | N/A | N/A | 61699 | 61715 | TATAAGCAGGAGTAAAA | 27 | 1276 |
| 741268 | N/A | N/A | 61969 | 61985 | GTTCCAAAAGATAGAGA | 55 | 1277 |
| 741269 | N/A | N/A | 62200 | 62216 | CGTACACAAACTAGAAA | 33 | 1278 |
| 741270 | N/A | N/A | 62492 | 62508 | TACTGTTGCATTCCAGC | 70 | 1279 |
| 741271 | N/A | N/A | 62729 | 62745 | TCTTAGTGTGGTGGCTC | 78 | 1280 |
| 741272 | N/A | N/A | 62955 | 62971 | TCAACAATAATAATGAC | 60 | 1281 |
| 741273 | N/A | N/A | 63197 | 63213 | CCTTTTCATCAACACAT | 71 | 1282 |
| 741274 | N/A | N/A | 63422 | 63438 | TATGCATCTAACACTTG | 52 | 1283 |
| 741275 | N/A | N/A | 63666 | 63682 | CCATCAACCAAGTATCT | 26 | 1284 |

TABLE 19 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741276 | N/A | N/A | 63891 | 63907 | CTTGAAACAGTAACTTG | 47 | 1285 |
| 741277 | N/A | N/A | 64116 | 64132 | AACATAGCAGATTAATA | 37 | 1286 |
| 741278 | N/A | N/A | 64349 | 64365 | TCATGTTATATAGTGGG | 97 | 1287 |
| 741279 | N/A | N/A | 64574 | 64590 | TGTAACCTAATGTAAAT | 37 | 1288 |
| 741280 | N/A | N/A | 64799 | 64815 | ACAAGTATCTGTACTCA | 94 | 1289 |
| 741281 | N/A | N/A | 65024 | 65040 | GTCTCTGTTAATGTTGG | 75 | 1290 |
| 741282 | N/A | N/A | 65249 | 65265 | GAACCAGCCTGACTTAA | 74 | 1291 |
| 741283 | N/A | N/A | 65474 | 65490 | TTGTATGGGTTACATAA | 61 | 1292 |
| 741284 | N/A | N/A | 65801 | 65817 | CAATTAAATGCAATTCC | 53 | 1293 |
| 741285 | N/A | N/A | 66026 | 66042 | TGACAGAAGTGTGCATA | 59 | 1294 |
| 741286 | N/A | N/A | 66251 | 66267 | CAACACATCCACATTGC | 75 | 1295 |
| 741287 | N/A | N/A | 66476 | 66492 | TTCACACCTCTCTCCCT | 51 | 1296 |
| 741288 | N/A | N/A | 66701 | 66717 | TGCTGGTCTAAGATGCA | 77 | 1297 |
| 741289 | N/A | N/A | 66926 | 66942 | ATGTGTTTTGAGGAAAA | 77 | 1298 |
| 741290 | N/A | N/A | 67151 | 67167 | CAGAAGTAAATGTGGAC | 85 | 1299 |
| 741291 | N/A | N/A | 67376 | 67392 | TGATTCTTTGGATTCAT | 79 | 1300 |
| 741292 | N/A | N/A | 67876 | 67892 | CATTCTTGTTTTTATTC | 86 | 1301 |
| 741293 | N/A | N/A | 68101 | 68117 | AATAGTGTCCCAGTGTA | 78 | 1302 |
| 741294 | N/A | N/A | 68326 | 68342 | TGAAAGCTGTTCAGTTA | 74 | 1303 |
| 741295 | N/A | N/A | 68551 | 68567 | CCCACATATACTACTTG | 86 | 1304 |
| 741296 | N/A | N/A | 68776 | 68792 | AGAATTTCAGGAAGTTA | 87 | 1305 |
| 741297 | N/A | N/A | 68798 | 68814 | CAAAGTAAGAGGAGATT | 62 | 1306 |
| 741298 | N/A | N/A | 68800 | 68816 | GCCAAAGTAAGAGGAGA | 90 | 1307 |
| 741299 | N/A | N/A | 68801 | 68817 | TGCCAAAGTAAGAGGAG | 61 | 397 |
| 741300 | N/A | N/A | 68804 | 68820 | CAGTGCCAAAGTAAGAG | 64 | 1308 |
| 741301 | N/A | N/A | 69001 | 69017 | TGAATCCATTTGTCCAG | 91 | 1309 |
| 741302 | N/A | N/A | 69227 | 69243 | CTCTAAAATACAAATGT | 72 | 1310 |
| 741303 | N/A | N/A | 69452 | 69468 | GAACAAAGGAATAAGTA | 59 | 1311 |
| 741304 | N/A | N/A | 69677 | 69693 | CTAGATGTAGATATCAT | 61 | 1312 |
| 741305 | N/A | N/A | 69902 | 69918 | AAGGGAATAAATTGTAG | 52 | 1313 |
| 741306 | N/A | N/A | 70127 | 70143 | CAACAGACCCTTTCAAT | 60 | 1314 |
| 741307 | N/A | N/A | 70352 | 70368 | GTCTTCCCACTGCCTAC | 62 | 1315 |
| 741308 | N/A | N/A | 70577 | 70593 | TTTAGATATACCTCCAA | 94 | 1316 |
| 741309 | N/A | N/A | 70880 | 70896 | GCTTCAGTTTCTTGAGT | 79 | 1317 |
| 741310 | N/A | N/A | 71105 | 71121 | CTGGTCTTTCTCACAAT | N.D. | 1318 |
| 741311 | N/A | N/A | 71375 | 71391 | ATCATTCTTAACAGAAA | 70 | 1319 |

TABLE 19 -continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741312 | N/A | N/A | 71600 | 71616 | GCTCTTGCTGTGCAGCC | 74 | 1320 |
| 741313 | N/A | N/A | 71844 | 71860 | ATTTAAAGCAGCAGTCC | 50 | 1321 |
| 741314 | N/A | N/A | 72076 | 72092 | AGGTAATTCTAATTTTA | 68 | 1322 |
| 741315 | N/A | N/A | 72301 | 72317 | GGCAAATGACAGGGTCT | 93 | 1323 |
| 741316 | N/A | N/A | 72632 | 72648 | TCTCAACTGCCTGAGTA | 22 | 1324 |
| 741317 | N/A | N/A | 72857 | 72873 | CATGTCAGCTTTTTAGT | 69 | 1325 |

TABLE 20

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 95 | 33 |
| 740432 | 270 | 286 | 4721 | 4737 | AGTCCTTTCATGAATAC | 94 | 591 |
| 741318 | N/A | N/A | 73090 | 73106 | ATACTCAGATATTTAAA | 64 | 1326 |
| 741319 | N/A | N/A | 73188 | 73204 | ACTTTCTGTGTGGTATG | 91 | 1327 |
| 741320 | N/A | N/A | 73190 | 73206 | AGACTTTCTGTGTGGTA | 95 | 1328 |
| 741321 | N/A | N/A | 73191 | 73207 | CAGACTTTCTGTGTGGT | 93 | 170 |
| 741322 | N/A | N/A | 73192 | 73208 | ACAGACTTTCTGTGTGG | 86 | 1329 |
| 741323 | N/A | N/A | 73194 | 73210 | AGACAGACTTTCTGTGT | 46 | 1330 |
| 741324 | N/A | N/A | 73315 | 73331 | GTTGAGAATTTTTCATT | 66 | 1331 |
| 741325 | N/A | N/A | 73540 | 73556 | AGTTATGGAGCATCTTT | 89 | 1332 |
| 741326 | N/A | N/A | 73765 | 73781 | GACTGAGTTTTTTATTC | 74 | 1333 |
| 741327 | N/A | N/A | 73990 | 74006 | TCCTGAATTAAAAATTT | 13 | 1334 |
| 741328 | N/A | N/A | 74215 | 74231 | GCTAAGCACAAACAATT | 62 | 1335 |
| 741329 | N/A | N/A | 74292 | 74308 | GAACTCTGTAGTCAGAA | 92 | 1336 |
| 741330 | N/A | N/A | 74294 | 74310 | TAGAACTCTGTAGTCAG | 93 | 1337 |
| 741331 | N/A | N/A | 74295 | 74311 | ATAGAACTCTGTAGTCA | 95 | 398 |
| 741332 | N/A | N/A | 74296 | 74312 | AATAGAACTCTGTAGTC | 92 | 1338 |
| 741333 | N/A | N/A | 74298 | 74314 | TGAATAGAACTCTGTAG | 85 | 1339 |
| 741334 | N/A | N/A | 74440 | 74456 | ACACAGAGCACTTCTTA | 70 | 1340 |
| 741335 | N/A | N/A | 74665 | 74681 | GGAGTTACAGAGTTGCC | 91 | 1341 |
| 741336 | N/A | N/A | 74890 | 74906 | TATCAGTCTATTAAGAA | 82 | 1342 |
| 741337 | N/A | N/A | 75115 | 75131 | AAGTTTCTCAGAGCCTG | 82 | 1343 |
| 741338 | N/A | N/A | 75340 | 75356 | AATACAGAAGTCTATTC | 68 | 1344 |
| 741339 | N/A | N/A | 75573 | 75589 | CATTGAATAAAAATTTG | 18 | 1345 |
| 741340 | N/A | N/A | 75945 | 75961 | CAGGTATAAAATTTTTT | 45 | 1346 |

TABLE 20-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741341 | N/A | N/A | 76170 | 76186 | GGTGTTAATCACTTGAA | 86 | 1347 |
| 741342 | N/A | N/A | 76398 | 76414 | TCTTGAAGCTAGTTGGG | 91 | 1348 |
| 741343 | N/A | N/A | 76623 | 76639 | AGGGCAACTAACCAACA | 75 | 1349 |
| 741344 | N/A | N/A | 76848 | 76864 | GTGGATACTTAGTATCA | 69 | 1350 |
| 741345 | N/A | N/A | 77073 | 77089 | CTCTCTCAGTTGTAGGT | 67 | 1351 |
| 741346 | N/A | N/A | 77298 | 77314 | AAAGTATGCTGTGTTCT | 92 | 1352 |
| 741347 | N/A | N/A | 77523 | 77539 | GTACCCGGCACTTTTCC | 53 | 1353 |
| 741348 | N/A | N/A | 77663 | 77679 | TCTAGAAAAGCTCTCTT | 57 | 1354 |
| 741349 | N/A | N/A | 77665 | 77681 | ACTCTAGAAAAGCTCTC | 81 | 1355 |
| 741350 | N/A | N/A | 77666 | 77682 | GACTCTAGAAAAGCTCT | 91 | 247 |
| 741351 | N/A | N/A | 77667 | 77683 | AGACTCTAGAAAAGCTC | 84 | 1356 |
| 741352 | N/A | N/A | 77748 | 77764 | TGGCACCCAGGAGTAAG | 65 | 1357 |
| 741353 | N/A | N/A | 77973 | 77989 | CATACACAAAATCCCCT | 83 | 1358 |
| 741354 | N/A | N/A | 78198 | 78214 | CACATGAAGCCAGGGAC | 77 | 1359 |
| 741355 | N/A | N/A | 78423 | 78439 | GCAGGCCCTAAACTGTG | 39 | 1360 |
| 741356 | N/A | N/A | 78648 | 78664 | AAATTTATCTATCATGC | 93 | 1361 |
| 741357 | N/A | N/A | 78873 | 78889 | GCTAAACACTTTATCAA | 75 | 1362 |
| 741358 | N/A | N/A | 79098 | 79114 | ACTTCATTCTTTCTGTT | 87 | 1363 |
| 741359 | N/A | N/A | 79323 | 79339 | CAATTAAAAGATTACTT | 0 | 1364 |
| 741360 | N/A | N/A | 79548 | 79564 | ACATTGTACAGTTAATT | 77 | 1365 |
| 741361 | N/A | N/A | 79773 | 79789 | TACAAACCTTACTATGC | 51 | 1366 |
| 741362 | N/A | N/A | 79998 | 80014 | AACAGACTTAAACAAAC | 88 | 1367 |
| 741363 | N/A | N/A | 80223 | 80239 | CTCAGACATCATGTTTT | 91 | 1368 |
| 741364 | N/A | N/A | 80448 | 80464 | AGGCACTCACAAACATT | 86 | 1369 |
| 741365 | N/A | N/A | 80673 | 80689 | TCTCGCATCCTAAATGT | 50 | 1370 |
| 741366 | N/A | N/A | 80898 | 80914 | TTCATATTTTATGTTAC | 89 | 1371 |
| 741367 | N/A | N/A | 80991 | 81007 | TGAAATTTCCAGCTAA | 93 | 1372 |
| 741368 | N/A | N/A | 80993 | 81009 | CTTGAAATTTTCCAGCT | 97 | 1373 |
| 741369 | N/A | N/A | 80995 | 81011 | ATCTTGAAATTTTCCAG | 86 | 1374 |
| 741370 | N/A | N/A | 81123 | 81139 | CTATAATTACATTCCTA | 73 | 1375 |
| 741371 | N/A | N/A | 81348 | 81364 | GCATGAACCTAGATATG | 58 | 1376 |
| 741372 | N/A | N/A | 81472 | 81488 | GCTGTTTGAAGTGACAA | 70 | 1377 |
| 741373 | N/A | N/A | 81474 | 81490 | GAGCTGTTTGAAGTGAC | 90 | 1378 |
| 741374 | N/A | N/A | 81475 | 81491 | AGAGCTGTTTGAAGTGA | 82 | 249 |
| 741375 | N/A | N/A | 81476 | 81492 | GAGAGCTGTTTGAAGTG | 76 | 1379 |
| 741376 | N/A | N/A | 81478 | 81494 | TGGAGAGCTGTTTGAAG | 69 | 1380 |

TABLE 20-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741377 | N/A | N/A | 81575 | 81591 | CTGCCACTATTCACAAT | 71 | 1381 |
| 741378 | N/A | N/A | 81800 | 81816 | TTATTGCATTAATGGAA | 94 | 1382 |
| 741379 | N/A | N/A | 82107 | 82123 | ATGGTGTTAGCTAGGAT | 91 | 1383 |
| 741380 | N/A | N/A | 82332 | 82348 | GTCTTTTTACATTATAA | 93 | 1384 |
| 741381 | N/A | N/A | 82557 | 82573 | ATAACCACTATTCAATG | 63 | 1385 |
| 741382 | N/A | N/A | 82783 | 82799 | AAAAATCACATTTGGCA | 95 | 1386 |
| 741383 | N/A | N/A | 83008 | 83024 | TTCTTTCACCTTATGAG | 72 | 1387 |
| 741384 | N/A | N/A | 83233 | 83249 | ATATATGTGTCAGTTCT | 90 | 1388 |
| 741385 | N/A | N/A | 83458 | 83474 | GTGTCACTTTTTAAGGT | 14 | 1389 |
| 741386 | N/A | N/A | 83528 | 83544 | AGAACAATGTCATCTTT | 94 | 1390 |
| 741387 | N/A | N/A | 83530 | 83546 | AAAGAACAATGTCATCT | 88 | 1391 |
| 741388 | N/A | N/A | 83531 | 83547 | GAAAGAACAATGTCATC | 89 | 98 |
| 741389 | N/A | N/A | 83532 | 83548 | GGAAAGAACAATGTCAT | 82 | 1392 |
| 741390 | N/A | N/A | 83534 | 83550 | CAGGAAAGAACAATGTC | 88 | 1393 |
| 741391 | N/A | N/A | 83683 | 83699 | CACAGGTATACACACTT | 90 | 1394 |
| 741392 | N/A | N/A | 83908 | 83924 | GTACAAAATCTGCATAT | 81 | 1395 |
| 741393 | N/A | N/A | 84133 | 84149 | ATAGGTATTTTATGCAT | 88 | 1396 |
| 741394 | N/A | N/A | 84616 | 84632 | CAAATTATGCATTTGTT | 66 | 1397 |

TABLE 21

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 95 | 33 |
| 740432 | 270 | 286 | 4721 | 4737 | AGTCCTTTCATGAATAC | 93 | 591 |
| 741395 | N/A | N/A | 84845 | 84861 | CTACAAAATTGCTAAAA | 9 | 1398 |
| 741396 | N/A | N/A | 85070 | 85086 | ACAATGTTACTTTGTCC | 90 | 1399 |
| 741397 | N/A | N/A | 85295 | 85311 | TACAAAATACCCCCCC | 12 | 1400 |
| 741398 | N/A | N/A | 85520 | 85536 | ATTTGTAGACCTATGTT | 62 | 1401 |
| 741399 | N/A | N/A | 85745 | 85761 | AAGCATCTCCTGTGGTG | 78 | 1402 |
| 741400 | N/A | N/A | 85970 | 85986 | CAACATGTTTTATCATG | 68 | 1403 |
| 741401 | N/A | N/A | 86195 | 86211 | AATATGACCACAATTTT | 73 | 1404 |
| 741402 | N/A | N/A | 86420 | 86436 | TGGCAATATGAATGTGC | 86 | 1405 |
| 741403 | N/A | N/A | 86645 | 86661 | GATAAGGGCACATTGTC | 64 | 1406 |
| 741404 | N/A | N/A | 86871 | 86887 | GTGATGGAGGGAAATCG | 53 | 1407 |
| 741405 | N/A | N/A | 87096 | 87112 | TGTGGTAATTGGAACAA | 34 | 1408 |

TABLE 21-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741406 | N/A | N/A | 87321 | 87337 | ACTGAACCCAAATGGCT | 68 | 1409 |
| 741407 | N/A | N/A | 87546 | 87562 | TCACATTCATCATATTC | 81 | 1410 |
| 741408 | N/A | N/A | 87772 | 87788 | CATTGCTGTTGTTGTTC | 92 | 1411 |
| 741409 | N/A | N/A | 87945 | 87961 | TAAGTTGTGACCATGCA | 87 | 1412 |
| 741410 | N/A | N/A | 87946 | 87962 | GTAAGTTGTGACCATGC | 95 | 402 |
| 741411 | N/A | N/A | 87947 | 87963 | AGTAAGTTGTGACCATG | 96 | 1413 |
| 741412 | N/A | N/A | 87949 | 87965 | TTAGTAAGTTGTGACCA | 76 | 1414 |
| 741413 | N/A | N/A | 87997 | 88013 | AATAAAAATGTGCATGC | 47 | 1415 |
| 741414 | N/A | N/A | 88222 | 88238 | AACAAAATACAGTCAGA | 91 | 1416 |
| 741415 | N/A | N/A | 88447 | 88463 | TTTGTACTGTGTGCTGT | 89 | 1417 |
| 741416 | N/A<br>N/A | N/A<br>N/A | 89657<br>88652 | 89673<br>88668 | TGACATACAAACCCAAA | 78 | 1418 |
| 741417 | N/A<br>N/A | N/A<br>N/A | 89658<br>88653 | 89674<br>88669 | TTGACATACAAACCCAA | 87 | 326 |
| 741418 | N/A<br>N/A | N/A<br>N/A | 89659<br>88654 | 89675<br>88670 | CTTGACATACAAACCCA | 82 | 1419 |
| 741419 | N/A<br>N/A | N/A<br>N/A | 89681<br>88676 | 89697<br>88692 | GTCCCCAATCCCCACCC | 19 | 100 |
| 741420 | N/A | N/A | 88705 | 88721 | GAAGTTAACTCCCTAGA | 83 | 1420 |
| 741421 | N/A | N/A | 88707 | 88723 | ATGAAGTTAACTCCCTA | 92 | 1421 |
| 741422 | N/A<br>N/A | N/A<br>N/A | 89713<br>88708 | 89729<br>88724 | GATGAAGTTAACTCCCT | 92 | 176 |
| 741423 | N/A<br>N/A | N/A<br>N/A | 89714<br>88709 | 89730<br>88725 | AGATGAAGTTAACTCCC | 86 | 1422 |
| 741424 | N/A<br>N/A | N/A<br>N/A | 89716<br>88711 | 89732<br>88727 | AGAGATGAAGTTAACTC | 78 | 252 |
| 741425 | N/A | N/A | 88754 | 88770 | TTTTCAAGAGCTTTTCG | 67 | 1423 |
| 741426 | N/A<br>N/A | N/A<br>N/A | 89761<br>88756 | 89777<br>88772 | CCTTTTCAAGAGCTTTT | 90 | 1424 |
| 741427 | N/A<br>N/A | N/A<br>N/A | 89763<br>88758 | 89779<br>88774 | TCCCTTTTCAAGAGCTT | 96 | 1425 |
| 741428 | N/A<br>N/A | N/A<br>N/A | 89765<br>88760 | 89781<br>88776 | TTTCCCTTTTCAAGAGC | 93 | 1426 |
| 741429 | N/A<br>N/A | N/A<br>N/A | 89767<br>88762 | 89783<br>88778 | TATTTCCCTTTTCAAGA | 32 | 1427 |
| 741430 | N/A | N/A | 88901 | 88917 | ACAAGTAGGTAGGTCAA | 83 | 1428 |
| 741431 | N/A | N/A | 89126 | 89142 | TGAGCCATATTCAATAT | 66 | 1429 |
| 741432 | N/A | N/A | 89351 | 89367 | AAATTGCTAGGTTCAAC | 77 | 1430 |
| 741433 | N/A | N/A | 89579 | 89595 | ATCAAATATTTACTAGA | 49 | 1431 |
| 741434 | N/A<br>N/A | N/A<br>N/A | 89655<br>88650 | 89671<br>88666 | ACATACAAACCCAAAGA | 43 | 1432 |
| 741435 | N/A<br>N/A | N/A<br>N/A | 89661<br>88656 | 89677<br>88672 | CACTTGACATACAAACC | 58 | 1433 |

TABLE 21-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741436 | N/A | N/A | 89710 | 89726 | GAAGTTAACTCCCTTGA | 69 | 1434 |
| 741437 | N/A | N/A | 89712 | 89728 | ATGAAGTTAACTCCCTT | 92 | 1435 |
| 741438 | N/A | N/A | 89759 | 89775 | TTTTCAAGAGCTTTTCT | 66 | 1436 |
| 741439 | N/A | N/A | 89804 | 89820 | TCTACAGGTTATATGTG | 46 | 1437 |
| 741440 | N/A | N/A | 90029 | 90045 | TCCCAAAGTGCAAGACT | 53 | 1438 |
| 741441 | N/A | N/A | 90321 | 90337 | CTCTATTGTTATATTTT | 86 | 1439 |
| 741442 | N/A | N/A | 90546 | 90562 | ATCTAACTCCTAGCACA | 37 | 1440 |
| 741443 | N/A | N/A | 90771 | 90787 | ATACTTTCTCTGCATAA | 65 | 1441 |
| 741444 | N/A | N/A | 91050 | 91066 | TAGCTATAGTGCAATGG | 52 | 1442 |
| 741445 | N/A | N/A | 91277 | 91293 | CTGGAATTCCAGAAAAA | 63 | 1443 |
| 741446 | N/A | N/A | 91502 | 91518 | CTTTCAAATCTCATTAC | 68 | 1444 |
| 741447 | N/A | N/A | 91727 | 91743 | TCTTCTTTTGCAGAGAT | 65 | 1445 |
| 741448 | N/A | N/A | 91952 | 91968 | TAGAGCATTAAGAACAT | 68 | 1446 |
| 741449 | N/A | N/A | 92177 | 92193 | GTTACTAAAAAAAACCA | 41 | 1447 |
| 741450 | N/A | N/A | 92402 | 92418 | TCCCATTGGACTGAGTT | 53 | 1448 |
| 741451 | N/A | N/A | 92627 | 92643 | TATCCATTTTCCAGTTA | 83 | 1449 |
| 741452 | N/A | N/A | 92852 | 92868 | CCAGGGTGCTATACAAA | 73 | 1450 |
| 741453 | N/A | N/A | 93077 | 93093 | CCTTAACAATCTTATTT | 48 | 1451 |
| 741454 | N/A | N/A | 93302 | 93318 | CACCACATTAATTAAAC | 52 | 1452 |
| 741455 | N/A | N/A | 93527 | 93543 | ATGTTTTGAGTTCCAGG | 97 | 1453 |
| 741456 | N/A | N/A | 93752 | 93768 | TAATTAATAATCATCTT | 20 | 1454 |
| 741457 | N/A | N/A | 93950 | 93966 | TTCTGGCTGACTGAATT | 48 | 1455 |
| 741458 | N/A | N/A | 93953 | 93969 | GGCTTCTGGCTGACTGA | 72 | 180 |
| 741459 | N/A | N/A | 93954 | 93970 | TGGCTTCTGGCTGACTG | 83 | 1456 |
| 741460 | N/A | N/A | 93956 | 93972 | TGTGGCTTCTGGCTGAC | 66 | 1457 |
| 741461 | N/A | N/A | 93983 | 93999 | GGCTTTTAACAAAACAA | 69 | 1458 |
| 741462 | N/A | N/A | 94052 | 94068 | ATAATTCAAGTCAGGGA | 67 | 1459 |
| 741463 | N/A | N/A | 94054 | 94070 | CCATAATTCAAGTCAGG | 80 | 1460 |
| 741464 | N/A | N/A | 94055 | 94071 | GCCATAATTCAAGTCAG | 89 | 331 |
| 741465 | N/A | N/A | 94056 | 94072 | TGCCATAATTCAAGTCA | 66 | 1461 |
| 741466 | N/A | N/A | 94058 | 94074 | ACTGCCATAATTCAAGT | 64 | 1462 |
| 741467 | N/A | N/A | 94208 | 94224 | TAATATTGTGACCACTT | 94 | 1463 |
| 741468 | N/A | N/A | 94433 | 94449 | TAAGACTATTGCTTTGG | 74 | 1464 |
| 741469 | N/A | N/A | 94658 | 94674 | CATAATAGATGAGTTAA | 62 | 1465 |
| 741470 | N/A | N/A | 94993 | 95009 | TTCAGTTTTGTGGCGGG | 72 | 1466 |
| 741471 | N/A | N/A | 95218 | 95234 | ATTACATTAAAGGTGG | 39 | 1467 |

TABLE 22

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 97 | 33 |
| 740432 | 270 | 286 | 4721 | 4737 | AGTCCTTTCATGAATAC | 95 | 591 |
| 741472 | N/A | N/A | 95443 | 95459 | CCACCGTCACTGCATAC | 85 | 1468 |
| 741473 | N/A | N/A | 95668 | 95684 | ACTCTGTTGAATTTTCT | 80 | 1469 |
| 741474 | N/A | N/A | 95893 | 95909 | TTTCCAGTGCTAGTATT | 68 | 1470 |
| 741475 | N/A | N/A | 96118 | 96134 | AATGAGATGAAAATTGA | 70 | 1471 |
| 741476 | N/A | N/A | 96343 | 96359 | AGCTAGTTTGTAAACAA | 72 | 1472 |
| 741477 | N/A | N/A | 96568 | 96584 | AGAAGCAGTGAATCCAA | 84 | 1473 |
| 741478 | N/A | N/A | 96793 | 96809 | CTGTTAATCACCCCTTT | 60 | 1474 |
| 741479 | N/A | N/A | 97018 | 97034 | CACAATACAGAGCAGAG | 72 | 1475 |
| 741480 | N/A | N/A | 97243 | 97259 | AGAAGTCAGACTTCAGG | 33 | 1476 |
| 741481 | N/A | N/A | 97474 | 97490 | ATGGAAGATGAAAAGG | 3 | 1477 |
| 741482 | N/A | N/A | 97699 | 97715 | GTTGAGTCTGAGATGCC | 75 | 1478 |
| 741483 | N/A | N/A | 97924 | 97940 | AAGGCTGTTCACTATAT | 81 | 1479 |
| 741484 | N/A | N/A | 98149 | 98165 | TCTTGCACTGATTCCTC | 61 | 1480 |
| 741485 | N/A | N/A | 98374 | 98390 | AGATAAGAAGCAAATGC | 61 | 1481 |
| 741486 | N/A | N/A | 98805 | 98821 | GAATGGGCGGATCACAA | 34 | 1482 |
| 741487 | N/A | N/A | 99032 | 99048 | GATTATTTTAAGCACTT | 90 | 1483 |
| 741488 | N/A | N/A | 99257 | 99273 | AGAAAAGGGCATTTAA | 26 | 1484 |
| 741489 | N/A | N/A | 99483 | 99499 | TGCAATGTGTAGGTGGG | 70 | 1485 |
| 741490 | N/A | N/A | 99708 | 99724 | ACTTTTAAGGCATCCAT | 74 | 1486 |
| 741491 | N/A | N/A | 99933 | 99949 | CCCTCCCAACAATTTCA | 26 | 1487 |
| 741492 | N/A | N/A | 100158 | 100174 | CTTTCCATTATTGTTCT | 67 | 1488 |
| 741493 | N/A | N/A | 100391 | 100407 | GGAAATGTTTATATATA | 58 | 1489 |
| 741494 | N/A | N/A | 100625 | 100641 | TAGGAAGTCTGGCTCCA | 22 | 1490 |
| 741495 | N/A | N/A | 100850 | 100866 | GATAATGGGCTAGGTGT | 69 | 1491 |
| 741496 | N/A | N/A | 101075 | 101091 | TGGAATATCTTTGCTTA | 22 | 1492 |
| 741497 | N/A | N/A | 101300 | 101316 | ATAGCTTCAAGATCGGT | 72 | 1493 |
| 741498 | N/A | N/A | 101525 | 101541 | GAGATAAAGAGTCTGCT | 61 | 1494 |
| 741499 | N/A | N/A | 101803 | 101819 | TCACGGGATCACGCCAT | 58 | 1495 |
| 741500 | N/A | N/A | 102028 | 102044 | TGACTGAATAAGACATT | 52 | 1496 |
| 741501 | N/A | N/A | 102253 | 102269 | GCAACAACTGCCAGCTT | 54 | 1497 |
| 741502 | N/A | N/A | 102478 | 102494 | CAGGTTTAAATACATTC | 85 | 1498 |
| 741503 | N/A | N/A | 102703 | 102719 | TTGGATAATCTGTTACT | 63 | 1499 |
| 741504 | N/A | N/A | 102968 | 102984 | TAATGCAGTGATACAAT | 57 | 1500 |
| 741505 | N/A | N/A | 103193 | 103209 | CTGGATCACTTGGGAAT | 69 | 1501 |
| 741506 | N/A | N/A | 103418 | 103434 | TGTTCTAATTAAAAAGT | 47 | 1502 |

TABLE 22-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741507 | N/A | N/A | 103643 | 103659 | ACTTTACAACAAGATAA | 36 | 1503 |
| 741508 | N/A | N/A | 103868 | 103884 | TGATACATTATAATACA | 58 | 1504 |
| 741509 | N/A | N/A | 104093 | 104109 | GGGAAAGTATAGTTATG | 63 | 1505 |
| 741510 | N/A | N/A | 104332 | 104348 | GCATAAGAAAGAACAAT | 42 | 1506 |
| 741511 | N/A | N/A | 104557 | 104573 | TCTTGAGGTCATAAATC | 56 | 1507 |
| 741512 | N/A | N/A | 104782 | 104798 | AAATGAAGGCGATAGAC | 76 | 1508 |
| 741513 | N/A | N/A | 105007 | 105023 | CTAAAAAGAACTTTGA | 0 | 1509 |
| 741514 | N/A | N/A | 105232 | 105248 | TGTGTGATCAACTTTCA | 88 | 1510 |
| 741515 | N/A | N/A | 105457 | 105473 | AGTAAGCTTCAATTGGT | 71 | 1511 |
| 741516 | N/A | N/A | 105682 | 105698 | AGGTTTCATCAATTATC | 89 | 1512 |
| 741517 | N/A | N/A | 105907 | 105923 | AGTGTCTTGTTAAGTAT | 64 | 1513 |
| 741518 | N/A | N/A | 106134 | 106150 | GAATTTACATAATCTTT | 69 | 1514 |
| 741519 | N/A | N/A | 106361 | 106377 | CTTTTTAAATAAACCTG | 58 | 1515 |
| 741520 | N/A | N/A | 106586 | 106602 | GAATAGCTGTAGACTTT | 67 | 1516 |
| 741521 | N/A | N/A | 106811 | 106827 | TACCAATATAACAAATG | 23 | 1517 |
| 741522 | N/A | N/A | 107037 | 107053 | TATTTACTGTTTCATAA | 40 | 1518 |
| 741523 | N/A | N/A | 107275 | 107291 | TCAGGTGTCCTAGTGGG | 68 | 1519 |
| 741524 | N/A | N/A | 107500 | 107516 | GCAACCCCAAAATACTA | 62 | 1520 |
| 741525 | N/A | N/A | 107725 | 107741 | GTGTGATGATATATTGC | 85 | 1521 |
| 741526 | N/A | N/A | 107954 | 107970 | ACAAGACAAAGAATACG | 47 | 1522 |
| 741527 | N/A | N/A | 108273 | 108289 | GTTCTCCTATAGTCCCA | 24 | 1523 |
| 741528 | N/A | N/A | 108498 | 108514 | ACTAGGGATGACAGCAC | 74 | 1524 |
| 741529 | N/A | N/A | 108724 | 108740 | TTCTTGCTTATATCAAT | 72 | 1525 |
| 741530 | N/A | N/A | 108970 | 108986 | GCAGTAATGGAACAGCG | 63 | 1526 |
| 741531 | N/A | N/A | 109195 | 109211 | ATTTTGATATGGACCAG | 73 | 1527 |
| 741532 | N/A | N/A | 109420 | 109436 | TGCTGAGAAGTTTCCTA | 52 | 1528 |
| 741533 | N/A | N/A | 109645 | 109661 | TGCCCTTTTTATAAACT | 18 | 1529 |
| 741534 | N/A | N/A | 109870 | 109886 | AGCCTAAAGGGACTTGG | 49 | 1530 |
| 741535 | N/A | N/A | 110095 | 110111 | AGACTGAGACTATACAT | 65 | 1531 |
| 741536 | N/A | N/A | 110320 | 110336 | GTCTATATTATAGATAC | 16 | 1532 |
| 741537 | N/A | N/A | 110626 | 110642 | TTACAATGAAACCCCAT | 38 | 1533 |
| 741538 | N/A | N/A | 110853 | 110869 | TTTACTATTTAGGAAAT | 10 | 1534 |
| 741539 | N/A | N/A | 111078 | 111094 | AAGTAAGAAGCACAAAA | 20 | 1535 |
| 741540 | N/A | N/A | 111303 | 111319 | AACTTGCAAGTTGTCCA | 79 | 1536 |
| 741541 | N/A | N/A | 111528 | 111544 | GATTTCCCTAACTTTCC | 61 | 1537 |
| 741542 | N/A | N/A | 111986 | 112002 | ATGTCTCCTCTTCTGTT | 43 | 1538 |

TABLE 22-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741543 | N/A | N/A | 112211 | 112227 | GTAACCTGGCCACTTTG | 49 | 1539 |
| 741544 | N/A | N/A | 112436 | 112452 | TGTCTGTGTGAGACAGT | 31 | 1540 |
| 741545 | N/A | N/A | 112661 | 112677 | ATCATAATGAAGAAATG | 12 | 1541 |
| 741546 | N/A | N/A | 112886 | 112902 | TGCCTTTGCTTCTGATA | 63 | 1542 |
| 741547 | N/A | N/A | 113111 | 113127 | ATATCAGGATTCTGCTT | 52 | 1543 |
| 741548 | N/A | N/A | 113336 | 113352 | GATGCTCTAATTCTCAG | 61 | 1544 |

TABLE 23

Percent reduction of human SNCA mRNA with 4-9-4 MOE and cEt gapmers with mixed internucleoside linkages

| Compound No | SEQ ID No: 3 start | SEQ ID No: 3 stop | SEQ ID No: 5 start | SEQ ID No: 5 stop | SEQ ID No: 6 start | SEQ ID No: 6 stop | Sequence (5' to 3') | % Reduction | SEQ ID NO |
|---|---|---|---|---|---|---|---|---|---|
| 740914 | N/A | N/A | 31 | 47 | N/a | N/a | CACTCTTTCAGAGCTGG | 49 | 1545 |
| 740915 | N/A | N/A | 34 | 50 | N/a | N/a | CCACACTCTTTCAGAGC | 12 | 1546 |
| 740916 | N/A | N/A | 37 | 53 | N/a | N/a | ACACCACACTCTTTCAG | 37 | 1547 |
| 740917 | N/A | N/A | 40 | 56 | N/a | N/a | TTTACACCACACTCTTT | 55 | 1548 |
| 740918 | N/A | N/A | 41 | 57 | N/a | N/a | CTTTACACCACACTCTT | 70 | 1549 |
| 740919 | N/A | N/A | 43 | 59 | 98 | 114 | TCCTTTACACCACACTC | 89 | 1550 |
| 740920 | N/A | N/A | 90 | 106 | 90 | 106 | ACCACACTCACTTCCGC | 23 | 1551 |
| 740921 | N/A | N/A | 93 | 109 | 93 | 109 | TACACCACACTCACTTC | 0 | 1552 |
| 740922 | N/A | N/A | 96 | 112 | 96 | 112 | CTTTACACCACACTCAC | 86 | 1553 |
| 740923 | 370 | 386 | N/A | N/A | N/A | N/A | CACTACATAGAGAACAC | 86 | 1554 |
| 740924 | 373 | 389 | N/A | N/A | N/A | N/A | AGCCACTACATAGAGAA | 8 | 1555 |
| 740925 | 376 | 392 | N/A | N/A | N/A | N/A | CTCAGCCACTACATAGA | 29 | 1556 |
| 740926 | 379 | 395 | N/A | N/A | N/A | N/A | CTTCTCAGCCACTACAT | 52 | 1557 |
| 740927 | 382 | 398 | N/A | N/A | N/A | N/A | GGTCTTCTCAGCCACTA | 83 | 1558 |
| 740928 | 513 | 529 | N/A | N/A | N/A | N/A | TCCTTGCCCAACTGGTC | 46 | 1559 |
| 740929 | 516 | 532 | N/A | N/A | N/A | N/A | CCTTCCTTGCCCAACTG | 19 | 1560 |
| 740930 | 519 | 535 | N/A | N/A | N/A | N/A | TACCCTTCCTTGCCCAA | 50 | 1561 |
| 740931 | 522 | 538 | N/A | N/A | N/A | N/A | TGATACCCTTCCTTGCC | 16 | 1562 |
| 740932 | 525 | 541 | N/A | N/A | N/A | N/A | TCTTGATACCCTTCCTT | 63 | 1563 |

Example 4: Effect of 5-8-4 MOE and cEt Gapmers with Mixed Internucleoside Linkages on Human SNCA In Vitro, Single Dose Modified oligonucleotides complementary to a human SNCA nucleic acid were designed and tested for their effect on SNCA mRNA in vitro. The modified oligonucleotides were tested in a series of experiments that had similar culture conditions.

Cultured SH-SY5Y cells at a density of 20,000 cells per well were transfected using electroporation with 1,000 nM concentration of modified oligonucleotide or no modified oligonucleotide for untreated controls. After approximately 24 hours, RNA was isolated from the cells and SNCA mRNA levels were measured by quantitative real-time PCR using human primer probe set RTS2621 as described in Example 1. SNCA mRNA levels were adjusted according to total RNA content, as measured by RIBOGREEN®. Results are presented in the tables below as percent reduction of the amount of SNCA mRNA, relative to untreated control cells.

The modified oligonucleotides in tables 24-28 are 4-9-4 MOE and cEt gapmers. The gapmers are 17 nucleobases in length, wherein the central gap segment comprises nine 2'-deoxynucleosides and is flanked by wing segments on both the 5' end on the 3' end comprising two 2'-MOE nucleosides and two cEt nucleosides. The sugar motif for the gapmers is (from 5' to 3'): eekkddddddddddkkee; wherein 'd' represents a 2'-deoxyribose sugar; 'e' represents a 2'-MOE modified sugar; and 'k' represents a cEt modified sugar. All cytosine residues throughout each gapmer are 5-methyl cytosines. The internucleoside linkages are mixed phosphodiester and phosphorothioate linkages. The internucleoside linkage motif for the gapmers is (from 5' to 3'): sooosssssssssoss; wherein 'o' represents a phosphodiester internucleoside linkage and 's' represents a phosphorothioate internucleoside linkage. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the Tables below is complementary to human SNCA nucleic acid sequences SEQ ID NO: 1, SEQ ID NO: 2, SEQ ID NO: 3, SEQ ID NO: 4, SEQ ID NO: 5, or SEQ ID NO: 6, as indicated. 'N/A' indicates that the modified oligonucleotide is not complementary to that particular nucleic acid with 100% complementarity. A value of 0% reduction indicates that the compound had no effect or increased mRNA concentrations in the cell. As shown below, modified oligonucleotides complementary to human SNCA reduced the amount of human SNCA mRNA.

TABLE 24

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 61 | 33 |
| 740432 | 270 | 286 | 4721 | 4737 | AGTCCTTTCATGAATAC | 87 | 591 |
| 741010 | N/A | N/A | 20549 | 20565 | CAATTTCTAGGTTCTAT | 28 | 1107 |
| 741011 | N/A | N/A | 20559 | 20575 | AACTATGCTGCAATTTC | 28 | 1108 |
| 741012 | N/A | N/A | 20561 | 20577 | ACAACTATGCTGCAATT | 25 | 1109 |
| 741013 | N/A | N/A | 20562 | 20578 | CACAACTATGCTGCAAT | 54 | 314 |
| 741014 | N/A | N/A | 20565 | 20581 | TTCCACAACTATGCTGC | 51 | 1110 |
| 741015 | N/A | N/A | 20774 | 20790 | GACCACAATTGCAGACA | 55 | 1111 |
| 741016 | N/A | N/A | 20985 | 21001 | GTGTGAGCAAACATTCT | 73 | 1112 |
| 741017 | N/A | N/A | 27412 | 27428 | CAGTGTGAGCAAACATT | 35 | 1113 |
| | N/A | N/A | 20987 | 21003 | | | |
| 741018 | N/A | N/A | 27413 | 27429 | ACAGTGTGAGCAAACAT | 67 | 468 |
| | N/A | N/A | 20988 | 21004 | | | |
| 741019 | N/A | N/A | 27414 | 27430 | CACAGTGTGAGCAAACA | 61 | 1114 |
| | N/A | N/A | 20989 | 21005 | | | |
| 741020 | N/A | N/A | 20991 | 21007 | GGCACAGTGTGAGCAAA | 53 | 1115 |
| 741021 | N/A | N/A | 20999 | 21015 | AAGTTTCTGGCACAGTG | 89 | 1116 |
| 741022 | N/A | N/A | 21224 | 21240 | GTTCAGAATTATGTCAT | 81 | 1117 |
| 741023 | N/A | N/A | 21449 | 21465 | TCTTATGTGCACATGAG | 16 | 1118 |
| 741024 | N/A | N/A | 21674 | 21690 | CATAGTAGCATTACAGA | 47 | 1119 |
| 741025 | N/A | N/A | 21899 | 21915 | TCAGGCAGTGGCTTCAC | 43 | 1120 |
| 741026 | N/A | N/A | 22129 | 22145 | TAAAAAAGTTGTTCAT | 0 | 1121 |
| 741027 | N/A | N/A | 22360 | 22376 | CACTCAAGTGTTTAAAA | 26 | 1122 |
| 741028 | N/A | N/A | 22454 | 22470 | TGTGACCTGTGCTTGTT | 83 | 1123 |
| 741029 | N/A | N/A | 22456 | 22472 | CCTGTGACCTGTGCTTG | 87 | 1124 |
| 741030 | N/A | N/A | 22457 | 22473 | GCCTGTGACCTGTGCTT | 62 | 88 |

TABLE 24-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741031 | N/A | N/A | 22458 | 22474 | TGCCTGTGACCTGTGCT | 54 | 1125 |
| 741032 | N/A | N/A | 22460 | 22476 | GTTGCCTGTGACCTGTG | 78 | 1126 |
| 741033 | N/A | N/A | 22599 | 22615 | TATTAGACACTTAAGGG | 28 | 1127 |
| 741034 | N/A | N/A | 22831 | 22847 | TCAATCTTAAATTTTTC | 56 | 1128 |
| 741035 | N/A | N/A | 23056 | 23072 | GTACTTTCCCACCTAGA | 39 | 1129 |
| 741036 | N/A | N/A | 23281 | 23297 | TCTCAGAGACCACAGCT | 56 | 1130 |
| 741037 | N/A | N/A | 23285 | 23301 | TTGTTCTCAGAGACCAC | 86 | 1131 |
| 741038 | N/A | N/A | 23286 | 23302 | ATTGTTCTCAGAGACCA | 72 | 164 |
| 741039 | N/A | N/A | 23287 | 23303 | TATTGTTCTCAGAGACC | 67 | 1132 |
| 741040 | N/A | N/A | 23289 | 23305 | CATATTGTTCTCAGAGA | 40 | 1133 |
| 741041 | N/A | N/A | 23506 | 23522 | ACTATTAACCACTGATC | 25 | 1134 |
| 741042 | N/A | N/A | 23731 | 23747 | GTTGCAGTCCACAGAAT | 34 | 1135 |
| 741043 | N/A | N/A | 23956 | 23972 | TAAAGATAAGTATCTCA | 70 | 1136 |
| 741044 | N/A | N/A | 24181 | 24197 | AAACAAACCTAAGTCA | 0 | 1137 |
| 741045 | N/A | N/A | 24406 | 24422 | AAAAGCTAACAGCCTAT | 14 | 1138 |
| 741046 | N/A | N/A | 24631 | 24647 | TTAAATTGATGAGATGT | 49 | 1139 |
| 741047 | N/A | N/A | 24856 | 24872 | GTATTCTTTGCATTAGT | 67 | 1140 |
| 741048 | N/A | N/A | 25081 | 25097 | TAAAAGTGTACATTATT | 22 | 1141 |
| 741049 | N/A | N/A | 25306 | 25322 | CTCAAGGCAAAGCTGTA | 57 | 1142 |
| 741050 | N/A | N/A | 25531 | 25547 | TGCCACTATAAGCAGTC | 55 | 1143 |
| 741051 | N/A | N/A | 25756 | 25772 | TTCAAGCCCATGCCCTC | 21 | 1144 |
| 741052 | N/A | N/A | 25801 | 25817 | ATCCAGTAGAGTGAGAG | 37 | 1145 |
| 741053 | N/A | N/A | 25803 | 25819 | TCATCCAGTAGAGTGAG | 41 | 1146 |
| 741054 | N/A | N/A | 25804 | 25820 | ATCATCCAGTAGAGTGA | 31 | 315 |
| 741055 | N/A | N/A | 25807 | 25823 | GACATCATCCAGTAGAG | 55 | 1147 |
| 741056 | N/A | N/A | 25923 | 25939 | TGAATACATTGTCTTAA | 18 | 1148 |
| 741057 | N/A | N/A | 25925 | 25941 | ATTGAATACATTGTCTT | 41 | 1149 |
| 741058 | N/A | N/A | 25926 | 25942 | AATTGAATACATTGTCT | 50 | 392 |
| 741059 | N/A | N/A | 25927 | 25943 | TAATTGAATACATTGTC | 29 | 1150 |
| 741060 | N/A | N/A | 25929 | 25945 | CATAATTGAATACATTG | 25 | 1151 |
| 741061 | N/A | N/A | 25981 | 25997 | TGAGTAGCTATGGTTTA | 37 | 1152 |
| 741062 | N/A | N/A | 26202 | 26218 | TCTTTGTGTTATACAAT | 0 | 1153 |
| 741063 | N/A | N/A | 26204 | 26220 | CCTCTTTGTGTTATACA | 53 | 1154 |
| 741064 | N/A | N/A | 26205 | 26221 | CCCTCTTTGTGTTATAC | 42 | 469 |
| 741065 | N/A | N/A | 26206 | 26222 | TCCCTCTTTGTGTTATA | 20 | 1155 |
| 741066 | N/A | N/A | 26208 | 26224 | TTTCCCTCTTTGTGTTA | 30 | 1156 |

TABLE 24-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741067 | N/A | N/A | 26431 | 26447 | TACATACAATATTAAGG | 0 | 1157 |
| 741068 | N/A | N/A | 26656 | 26672 | AAAAGAATGGATTCTGA | 34 | 1158 |
| 741069 | N/A | N/A | 26881 | 26897 | AAGGAAAAACTCTGCCC | 15 | 1159 |
| 741070 | N/A | N/A | 27106 | 27122 | TCACCCCAAGGCATTTG | 6 | 1160 |
| 741071 | N/A | N/A | 27331 | 27347 | ACACCCTGATTCCCAAG | 31 | 1161 |
| 741072 | N/A | N/A | 27410 | 27426 | GTGTGAGCAAACATTCA | 52 | 1162 |
| 741073 | N/A | N/A | 27416 | 27432 | GTCACAGTGTGAGCAAA | 72 | 1163 |
| 741074 | N/A | N/A | 27556 | 27572 | GGGAAGTATTAGTGGAA | 27 | 1164 |
| 741075 | N/A | N/A | 27782 | 27798 | GCTGAAAATATGAAACA | 32 | 1165 |
| 741076 | N/A | N/A | 28007 | 28023 | ACTTCTAGCACTATTTT | 9 | 1166 |
| 741077 | N/A | N/A | 28232 | 28248 | TTGTGCATTTATTCCAC | 78 | 1167 |
| 741078 | N/A | N/A | 28457 | 28473 | GACTGTAATCTAGGACC | 74 | 1168 |
| 741079 | N/A | N/A | 28682 | 28698 | TGACTTTTGAATCAGTC | 14 | 1169 |
| 741080 | N/A | N/A | 29010 | 29026 | GAGCGATTCTCCTGGTT | 61 | 1170 |
| 741081 | N/A | N/A | 29235 | 29251 | CACAGTCCATAATATTG | 34 | 1171 |
| 741082 | N/A | N/A | 29460 | 29476 | TTTTTGTTAATAGTTCT | 73 | 1172 |
| 741083 | N/A | N/A | 29685 | 29701 | GCTTTCTCAGAGCCCAA | 74 | 1173 |
| 741084 | N/A | N/A | 29912 | 29928 | ATCTCTCTACCATGTGA | 34 | 1174 |
| 741085 | N/A | N/A | 30137 | 30153 | GTGGATAAAGTACATTA | 16 | 1175 |
| 741086 | N/A | N/A | 30362 | 30378 | AAATGGTATTCAGAGAT | 42 | 1176 |

TABLE 25

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 55 | 33 |
| 740432 | 270 | 286 | 4721 | 4737 | AGTCCTTTCATGAATAC | 84 | 591 |
| 741087 | N/A | N/A | 30587 | 30603 | TTTTCTCCTAAAGCCTT | 42 | 1177 |
| 741088 | N/A | N/A | 31037 | 31053 | CAGATTTCCAGCACACT | 30 | 1178 |
| 741089 | N/A | N/A | 31262 | 31278 | CCTTCTTAGTGGTAAGA | 0 | 1179 |
| 741090 | N/A | N/A | 31487 | 31503 | AATTACAGTGTAGGTAA | 18 | 1180 |
| 741091 | N/A | N/A | 31712 | 31728 | ATAAGAGGTCACTGGAT | 25 | 1181 |
| 741092 | N/A | N/A | 31937 | 31953 | AAGGAAACAGTCTACAT | 14 | 1182 |
| 741093 | N/A | N/A | 32162 | 32178 | CTATCATGATAAGTATA | 10 | 1183 |
| 741094 | N/A | N/A | 32387 | 32403 | TGTGGTTCTGCCCATCT | 54 | 1184 |
| 741095 | N/A | N/A | 32624 | 32640 | GCCTAAACATTTTACTT | 5 | 1185 |

TABLE 25-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741096 | N/A | N/A | 32858 | 32874 | GAAGTTTCTGAAGAAAT | 40 | 1186 |
| 741097 | N/A | N/A | 33083 | 33099 | TTTTCAGTAGATTTGAC | 24 | 1187 |
| 741098 | N/A | N/A | 33308 | 33324 | GCTATGACCCTCAAGCC | 11 | 1188 |
| 741099 | N/A | N/A | 33533 | 33549 | AATAGAGCAAAATTTCG | 35 | 1189 |
| 741100 | N/A | N/A | 33762 | 33778 | ATAATCAAACAAAAGGG | 16 | 1190 |
| 741101 | N/A | N/A | 33987 | 34003 | AAAGTTCAATGCTGTGT | 69 | 1191 |
| 741102 | N/A | N/A | 34212 | 34228 | GAAATGGGCATGTAAAC | 10 | 1192 |
| 741103 | N/A | N/A | 34443 | 34459 | CAAAATACAATGTTCAA | 15 | 1193 |
| 741104 | N/A | N/A | 34668 | 34684 | ATTCTTCTATCCTAGAA | 5 | 1194 |
| 741105 | N/A | N/A | 34893 | 34909 | ATTATCATGGTTGCCCA | 38 | 1195 |
| 741106 | N/A | N/A | 35118 | 35134 | ATGAGATCTTTTTGCAT | 39 | 1196 |
| 741107 | N/A | N/A | 35343 | 35359 | AAGCAAGTTGTCCATGG | 47 | 1197 |
| 741108 | N/A | N/A | 35568 | 35584 | TGTTGGAGTTTACAATT | 20 | 1198 |
| 741109 | N/A | N/A | 35793 | 35809 | CTCACTAGCCCTGTGAC | 0 | 1199 |
| 741110 | N/A | N/A | 36018 | 36034 | TCTCTTTCATGGGTATT | 57 | 1200 |
| 741111 | N/A | N/A | 36252 | 36268 | GTCATTTTAATAAGTGT | 65 | 1201 |
| 741112 | N/A | N/A | 36484 | 36500 | CAATTAAATAAACCTCT | 10 | 1202 |
| 741113 | N/A | N/A | 36790 | 36806 | TATGGTGATATGGTTAG | 53 | 1203 |
| 741114 | N/A | N/A | 37018 | 37034 | CCATGTGTTTTTGTGGC | 33 | 1204 |
| 741115 | N/A | N/A | 37243 | 37259 | CAAAGGTATAAGGTCAT | 49 | 1205 |
| 741116 | N/A | N/A | 37468 | 37484 | AGCTTGTATTTTTGAAA | 24 | 1206 |
| 741117 | N/A | N/A | 37788 | 37804 | CGCATCTGTCTTTCTTT | 25 | 1207 |
| 741118 | N/A | N/A | 38013 | 38029 | TAGGACAGGTGAAATAA | 12 | 1208 |
| 741119 | N/A | N/A | 38238 | 38254 | AGTTATTAGAATAACAC | 0 | 1209 |
| 741120 | N/A | N/A | 38464 | 38480 | AATAAAATGTCTTAATC | 0 | 1210 |
| 741121 | N/A | N/A | 38691 | 38707 | ACTCAAAAAGAAGAAT | 0 | 1211 |
| 741122 | N/A | N/A | 38916 | 38932 | GTTTTCTCTGTATTGGC | 87 | 1212 |
| 741123 | N/A | N/A | 39141 | 39157 | TGGCCTAGTGGTTATAA | 0 | 1213 |
| 741124 | N/A | N/A | 39366 | 39382 | CACAAAGAGGAAACAGG | 27 | 1214 |
| 741125 | N/A | N/A | 39591 | 39607 | ACATTTTTAACTGGAT | 76 | 1215 |
| 741126 | N/A | N/A | 39816 | 39832 | AGGCTAAATTTTAATAA | 0 | 1216 |
| 741127 | N/A | N/A | 40041 | 40057 | TAGCCTTTCATAGTACG | 38 | 1217 |
| 741128 | N/A | N/A | 40266 | 40282 | AAGAGGAAAAGCTTGGA | 0 | 1218 |
| 741129 | N/A | N/A | 40491 | 40507 | AAAAATTCTGGTGCCAA | 57 | 1219 |
| 741130 | N/A | N/A | 40716 | 40732 | AAGCTAAACTACCGCTG | 2 | 1220 |
| 741131 | N/A | N/A | 40941 | 40957 | GAATTTCCTGGATGCTC | 44 | 1221 |

TABLE 25-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741132 | N/A | N/A | 41130 | 41146 | AGATTCCAGCAGAGATT | 20 | 1222 |
| 741133 | N/A | N/A | 41132 | 41148 | ACAGATTCCAGCAGAGA | 44 | 1223 |
| 741134 | N/A | N/A | 41133 | 41149 | AACAGATTCCAGCAGAG | 40 | 90 |
| 741135 | N/A | N/A | 41134 | 41150 | GAACAGATTCCAGCAGA | 24 | 1224 |
| 741136 | N/A | N/A | 41136 | 41152 | GTGAACAGATTCCAGCA | 34 | 1225 |
| 741137 | N/A | N/A | 41166 | 41182 | ATCTGTAAGAAGTTTAG | 10 | 1226 |
| 741138 | N/A | N/A | 41391 | 41407 | TGAGAAATTTTATGGGT | 47 | 1227 |
| 741139 | N/A | N/A | 41620 | 41636 | TCATTCAAAACCATCCT | 21 | 1228 |
| 741140 | N/A | N/A | 41845 | 41861 | GATCACACTGCTTATAG | 16 | 1229 |
| 741141 | N/A | N/A | 42070 | 42086 | CAAGTTGATGGCATATA | 34 | 1230 |
| 741142 | N/A | N/A | 42295 | 42311 | GTGTACCAACCTCAAGT | 34 | 1231 |
| 741143 | N/A | N/A | 42532 | 42548 | TAAGTAAATACCTAGGG | 20 | 1232 |
| 741144 | N/A | N/A | 42757 | 42773 | GATTTGTGCCTGGCATC | 38 | 1233 |
| 741145 | N/A | N/A | 42835 | 42851 | TGCCTCTACCTCCAGCA | 39 | 1234 |
| 741146 | N/A | N/A | 42837 | 42853 | GATGCCTCTACCTCCAG | 42 | 1235 |
| 741147 | N/A | N/A | 42838 | 42854 | TGATGCCTCTACCTCCA | 40 | 166 |
| 741148 | N/A | N/A | 42839 | 42855 | CTGATGCCTCTACCTCC | 33 | 1236 |
| 741149 | N/A | N/A | 42982 | 42998 | TATCACAACTACATTGT | 0 | 1237 |
| 741150 | N/A | N/A | 43208 | 43224 | GGCCTCCTGCTGCAGCA | 0 | 1238 |
| 741151 | N/A | N/A | 43440 | 43456 | GCACTCATTTTAAATGT | 20 | 1239 |
| 741152 | N/A | N/A | 43665 | 43681 | TGGTAACTTAGGACAAG | 44 | 1240 |
| 741153 | N/A | N/A | 43818 | 43834 | TTCTCTGGACCTCTTAA | 6 | 1241 |
| 741154 | N/A | N/A | 43820 | 43836 | ACTTCTCTGGACCTCTT | 41 | 1242 |
| 741155 | N/A | N/A | 43821 | 43837 | TACTTCTCTGGACCTCT | 49 | 242 |
| 741156 | N/A | N/A | 43822 | 43838 | TTACTTCTCTGGACCTC | 44 | 1243 |
| 741157 | N/A | N/A | 43890 | 43906 | TCAATACAACTTAATTC | 0 | 1244 |
| 741158 | N/A | N/A | 44376 | 44392 | TTGGGCTGGAAGCAGTG | 9 | 1245 |
| 741159 | N/A | N/A | 44601 | 44617 | AAGATATGCAGAGGGTT | 49 | 1246 |
| 741160 | N/A | N/A | 44828 | 44844 | TGGTCTAACTGTGTTGC | 40 | 1247 |
| 741161 | N/A | N/A | 45053 | 45069 | GTTTATGGACTTTTTAA | 29 | 1248 |
| 741162 | N/A | N/A | 45278 | 45294 | TTTTGTACTTTATGGAA | 40 | 1249 |
| 741163 | N/A | N/A | 45503 | 45519 | ACTTCTCCTTCAATTAA | 11 | 1250 |

TABLE 26

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 64 | 33 |
| 740432 | 270 | 286 | 4721 | 4737 | AGTCCTTTCATGAATAC | 82 | 591 |
| 741164 | N/A | N/A | 45728 | 45744 | GTCAAAATATTCTTACT | 30 | 1564 |
| 741165 | N/A | N/A | 45953 | 45969 | CACATAAAATTAAAGCT | 2 | 1565 |
| 741166 | N/A | N/A | 46157 | 46173 | TCCATGAAGCCAAGTAA | 38 | 1566 |
| 741167 | N/A | N/A | 46159 | 46175 | TTTCCATGAAGCCAAGT | 74 | 1567 |
| 741168 | N/A | N/A | 53645 | 53661 | ATTTCCATGAAGCCAAG | 67 | 317 |
|  | N/A | N/A | 46160 | 46176 |  |  |  |
| 741169 | N/A | N/A | 46161 | 46177 | GATTTCCATGAAGCCAA | 84 | 1568 |
| 741170 | N/A | N/A | 46163 | 46179 | GAGATTTCCATGAAGCC | 87 | 1569 |
| 741171 | N/A | N/A | 46178 | 46194 | GGAATTGGAGTGAGAGA | 29 | 1570 |
| 741172 | N/A | N/A | 46403 | 46419 | ATCCCTACATACTCACA | 20 | 1571 |
| 741173 | N/A | N/A | 46628 | 46644 | TTCTACCACCCACAGCT | 0 | 1572 |
| 741174 | N/A | N/A | 46880 | 46896 | GAAAACATTGTATTATT | 39 | 1573 |
| 741175 | N/A | N/A | 47105 | 47121 | CCTTAAAATGATGCCTG | 43 | 1574 |
| 741176 | N/A | N/A | 47330 | 47346 | CTAAAGTTAAGGTGTCG | 25 | 1575 |
| 741177 | N/A | N/A | 47557 | 47573 | GCATGAATTACTTTACG | 40 | 1576 |
| 741178 | N/A | N/A | 47952 | 47968 | GGTTGTTCAAGTGATTC | 58 | 1577 |
| 741179 | N/A | N/A | 48177 | 48193 | GATCTTTTCATCATGCC | 75 | 1578 |
| 741180 | N/A | N/A | 48225 | 48241 | GGTCATGACTCTGACAC | 14 | 1579 |
| 741181 | N/A | N/A | 48227 | 48243 | CTGGTCATGACTCTGAC | 34 | 1580 |
| 741182 | N/A | N/A | 48228 | 48244 | CCTGGTCATGACTCTGA | 39 | 394 |
| 741183 | N/A | N/A | 48229 | 48245 | CCCTGGTCATGACTCTG | 46 | 1581 |
| 741184 | N/A | N/A | 48231 | 48247 | TCCCCTGGTCATGACTC | 35 | 1582 |
| 741185 | N/A | N/A | 48402 | 48418 | AGGGCCATCCTGTTCAA | 9 | 1583 |
| 741186 | N/A | N/A | 48648 | 48664 | AGAATACTTATTTTTG | 14 | 1584 |
| 741187 | N/A | N/A | 48713 | 48729 | ATTTTGGATGCTTCTGA | 56 | 1585 |
| 741188 | N/A | N/A | 48715 | 48731 | GTATTTTGGATGCTTCT | 70 | 1586 |
| 741189 | N/A | N/A | 48716 | 48732 | TGTATTTTGGATGCTTC | 80 | 471 |
| 741190 | N/A | N/A | 48717 | 48733 | TTGTATTTTGGATGCTT | 78 | 1587 |
| 741191 | N/A | N/A | 48719 | 48735 | GTTTGTATTTTGGATGC | 69 | 1588 |
| 741192 | N/A | N/A | 48873 | 48889 | TTTAAAGATGGATATTG | 0 | 1589 |
| 741193 | N/A | N/A | 49111 | 49127 | TAAGGTCCCTCCCTCAA | 0 | 1590 |
| 741194 | N/A | N/A | 49373 | 49389 | TTACCTGGCTACCTTTT | 31 | 1591 |
| 741195 | N/A | N/A | 49480 | 49496 | TGAAATTTTCCAGCTAT | 60 | 1592 |
| 741196 | N/A | N/A | 80992 | 81008 | TTGAAATTTTCCAGCTA | 37 | 167 |
|  | N/A | N/A | 49481 | 49497 |  |  |  |
| 741197 | N/A | N/A | 49482 | 49498 | ATTGAAATTTTCCAGCT | 60 | 1593 |

TABLE 26-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741198 | N/A | N/A | 49484 | 49500 | TGATTGAAATTTTCCAG | 33 | 1594 |
| 741199 | N/A | N/A | 49598 | 49614 | TGGGAATCACCTCCCCT | 14 | 1595 |
| 741200 | N/A | N/A | 49825 | 49841 | CATTGAATTAATTTGTT | 30 | 1596 |
| 741201 | N/A | N/A | 50050 | 50066 | CACCATTTTATAGCATG | 64 | 1597 |
| 741202 | N/A | N/A | 50275 | 50291 | TGGAAAGAGGTATGAGT | 0 | 1598 |
| 741203 | N/A | N/A | 50500 | 50516 | ATTAAAATGAGAGGTCC | 18 | 1599 |
| 741204 | N/A | N/A | 50725 | 50741 | TTCCACCACACAAGTTA | 43 | 1600 |
| 741205 | N/A | N/A | 50920 | 50936 | TTCATCAATATCTGCAA | 66 | 1601 |
| 741206 | N/A | N/A | 50921 | 50937 | TTTCATCAATATCTGCA | 85 | 243 |
| 741207 | N/A | N/A | 50922 | 50938 | TTTTCATCAATATCTGC | 86 | 1602 |
| 741208 | N/A | N/A | 50924 | 50940 | GGTTTTCATCAATATCT | 76 | 1603 |
| 741209 | N/A | N/A | 50950 | 50966 | CTTTGATGAATTAAGAG | 22 | 1604 |
| 741210 | N/A | N/A | 51175 | 51191 | AGGTATAAGATTCCTGC | 31 | 1605 |
| 741211 | N/A | N/A | 51412 | 51428 | ACAAGGCCTTACTTACG | 9 | 1606 |
| 741212 | N/A | N/A | 51637 | 51653 | CTGCCCAACTTACAATT | 9 | 1607 |
| 741213 | N/A | N/A | 51868 | 51884 | CATGGCAAGAACAAGGG | 27 | 1608 |
| 741214 | N/A | N/A | 52093 | 52109 | TATTATGTGCTTATTGG | 56 | 1609 |
| 741215 | N/A | N/A | 52318 | 52334 | CCTAACACATGGATGTA | 5 | 1610 |
| 741216 | N/A | N/A | 52417 | 52433 | CAAATGTATAGAGAAGT | 15 | 1611 |
| 741217 | N/A | N/A | 52419 | 52435 | ATCAAATGTATAGAGAA | 41 | 1612 |
| 741218 | N/A | N/A | 52420 | 52436 | GATCAAATGTATAGAGA | 36 | 395 |
| 741219 | N/A | N/A | 52421 | 52437 | AGATCAAATGTATAGAG | 31 | 1613 |
| 741220 | N/A | N/A | 52423 | 52439 | ACAGATCAAATGTATAG | 55 | 1614 |
| 741221 | N/A | N/A | 52543 | 52559 | CTCTACTGTGTTTGAGC | 14 | 1615 |
| 741222 | N/A | N/A | 52768 | 52784 | CTATATACTACAATTTT | 7 | 1616 |
| 741223 | N/A | N/A | 52993 | 53009 | TGAGCTCACTGACAGAA | 13 | 1617 |
| 741224 | N/A | N/A | 53239 | 53255 | CAAGTATAAATATGTTT | 10 | 1618 |
| 741225 | N/A | N/A | 53464 | 53480 | CCAAGGAGCATTTGGAT | 7 | 1619 |
| 741226 | N/A | N/A | 53642 | 53658 | TCCATGAAGCCAAGATC | 52 | 1620 |
| 741227 | N/A | N/A | 53644 | 53660 | TTTCCATGAAGCCAAGA | 65 | 1621 |
| 741228 | N/A | N/A | 53646 | 53662 | TATTTCCATGAAGCCAA | 79 | 1622 |
| 741229 | N/A | N/A | 53648 | 53664 | ATTATTTCCATGAAGCC | 81 | 1623 |
| 741230 | N/A | N/A | 53689 | 53705 | ATCCATAAATGCTTTGT | 68 | 1624 |
| 741231 | N/A | N/A | 53914 | 53930 | TATCTTCATCATAGCTC | 60 | 1625 |
| 741232 | N/A | N/A | 54139 | 54155 | AGACCACACTCCAACTA | 20 | 1626 |
| 741233 | N/A | N/A | 54364 | 54380 | ATGTAAGGATGATCATT | 32 | 1627 |

TABLE 26-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741234 | N/A | N/A | 54589 | 54605 | TGACTTTATATGCATTT | 54 | 1628 |
| 741235 | N/A | N/A | 54814 | 54830 | CATATATACTTACTTAC | 2 | 1629 |
| 741236 | N/A | N/A | 55039 | 55055 | ATATGTTTGATCGAAAG | 20 | 1630 |
| 741237 | N/A | N/A | 55269 | 55285 | CAGATGGTTTTTCTTT | 31 | 1631 |
| 741238 | N/A | N/A | 55494 | 55510 | ACAAAAGGGATTGTTCT | 8 | 1632 |
| 741239 | N/A | N/A | 55719 | 55735 | ACTTGACTATAACACTT | 40 | 1633 |
| 741240 | N/A | N/A | 56172 | 56188 | ATAGAAAACAGATGAAG | 2 | 1634 |

TABLE 27

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 57 | 33 |
| 740432 | 270 | 286 | 4721 | 4737 | AGTCCTTTCATGAATAC | 87 | 591 |
| 741241 | N/A | N/A | 56397 | 56413 | AAAATTTTTGCACACTT | 46 | 1251 |
| 741242 | N/A | N/A | 56622 | 56638 | GCCAAATCAATGGATGA | 33 | 1252 |
| 741243 | N/A | N/A | 56847 | 56863 | AGTGACCAAGAGAATGA | 4 | 1253 |
| 741244 | N/A | N/A | 57072 | 57088 | TTTTAAAACACTGGCCT | 0 | 1254 |
| 741245 | N/A | N/A | 57297 | 57313 | TAGGATTAAACAGTCCA | 0 | 1255 |
| 741246 | N/A | N/A | 57522 | 57538 | TTATCTGTTGCTATGTG | 51 | 1256 |
| 741247 | N/A | N/A | 57747 | 57763 | AAGAAGGAGAATAGCAG | 14 | 1257 |
| 741248 | N/A | N/A | 57981 | 57997 | CGGGCAAACATGTTTTG | 8 | 1258 |
| 741249 | N/A | N/A | 58206 | 58222 | ATGACCTACATGCTAAA | 11 | 1259 |
| 741250 | N/A | N/A | 58431 | 58447 | AGAAGCAAAATGTCAGT | 40 | 1260 |
| 741251 | N/A | N/A | 58656 | 58672 | CCTAACAGCTTTACTTT | 0 | 1261 |
| 741252 | N/A | N/A | 58881 | 58897 | CTTTCACACATCTCTAA | 0 | 1262 |
| 741253 | N/A | N/A | 58991 | 59007 | TTTCATTAATCTGTGAA | 14 | 1263 |
| 741254 | N/A | N/A | 58992 | 59008 | ATTTCATTAATCTGTGA | 20 | 169 |
| 741255 | N/A | N/A | 58993 | 59009 | TATTTCATTAATCTGTG | 39 | 1264 |
| 741256 | N/A | N/A | 58995 | 59011 | TATATTTCATTAATCTG | 27 | 1265 |
| 741257 | N/A | N/A | 59106 | 59122 | CCTTACACAAAATATAA | 0 | 1266 |
| 741258 | N/A | N/A | 59354 | 59370 | ACACCAATATATTATTT | 13 | 1267 |
| 741259 | N/A | N/A | 59594 | 59610 | TAAAGGATGCAAAGGCA | 0 | 1268 |
| 741260 | N/A | N/A | 59948 | 59964 | TTCCAGCGATCCCACTC | 21 | 1269 |
| 741261 | N/A | N/A | 60173 | 60189 | CTCAACATCTTTAATGA | 6 | 1270 |
| 741262 | N/A | N/A | 60421 | 60437 | GGGACCTAAAACTATAA | 0 | 1271 |

TABLE 27-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741263 | N/A | N/A | 60758 | 60774 | AGCAGAATAGAAAATCC | 14 | 1272 |
| 741264 | N/A | N/A | 60983 | 60999 | TTCAATGCGACTCCCAT | 23 | 1273 |
| 741265 | N/A | N/A | 61216 | 61232 | CAACAAAACTGAGAATC | 0 | 1274 |
| 741266 | N/A | N/A | 61474 | 61490 | AATGCCTGCTTTCACCA | 26 | 1275 |
| 741267 | N/A | N/A | 61699 | 61715 | TATAAGCAGGAGTAAAA | 2 | 1276 |
| 741268 | N/A | N/A | 61969 | 61985 | GTTCCAAAGATAGAGA | 11 | 1277 |
| 741269 | N/A | N/A | 62200 | 62216 | CGTACACAAACTAGAAA | 1 | 1278 |
| 741270 | N/A | N/A | 62492 | 62508 | TACTGTTGCATTCCAGC | 6 | 1279 |
| 741271 | N/A | N/A | 62729 | 62745 | TCTTAGTGTGGTGGCTC | 15 | 1280 |
| 741272 | N/A | N/A | 62955 | 62971 | TCAACAATAATAATGAC | 0 | 1281 |
| 741273 | N/A | N/A | 63197 | 63213 | CCTTTTCATCAACACAT | 12 | 1282 |
| 741274 | N/A | N/A | 63422 | 63438 | TATGCATCTAACACTTG | 8 | 1283 |
| 741275 | N/A | N/A | 63666 | 63682 | CCATCAACCAAGTATCT | 0 | 1284 |
| 741276 | N/A | N/A | 63891 | 63907 | CTTGAAACAGTAACTTG | 0 | 1285 |
| 741277 | N/A | N/A | 64116 | 64132 | AACATAGCAGATTAATA | 12 | 1286 |
| 741278 | N/A | N/A | 64349 | 64365 | TCATGTTATATAGTGGG | 73 | 1287 |
| 741279 | N/A | N/A | 64574 | 64590 | TGTAACCTAATGTAAAT | 0 | 1288 |
| 741280 | N/A | N/A | 64799 | 64815 | ACAAGTATCTGTACTCA | 59 | 1289 |
| 741281 | N/A | N/A | 65024 | 65040 | GTCTCTGTTAATGTTGG | 26 | 1290 |
| 741282 | N/A | N/A | 65249 | 65265 | GAACCAGCCTGACTTAA | 21 | 1291 |
| 741283 | N/A | N/A | 65474 | 65490 | TTGTATGGGTTACATAA | 3 | 1292 |
| 741284 | N/A | N/A | 65801 | 65817 | CAATTAAATGCAATTCC | 0 | 1293 |
| 741285 | N/A | N/A | 66026 | 66042 | TGACAGAAGTGTGCATA | 14 | 1294 |
| 741286 | N/A | N/A | 66251 | 66267 | CAACACATCCACATTGC | 8 | 1295 |
| 741287 | N/A | N/A | 66476 | 66492 | TTCACACCTCTCTCCCT | 0 | 1296 |
| 741288 | N/A | N/A | 66701 | 66717 | TGCTGGTCTAAGATGCA | 24 | 1297 |
| 741289 | N/A | N/A | 66926 | 66942 | ATGTGTTTGAGGAAAA | 13 | 1298 |
| 741290 | N/A | N/A | 67151 | 67167 | CAGAAGTAAATGTGGAC | 24 | 1299 |
| 741291 | N/A | N/A | 67376 | 67392 | TGATTCTTTGGATTCAT | 27 | 1300 |
| 741292 | N/A | N/A | 67876 | 67892 | CATTCTTGTTTTTATTC | 37 | 1301 |
| 741293 | N/A | N/A | 68101 | 68117 | AATAGTGTCCCAGTGTA | 40 | 1302 |
| 741294 | N/A | N/A | 68326 | 68342 | TGAAAGCTGTTCAGTTA | 12 | 1303 |
| 741295 | N/A | N/A | 68551 | 68567 | CCCACATATACTACTTG | 32 | 1304 |
| 741296 | N/A | N/A | 68776 | 68792 | AGAATTTCAGGAAGTTA | 33 | 1305 |
| 741297 | N/A | N/A | 68798 | 68814 | CAAAGTAAGAGGAGATT | 13 | 1306 |
| 741298 | N/A | N/A | 68800 | 68816 | GCCAAAGTAAGAGGAGA | 37 | 1307 |

TABLE 27-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741299 | N/A | N/A | 68801 | 68817 | TGCCAAAGTAAGAGGAG | 11 | 397 |
| 741300 | N/A | N/A | 68804 | 68820 | CAGTGCCAAAGTAAGAG | 0 | 1308 |
| 741301 | N/A | N/A | 69001 | 69017 | TGAATCCATTTGTCCAG | 52 | 1309 |
| 741302 | N/A | N/A | 69227 | 69243 | CTCTAAAATACAAATGT | 13 | 1310 |
| 741303 | N/A | N/A | 69452 | 69468 | GAACAAAGGAATAAGTA | 0 | 1311 |
| 741304 | N/A | N/A | 69677 | 69693 | CTAGATGTAGATATCAT | 13 | 1312 |
| 741305 | N/A | N/A | 69902 | 69918 | AAGGGAATAAATTGTAG | 28 | 1313 |
| 741306 | N/A | N/A | 70127 | 70143 | CAACAGACCCTTTCAAT | 3 | 1314 |
| 741307 | N/A | N/A | 70352 | 70368 | GTCTTCCCACTGCCTAC | 7 | 1315 |
| 741308 | N/A | N/A | 70577 | 70593 | TTTAGATATACCTCCAA | 37 | 1316 |
| 741309 | N/A | N/A | 70880 | 70896 | GCTTCAGTTTCTTGAGT | 18 | 1317 |
| 741310 | N/A | N/A | 71105 | 71121 | CTGGTCTTTCTCACAAT | 8 | 1318 |
| 741311 | N/A | N/A | 71375 | 71391 | ATCATTCTTAACAGAAA | 15 | 1319 |
| 741312 | N/A | N/A | 71600 | 71616 | GCTCTTGCTGTGCAGCC | 11 | 1320 |
| 741313 | N/A | N/A | 71844 | 71860 | ATTTAAAGCAGCAGTCC | 4 | 1321 |
| 741314 | N/A | N/A | 72076 | 72092 | AGGTAATTCTAATTTTA | 17 | 1322 |
| 741315 | N/A | N/A | 72301 | 72317 | GGCAAATGACAGGGTCT | 69 | 1323 |
| 741316 | N/A | N/A | 72632 | 72648 | TCTCAACTGCCTGAGTA | 0 | 1324 |
| 741317 | N/A | N/A | 72857 | 72873 | CATGTCAGCTTTTAGT | 19 | 1325 |

TABLE 28

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 57 | 33 |
| 740432 | 270 | 286 | 4721 | 4737 | AGTCCTTTCATGAATAC | 85 | 591 |
| 741318 | N/A | N/A | 73090 | 73106 | ATACTCAGATATTTAAA | 0 | 1326 |
| 741319 | N/A | N/A | 73188 | 73204 | ACTTTCTGTGTGGTATG | 42 | 1327 |
| 741320 | N/A | N/A | 73190 | 73206 | AGACTTTCTGTGTGGTA | 59 | 1328 |
| 741321 | N/A | N/A | 73191 | 73207 | CAGACTTTCTGTGTGGT | 83 | 170 |
| 741322 | N/A | N/A | 73192 | 73208 | ACAGACTTTCTGTGTGG | 37 | 1329 |
| 741323 | N/A | N/A | 73194 | 73210 | AGACAGACTTTCTGTGT | 0 | 1330 |
| 741324 | N/A | N/A | 73315 | 73331 | GTTGAGAATTTTTCATT | 14 | 1331 |
| 741325 | N/A | N/A | 73540 | 73556 | AGTTATGGAGCATCTTT | 46 | 1332 |
| 741326 | N/A | N/A | 73765 | 73781 | GACTGAGTTTTTATTC | 16 | 1333 |
| 741327 | N/A | N/A | 73990 | 74006 | TCCTGAATTAAAAATTT | 0 | 1334 |

TABLE 28-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741328 | N/A | N/A | 74215 | 74231 | GCTAAGCACAAACAATT | 15 | 1335 |
| 741329 | N/A | N/A | 74292 | 74308 | GAACTCTGTAGTCAGAA | 58 | 1336 |
| 741330 | N/A | N/A | 74294 | 74310 | TAGAACTCTGTAGTCAG | 63 | 1337 |
| 741331 | N/A | N/A | 74295 | 74311 | ATAGAACTCTGTAGTCA | 42 | 398 |
| 741332 | N/A | N/A | 74296 | 74312 | AATAGAACTCTGTAGTC | 42 | 1338 |
| 741333 | N/A | N/A | 74298 | 74314 | TGAATAGAACTCTGTAG | 25 | 1339 |
| 741334 | N/A | N/A | 74440 | 74456 | ACACAGAGCACTTCTTA | 15 | 1340 |
| 741335 | N/A | N/A | 74665 | 74681 | GGAGTTACAGAGTTGCC | 64 | 1341 |
| 741336 | N/A | N/A | 74890 | 74906 | TATCAGTCTATTAAGAA | 11 | 1342 |
| 741337 | N/A | N/A | 75115 | 75131 | AAGTTTCTCAGAGCCTG | 24 | 1343 |
| 741338 | N/A | N/A | 75340 | 75356 | AATACAGAAGTCTATTC | 0 | 1344 |
| 741339 | N/A | N/A | 75573 | 75589 | CATTGAATAAAAATTTG | 0 | 1345 |
| 741340 | N/A | N/A | 75945 | 75961 | CAGGTATAAAATTTTTT | 2 | 1346 |
| 741341 | N/A | N/A | 76170 | 76186 | GGTGTTAATCACTTGAA | 18 | 1347 |
| 741342 | N/A | N/A | 76398 | 76414 | TCTTGAAGCTAGTTGGG | 39 | 1348 |
| 741343 | N/A | N/A | 76623 | 76639 | AGGGCAACTAACCAACA | 20 | 1349 |
| 741344 | N/A | N/A | 76848 | 76864 | GTGGATACTTAGTATCA | 13 | 1350 |
| 741345 | N/A | N/A | 77073 | 77089 | CTCTCTCAGTTGTAGGT | 19 | 1351 |
| 741346 | N/A | N/A | 77298 | 77314 | AAAGTATGCTGTGTTCT | 46 | 1352 |
| 741347 | N/A | N/A | 77523 | 77539 | GTACCCGGCACTTTTCC | 15 | 1353 |
| 741348 | N/A | N/A | 77663 | 77679 | TCTAGAAAAGCTCTCTT | 0 | 1354 |
| 741349 | N/A | N/A | 77665 | 77681 | ACTCTAGAAAGCTCTC | 13 | 1355 |
| 741350 | N/A | N/A | 77666 | 77682 | GACTCTAGAAAAGCTCT | 36 | 247 |
| 741351 | N/A | N/A | 77667 | 77683 | AGACTCTAGAAAAGCTC | 26 | 1356 |
| 741352 | N/A | N/A | 77748 | 77764 | TGGCACCCAGGAGTAAG | 8 | 1357 |
| 741353 | N/A | N/A | 77973 | 77989 | CATACACAAAATCCCCT | 28 | 1358 |
| 741354 | N/A | N/A | 78198 | 78214 | CACATGAAGCCAGGGAC | 19 | 1359 |
| 741355 | N/A | N/A | 78423 | 78439 | GCAGGCCCTAAACTGTG | 5 | 1360 |
| 741356 | N/A | N/A | 78648 | 78664 | AAATTTATCTATCATGC | 30 | 1361 |
| 741357 | N/A | N/A | 78873 | 78889 | GCTAAACACTTTATCAA | 22 | 1362 |
| 741358 | N/A | N/A | 79098 | 79114 | ACTTCATTCTTTCTGTT | 30 | 1363 |
| 741359 | N/A | N/A | 79323 | 79339 | CAATTAAAAGATTACTT | 0 | 1364 |
| 741360 | N/A | N/A | 79548 | 79564 | ACATTGTACAGTTAATT | 9 | 1365 |
| 741361 | N/A | N/A | 79773 | 79789 | TACAAACCTTACTATGC | 9 | 1366 |
| 741362 | N/A | N/A | 79998 | 80014 | AACAGACTTAAACAAAC | 40 | 1367 |
| 741363 | N/A | N/A | 80223 | 80239 | CTCAGACATCATGTTTT | 52 | 1368 |

TABLE 28-continued

Percent reduction of human SNCA mRNA with 4-9-4 MOE and cEt gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 741364 | N/A | N/A | 80448 | 80464 | AGGCACTCACAAACATT | 33 | 1369 |
| 741365 | N/A | N/A | 80673 | 80689 | TCTCGCATCCTAAATGT | 0 | 1370 |
| 741366 | N/A | N/A | 80898 | 80914 | TTCATATTTTATGTTAC | 23 | 1371 |
| 741367 | N/A | N/A | 80991 | 81007 | TGAAATTTTCCAGCTAA | 52 | 1372 |
| 741368 | N/A | N/A | 80993 | 81009 | CTTGAAATTTTCCAGCT | 72 | 1373 |
| 741369 | N/A | N/A | 80995 | 81011 | ATCTTGAAATTTTCCAG | 33 | 1374 |
| 741370 | N/A | N/A | 81123 | 81139 | CTATAATTACATTCCTA | 9 | 1375 |
| 741371 | N/A | N/A | 81348 | 81364 | GCATGAACCTAGATATG | 4 | 1376 |
| 741372 | N/A | N/A | 81472 | 81488 | GCTGTTTGAAGTGACAA | 21 | 1377 |
| 741373 | N/A | N/A | 81474 | 81490 | GAGCTGTTTGAAGTGAC | 54 | 1378 |
| 741374 | N/A | N/A | 81475 | 81491 | AGAGCTGTTTGAAGTGA | 52 | 249 |
| 741375 | N/A | N/A | 81476 | 81492 | GAGAGCTGTTTGAAGTG | 22 | 1379 |
| 741376 | N/A | N/A | 81478 | 81494 | TGGAGAGCTGTTTGAAG | 12 | 1380 |
| 741377 | N/A | N/A | 81575 | 81591 | CTGCCACTATTCACAAT | 27 | 1381 |
| 741378 | N/A | N/A | 81800 | 81816 | TTATTGCATTAATGGAA | 76 | 1382 |
| 741379 | N/A | N/A | 82107 | 82123 | ATGGTGTTAGCTAGGAT | 84 | 1383 |
| 741380 | N/A | N/A | 82332 | 82348 | GTCTTTTTACATTATAA | 31 | 1384 |
| 741381 | N/A | N/A | 82557 | 82573 | ATAACCACTATTCAATG | 2 | 1385 |
| 741382 | N/A | N/A | 82783 | 82799 | AAAAATCACATTTGGCA | 48 | 1386 |
| 741383 | N/A | N/A | 83008 | 83024 | TTCTTTCACCTTATGAG | 21 | 1387 |
| 741384 | N/A | N/A | 83233 | 83249 | ATATATGTGTCAGTTCT | 22 | 1388 |
| 741385 | N/A | N/A | 83458 | 83474 | GTGTCACTTTTTAAGGT | 18 | 1389 |
| 741386 | N/A | N/A | 83528 | 83544 | AGAACAATGTCATCTTT | 43 | 1390 |
| 741387 | N/A | N/A | 83530 | 83546 | AAAGAACAATGTCATCT | 42 | 1391 |
| 741388 | N/A | N/A | 83531 | 83547 | GAAAGAACAATGTCATC | 25 | 98 |
| 741389 | N/A | N/A | 83532 | 83548 | GGAAAGAACAATGTCAT | 27 | 1392 |
| 741390 | N/A | N/A | 83534 | 83550 | CAGGAAAGAACAATGTC | 47 | 1393 |
| 741391 | N/A | N/A | 83683 | 83699 | CACAGGTATACACACTT | 42 | 1394 |
| 741392 | N/A | N/A | 83908 | 83924 | GTACAAAATCTGCATAT | 3 | 1395 |
| 741393 | N/A | N/A | 84133 | 84149 | ATAGGTATTTTATGCAT | 58 | 1396 |
| 741394 | N/A | N/A | 84616 | 84632 | CAAATTATGCATTTGTT | 0 | 1397 |

Example 5: Effect of 5-10-5 MOE Gapmers with Mixed Internucleoside Linkages on Human SNCA In Vitro, Single Dose Modified oligonucleotides complementary to a human SNCA nucleic acid were designed and tested for their effect on SNCA mRNA in vitro. The modified oligonucleotides were tested in a series of experiments that had similar culture conditions.

Cultured SH-SY5Y cells at a density of 20,000 cells per well were transfected using electroporation with 4,000 nM concentration of modified oligonucleotide or no modified oligonucleotide for untreated controls. After approximately 24 hours, RNA was isolated from the cells and SNCA mRNA levels were measured by quantitative real-time PCR using human primer probe set RTS2621 as described in Example 1. SNCA mRNA levels were adjusted according to total RNA content, as measured by RIBOGREEN®. Results are presented in the tables below as percent reduction of the amount of SNCA mRNA, relative to untreated control cells.

The modified oligonucleotides in tables 29-44 are 5-10-5 MOE gapmers. The gapmers are 20 nucleobases in length, wherein the central gap segment comprises ten 2'-deoxynucleosides and is flanked by wing segments on both the 5' end on the 3' end, each comprising five 2'-MOE nucleosides. The sugar motif for the gapmers is (from 5' to 3'): eeeeedddddddddeeeee; wherein 'd' represents a 2'-deoxyribose sugar and 'e' represents a 2'-MOE modified sugar. All cytosine residues throughout each gapmer are 5-methyl cytosines. The internucleoside linkages are mixed phosphodiester and phosphorothioate linkages. The internucleoside linkage motif for the gapmers is (from 5' to 3'): sooosssssssssssooss; wherein 'o' represents a phosphodiester internucleoside linkage and 's' represents a phosphorothioate internucleoside linkage. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the Tables below is complementary to human SNCA nucleic acid sequences SEQ ID NO: 1 or SEQ ID NO:2, as indicated. 'N/A' indicates that the modified oligonucleotide is not complementary to that particular nucleic acid with 100% complementarity. A value of 0% reduction indicates that the compound had no effect or increased mRNA concentrations in the cell. As shown below, modified oligonucleotides complementary to human SNCA reduced the amount of human SNCA mRNA.

TABLE 29

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 693413 | 19 | 38 | 4687 | 4706 | AATTCCTTTACACCACACTG | 53 | 28 |
| 693416 | 39 | 58 | 4707 | 4726 | GAATACATCCATGGCTAATG | 38 | 29 |
| 740410 | 240 | 256 | 4691 | 4707 | GAATTCCTTTACACCAC | 72 | 33 |
| 741410 | N/A | N/A | 87946 | 87962 | GTAAGTTGTGACCATGC | 64 | 402 |
| 762833 | 233 | 252 | N/A | N/A | TCCTTTACACCACACTGTCG | 50 | 1635 |
| 762834 | 234 | 253 | N/A | N/A | TTCCTTTACACCACACTGTC | 49 | 1636 |
| 762835 | 235 | 254 | N/A | N/A | ATTCCTTTACACCACACTGT | 39 | 1637 |
| 762836 | 237 | 256 | 4688 | 4707 | GAATTCCTTTACACCACACT | 50 | 1638 |
| 762837 | 238 | 257 | 4689 | 4708 | TGAATTCCTTTACACCACAC | 45 | 1639 |
| 762838 | 239 | 258 | 4690 | 4709 | ATGAATTCCTTTACACCACA | 47 | 1640 |
| 762839 | 240 | 259 | 4691 | 4710 | AATGAATTCCTTTACACCAC | 51 | 1641 |
| 762840 | 241 | 260 | 4692 | 4711 | TAATGAATTCCTTTACACCA | 41 | 1642 |
| 762841 | 242 | 261 | 4693 | 4712 | CTAATGAATTCCTTTACACC | 44 | 1643 |
| 762842 | 243 | 262 | 4694 | 4713 | GCTAATGAATTCCTTTACAC | 51 | 1644 |
| 762843 | 244 | 263 | 4695 | 4714 | GGCTAATGAATTCCTTTACA | 50 | 1645 |
| 762844 | 252 | 271 | 4703 | 4722 | ACATCCATGGCTAATGAATT | 45 | 1646 |
| 762845 | 253 | 272 | 4704 | 4723 | TACATCCATGGCTAATGAAT | 32 | 1647 |
| 762846 | 254 | 273 | 4705 | 4724 | ATACATCCATGGCTAATGAA | 34 | 1648 |
| 762847 | 255 | 274 | 4706 | 4725 | AATACATCCATGGCTAATGA | 32 | 1649 |
| 762848 | 257 | 276 | 4708 | 4727 | TGAATACATCCATGGCTAAT | 47 | 1650 |
| 762849 | 258 | 277 | 4709 | 4728 | ATGAATACATCCATGGCTAA | 43 | 1651 |

TABLE 29-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 762850 | 259 | 278 | 4710 | 4729 | CATGAATACATCCATGGCTA | 41 | 1652 |
| 762851 | 260 | 279 | 4711 | 4730 | TCATGAATACATCCATGGCT | 61 | 1653 |
| 762852 | 261 | 280 | 4712 | 4731 | TTCATGAATACATCCATGGC | 48 | 1654 |
| 762853 | 262 | 281 | 4713 | 4732 | TTTCATGAATACATCCATGG | 42 | 1655 |
| 762854 | 263 | 282 | 4714 | 4733 | CTTTCATGAATACATCCATG | 56 | 1656 |
| 762855 | 265 | 284 | 4716 | 4735 | TCCTTTCATGAATACATCCA | 61 | 1657 |
| 762856 | 49 | 68 | 4717 | 4736 | GTCCTTTCATGAATACATCC | 52 | 1658 |
| 762857 | 267 | 286 | 4718 | 4737 | AGTCCTTTCATGAATACATC | 38 | 1659 |
| 762858 | 268 | 287 | 4719 | 4738 | AAGTCCTTTCATGAATACAT | 60 | 1660 |
| 762859 | 269 | 288 | 4720 | 4739 | AAAGTCCTTTCATGAATACA | 51 | 1661 |
| 762860 | 270 | 289 | 4721 | 4740 | GAAAGTCCTTTCATGAATAC | 55 | 1662 |
| 762861 | 271 | 290 | 4722 | 4741 | TGAAAGTCCTTTCATGAATA | 44 | 1663 |
| 762862 | 272 | 291 | 4723 | 4742 | TTGAAAGTCCTTTCATGAAT | 34 | 1664 |
| 762863 | 56 | 75 | 4724 | 4743 | TTTGAAAGTCCTTTCATGAA | 28 | 1665 |
| 762864 | 432 | 451 | 17999 | 18018 | ACTTGCTCTTTGGTCTTCTC | 36 | 1666 |
| 762865 | 433 | 452 | 18000 | 18019 | CACTTGCTCTTTGGTCTTCT | 36 | 1667 |
| 762866 | 434 | 453 | 18001 | 18020 | TCACTTGCTCTTTGGTCTTC | 40 | 1668 |
| 762867 | 435 | 454 | 18002 | 18021 | GTCACTTGCTCTTTGGTCTT | 50 | 1669 |
| 762868 | 436 | 455 | 18003 | 18022 | TGTCACTTGCTCTTTGGTCT | 45 | 1670 |
| 762869 | 437 | 456 | 18004 | 18023 | TTGTCACTTGCTCTTTGGTC | 36 | 1671 |
| 762870 | 438 | 457 | 18005 | 18024 | TTTGTCACTTGCTCTTTGGT | 28 | 1672 |
| 762871 | 439 | 458 | 18006 | 18025 | ATTTGTCACTTGCTCTTTGG | 34 | 1673 |
| 762872 | 440 | 459 | 18007 | 18026 | CATTTGTCACTTGCTCTTTG | 41 | 1674 |
| 762873 | 441 | 460 | 18008 | 18027 | ACATTTGTCACTTGCTCTTT | 7 | 1675 |
| 762874 | 442 | 461 | 18009 | 18028 | AACATTTGTCACTTGCTCTT | 22 | 1676 |
| 762875 | N/A | N/A | 4681 | 4700 | TTTACACCACACTGGAAAAC | 13 | 1677 |
| 762876 | N/A | N/A | 4682 | 4701 | CTTTACACCACACTGGAAAA | 22 | 1678 |
| 762877 | N/A | N/A | 4683 | 4702 | CCTTTACACCACACTGGAAA | 44 | 1679 |
| 762878 | N/A | N/A | 4684 | 4703 | TCCTTTACACCACACTGGAA | 44 | 1680 |
| 762879 | N/A | N/A | 4685 | 4704 | TTCCTTTACACCACACTGGA | 45 | 1681 |
| 762880 | N/A | N/A | 4686 | 4705 | ATTCCTTTACACCACACTGG | 59 | 1682 |
| 762881 | N/A | N/A | 18150 | 18169 | TATAAATGTAACACAAAACG | 0 | 1683 |
| 762882 | N/A | N/A | 18255 | 18274 | GTAGCACTTTTTCACAAGGG | 67 | 1684 |
| 762883 | N/A | N/A | 18349 | 18368 | CTTTCTTCCAGAAATTGAAA | 49 | 1685 |
| 762884 | N/A | N/A | 18442 | 18461 | AAATTCCAAGACTTACAATT | 28 | 1686 |
| 762885 | N/A | N/A | 18535 | 18554 | AGAGATGATGTCACTATAAA | 50 | 1687 |

TABLE 29-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 762886 | N/A | N/A | 18628 | 18647 | TCTCTGGTTGGTATGTATTT | 62 | 1688 |
| 762887 | N/A | N/A | 18721 | 18740 | TATCTTTGGTATAATCTTAT | 41 | 1689 |
| 762888 | N/A | N/A | 18814 | 18833 | TTATTTTGCTGTTGTAGTGG | 35 | 1690 |
| 762889 | N/A | N/A | 18907 | 18926 | GGCAGGCCTCCCCAAGAACG | 35 | 1691 |
| 762890 | N/A | N/A | 19176 | 19195 | GGCAAAGAAAGGAAAAAGAA | 5 | 1692 |
| 762891 | N/A | N/A | 19269 | 19288 | ATGGTGCCTACATTCTAGAA | 69 | 1693 |
| 762892 | N/A | N/A | 19368 | 19387 | CTTAATTTAATAAATGTTTG | 7 | 1694 |
| 762893 | N/A | N/A | 19461 | 19480 | TTGGATAGCTGAATAGCACT | 58 | 1695 |
| 762894 | N/A | N/A | 19556 | 19575 | TGAAGTGGAAACAACCCAGA | 46 | 1696 |
| 762895 | N/A | N/A | 19627 | 19646 | ATTTTGTTCTGCCTTTTTA | 39 | 1697 |
| 762896 | N/A | N/A | 19628 | 19647 | TATTTTGTTCTGCCTTTTT | 49 | 1698 |
| 762897 | N/A | N/A | 19629 | 19648 | ATATTTTGTTCTGCCTTTT | 34 | 1699 |
| 762898 | N/A | N/A | 19630 | 19649 | GATATTTTGTTCTGCCTTT | 57 | 1700 |
| 762899 | N/A | N/A | 19631 | 19650 | AGATATTTTGTTCTGCCTT | 60 | 1701 |
| 762900 | N/A | N/A | 19632 | 19651 | CAGATATTTTGTTCTGCCT | 74 | 1702 |
| 762901 | N/A | N/A | 19633 | 19652 | ACAGATATTTTGTTCTGCC | 70 | 1703 |
| 762902 | N/A | N/A | 19634 | 19653 | CACAGATATTTTGTTCTGC | 48 | 1704 |
| 762903 | N/A | N/A | 19635 | 19654 | TCACAGATATTTTGTTCTG | 58 | 1705 |
| 762904 | N/A | N/A | 19636 | 19655 | ATCACAGATATTTTGTTCT | 55 | 1706 |
| 762905 | N/A | N/A | 19637 | 19656 | TATCACAGATATTTTGTTC | 56 | 1707 |
| 762906 | N/A | N/A | 19649 | 19668 | TAAATCTAAATATATCACAG | 15 | 1708 |
| 762907 | N/A | N/A | 19742 | 19761 | AACATTAGCTGAAGAACTTC | 36 | 1709 |
| 762908 | N/A | N/A | 19835 | 19854 | AACCAGGAATTAATATAATT | 33 | 1710 |

TABLE 30

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 60 | 33 |
| 741410 | N/A | N/A | 87946 | 87962 | GTAAGTTGTGACCATGC | 72 | 402 |
| 762837 | 238 | 257 | 4689 | 4708 | TGAATTCCTTTACACCACAC | 49 | 1639 |
| 762909 | N/A | N/A | 19928 | 19947 | CTGATTAATTGCCTGTGTAC | 48 | 1711 |
| 762910 | N/A | N/A | 20026 | 20045 | ATTAAGCTCTTTGATGTGCG | 65 | 1712 |
| 762911 | N/A | N/A | 20119 | 20138 | TCTTGGACTACCCACTTCCT | 45 | 1713 |
| 762912 | N/A | N/A | 20212 | 20231 | AAGGAAGGTAAGTTTTGAGG | 0 | 1714 |
| 762913 | N/A | N/A | 20305 | 20324 | AGACGGTACATGTTTCCCTG | 47 | 1715 |

TABLE 30-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 762914 | N/A | N/A | 20332 | 20351 | TGTATGCCTTAAATGCAGGT | 69 | 1716 |
| 762915 | N/A | N/A | 20398 | 20417 | TGGGTGGAAAGCAAACCCAG | 16 | 1717 |
| 762916 | N/A | N/A | 20491 | 20510 | CTACCTATAAGGGAAATATC | 20 | 1718 |
| 762917 | N/A | N/A | 20584 | 20603 | TCACTCTCAGTCCAATGTTT | 55 | 1719 |
| 762918 | N/A | N/A | 20677 | 20696 | GAGCTTCCTCATTTTATGAG | 41 | 1720 |
| 762919 | N/A | N/A | 20770 | 20789 | ACCACAATTGCAGACATTTA | 41 | 1721 |
| 762920 | N/A | N/A | 20871 | 20890 | TCAAAGTTTAAAAAATGAAA | 6 | 1722 |
| 762921 | N/A | N/A | 20964 | 20983 | TCTTGAATGATGAATGAGTG | 59 | 1723 |
| 762922 | N/A | N/A | 20979 | 20998 | TGAGCAAACATTCTTTCTTG | 59 | 1724 |
| 762923 | N/A | N/A | 20980 | 20999 | GTGAGCAAACATTCTTTCTT | 62 | 1725 |
| 762924 | N/A | N/A | 20981 | 21000 | TGTGAGCAAACATTCTTTCT | 74 | 1726 |
| 762925 | N/A | N/A | 20982 | 21001 | GTGTGAGCAAACATTCTTTC | 52 | 1727 |
| 762926 | N/A | N/A | 20983 | 21002 | AGTGTGAGCAAACATTCTTT | 75 | 1728 |
| 762927 | N/A | N/A | 20984 | 21003 | CAGTGTGAGCAAACATTCTT | 50 | 1729 |
| 762928 | N/A | N/A | 20985 | 21004 | ACAGTGTGAGCAAACATTCT | 57 | 1730 |
| 762929 | N/A | N/A | 20986 | 21005 | CACAGTGTGAGCAAACATTC | 63 | 1731 |
| 762929 | N/A | N/A | 27411 | 27430 | CACAGTGTGAGCAAACATTC | 63 | 1731 |
| 762930 | N/A | N/A | 20987 | 21006 | GCACAGTGTGAGCAAACATT | 75 | 1732 |
| 762931 | N/A | N/A | 20988 | 21007 | GGCACAGTGTGAGCAAACAT | 51 | 1733 |
| 762932 | N/A | N/A | 20989 | 21008 | TGGCACAGTGTGAGCAAACA | 72 | 1734 |
| 762933 | N/A | N/A | 20993 | 21012 | TTTCTGGCACAGTGTGAGCA | 43 | 1735 |
| 762934 | N/A | N/A | 20994 | 21013 | GTTTCTGGCACAGTGTGAGC | 59 | 1736 |
| 762935 | N/A | N/A | 20995 | 21014 | AGTTTCTGGCACAGTGTGAG | 53 | 1737 |
| 762936 | N/A | N/A | 20996 | 21015 | AAGTTTCTGGCACAGTGTGA | 44 | 1738 |
| 762937 | N/A | N/A | 20997 | 21016 | CAAGTTTCTGGCACAGTGTG | 50 | 1739 |
| 762938 | N/A | N/A | 20998 | 21017 | CCAAGTTTCTGGCACAGTGT | 42 | 1740 |
| 762939 | N/A | N/A | 20999 | 21018 | TCCAAGTTTCTGGCACAGTG | 51 | 1741 |
| 762940 | N/A | N/A | 21000 | 21019 | CTCCAAGTTTCTGGCACAGT | 40 | 1742 |
| 762941 | N/A | N/A | 21001 | 21020 | CCTCCAAGTTTCTGGCACAG | 51 | 1743 |
| 762942 | N/A | N/A | 21002 | 21021 | TCCTCCAAGTTTCTGGCACA | 57 | 1744 |
| 762943 | N/A | N/A | 21003 | 21022 | TTCCTCCAAGTTTCTGGCAC | 32 | 1745 |
| 762944 | N/A | N/A | 21057 | 21076 | ATTAATCCACTTCTACAAGC | 30 | 1746 |
| 762945 | N/A | N/A | 21150 | 21169 | GAGGGTGATGGACCAGATAC | 51 | 1747 |
| 762946 | N/A | N/A | 21218 | 21237 | CAGAATTATGTCATTTAATT | 40 | 1748 |
| 762947 | N/A | N/A | 21219 | 21238 | TCAGAATTATGTCATTTAAT | 58 | 1749 |
| 762948 | N/A | N/A | 21220 | 21239 | TTCAGAATTATGTCATTTAA | 59 | 1750 |

TABLE 30-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 762949 | N/A | N/A | 21221 | 21240 | GTTCAGAATTATGTCATTTA | 56 | 1751 |
| 762950 | N/A | N/A | 21222 | 21241 | TGTTCAGAATTATGTCATTT | 66 | 1752 |
| 762951 | N/A | N/A | 21223 | 21242 | TTGTTCAGAATTATGTCATT | 61 | 1753 |
| 762952 | N/A | N/A | 21224 | 21243 | GTTGTTCAGAATTATGTCAT | 68 | 1754 |
| 762953 | N/A | N/A | 21225 | 21244 | GGTTGTTCAGAATTATGTCA | 75 | 1755 |
| 762954 | N/A | N/A | 21226 | 21245 | TGGTTGTTCAGAATTATGTC | 51 | 1756 |
| 762955 | N/A | N/A | 21227 | 21246 | TTGGTTGTTCAGAATTATGT | 67 | 1757 |
| 762956 | N/A | N/A | 21228 | 21247 | ATTGGTTGTTCAGAATTATG | 57 | 1758 |
| 762957 | N/A | N/A | 21243 | 21262 | ATTTACTCTCGATTTATTGG | 65 | 1759 |
| 762958 | N/A | N/A | 21336 | 21355 | TCATTTGTCCTTTAACTAGT | 55 | 1760 |
| 762959 | N/A | N/A | 21429 | 21448 | TAAAAATATGGATCAAAAGA | 0 | 1761 |
| 762960 | N/A | N/A | 21522 | 21541 | TGTGCACTTTTAACCTGTTT | 69 | 1762 |
| 762961 | N/A | N/A | 21616 | 21635 | TTAGAACAAGCAGATCTTTC | 63 | 1763 |
| 762962 | N/A | N/A | 21709 | 21728 | ATAGACCAAGTGTTCTAGTG | 68 | 1764 |
| 762963 | N/A | N/A | 21802 | 21821 | GAGCATTCCATGTGGCATGA | 62 | 1765 |
| 762964 | N/A | N/A | 21895 | 21914 | CAGGCAGTGGCTTCACAGTT | 40 | 1766 |
| 762965 | N/A | N/A | 21993 | 22012 | TTTCAAGCTTATTTCTTGCG | 69 | 1767 |
| 762966 | N/A | N/A | 22086 | 22105 | AAATGGCATTGCTTAGGAAC | 39 | 1768 |
| 762967 | N/A | N/A | 22179 | 22198 | AAGTCAGGATTATTACAGAA | 51 | 1769 |
| 762968 | N/A | N/A | 22273 | 22292 | GATATTATATTCACAATGTC | 34 | 1770 |
| 762969 | N/A | N/A | 22366 | 22385 | GGTCCATAACACTCAAGTGT | 79 | 1771 |
| 762970 | N/A | N/A | 22448 | 22467 | GACCTGTGCTTGTTTGTGAA | 60 | 1772 |
| 762971 | N/A | N/A | 22449 | 22468 | TGACCTGTGCTTGTTTGTGA | 58 | 1773 |
| 762972 | N/A | N/A | 22450 | 22469 | GTGACCTGTGCTTGTTTGTG | 56 | 1774 |
| 762973 | N/A | N/A | 22451 | 22470 | TGTGACCTGTGCTTGTTTGT | 48 | 1775 |
| 762974 | N/A | N/A | 22452 | 22471 | CTGTGACCTGTGCTTGTTTG | 61 | 1776 |
| 762975 | N/A | N/A | 22453 | 22472 | CCTGTGACCTGTGCTTGTTT | 47 | 1777 |
| 762976 | N/A | N/A | 22454 | 22473 | GCCTGTGACCTGTGCTTGTT | 50 | 1778 |
| 762977 | N/A | N/A | 22455 | 22474 | TGCCTGTGACCTGTGCTTGT | 54 | 1779 |
| 762978 | N/A | N/A | 22456 | 22475 | TTGCCTGTGACCTGTGCTTG | 59 | 1780 |
| 762979 | N/A | N/A | 22457 | 22476 | GTTGCCTGTGACCTGTGCTT | 68 | 1781 |
| 762980 | N/A | N/A | 22458 | 22477 | TGTTGCCTGTGACCTGTGCT | 54 | 1782 |
| 762981 | N/A | N/A | 22459 | 22478 | ATGTTGCCTGTGACCTGTGC | 40 | 1783 |
| 762982 | N/A | N/A | 22460 | 22479 | AATGTTGCCTGTGACCTGTG | 28 | 1784 |

TABLE 30-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 762983 | N/A | N/A | 22461 | 22480 | AAATGTTGCCTGTGACCTGT | 49 | 1785 |
| 762984 | N/A | N/A | 22462 | 22481 | GAAATGTTGCCTGTGACCTG | 30 | 1786 |
| 762985 | N/A | N/A | 22463 | 22482 | TGAAATGTTGCCTGTGACCT | 49 | 1787 |

TABLE 31

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 83 | 33 |
| 741410 | N/A | N/A | 87946 | 87962 | GTAAGTTGTGACCATGC | 94 | 402 |
| 762837 | 238 | 257 | 4689 | 4708 | TGAATTCCTTTACACCACAC | 52 | 1639 |
| 762986 | N/A | N/A | 22464 | 22483 | CTGAAATGTTGCCTGTGACC | 58 | 1788 |
| 762987 | N/A | N/A | 22552 | 22571 | CTCCAGTCCTGACATCTCTT | 77 | 1789 |
| 762988 | N/A | N/A | 22645 | 22664 | ACAAGAACCAAACTTTTAAT | 57 | 1790 |
| 762989 | N/A | N/A | 22738 | 22757 | CAAATCAGGCAATTCATTGT | 57 | 1791 |
| 762990 | N/A | N/A | 22831 | 22850 | AAATCAATCTTAAATTTTTC | 0 | 1792 |
| 762991 | N/A | N/A | 22924 | 22943 | TTTATGTACCATTAGTGGGC | 63 | 1793 |
| 762992 | N/A | N/A | 23017 | 23036 | CATTAGAATTCACTATTCAT | 54 | 1794 |
| 762993 | N/A | N/A | 23110 | 23129 | TTAATGAAAACATAGCAGTA | 37 | 1795 |
| 762994 | N/A | N/A | 23203 | 23222 | AAGGCAGGAGCCACCCATAT | 56 | 1796 |
| 762995 | N/A | N/A | 23279 | 23298 | TTCTCAGAGACCACAGCTGC | 70 | 1797 |
| 762996 | N/A | N/A | 23280 | 23299 | GTTCTCAGAGACCACAGCTG | 70 | 1798 |
| 762997 | N/A | N/A | 23281 | 23300 | TGTTCTCAGAGACCACAGCT | 64 | 1799 |
| 762998 | N/A | N/A | 23282 | 23301 | TTGTTCTCAGAGACCACAGC | 68 | 1800 |
| 762999 | N/A | N/A | 23283 | 23302 | ATTGTTCTCAGAGACCACAG | 67 | 1801 |
| 763000 | N/A | N/A | 23284 | 23303 | TATTGTTCTCAGAGACCACA | 57 | 1802 |
| 763001 | N/A | N/A | 23285 | 23304 | ATATTGTTCTCAGAGACCAC | 71 | 1803 |
| 763002 | N/A | N/A | 23286 | 23305 | CATATTGTTCTCAGAGACCA | 81 | 1804 |
| 763003 | N/A | N/A | 23287 | 23306 | CCATATTGTTCTCAGAGACC | 67 | 1805 |
| 763004 | N/A | N/A | 23288 | 23307 | ACCATATTGTTCTCAGAGAC | 69 | 1806 |
| 763005 | N/A | N/A | 23289 | 23308 | AACCATATTGTTCTCAGAGA | 65 | 1807 |
| 763006 | N/A | N/A | 23290 | 23309 | AAACCATATTGTTCTCAGAG | 68 | 1808 |
| 763007 | N/A | N/A | 23291 | 23310 | CAAACCATATTGTTCTCAGA | 64 | 1809 |
| 763008 | N/A | N/A | 23296 | 23315 | TGTAACAAACCATATTGTTC | 73 | 1810 |
| 763009 | N/A | N/A | 23389 | 23408 | CAAAAACACAATTTAATGTA | 14 | 1811 |
| 763010 | N/A | N/A | 23482 | 23501 | GATTTGGGTGGAAGTATTTG | 47 | 1812 |

TABLE 31-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763011 | N/A | N/A | 23575 | 23594 | CGCAATCAGTTCTTTGAATA | 73 | 1813 |
| 763012 | N/A | N/A | 23668 | 23687 | CAAATATGATTTAAACCTAT | 4 | 1814 |
| 763013 | N/A | N/A | 23761 | 23780 | ATGGGTTCACAGAAGTGTGG | 65 | 1815 |
| 763014 | N/A | N/A | 23854 | 23873 | ACAGTATCTCATTAATGAAA | 45 | 1816 |
| 763015 | N/A | N/A | 23948 | 23967 | ATAAGTATCTCAAAACATCA | 52 | 1817 |
| 763016 | N/A | N/A | 24041 | 24060 | AAGATAACCATATGATGATG | 42 | 1818 |
| 763017 | N/A | N/A | 24160 | 24179 | GTAAGATGAGTAAGTCTAAA | 59 | 1819 |
| 763018 | N/A | N/A | 24253 | 24272 | ACATATAAGTGCTATTTTTC | 42 | 1820 |
| 763019 | N/A | N/A | 24346 | 24365 | AGGGACAAACAGGTTGTTTA | 83 | 1821 |
| 763020 | N/A | N/A | 24439 | 24458 | AAAGCAAATAGCATCATCAA | 44 | 1822 |
| 763021 | N/A | N/A | 24539 | 24558 | CTGTACCCTTGAATATCACG | 69 | 1823 |
| 763022 | N/A | N/A | 24632 | 24651 | ACAATTAAATTGATGAGATG | 18 | 1824 |
| 763023 | N/A | N/A | 24731 | 24750 | CTTAAAAATCCAAATGTTGT | 51 | 1825 |
| 763024 | N/A | N/A | 24825 | 24844 | CATTAATAAGAATTAAATGC | 6 | 1826 |
| 763025 | N/A | N/A | 24850 | 24869 | TTCTTTGCATTAGTATTCAC | 53 | 1827 |
| 763026 | N/A | N/A | 24851 | 24870 | ATTCTTTGCATTAGTATTCA | 48 | 1828 |
| 763027 | N/A | N/A | 24852 | 24871 | TATTCTTTGCATTAGTATTC | 48 | 1829 |
| 763028 | N/A | N/A | 24853 | 24872 | GTATTCTTTGCATTAGTATT | 60 | 1830 |
| 763029 | N/A | N/A | 24854 | 24873 | AGTATTCTTTGCATTAGTAT | 72 | 1831 |
| 763030 | N/A | N/A | 24855 | 24874 | CAGTATTCTTTGCATTAGTA | 69 | 1832 |
| 763031 | N/A | N/A | 24856 | 24875 | TCAGTATTCTTTGCATTAGT | 70 | 1833 |
| 763032 | N/A | N/A | 24857 | 24876 | CTCAGTATTCTTTGCATTAG | 77 | 1834 |
| 763033 | N/A | N/A | 24858 | 24877 | GCTCAGTATTCTTTGCATTA | 79 | 1835 |
| 763034 | N/A | N/A | 24859 | 24878 | GGCTCAGTATTCTTTGCATT | 69 | 1836 |
| 763035 | N/A | N/A | 24860 | 24879 | TGGCTCAGTATTCTTTGCAT | 77 | 1837 |
| 763036 | N/A | N/A | 24918 | 24937 | TCCATTTTTTCACTTACTTG | 75 | 1838 |
| 763037 | N/A | N/A | 25011 | 25030 | TTAGATTTATCATATTGTTG | 50 | 1839 |
| 763038 | N/A | N/A | 25104 | 25123 | TTAAAATCTATTTGATTTCA | 32 | 1840 |
| 763039 | N/A | N/A | 25198 | 25217 | CCAAATAGAAAAAAGTGTG | 18 | 1841 |
| 763040 | N/A | N/A | 25291 | 25310 | CTGTATGTACAACCTCAGAA | 82 | 1842 |
| 763041 | N/A | N/A | 25384 | 25403 | CCTGACATAAGTAGGAAGCA | 63 | 1843 |
| 763042 | N/A | N/A | 25477 | 25496 | CCTACTTTAGATATGTCATA | 69 | 1844 |
| 763043 | N/A | N/A | 25570 | 25589 | TGTTAGTATACCTTTGTAGG | 72 | 1845 |
| 763044 | N/A | N/A | 25663 | 25682 | GAGGGCCAGCTGGCCATCAT | 15 | 1846 |
| 763045 | N/A | N/A | 25756 | 25775 | GAATTCAAGCCCATGCCCTC | 44 | 1847 |
| 763046 | N/A | N/A | 25854 | 25873 | CAACATTTTTATTTCACAGA | 54 | 1848 |

TABLE 31-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763047 | N/A | N/A | 25947 | 25966 | GTTGCCAGGGATCTGGCAAC | 15 | 1849 |
| 763048 | N/A | N/A | 26040 | 26059 | TGTCTGCATTATCTTATTTC | 67 | 1850 |
| 763049 | N/A | N/A | 26133 | 26152 | TGTGATCATGTATCGACACA | 78 | 1851 |
| 763050 | N/A | N/A | 26226 | 26245 | AACGGCATGTTCAGTGATGC | 82 | 1852 |
| 763051 | N/A | N/A | 26319 | 26338 | ATTATACCATGTGCATAATA | 54 | 1853 |
| 763052 | N/A | N/A | 26412 | 26431 | GCCTTTGAGATTTGCTTCAG | 91 | 1854 |
| 763053 | N/A | N/A | 26505 | 26524 | TTTTACTGAACACCTAGAAC | 54 | 1855 |
| 763054 | N/A | N/A | 26598 | 26617 | TTCATCTAGGACCTGCAATC | 39 | 1856 |
| 763055 | N/A | N/A | 26691 | 26710 | TTGGTGTTGTCCCAAGAAAT | 63 | 1857 |
| 763056 | N/A | N/A | 26784 | 26803 | CTGCAATCTACTTAGACCTG | 71 | 1858 |
| 763057 | N/A | N/A | 26877 | 26896 | AGGAAAAACTCTGCCCTCCT | 46 | 1859 |
| 763058 | N/A | N/A | 26978 | 26997 | CAAATGAACTTGGGAGGAGG | 14 | 1860 |
| 763059 | N/A | N/A | 27071 | 27090 | AGTGCAGGATGAAACCAGAC | 76 | 1861 |
| 763060 | N/A | N/A | 27164 | 27183 | TGAAGTATTAGAGAGGATCA | 46 | 1862 |
| 763061 | N/A | N/A | 27257 | 27276 | CTCGGACGGAAGTGAAGGCA | 57 | 1863 |
| 763062 | N/A | N/A | 27350 | 27369 | GCTCACTTCCTGTCACCCCC | 49 | 1864 |

TABLE 32

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 76 | 33 |
| 741410 | N/A | N/A | 87946 | 87962 | GTAAGTTGTGACCATGC | 64 | 402 |
| 762837 | 238 | 257 | 4689 | 4708 | TGAATTCCTTTACACCACAC | 61 | 1639 |
| 763063 | N/A | N/A | 27443 | 27462 | TAGGATGCAGCCTGAGGAGC | 29 | 1865 |
| 763064 | N/A | N/A | 27536 | 27555 | CATTAGAGTTTGTCTCTGGT | 58 | 1866 |
| 763065 | N/A | N/A | 27629 | 27648 | GACCCTTTCATTACCTTTCA | 81 | 1867 |
| 763066 | N/A | N/A | 27722 | 27741 | TCCTAGCCCACATCTTAGTA | 19 | 1868 |
| 763067 | N/A | N/A | 27815 | 27834 | ATTGTTCTGATTGATGGACA | 59 | 1869 |
| 763068 | N/A | N/A | 27908 | 27927 | TGCGACTGGTCAGAGCATGC | 63 | 1870 |
| 763069 | N/A | N/A | 28001 | 28020 | TCTAGCACTATTTTTTTCAA | 31 | 1871 |
| 763070 | N/A | N/A | 28094 | 28113 | TTAATAATTATTCTACAACA | 0 | 1872 |
| 763071 | N/A | N/A | 28192 | 28211 | CACATACAGGTTTTTAAAAA | 21 | 1873 |
| 763072 | N/A | N/A | 28231 | 28250 | CCTTGTGCATTTATTCCACG | 84 | 1874 |
| 763073 | N/A | N/A | 28232 | 28251 | ACCTTGTGCATTTATTCCAC | 67 | 1875 |
| 763074 | N/A | N/A | 28233 | 28252 | TACCTTGTGCATTTATTCCA | 64 | 1876 |

TABLE 32-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763075 | N/A | N/A | 28234 | 28253 | GTACCTTGTGCATTTATTCC | 70 | 1877 |
| 763076 | N/A | N/A | 28235 | 28254 | AGTACCTTGTGCATTTATTC | 68 | 1878 |
| 763077 | N/A | N/A | 28236 | 28255 | GAGTACCTTGTGCATTTATT | 67 | 1879 |
| 763078 | N/A | N/A | 28286 | 28305 | CGAAGAATTACCCAGCCCAA | 28 | 1880 |
| 763079 | N/A | N/A | 28379 | 28398 | GTGCTTGTTGCCATGCTGGG | 78 | 1881 |
| 763080 | N/A | N/A | 28451 | 28470 | TGTAATCTAGGACCCAGTAA | 56 | 1882 |
| 763081 | N/A | N/A | 28452 | 28471 | CTGTAATCTAGGACCCAGTA | 70 | 1883 |
| 763082 | N/A | N/A | 28453 | 28472 | ACTGTAATCTAGGACCCAGT | 63 | 1884 |
| 763083 | N/A | N/A | 28454 | 28473 | GACTGTAATCTAGGACCCAG | 69 | 1885 |
| 763084 | N/A | N/A | 28455 | 28474 | AGACTGTAATCTAGGACCCA | 72 | 1886 |
| 763085 | N/A | N/A | 28456 | 28475 | CAGACTGTAATCTAGGACCC | 70 | 1887 |
| 763086 | N/A | N/A | 28457 | 28476 | CCAGACTGTAATCTAGGACC | 64 | 1888 |
| 763087 | N/A | N/A | 28458 | 28477 | TCCAGACTGTAATCTAGGAC | 92 | 1889 |
| 763088 | N/A | N/A | 28459 | 28478 | ATCCAGACTGTAATCTAGGA | 83 | 1890 |
| 763089 | N/A | N/A | 28460 | 28479 | AATCCAGACTGTAATCTAGG | 51 | 1891 |
| 763090 | N/A | N/A | 28461 | 28480 | TAATCCAGACTGTAATCTAG | 49 | 1892 |
| 763091 | N/A | N/A | 28472 | 28491 | AAGGAACGCAATAATCCAGA | 47 | 1893 |
| 763092 | N/A | N/A | 28565 | 28584 | ACCAGTGCGGAATATTGTAA | 64 | 1894 |
| 763093 | N/A | N/A | 28669 | 28688 | ATCAGTCGAATGAATGTACG | 36 | 1895 |
| 763094 | N/A | N/A | 28765 | 28784 | CAGATGGATGGGTGGACAAA | 52 | 1896 |
| 763095 | N/A | N/A | 29117 | 29136 | TTGGCATTGTATTTTTTTTG | 60 | 1897 |
| 763096 | N/A | N/A | 29210 | 29229 | TAGACTCCTACACATATTAA | 32 | 1898 |
| 763097 | N/A | N/A | 29303 | 29322 | GATACTTCACTCAGAAAACC | 34 | 1899 |
| 763098 | N/A | N/A | 29396 | 29415 | AAAATGGTTTGATAGTTGGG | 55 | 1900 |
| 763099 | N/A | N/A | 29454 | 29473 | TTGTTAATAGTTCTCTGTTT | 62 | 1901 |
| 763100 | N/A | N/A | 29455 | 29474 | TTTGTTAATAGTTCTCTGTT | 45 | 1902 |
| 763101 | N/A | N/A | 29456 | 29475 | TTTTGTTAATAGTTCTCTGT | 54 | 1903 |
| 763102 | N/A | N/A | 29457 | 29476 | TTTTTGTTAATAGTTCTCTG | 70 | 1904 |
| 763103 | N/A | N/A | 29489 | 29508 | GGATACCATACAACCAATTA | 57 | 1905 |
| 763104 | N/A | N/A | 29582 | 29601 | ACAACTAAATCACTCAATTC | 8 | 1906 |
| 763105 | N/A | N/A | 29675 | 29694 | CAGAGCCCAAAACATTTATA | 33 | 1907 |
| 763106 | N/A | N/A | 29801 | 29820 | CAAATGCCTTGATCTTGGAG | 42 | 1908 |
| 763107 | N/A | N/A | 29894 | 29913 | GAGAACACAGCATTTGGCCC | 68 | 1909 |
| 763108 | N/A | N/A | 29997 | 30016 | AGAGGTAATAAAGTCACGGG | 46 | 1910 |
| 763109 | N/A | N/A | 30090 | 30109 | ATATGAAAATGAAAGGATGG | 28 | 1911 |
| 763110 | N/A | N/A | 30193 | 30212 | TTACAGTTTCCTATATATCG | 25 | 1912 |

TABLE 32-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763111 | N/A | N/A | 30287 | 30306 | TCATACACAAAATAAACACA | 33 | 1913 |
| 763112 | N/A | N/A | 30380 | 30399 | GAATAGCAGTATGTACTAAT | 40 | 1914 |
| 763113 | N/A | N/A | 30473 | 30492 | ACCTTTCAATAAACTGTTAA | 33 | 1915 |
| 763114 | N/A | N/A | 30566 | 30585 | ATTTTTTCATATATAGTGAG | 49 | 1916 |
| 763115 | N/A | N/A | 30659 | 30678 | CTGTAACAAATATACATTTT | 36 | 1917 |
| 763116 | N/A | N/A | 30752 | 30771 | ACCAATTAGTTTCTAATAAG | 38 | 1918 |
| 763117 | N/A | N/A | 30885 | 30904 | TTATATACACACACAGCTAC | 14 | 1919 |
| 763118 | N/A | N/A | 30978 | 30997 | CCAAAAATAGAGATCAATGT | 31 | 1920 |
| 763119 | N/A | N/A | 31078 | 31097 | AAACCACTGGCTAATTTTTT | 57 | 1921 |
| 763120 | N/A | N/A | 31171 | 31190 | TGAGAGCTATATGGCTGAAA | 47 | 1922 |
| 763121 | N/A | N/A | 31264 | 31283 | AAAAGCCTTCTTAGTGGTAA | 53 | 1923 |
| 763122 | N/A | N/A | 31357 | 31376 | ATTACTGTGTTTCAGCAGTT | 51 | 1924 |
| 763123 | N/A | N/A | 31450 | 31469 | TTAGATATAAAAGGTATGAA | 0 | 1925 |
| 763124 | N/A | N/A | 31543 | 31562 | CTAGCCTAGGGTGGTAACAG | 17 | 1926 |
| 763125 | N/A | N/A | 31636 | 31655 | TGCTCAAGAATGGACTAGGT | 57 | 1927 |
| 763126 | N/A | N/A | 31729 | 31748 | TGCATTTCATTCTATGTATG | 62 | 1928 |
| 763127 | N/A | N/A | 31822 | 31841 | AGTTGGAGGGTGGCATACAA | 25 | 1929 |
| 763128 | N/A | N/A | 31915 | 31934 | AACAAACAATTCATTTTCTA | 0 | 1930 |
| 763129 | N/A | N/A | 32011 | 32030 | GTCTTTTTAAAATTAAAATC | 0 | 1931 |
| 763130 | N/A | N/A | 32104 | 32123 | TATAATATACAAAATTACTA | 0 | 1932 |
| 763131 | N/A | N/A | 32197 | 32216 | CAATAAGTAGTGCTGTTATA | 51 | 1933 |
| 763132 | N/A | N/A | 32290 | 32309 | AGTAGTTTTTAAATCTTCAA | 51 | 1934 |
| 763133 | N/A | N/A | 32383 | 32402 | GTGGTTCTGCCCATCTGTCC | 64 | 1935 |
| 763134 | N/A | N/A | 32476 | 32495 | TGTTTTCAAGAGCGATCGGA | 58 | 1936 |
| 763135 | N/A | N/A | 32569 | 32588 | GAGTAAGTTTAGATATAAAA | 36 | 1937 |
| 763136 | N/A | N/A | 32662 | 32681 | GCATAAAAGGCAGAGGGAGG | 35 | 1938 |
| 763137 | N/A | N/A | 32755 | 32774 | GCAACCTTTCTCTCCCTCTC | 65 | 1939 |
| 763138 | N/A | N/A | 32848 | 32867 | CTGAAGAAATAAATAAAGAA | 0 | 1940 |
| 763139 | N/A | N/A | 32941 | 32960 | TCAATATTCAGAGATGACTA | 27 | 1941 |

TABLE 33

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No:2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 78 | 33 |
| 741410 | N/A | N/A | 87946 | 87962 | GTAAGTTGTGACCATGC | 72 | 402 |

TABLE 33-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No:2 stop | Sequence (5' to 3') | % Reduction | SEQ ID NO |
|---|---|---|---|---|---|---|---|
| 762837 | 238 | 257 | 4689 | 4708 | TGAATTCCTTTACACCACAC | 46 | 1639 |
| 763140 | N/A | N/A | 33034 | 33053 | CACACCCGAAATACCACCTG | 49 | 1942 |
| 763141 | N/A | N/A | 33127 | 33146 | TAAGCTAAAATGGTTTCAAC | 45 | 1943 |
| 763142 | N/A | N/A | 33220 | 33239 | GGCAAAATTTGCATTGGATG | 79 | 1944 |
| 763143 | N/A | N/A | 33313 | 33332 | TGAAAAAGCTATGACCCTC | 30 | 1945 |
| 763144 | N/A | N/A | 33406 | 33425 | TTACTTCTACTTTTGTGAGG | 46 | 1946 |
| 763145 | N/A | N/A | 33499 | 33518 | CCAACATTTTAAGGAAGGTA | 73 | 1947 |
| 763146 | N/A | N/A | 33592 | 33611 | GGTAGAGAACACTTAAGTGA | 67 | 1948 |
| 763147 | N/A | N/A | 33689 | 33708 | CAAATTTTAAAAGTTAACTT | 0 | 1949 |
| 763148 | N/A | N/A | 33785 | 33804 | AATTTCTACAAGAAAAATAT | 0 | 1950 |
| 763149 | N/A | N/A | 33878 | 33897 | CCAGAAAGAAACATTTAGAA | 39 | 1951 |
| 763150 | N/A | N/A | 33971 | 33990 | GTGTTAACTGGCAATTCCAT | 82 | 1952 |
| 763151 | N/A | N/A | 33981 | 34000 | GTTCAATGCTGTGTTAACTG | 74 | 1953 |
| 763152 | N/A | N/A | 33982 | 34001 | AGTTCAATGCTGTGTTAACT | 63 | 1954 |
| 763153 | N/A | N/A | 33983 | 34002 | AAGTTCAATGCTGTGTTAAC | 50 | 1955 |
| 763154 | N/A | N/A | 33984 | 34003 | AAAGTTCAATGCTGTGTTAA | 38 | 1956 |
| 763155 | N/A | N/A | 33985 | 34004 | AAAAGTTCAATGCTGTGTTA | 49 | 1957 |
| 763156 | N/A | N/A | 33986 | 34005 | AAAAAGTTCAATGCTGTGTT | 63 | 1958 |
| 763157 | N/A | N/A | 33987 | 34006 | GAAAAAGTTCAATGCTGTGT | 56 | 1959 |
| 763158 | N/A | N/A | 33988 | 34007 | AGAAAAAGTTCAATGCTGTG | 62 | 1960 |
| 763159 | N/A | N/A | 33989 | 34008 | AAGAAAAAGTTCAATGCTGT | 42 | 1961 |
| 763160 | N/A | N/A | 33990 | 34009 | CAAGAAAAAGTTCAATGCTG | 52 | 1962 |
| 763161 | N/A | N/A | 33991 | 34010 | ACAAGAAAAAGTTCAATGCT | 28 | 1963 |
| 763162 | N/A | N/A | 34064 | 34083 | TAATATCAGCCAAAGACATT | 34 | 1964 |
| 763163 | N/A | N/A | 34157 | 34176 | TTGAAAAAAGTATTGACTCT | 16 | 1965 |
| 763164 | N/A | N/A | 34250 | 34269 | CTGTTAAAATGCATTTCTAG | 64 | 1966 |
| 763165 | N/A | N/A | 34383 | 34402 | GTATCCCAGCACTGTTGGGA | 25 | 1967 |
| 763166 | N/A | N/A | 34476 | 34495 | CTGGTTGCTATCTAGGGATC | 82 | 1968 |
| 763167 | N/A | N/A | 34569 | 34588 | AATAGAACCTAATATAATTT | 0 | 1969 |
| 763168 | N/A | N/A | 34662 | 34681 | CTTCTATCCTAGAATTCATA | 40 | 1970 |
| 763169 | N/A | N/A | 34755 | 34774 | ATGGGAATGAGGTGTAAAAG | 56 | 1971 |
| 763170 | N/A | N/A | 34848 | 34867 | CAGTCTGATAAGGAGAACAA | 45 | 1972 |
| 763171 | N/A | N/A | 34941 | 34960 | GGATAGAATATCAAGATAAA | 38 | 1973 |
| 763172 | N/A | N/A | 35034 | 35053 | TCACAGTGTTCTTTTCTCTT | 71 | 1974 |
| 763173 | N/A | N/A | 35127 | 35146 | TTGTGCTAGAATATGAGATC | 0 | 1975 |
| 763174 | N/A | N/A | 35220 | 35239 | TCTAGAATTCAAGCCACACC | 41 | 1976 |

TABLE 33-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No:2 stop | Sequence (5' to 3') | % Reduction | SEQ ID NO |
|---|---|---|---|---|---|---|---|
| 763175 | N/A | N/A | 35313 | 35332 | AATAATGATAGTATTTTCCT | 15 | 1977 |
| 763176 | N/A | N/A | 35406 | 35425 | CCATCACACCTTGCAGATGT | 70 | 1978 |
| 763177 | N/A | N/A | 35499 | 35518 | ACTTCCTTTAGAGTATACGG | 79 | 1979 |
| 763178 | N/A | N/A | 35594 | 35613 | GCACTATATAAAATGTAACG | 68 | 1980 |
| 763179 | N/A | N/A | 35687 | 35706 | GTTGTAATAATAATATTGAC | 51 | 1981 |
| 763180 | N/A | N/A | 35780 | 35799 | CTGTGACTTTGGTCTATTTG | 34 | 1982 |
| 763181 | N/A | N/A | 35873 | 35892 | GGATTGTGTAATAGCCTTTA | 60 | 1983 |
| 763182 | N/A | N/A | 35966 | 35985 | TGACTATCAGTATCTGTTGA | 75 | 1984 |
| 763183 | N/A | N/A | 36059 | 36078 | AAGTTGACTTGTGACATACA | 45 | 1985 |
| 763184 | N/A | N/A | 36152 | 36171 | TTCTACCGAAGGAAATATGT | 27 | 1986 |
| 763185 | N/A | N/A | 36250 | 36269 | AGTCATTTTAATAAGTGTTT | 72 | 1987 |
| 763186 | N/A | N/A | 36360 | 36379 | ATCTTCCAAAGTTACTGTAC | 49 | 1988 |
| 763187 | N/A | N/A | 36453 | 36472 | ATTTCCCAGTCTCGGGAACT | 17 | 1989 |
| 763188 | N/A | N/A | 36625 | 36644 | GCTAATGGTTTTATGTGTTT | 73 | 1990 |
| 763189 | N/A | N/A | 36789 | 36808 | CATATGGTGATATGGTTAGG | 55 | 1991 |
| 763190 | N/A | N/A | 36933 | 36952 | TCATTCACCTATTGAGGAAC | 50 | 1992 |
| 763191 | N/A | N/A | 37026 | 37045 | CTAAGTTTTCTCCATGTGTT | 52 | 1993 |
| 763192 | N/A | N/A | 37135 | 37154 | GAGCCCCAGGCAATCACTGA | 0 | 1994 |
| 763193 | N/A | N/A | 37229 | 37248 | GGTCATGTATCCACCATGAC | 44 | 1995 |
| 763194 | N/A | N/A | 37322 | 37341 | AAATAACATTGATACCTTAT | 40 | 1996 |
| 763195 | N/A | N/A | 37415 | 37434 | ATTACAGTGCATTCCCATAT | 41 | 1997 |
| 763196 | N/A | N/A | 37523 | 37542 | GGGTCTTGACTTCCCAAAGT | 74 | 1998 |
| 763197 | N/A | N/A | 37649 | 37668 | TCTTTTATTTCTTCTGTTCT | 34 | 1999 |
| 763198 | N/A | N/A | 37785 | 37804 | CGCATCTGTCTTTCTTTTCT | 31 | 2000 |
| 763199 | N/A | N/A | 37878 | 37897 | GTAATCTCACCCTACTGCAA | 4 | 2001 |
| 763200 | N/A | N/A | 37971 | 37990 | TATCTAGACTGAGCTTTACA | 39 | 2002 |
| 763201 | N/A | N/A | 38064 | 38083 | CATTCACATATTTGGATTCT | 60 | 2003 |
| 763202 | N/A | N/A | 38157 | 38176 | TGAAACATTAACTGCTTTAT | 51 | 2004 |
| 763203 | N/A | N/A | 38250 | 38269 | ACAATGCTATGTGGAAGTTA | 44 | 2005 |
| 763204 | N/A | N/A | 38343 | 38362 | CCTCAGTGCTAGCGAAGGAC | 67 | 2006 |
| 763205 | N/A | N/A | 38436 | 38455 | AATTTACAATCTACACAGGC | 53 | 2007 |
| 763206 | N/A | N/A | 38529 | 38548 | TCAATTCTTGAGGCCAATTG | 27 | 2008 |
| 763207 | N/A | N/A | 38622 | 38641 | TCAGTATTTCATTGTCATAC | 89 | 2009 |
| 763208 | N/A | N/A | 38715 | 38734 | GTTAGTGGAATTGTAAAATA | 54 | 2010 |
| 763209 | N/A | N/A | 38808 | 38827 | CTAGTTATAAAAAACAAGAT | 34 | 2011 |
| 763210 | N/A | N/A | 38901 | 38920 | TTGGCCCCAATCATTGGAAT | 43 | 2012 |
| 763211 | N/A | N/A | 38910 | 38929 | TTCTCTGTATTGGCCCCAAT | 52 | 2013 |

TABLE 33-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No:2 stop | Sequence (5' to 3') | % Reduction | SEQ ID NO |
|---|---|---|---|---|---|---|---|
| 763212 | N/A | N/A | 38911 | 38930 | TTTCTCTGTATTGGCCCCAA | 59 | 2014 |
| 763213 | N/A | N/A | 38912 | 38931 | TTTTCTCTGTATTGGCCCCA | 51 | 2015 |
| 763214 | N/A | N/A | 38913 | 38932 | GTTTTCTCTGTATTGGCCCC | 60 | 2016 |
| 763215 | N/A | N/A | 38914 | 38933 | TGTTTTCTCTGTATTGGCCC | 70 | 2017 |
| 763216 | N/A | N/A | 38915 | 38934 | ATGTTTTCTCTGTATTGGCC | 74 | 2018 |

TABLE 34

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 67 | 33 |
| 741410 | N/A | N/A | 87946 | 87962 | GTAAGTTGTGACCATGC | 95 | 402 |
| 762837 | 238 | 257 | 4689 | 4708 | TGAATTCCTTTACACCACAC | 47 | 1639 |
| 763217 | N/A | N/A | 38916 | 38935 | GATGTTTTCTCTGTATTGGC | 54 | 2019 |
| 763218 | N/A | N/A | 38917 | 38936 | AGATGTTTTCTCTGTATTGG | 61 | 2020 |
| 763219 | N/A | N/A | 38918 | 38937 | GAGATGTTTTCTCTGTATTG | 61 | 2021 |
| 763220 | N/A | N/A | 38919 | 38938 | TGAGATGTTTTCTCTGTATT | 48 | 2022 |
| 763221 | N/A | N/A | 38920 | 38939 | TTGAGATGTTTTCTCTGTAT | 52 | 2023 |
| 763222 | N/A | N/A | 38994 | 39013 | TTTTCAGCAGGAGTTATAAT | 43 | 2024 |
| 763223 | N/A | N/A | 39087 | 39106 | TATTCCGTGTGTTTTTCCTA | 31 | 2025 |
| 763224 | N/A | N/A | 39180 | 39199 | TTTTCTGATAAATGGTAATC | 12 | 2026 |
| 763225 | N/A | N/A | 39273 | 39292 | CAGGTGGTATCAGTCCAAAG | 69 | 2027 |
| 763226 | N/A | N/A | 39366 | 39385 | CACCACAAAGAGGAAACAGG | 41 | 2028 |
| 763227 | N/A | N/A | 39459 | 39478 | AATGTTCCCTGGGAGCACAA | 58 | 2029 |
| 763228 | N/A | N/A | 39555 | 39574 | ATGTCCTGTGCATTGTAGAT | 64 | 2030 |
| 763229 | N/A | N/A | 39585 | 39604 | TTTTTTAACTGGATACTTTG | 27 | 2031 |
| 763230 | N/A | N/A | 39586 | 39605 | ATTTTTTAACTGGATACTTT | 26 | 2032 |
| 763231 | N/A | N/A | 39587 | 39606 | CATTTTTTAACTGGATACTT | 44 | 2033 |
| 763232 | N/A | N/A | 39588 | 39607 | ACATTTTTTAACTGGATACT | 48 | 2034 |
| 763233 | N/A | N/A | 39589 | 39608 | GACATTTTTTAACTGGATAC | 66 | 2035 |
| 763234 | N/A | N/A | 39590 | 39609 | TGACATTTTTTAACTGGATA | 55 | 2036 |
| 763235 | N/A | N/A | 39591 | 39610 | ATGACATTTTTTAACTGGAT | 51 | 2037 |
| 763236 | N/A | N/A | 39592 | 39611 | AATGACATTTTTTAACTGGA | 64 | 2038 |
| 763237 | N/A | N/A | 39593 | 39612 | TAATGACATTTTTTAACTGG | 38 | 2039 |
| 763238 | N/A | N/A | 39594 | 39613 | GTAATGACATTTTTTAACTG | 53 | 2040 |

TABLE 34-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763239 | N/A | N/A | 39595 | 39614 | AGTAATGACATTTTTAACT | 38 | 2041 |
| 763240 | N/A | N/A | 39648 | 39667 | GTGCCTGGAGAAGATGAATT | 44 | 2042 |
| 763241 | N/A | N/A | 39741 | 39760 | CTTTTCCTATTTGGTATTTG | 53 | 2043 |
| 763242 | N/A | N/A | 39834 | 39853 | TTGCTAAATATTACTCACTC | 40 | 2044 |
| 763243 | N/A | N/A | 39927 | 39946 | ACCAGACTGACTGTAATATG | 60 | 2045 |
| 763244 | N/A | N/A | 40020 | 40039 | AAGTGAAAGCATTAGAGGAT | 54 | 2046 |
| 763245 | N/A | N/A | 40113 | 40132 | TGGTGTGTGCAAACATGTAT | 27 | 2047 |
| 763246 | N/A | N/A | 40206 | 40225 | TTGTGAGAAAGTTTTTATGG | 17 | 2048 |
| 763247 | N/A | N/A | 40299 | 40318 | ATAAATAGTCATAAGACTAT | 5 | 2049 |
| 763248 | N/A | N/A | 40392 | 40411 | AGTGTGATATCTAAATAAAA | 11 | 2050 |
| 763249 | N/A | N/A | 40485 | 40504 | AATTCTGGTGCCAATGGTGA | 70 | 2051 |
| 763250 | N/A | N/A | 40578 | 40597 | ATCATCTTATGGCTAAATTT | 42 | 2052 |
| 763251 | N/A | N/A | 40671 | 40690 | ATCTAGGCATGAGTTGTGTC | 39 | 2053 |
| 763252 | N/A | N/A | 40775 | 40794 | CGTTTGAATGAAAAATGACG | 37 | 2054 |
| 763253 | N/A | N/A | 40868 | 40887 | ATTAGAACGAGGATGGAGAA | 32 | 2055 |
| 763254 | N/A | N/A | 40961 | 40980 | AGAGAATTCACATGATAGAT | 44 | 2056 |
| 763255 | N/A | N/A | 41054 | 41073 | TAAGAAAGAATTTTAGGCAT | 35 | 2057 |
| 763256 | N/A | N/A | 41147 | 41166 | GCAGGAGCAACACAGTGAAC | 40 | 2058 |
| 763257 | N/A | N/A | 41241 | 41260 | GATCAACAGGAAACATTTAT | 45 | 2059 |
| 763258 | N/A | N/A | 41334 | 41353 | TACCCCTATATCTCAACTCA | 43 | 2060 |
| 763259 | N/A | N/A | 41427 | 41446 | AATGTTATAGTTTCTACATG | 34 | 2061 |
| 763260 | N/A | N/A | 41521 | 41540 | CCAATTATGTAATTTTAAAT | 0 | 2062 |
| 763261 | N/A | N/A | 41619 | 41638 | TCTCATTCAAAACCATCCTG | 59 | 2063 |
| 763262 | N/A | N/A | 41740 | 41759 | TAATTGTCTTGAGCCATGCA | 48 | 2064 |
| 763263 | N/A | N/A | 41833 | 41852 | GCTTATAGTACACATTAACT | 56 | 2065 |
| 763264 | N/A | N/A | 41933 | 41952 | GCCCTCTCTCATTACCGTCG | 44 | 2066 |
| 763265 | N/A | N/A | 42026 | 42045 | AATACAAATTAGTTGAGTTA | 22 | 2067 |
| 763266 | N/A | N/A | 42119 | 42138 | ATACCACATACTCATTTTAA | 46 | 2068 |
| 763267 | N/A | N/A | 42212 | 42231 | TAGTTACATGTAGAATGCAT | 41 | 2069 |
| 763268 | N/A | N/A | 42305 | 42324 | TCTGGGATACAAGGTGTACC | 54 | 2070 |
| 763269 | N/A | N/A | 42398 | 42417 | CTTCATGGGAAGAAAAGCTA | 33 | 2071 |
| 763270 | N/A | N/A | 42491 | 42510 | ACAGAAGTACAGCATGTAAG | 51 | 2072 |
| 763271 | N/A | N/A | 42598 | 42617 | TATTAAGAGTAATGCTATCG | 48 | 2073 |
| 763272 | N/A | N/A | 42691 | 42710 | AGTAGTCCATTCCATTTTTG | 76 | 2074 |
| 763273 | N/A | N/A | 42785 | 42804 | ATTTGTCTTTTCTGGAATTA | 47 | 2075 |
| 763274 | N/A | N/A | 42878 | 42897 | AATTCTAACACCATCTTGGA | 22 | 2076 |
| 763275 | N/A | N/A | 42971 | 42990 | CTACATTGTGGTTTTTCCTT | 31 | 2077 |

TABLE 34-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763276 | N/A | N/A | 43064 | 43083 | GGAAGCCAAGACTTTCTTGT | 55 | 2078 |
| 763277 | N/A | N/A | 43157 | 43176 | GACTGGCCTCCAGCCAATGA | 45 | 2079 |
| 763278 | N/A | N/A | 43250 | 43269 | ACCTCTTGGATCTTTTCTCT | 41 | 2080 |
| 763279 | N/A | N/A | 43343 | 43362 | TTCCCCAATTTTCCTTTGTG | 37 | 2081 |
| 763280 | N/A | N/A | 43436 | 43455 | CACTCATTTTAAATGTACAT | 49 | 2082 |
| 763281 | N/A | N/A | 43529 | 43548 | GTCTTAGGTTTATGTTCATG | 73 | 2083 |
| 763282 | N/A | N/A | 43622 | 43641 | AATGTCACAAGACTTCATCT | 59 | 2084 |
| 763283 | N/A | N/A | 43715 | 43734 | CCCCTTGAAAATGTATGTTA | 47 | 2085 |
| 763284 | N/A | N/A | 43808 | 43827 | GACCTCTTAATGTTTCTTTG | 53 | 2086 |
| 763285 | N/A | N/A | 43901 | 43920 | AGATCAGATCATAATCAATA | 42 | 2087 |
| 763286 | N/A | N/A | 43994 | 44013 | ACTAGAACTGAGGGACAAGG | 13 | 2088 |
| 763287 | N/A | N/A | 44376 | 44395 | ATTTTGGGCTGGAAGCAGTG | 6 | 2089 |
| 763288 | N/A | N/A | 44469 | 44488 | GGCAGGAACAACTCTGTCAG | 62 | 2090 |
| 763289 | N/A | N/A | 44574 | 44593 | AGCACCAACCAACCAGAGGG | 51 | 2091 |
| 763290 | N/A | N/A | 44667 | 44686 | CCCTGTCAAATTTTAGAAAT | 25 | 2092 |
| 763291 | N/A | N/A | 44826 | 44845 | TTGGTCTAACTGTGTTGCCC | 65 | 2093 |
| 763292 | N/A | N/A | 45028 | 45047 | GAGGATTCACTAATTTTTTT | 43 | 2094 |
| 763293 | N/A | N/A | 45121 | 45140 | AAACAAAAGAGAAGCAACC | 40 | 2095 |

TABLE 35

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 62 | 33 |
| 741410 | N/A | N/A | 87946 | 87962 | GTAAGTTGTGACCATGC | 72 | 402 |
| 762837 | 238 | 257 | 4689 | 4708 | TGAATTCCTTTACACCACAC | 34 | 1639 |
| 763294 | N/A | N/A | 45214 | 45233 | GTCTCTAGTTTTCCTAAAAT | 53 | 2096 |
| 763295 | N/A | N/A | 45307 | 45326 | AGGATACTCAATCTCTTAAT | 63 | 2097 |
| 763296 | N/A | N/A | 45400 | 45419 | CGAATAGAAAAATTTAACTT | 0 | 2098 |
| 763297 | N/A | N/A | 45493 | 45512 | CTTCAATTAATATTCCAAGA | 54 | 2099 |
| 763298 | N/A | N/A | 45586 | 45605 | CACTGTGGATGAAGGTTACT | 47 | 2100 |
| 763299 | N/A | N/A | 45679 | 45698 | GGACTACTTGATGTCTAGAT | 68 | 2101 |
| 763300 | N/A | N/A | 45773 | 45792 | TTTAATAATACAGTATTATT | 0 | 2102 |
| 763301 | N/A | N/A | 45866 | 45885 | AACCTACAGAGAGTGGACTT | 34 | 2103 |
| 763302 | N/A | N/A | 45959 | 45978 | TTTATTTCCCACATAAAATT | 4 | 2104 |

TABLE 35-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763303 | N/A | N/A | 46052 | 46071 | TACTTAAGAGAAAAAATAGT | 0 | 2105 |
| 763304 | N/A | N/A | 46145 | 46164 | CCAAGTAAATAGTATTTTGG | 28 | 2106 |
| 763305 | N/A | N/A | 46155 | 46174 | TTCCATGAAGCCAAGTAAAT | 63 | 2107 |
| 763306 | N/A | N/A | 46156 | 46175 | TTTCCATGAAGCCAAGTAAA | 44 | 2108 |
| 763307 | N/A | N/A | 46157 | 46176 | ATTTCCATGAAGCCAAGTAA | 48 | 2109 |
| 763308 | N/A | N/A | 46158 | 46177 | GATTTCCATGAAGCCAAGTA | 50 | 2110 |
| 763309 | N/A | N/A | 46159 | 46178 | AGATTTCCATGAAGCCAAGT | 66 | 2111 |
| 763310 | N/A | N/A | 46160 | 46179 | GAGATTTCCATGAAGCCAAG | 50 | 2112 |
| 763311 | N/A | N/A | 46161 | 46180 | AGAGATTTCCATGAAGCCAA | 34 | 2113 |
| 763312 | N/A | N/A | 46162 | 46181 | GAGAGATTTCCATGAAGCCA | 65 | 2114 |
| 763313 | N/A | N/A | 46163 | 46182 | AGAGAGATTTCCATGAAGCC | 41 | 2115 |
| 763314 | N/A | N/A | 46164 | 46183 | GAGAGAGATTTCCATGAAGC | 61 | 2116 |
| 763315 | N/A | N/A | 46165 | 46184 | TGAGAGAGATTTCCATGAAG | 30 | 2117 |
| 763316 | N/A | N/A | 46166 | 46185 | GTGAGAGAGATTTCCATGAA | 47 | 2118 |
| 763317 | N/A | N/A | 46167 | 46186 | AGTGAGAGAGATTTCCATGA | 44 | 2119 |
| 763318 | N/A | N/A | 46238 | 46257 | GGATTTATGTAACAGGAATA | 53 | 2120 |
| 763319 | N/A | N/A | 46331 | 46350 | TGATTTAATACATATTTGCA | 33 | 2121 |
| 763320 | N/A | N/A | 46424 | 46443 | TCCACACTTCCCTCGATACT | 18 | 2122 |
| 763321 | N/A | N/A | 46529 | 46548 | GTGGTGGTGCCAGCAGTGGG | 39 | 2123 |
| 763322 | N/A | N/A | 46622 | 46641 | TACCACCCACAGCTGTGCCC | 43 | 2124 |
| 763323 | N/A | N/A | 46715 | 46734 | TAGAATAGTGCCTGTTTAAA | 19 | 2125 |
| 763324 | N/A | N/A | 46808 | 46827 | AATTGCCTTTTCTGTTTCTT | 48 | 2126 |
| 763325 | N/A | N/A | 46905 | 46924 | TACTAGCATAGTGTCTAGCA | 43 | 2127 |
| 763326 | N/A | N/A | 46998 | 47017 | ATACTCAGACATCTTAAGTC | 52 | 2128 |
| 763327 | N/A | N/A | 47093 | 47112 | GATGCCTGACACAAAATAGG | 54 | 2129 |
| 763328 | N/A | N/A | 47186 | 47205 | ATTATATTTTGCCTAACCTC | 0 | 2130 |
| 763329 | N/A | N/A | 47279 | 47298 | GAGAAAATCTGTCTCCTTGC | 27 | 2131 |
| 763330 | N/A | N/A | 47372 | 47391 | CATTGTGGGATTGTAAGTCT | 31 | 2132 |
| 763331 | N/A | N/A | 47465 | 47484 | TCACAATTACATTTTCTTGT | 53 | 2133 |
| 763332 | N/A | N/A | 47558 | 47577 | TATAGCATGAATTACTTTAC | 44 | 2134 |
| 763333 | N/A | N/A | 47651 | 47670 | TACCTCCTCTTCAGCAAGGA | 78 | 2135 |
| 763334 | N/A | N/A | 47744 | 47763 | CCTCTTGTAGTTTTTAAAAT | 27 | 2136 |
| 763335 | N/A | N/A | 47951 | 47970 | TTGGTTGTTCAAGTGATTCT | 33 | 2137 |
| 763336 | N/A | N/A | 48081 | 48100 | TCTCACAGTTTTGTTGTTGT | 57 | 2138 |
| 763337 | N/A | N/A | 48171 | 48190 | CTTTTCATCATGCCTTTATT | 40 | 2139 |
| 763338 | N/A | N/A | 48172 | 48191 | TCTTTTCATCATGCCTTTAT | 40 | 2140 |
| 763339 | N/A | N/A | 48173 | 48192 | ATCTTTTCATCATGCCTTTA | 37 | 2141 |

TABLE 35-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763340 | N/A | N/A | 48174 | 48193 | GATCTTTTCATCATGCCTTT | 55 | 2142 |
| 763341 | N/A | N/A | 48175 | 48194 | TGATCTTTTCATCATGCCTT | 70 | 2143 |
| 763342 | N/A | N/A | 48176 | 48195 | TTGATCTTTTCATCATGCCT | 51 | 2144 |
| 763343 | N/A | N/A | 48177 | 48196 | CTTGATCTTTTCATCATGCC | 59 | 2145 |
| 763344 | N/A | N/A | 48178 | 48197 | TCTTGATCTTTTCATCATGC | 60 | 2146 |
| 763345 | N/A | N/A | 48179 | 48198 | CTCTTGATCTTTTCATCATG | 38 | 2147 |
| 763346 | N/A | N/A | 48180 | 48199 | TCTCTTGATCTTTTCATCAT | 43 | 2148 |
| 763347 | N/A | N/A | 48181 | 48200 | ATCTCTTGATCTTTTCATCA | 36 | 2149 |
| 763348 | N/A | N/A | 48267 | 48286 | GGATTACTCCTGGCACAGCT | 62 | 2150 |
| 763349 | N/A | N/A | 48360 | 48379 | CGATGGAGTACCTACCAACT | 36 | 2151 |
| 763350 | N/A | N/A | 48453 | 48472 | TACGAGTAGAAGTGACTTGC | 53 | 2152 |
| 763351 | N/A | N/A | 48546 | 48565 | TCAGTGGAGAGCTATGCAAT | 5 | 2153 |
| 763352 | N/A | N/A | 48648 | 48667 | TGTAGAATACTTATTTTTTG | 28 | 2154 |
| 763353 | N/A | N/A | 48710 | 48729 | ATTTTGGATGCTTCTGAAGA | 24 | 2155 |
| 763354 | N/A | N/A | 48711 | 48730 | TATTTTGGATGCTTCTGAAG | 17 | 2156 |
| 763355 | N/A | N/A | 48712 | 48731 | GTATTTTGGATGCTTCTGAA | 63 | 2157 |
| 763356 | N/A | N/A | 48713 | 48732 | TGTATTTTGGATGCTTCTGA | 59 | 2158 |
| 763357 | N/A | N/A | 48714 | 48733 | TTGTATTTTGGATGCTTCTG | 54 | 2159 |
| 763358 | N/A | N/A | 48715 | 48734 | TTTGTATTTTGGATGCTTCT | 61 | 2160 |
| 763359 | N/A | N/A | 48716 | 48735 | GTTTGTATTTTGGATGCTTC | 63 | 2161 |
| 763360 | N/A | N/A | 48717 | 48736 | GGTTTGTATTTTGGATGCTT | 61 | 2162 |
| 763361 | N/A | N/A | 48718 | 48737 | TGGTTTGTATTTTGGATGCT | 40 | 2163 |
| 763362 | N/A | N/A | 48719 | 48738 | ATGGTTTGTATTTTGGATGC | 41 | 2164 |
| 763363 | N/A | N/A | 48720 | 48739 | GATGGTTTGTATTTTGGATG | 55 | 2165 |
| 763364 | N/A | N/A | 48741 | 48760 | ACGACATTTTCTTGCCTCTT | 74 | 2166 |
| 763365 | N/A | N/A | 48842 | 48861 | ATGCTTTCACTTGAAAAAAA | 25 | 2167 |
| 763366 | N/A | N/A | 48975 | 48994 | CTTTTTTTATTTAAATTCTT | 1 | 2168 |
| 763367 | N/A | N/A | 49144 | 49163 | ATGGAGAAACTACCCCCATG | 27 | 2169 |
| 763368 | N/A | N/A | 49239 | 49258 | ACCTCACATGGCAGGAGAAA | 32 | 2170 |
| 763369 | N/A | N/A | 49341 | 49360 | TTTTTATAAAGAAAGAAGTT | 0 | 2171 |
| 763370 | N/A | N/A | 49434 | 49453 | TCTTGCTTCTATGTTATATG | 65 | 2172 |

TABLE 36

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 79 | 33 |
| 741410 | N/A | N/A | 87946 | 87962 | GTAAGTTGTGACCATGC | 82 | 402 |
| 762837 | 238 | 257 | 4689 | 4708 | TGAATTCCTTTACACCACAC | 57 | 1639 |
| 763371 | N/A | N/A | 49527 | 49546 | CACCCACCATAAAAGGTGAT | 10 | 2173 |
| 763372 | N/A | N/A | 49620 | 49639 | TGCCTCTGTTTACAAAGCAA | 58 | 2174 |
| 763373 | N/A | N/A | 49713 | 49732 | TGGTTTCCTTTGGTGGCTTT | 74 | 2175 |
| 763374 | N/A | N/A | 49806 | 49825 | TTTCCTTAAGAGGAGCTCTC | 53 | 2176 |
| 763375 | N/A | N/A | 49899 | 49918 | GATGTAAGTGAGACAGCTCA | 56 | 2177 |
| 763376 | N/A | N/A | 49992 | 50011 | TTTAGGTAATGGTTTGGTAT | 47 | 2178 |
| 763377 | N/A | N/A | 50085 | 50104 | ATAGAGGTTATTATTCAGTA | 49 | 2179 |
| 763378 | N/A | N/A | 50178 | 50197 | AGGAAAACCATCTCTGCTAT | 36 | 2180 |
| 763379 | N/A | N/A | 50271 | 50290 | GGAAAGAGGTATGAGTGATG | 24 | 2181 |
| 763380 | N/A | N/A | 50364 | 50383 | GAGTGCTGCCTAAGTCTTGG | 50 | 2182 |
| 763381 | N/A | N/A | 50457 | 50476 | TTGCTAGCTAAAAGGAGGGT | 9 | 2183 |
| 763382 | N/A | N/A | 50550 | 50569 | CCAGTTCTAGTTGTACTAGT | 52 | 2184 |
| 763383 | N/A | N/A | 50660 | 50679 | AAAATGAACTTTTTTATTCG | 14 | 2185 |
| 763384 | N/A | N/A | 50753 | 50772 | TGCACATCTTTTGCCTGAAA | 70 | 2186 |
| 763385 | N/A | N/A | 50846 | 50865 | AACTAATCATTATTTTAGAC | 0 | 2187 |
| 763386 | N/A | N/A | 50915 | 50934 | CATCAATATCTGCAATAATA | 63 | 2188 |
| 763387 | N/A | N/A | 50916 | 50935 | TCATCAATATCTGCAATAAT | 64 | 2189 |
| 763388 | N/A | N/A | 50917 | 50936 | TTCATCAATATCTGCAATAA | 45 | 2190 |
| 763389 | N/A | N/A | 50918 | 50937 | TTTCATCAATATCTGCAATA | 64 | 2191 |
| 763390 | N/A | N/A | 50919 | 50938 | TTTTCATCAATATCTGCAAT | 49 | 2192 |
| 763391 | N/A | N/A | 50920 | 50939 | GTTTTCATCAATATCTGCAA | 76 | 2193 |
| 763392 | N/A | N/A | 50921 | 50940 | GGTTTTCATCAATATCTGCA | 60 | 2194 |
| 763393 | N/A | N/A | 50922 | 50941 | AGGTTTTCATCAATATCTGC | 73 | 2195 |
| 763394 | N/A | N/A | 50923 | 50942 | AAGGTTTTCATCAATATCTG | 77 | 2196 |
| 763395 | N/A | N/A | 50924 | 50943 | AAAGGTTTTCATCAATATCT | 65 | 2197 |
| 763396 | N/A | N/A | 50925 | 50944 | TAAAGGTTTTCATCAATATC | 36 | 2198 |
| 763397 | N/A | N/A | 50926 | 50945 | GTAAAGGTTTTCATCAATAT | 54 | 2199 |
| 763398 | N/A | N/A | 50939 | 50958 | AATTAAGAGGAAGGTAAAGG | 2 | 2200 |
| 763399 | N/A | N/A | 51032 | 51051 | AAATAATTTCAACATCAGTT | 20 | 2201 |
| 763400 | N/A | N/A | 51125 | 51144 | CAATAGCTTGCCAAAAATTC | 38 | 2202 |
| 763401 | N/A | N/A | 51218 | 51237 | ATTTTGTTTCATGGATGTTT | 53 | 2203 |
| 763402 | N/A | N/A | 51318 | 51337 | AGTCAACATAATTTTTTTG | 34 | 2204 |
| 763403 | N/A | N/A | 51412 | 51431 | TCAACAAGGCCTTACTTACG | 55 | 2205 |
| 763404 | N/A | N/A | 51505 | 51524 | TTATAAAATATCTTCCTAGG | 3 | 2206 |

TABLE 36-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763405 | N/A | N/A | 51598 | 51617 | TTTTGGCTGCCTCTCAAAAT | 21 | 2207 |
| 763406 | N/A | N/A | 51691 | 51710 | TTCATTAAAAATTCTGAGTT | 3 | 2208 |
| 763407 | N/A | N/A | 51792 | 51811 | ATTTTTAATATAATGCTACG | 0 | 2209 |
| 763408 | N/A | N/A | 51885 | 51904 | CACCAGTGTTTGCATGTCCC | 67 | 2210 |
| 763409 | N/A | N/A | 51978 | 51997 | CCTCCTACTTCCTAGGCTGC | 7 | 2211 |
| 763410 | N/A | N/A | 52071 | 52090 | GCTCAATTGGGTGTTCAGCA | 62 | 2212 |
| 763411 | N/A | N/A | 52164 | 52183 | ACACTGTAAAACTGTCACAA | 52 | 2213 |
| 763412 | N/A | N/A | 52310 | 52329 | CACATGGATGTATTTGTGCG | 49 | 2214 |
| 763413 | N/A | N/A | 52403 | 52422 | AGAAGTTTCAAGAACAGTCA | 45 | 2215 |
| 763414 | N/A | N/A | 52496 | 52515 | TTTAATATACAGATGTTCAG | 11 | 2216 |
| 763415 | N/A | N/A | 52589 | 52608 | CCCACCTGCCAAAAACACCT | 36 | 2217 |
| 763416 | N/A | N/A | 52682 | 52701 | TCGAAGTGGGTATGGATGCA | 50 | 2218 |
| 763417 | N/A | N/A | 52775 | 52794 | GGGCATATGGCTATATACTA | 51 | 2219 |
| 763418 | N/A | N/A | 52868 | 52887 | TCTAGTTAGCATCTATCCAC | 73 | 2220 |
| 763419 | N/A | N/A | 52961 | 52980 | TCTTATAAAATTTCTATACT | 13 | 2221 |
| 763420 | N/A | N/A | 53054 | 53073 | TCATTTTACTTAAGTGGCAC | 51 | 2222 |
| 763421 | N/A | N/A | 53147 | 53166 | GTCTTTTTCCCATCCTTGAC | 53 | 2223 |
| 763422 | N/A | N/A | 53240 | 53259 | TTAGCAAGTATAAATATGTT | 4 | 2224 |
| 763423 | N/A | N/A | 53333 | 53352 | TAGTTGATTGTAGGAAATGT | 48 | 2225 |
| 763424 | N/A | N/A | 53426 | 53445 | TTGCAAAACAGATGGACTTC | 43 | 2226 |
| 763425 | N/A | N/A | 53519 | 53538 | TGATGATCTAGCCAAGAGGG | 27 | 2227 |
| 763426 | N/A | N/A | 53612 | 53631 | ACAAGCTGTACATTAATTAC | 42 | 2228 |
| 763427 | N/A | N/A | 53640 | 53659 | TTCCATGAAGCCAAGATCAA | 46 | 2229 |
| 763428 | N/A | N/A | 53641 | 53660 | TTTCCATGAAGCCAAGATCA | 62 | 2230 |
| 763429 | N/A | N/A | 53642 | 53661 | ATTTCCATGAAGCCAAGATC | 63 | 2231 |
| 763430 | N/A | N/A | 53643 | 53662 | TATTTCCATGAAGCCAAGAT | 66 | 2232 |
| 763431 | N/A | N/A | 53644 | 53663 | TTATTTCCATGAAGCCAAGA | 61 | 2233 |
| 763432 | N/A | N/A | 53645 | 53664 | ATTATTTCCATGAAGCCAAG | 53 | 2234 |
| 763433 | N/A | N/A | 53646 | 53665 | AATTATTTCCATGAAGCCAA | 67 | 2235 |
| 763434 | N/A | N/A | 53647 | 53666 | GAATTATTTCCATGAAGCCA | 77 | 2236 |
| 763435 | N/A | N/A | 53648 | 53667 | TGAATTATTTCCATGAAGCC | 66 | 2237 |
| 763436 | N/A | N/A | 53649 | 53668 | GTGAATTATTTCCATGAAGC | 68 | 2238 |
| 763437 | N/A | N/A | 53650 | 53669 | AGTGAATTATTTCCATGAAG | 69 | 2239 |
| 763438 | N/A | N/A | 53705 | 53724 | AAGTAAGTTCTGAGCTGACA | 34 | 2240 |
| 763439 | N/A | N/A | 53798 | 53817 | TATTAAGTCTGTTAAGAGGT | 54 | 2241 |
| 763440 | N/A | N/A | 53891 | 53910 | ATGTTGTATGATGCTCTGGC | 74 | 2242 |

TABLE 36-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763441 | N/A | N/A | 53984 | 54003 | GTAGATTGCTATTTTGCCAC | 55 | 2243 |
| 763442 | N/A | N/A | 54080 | 54099 | AATGGGTTTATGTATAATCG | 58 | 2244 |
| 763443 | N/A | N/A | 54173 | 54192 | CTCCAGACATAGATCTCTCT | 63 | 2245 |
| 763444 | N/A | N/A | 54266 | 54285 | ACAAGTAAACTGAAACCAGA | 23 | 2246 |
| 763445 | N/A | N/A | 54359 | 54378 | GTAAGGATGATCATTATAAC | 55 | 2247 |
| 763446 | N/A | N/A | 54452 | 54471 | ATTAAACATTTTTAATAGCC | 27 | 2248 |
| 763447 | N/A | N/A | 54545 | 54564 | AGGTGAATAAACTTCGAAAT | 51 | 2249 |

TABLE 37

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 86 | 33 |
| 741410 | N/A | N/A | 87946 | 87962 | GTAAGTTGTGACCATGC | 93 | 402 |
| 762837 | 238 | 257 | 4689 | 4708 | TGAATTCCTTTACACCACAC | 68 | 1639 |
| 763448 | N/A | N/A | 54638 | 54657 | TATCAAAAGATTATATATAG | 0 | 2250 |
| 763449 | N/A | N/A | 54731 | 54750 | TAAATAACATGAATAAGACC | 21 | 2251 |
| 763450 | N/A | N/A | 54824 | 54843 | TTTTACACATAAGCATATAT | 18 | 2252 |
| 763451 | N/A | N/A | 54917 | 54936 | AATGAATGTTACCATTTTAT | 45 | 2253 |
| 763452 | N/A | N/A | 55011 | 55030 | CAATATATTTATTAGGAGAA | 30 | 2254 |
| 763453 | N/A | N/A | 55104 | 55123 | TCATAAATCAGTCCTCTATA | 36 | 2255 |
| 763454 | N/A | N/A | 55197 | 55216 | AAAAAGAAGTCAGATATTTC | 26 | 2256 |
| 763455 | N/A | N/A | 55290 | 55309 | TTTCGGCAGAATTCCAGAGA | 56 | 2257 |
| 763456 | N/A | N/A | 55383 | 55402 | TGGTTTTCTTTTTCTAGTCA | 73 | 2258 |
| 763457 | N/A | N/A | 55476 | 55495 | CTCACAAATCATAGGTTTGT | 25 | 2259 |
| 763458 | N/A | N/A | 55569 | 55588 | GACTATCAATCGGTACTTAT | 67 | 2260 |
| 763459 | N/A | N/A | 55663 | 55682 | ATTTTATTTGAAATATGTGA | 12 | 2261 |
| 763460 | N/A | N/A | 55756 | 55775 | GATCTTAGAAATTCATTTAG | 42 | 2262 |
| 763461 | N/A | N/A | 55849 | 55868 | TTCTCTAAGTACAACACTGC | 33 | 2263 |
| 763462 | N/A | N/A | 55942 | 55961 | CCACAGTTACATCTGGAAAC | 46 | 2264 |
| 763463 | N/A | N/A | 56051 | 56070 | AAGTTGTGCGACTTTGGGCA | 66 | 2265 |
| 763464 | N/A | N/A | 56144 | 56163 | TATCATCAGCAGAACATAGA | 36 | 2266 |
| 763465 | N/A | N/A | 56237 | 56256 | TAAATATTGTTTTTCTAAG | 1 | 2267 |
| 763466 | N/A | N/A | 56330 | 56349 | GACACATTTATATTAGATGT | 79 | 2268 |
| 763467 | N/A | N/A | 56423 | 56442 | AAGGAGGGAAACAAAGCTCC | 22 | 2269 |
| 763468 | N/A | N/A | 56516 | 56535 | TACTATATGACATGCTTTCT | 31 | 2270 |

TABLE 37-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763469 | N/A | N/A | 56612 | 56631 | CAATGGATGAATAGGTGGAT | 45 | 2271 |
| 763470 | N/A | N/A | 56705 | 56724 | ATGTTGTGGCTTAACCCCAT | 54 | 2272 |
| 763471 | N/A | N/A | 56798 | 56817 | AAAAAACCTGAAGTACAACA | 16 | 2273 |
| 763472 | N/A | N/A | 56891 | 56910 | TACTGTGGGTCATTTTTTCT | 44 | 2274 |
| 763473 | N/A | N/A | 56987 | 57006 | ATAATATCTATATTTAAAAC | 0 | 2275 |
| 763474 | N/A | N/A | 57082 | 57101 | TATAAAGATGGATTTTTAAA | 0 | 2276 |
| 763475 | N/A | N/A | 57175 | 57194 | AAATGGATGCTAAGACAATT | 35 | 2277 |
| 763476 | N/A | N/A | 57268 | 57287 | CCTTCTCTAACTGCCTTTAC | 24 | 2278 |
| 763477 | N/A | N/A | 57361 | 57380 | GTATAGTTAAAGCTACATTT | 59 | 2279 |
| 763478 | N/A | N/A | 57454 | 57473 | CAAATTTTGCTTTTACACCC | 63 | 2280 |
| 763479 | N/A | N/A | 57547 | 57566 | CTTACTTGAGCTAGGTGATC | 54 | 2281 |
| 763480 | N/A | N/A | 57640 | 57659 | TTCCTCTATTTAATGTATTT | 69 | 2282 |
| 763481 | N/A | N/A | 57733 | 57752 | TAGCAGTTCCAGGTTCCACA | 84 | 2283 |
| 763482 | N/A | N/A | 57826 | 57845 | ATCACTTTGGTGTGAGAAGA | 14 | 2284 |
| 763483 | N/A | N/A | 57919 | 57938 | ATTCCATAGACTTCCAAGTC | 60 | 2285 |
| 763484 | N/A | N/A | 58012 | 58031 | AGCATCCACATGAAATTGGT | 48 | 2286 |
| 763485 | N/A | N/A | 58105 | 58124 | GATGTCTTGATACCTTCAGA | 79 | 2287 |
| 763486 | N/A | N/A | 58198 | 58217 | CTACATGCTAAACTTGTTTT | 11 | 2288 |
| 763487 | N/A | N/A | 58291 | 58310 | GTGAGAATAAATGTGATCTA | 41 | 2289 |
| 763488 | N/A | N/A | 58384 | 58403 | CTGTTTCATTAGGAATTTTT | 68 | 2290 |
| 763489 | N/A | N/A | 58477 | 58496 | TTTATGTACATGGCCAGAAA | 32 | 2291 |
| 763490 | N/A | N/A | 58571 | 58590 | ACAAAAAATTTCCTAACATT | 2 | 2292 |
| 763491 | N/A | N/A | 58664 | 58683 | TGTAGCATTTACCTAACAGC | 83 | 2293 |
| 763492 | N/A | N/A | 58757 | 58776 | AGTGCAGAATCCTGATTGCA | 75 | 2294 |
| 763493 | N/A | N/A | 58850 | 58869 | CACATTGTAACATAAGCTGT | 48 | 2295 |
| 763494 | N/A | N/A | 58943 | 58962 | AGTTTGAACTCCGCCCAAGA | 32 | 2296 |
| 763495 | N/A | N/A | 59036 | 59055 | ACAAGGTTTGCACAAATAAA | 48 | 2297 |
| 763496 | N/A | N/A | 59129 | 59148 | CCTCATATATAGGGCCTCAC | 46 | 2298 |
| 763497 | N/A | N/A | 59222 | 59241 | AATTATAAAGCCCTGAAGGC | 1 | 2299 |
| 763498 | N/A | N/A | 59315 | 59334 | AATGTATTGTTATTTGTCAT | 68 | 2300 |
| 763499 | N/A | N/A | 59439 | 59458 | CAACTTCTCCATATAACCAA | 52 | 2301 |
| 763500 | N/A | N/A | 59592 | 59611 | CTAAAGGATGCAAAGGCATA | 23 | 2302 |
| 763501 | N/A | N/A | 59685 | 59704 | CGTAGATAGAGTTGGAGACC | 76 | 2303 |
| 763502 | N/A | N/A | 59788 | 59807 | GTGATATATTTACATATATA | 60 | 2304 |
| 763503 | N/A | N/A | 59945 | 59964 | TTCCAGCGATCCCACTCCTA | 26 | 2305 |
| 763504 | N/A | N/A | 60040 | 60059 | TTTTTTTACACTGCTGGTAG | 31 | 2306 |

TABLE 37-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763505 | N/A | N/A | 60161 | 60180 | TTTAATGACCAGGGAAATGC | 19 | 2307 |
| 763506 | N/A | N/A | 60418 | 60437 | GGGACCTAAAACTATAAAGC | 40 | 2308 |
| 763507 | N/A | N/A | 60540 | 60559 | CAAAACCTTAAAAATTATAG | 0 | 2309 |
| 763508 | N/A | N/A | 60744 | 60763 | AAATCCAGAAATAAAGCTAA | 18 | 2310 |
| 763509 | N/A | N/A | 60844 | 60863 | CTAGATTACCCAACTTCAAA | 4 | 2311 |
| 763510 | N/A | N/A | 60972 | 60991 | GACTCCCATCAAAATGCCAC | 37 | 2312 |
| 763511 | N/A | N/A | 61069 | 61088 | ACAGAAACTAATGAAAACAC | 0 | 2313 |
| 763512 | N/A | N/A | 61183 | 61202 | GAGCCTTTTACAACAGCTG | 61 | 2314 |
| 763513 | N/A | N/A | 61282 | 61301 | TTAATTCAGTAAAGTTTCCA | 11 | 2315 |
| 763514 | N/A | N/A | 61391 | 61410 | AGCATCCAAACTGCTAAAGA | 35 | 2316 |
| 763515 | N/A | N/A | 61499 | 61518 | TTTCCCCCGAGAACTGGAAT | 0 | 2317 |
| 763516 | N/A | N/A | 61592 | 61611 | CTGGCATATAAGATACACAC | 45 | 2318 |
| 763517 | N/A | N/A | 61691 | 61710 | GCAGGAGTAAAAACAAAAAT | 29 | 2319 |
| 763518 | N/A | N/A | 61966 | 61985 | GTTCCAAAAGATAGAGACAG | 37 | 2320 |
| 763519 | N/A | N/A | 62059 | 62078 | GTCAGGAAACAAAAAAAGTC | 15 | 2321 |
| 763520 | N/A | N/A | 62154 | 62173 | CATATATACAAACCTCCTAG | 14 | 2322 |
| 763521 | N/A | N/A | 62296 | 62315 | AAAGATCTAAACAAGCTCAA | 16 | 2323 |
| 763522 | N/A | N/A | 62399 | 62418 | CACAAAATACAATACAAAAG | 0 | 2324 |
| 763523 | N/A | N/A | 62496 | 62515 | AAGATCATACTGTTGCATTC | 14 | 2325 |
| 763524 | N/A | N/A | 62674 | 62693 | AGGCGGATCACCATAAGTCA | 0 | 2326 |

TABLE 38

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 80 | 33 |
| 741410 | N/A | N/A | 87946 | 87962 | GTAAGTTGTGACCATGC | 83 | 402 |
| 762837 | 238 | 257 | 4689 | 4708 | TGAATTCCTTTACACCACAC | 69 | 1639 |
| 763604 | N/A | N/A | 70405 | 70424 | TCATTTCCTTAGTTCCATAT | 45 | 2327 |
| 763605 | N/A | N/A | 70498 | 70517 | TCTGCCTTGTTTTTCTTTC | 65 | 2328 |
| 763606 | N/A | N/A | 70594 | 70613 | TATATAGTTATATATTTACG | 0 | 2329 |
| 763607 | N/A | N/A | 70687 | 70706 | TTTATATTATATTAACTCTA | 13 | 2330 |
| 763608 | N/A | N/A | 70780 | 70799 | GGCTTGTCTCTATCCCTGT | 65 | 2331 |
| 763609 | N/A | N/A | 70908 | 70927 | GCCCCAGCTTCCGGGTTCAA | 24 | 2332 |
| 763610 | N/A | N/A | 71001 | 71020 | GAAATATTATTTATACTATT | 0 | 2333 |
| 763611 | N/A | N/A | 71094 | 71113 | TCTCACAATCACAGAAAACA | 31 | 2334 |

TABLE 38-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763612 | N/A | N/A | 71187 | 71206 | GACTGCATTTGTATTTCATC | 89 | 2335 |
| 763613 | N/A | N/A | 71280 | 71299 | AGATTAACAAAATATTAATT | 10 | 2336 |
| 763614 | N/A | N/A | 71373 | 71392 | TATCATTCTTAACAGAAAAA | 20 | 2337 |
| 763615 | N/A | N/A | 71471 | 71490 | CTAAGCCATTTTATAACAGG | 33 | 2338 |
| 763616 | N/A | N/A | 71568 | 71587 | GCCTAACAGGCTATGGACCA | 47 | 2339 |
| 763617 | N/A | N/A | 71778 | 71797 | CACGGACAGGGATGGTGAGG | 52 | 2340 |
| 763618 | N/A | N/A | 71871 | 71890 | GTATTGGGCATTATCAGTAA | 65 | 2341 |
| 763619 | N/A | N/A | 71964 | 71983 | ACTTATCAACACTTAAACTG | 23 | 2342 |
| 763620 | N/A | N/A | 72074 | 72093 | TAGGTAATTCTAATTTTAAT | 6 | 2343 |
| 763621 | N/A | N/A | 72201 | 72220 | TACCTAGGTGGTTTCCATAT | 46 | 2344 |
| 763622 | N/A | N/A | 72294 | 72313 | AATGACAGGGTCTTCTCCTT | 58 | 2345 |
| 763623 | N/A | N/A | 72295 | 72314 | AAATGACAGGGTCTTCTCCT | 66 | 2346 |
| 763624 | N/A | N/A | 72296 | 72315 | CAAATGACAGGGTCTTCTCC | 60 | 2347 |
| 763625 | N/A | N/A | 72297 | 72316 | GCAAATGACAGGGTCTTCTC | 76 | 2348 |
| 763626 | N/A | N/A | 72298 | 72317 | GGCAAATGACAGGGTCTTCT | 68 | 2349 |
| 763627 | N/A | N/A | 72299 | 72318 | TGGCAAATGACAGGGTCTTC | 83 | 2350 |
| 763628 | N/A | N/A | 72300 | 72319 | GTGGCAAATGACAGGGTCTT | 77 | 2351 |
| 763629 | N/A | N/A | 72301 | 72320 | TGTGGCAAATGACAGGGTCT | 89 | 2352 |
| 763630 | N/A | N/A | 72302 | 72321 | TTGTGGCAAATGACAGGGTC | 73 | 2353 |
| 763631 | N/A | N/A | 72408 | 72427 | ACTTTTCTTTTTAGATTCC | 67 | 2354 |
| 763632 | N/A | N/A | 72630 | 72649 | TTCTCAACTGCCTGAGTAGC | 41 | 2355 |
| 763633 | N/A | N/A | 72756 | 72775 | TGTGTGGACTGTGTTTTTTG | 70 | 2356 |
| 763634 | N/A | N/A | 72849 | 72868 | CAGCTTTTTAGTTCCTCCTA | 84 | 2357 |
| 763635 | N/A | N/A | 72942 | 72961 | TTCCCCTGTGGCAAGAGCAG | 47 | 2358 |
| 763636 | N/A | N/A | 73035 | 73054 | ATGCTGTTATAAGATGAATG | 58 | 2359 |
| 763637 | N/A | N/A | 73128 | 73147 | AAATTATTATAATTCACTCT | 5 | 2360 |
| 763638 | N/A | N/A | 73185 | 73204 | ACTTTCTGTGTGGTATGTTC | 74 | 2361 |
| 763639 | N/A | N/A | 73186 | 73205 | GACTTTCTGTGTGGTATGTT | 76 | 2362 |
| 763640 | N/A | N/A | 73187 | 73206 | AGACTTTCTGTGTGGTATGT | 88 | 2363 |
| 763641 | N/A | N/A | 73188 | 73207 | CAGACTTTCTGTGTGGTATG | 86 | 2364 |
| 763642 | N/A | N/A | 73189 | 73208 | ACAGACTTTCTGTGTGGTAT | 70 | 2365 |
| 763643 | N/A | N/A | 73190 | 73209 | GACAGACTTTCTGTGTGGTA | 78 | 2366 |
| 763644 | N/A | N/A | 73191 | 73210 | AGACAGACTTTCTGTGTGGT | 65 | 2367 |
| 763645 | N/A | N/A | 73192 | 73211 | CAGACAGACTTTCTGTGTGG | 81 | 2368 |
| 763646 | N/A | N/A | 73193 | 73212 | TCAGACAGACTTTCTGTGTG | 51 | 2369 |
| 763647 | N/A | N/A | 73194 | 73213 | TTCAGACAGACTTTCTGTGT | 58 | 2370 |

TABLE 38-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763648 | N/A | N/A | 73195 | 73214 | CTTCAGACAGACTTTCTGTG | 60 | 2371 |
| 763649 | N/A | N/A | 73221 | 73240 | TTGTATTGGTGGAGAAAACA | 20 | 2372 |
| 763650 | N/A | N/A | 73314 | 73333 | GTGTTGAGAATTTTTCATTG | 82 | 2373 |
| 763651 | N/A | N/A | 73407 | 73426 | TAGCATCTCTAATGTAGTCT | 85 | 2374 |
| 763652 | N/A | N/A | 73500 | 73519 | GTAGCTGAATTTCTTCAGCA | 22 | 2375 |
| 763653 | N/A | N/A | 73593 | 73612 | ATTACAGTGAAATGAAACAT | 4 | 2376 |
| 763654 | N/A | N/A | 73686 | 73705 | AAATACATTTTGCCTCTGTC | 55 | 2377 |
| 763655 | N/A | N/A | 73779 | 73798 | CTTTAAGACTTTCCTTAGAC | 54 | 2378 |
| 763656 | N/A | N/A | 73872 | 73891 | TTTGTTTTAAAACTAGACTT | 27 | 2379 |
| 763657 | N/A | N/A | 73965 | 73984 | AAAAGAGATGAAAAGTGTG | 22 | 2380 |
| 763658 | N/A | N/A | 74058 | 74077 | AGATATGGAGGAGAGTGAAA | 28 | 2381 |
| 763659 | N/A | N/A | 74159 | 74178 | CTTCCCTCAGCAACAGGCGC | 51 | 2382 |
| 763660 | N/A | N/A | 74252 | 74271 | GGTCTAGAATCATTCTGAAG | 55 | 2383 |
| 763661 | N/A | N/A | 74345 | 74364 | AAGGACCTTTCTTCTGAAAG | 66 | 2384 |
| 763662 | N/A | N/A | 74438 | 74457 | TACACAGAGCACTTCTTATT | 41 | 2385 |
| 763663 | N/A | N/A | 74531 | 74550 | CTCCCTTTTTCCCACATCTA | 48 | 2386 |
| 763664 | N/A | N/A | 74624 | 74643 | AAATTAAGTGTTAAGCACAC | 60 | 2387 |
| 763665 | N/A | N/A | 74717 | 74736 | AAATATTTGCTCAGAGACAC | 59 | 2388 |
| 763666 | N/A | N/A | 74810 | 74829 | GAATAAAAATGTATAACTAT | 6 | 2389 |
| 763667 | N/A | N/A | 75104 | 75123 | CAGAGCCTGGCCAAAATGGC | 33 | 2390 |
| 763668 | N/A | N/A | 75197 | 75216 | AGCACTTAAACAGAAAAAAT | 27 | 2391 |
| 763669 | N/A | N/A | 75290 | 75309 | TCTATTGTATATTAGGTTGA | 67 | 2392 |
| 763670 | N/A | N/A | 75383 | 75402 | GATGAAGGAAGAATGATTTT | 49 | 2393 |
| 763671 | N/A | N/A | 75476 | 75495 | GCTAGTTCATTGTATGTGTC | 81 | 2394 |
| 763672 | N/A | N/A | 75569 | 75588 | ATTGAATAAAAATTTGTATT | 0 | 2395 |
| 763673 | N/A | N/A | 75943 | 75962 | CCAGGTATAAAATTTTTTTT | 35 | 2396 |
| 763674 | N/A | N/A | 76036 | 76055 | GATCTAAGAATACCCCTAGT | 25 | 2397 |
| 763675 | N/A | N/A | 76129 | 76148 | TTAGATAAAAGTATACTGT | 8 | 2398 |
| 763676 | N/A | N/A | 76222 | 76241 | GACAGTTTTCTAATTTTACA | 64 | 2399 |
| 763677 | N/A | N/A | 76315 | 76334 | GGGTTGGAAATAATACAGAG | 43 | 2400 |
| 763678 | N/A | N/A | 76408 | 76427 | TTGACCTGCAGTATCTTGAA | 28 | 2401 |
| 763679 | N/A | N/A | 76501 | 76520 | TACATATTCTTATTCAACTC | 46 | 2402 |
| 763680 | N/A | N/A | 76594 | 76613 | ATATTATTGATTGTTCTAAA | 14 | 2403 |

TABLE 39

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 57 | 33 |
| 741410 | N/A | N/A | 87946 | 87962 | GTAAGTTGTGACCATGC | 73 | 402 |
| 762837 | 238 | 257 | 4689 | 4708 | TGAATTCCTTTACACCACAC | 65 | 1639 |
| 763681 | N/A | N/A | 76687 | 76706 | GGATATTCGATTCAAGAACA | 56 | 2404 |
| 763682 | N/A | N/A | 76780 | 76799 | ATAAATTTGGAAGCTAATGT | 2 | 2405 |
| 763683 | N/A | N/A | 76873 | 76892 | ACCACATTTTGAAAATAAAG | 40 | 2406 |
| 763684 | N/A | N/A | 76966 | 76985 | AGCACAGGAAATTAACATAT | 62 | 2407 |
| 763685 | N/A | N/A | 77059 | 77078 | GTAGGTGTGTTTATTTCTAT | 66 | 2408 |
| 763686 | N/A | N/A | 77164 | 77183 | CTTTTCATCAGAGATTTTTT | 60 | 2409 |
| 763687 | N/A | N/A | 77257 | 77276 | GAAATCTAAAAACAGCAAAG | 3 | 2410 |
| 763688 | N/A | N/A | 77350 | 77369 | GACTATTGTTTAATGTGTT | 48 | 2411 |
| 763689 | N/A | N/A | 77443 | 77462 | GGGAGATTTGAGAGAGAGGC | 44 | 2412 |
| 763690 | N/A | N/A | 77536 | 77555 | ATAGTGGGCTTATGGTGTAC | 51 | 2413 |
| 763691 | N/A | N/A | 77630 | 77649 | ATTTCTCCATTTCTGTCACT | 41 | 2414 |
| 763692 | N/A | N/A | 77738 | 77757 | CAGGAGTAAGGACACAGACG | 42 | 2415 |
| 763693 | N/A | N/A | 77831 | 77850 | CCTCCAGAAAAGGTTTTTAG | 62 | 2416 |
| 763694 | N/A | N/A | 77924 | 77943 | GAATTGAAACTGCTTAGAAG | 28 | 2417 |
| 763695 | N/A | N/A | 78027 | 78046 | CCTGACTTTGAATTATTTTG | 55 | 2418 |
| 763696 | N/A | N/A | 78120 | 78139 | AAAATCAGATAGCAGTGGTG | 36 | 2419 |
| 763697 | N/A | N/A | 78213 | 78232 | AGGGTACAGAAGGAAAGACA | 37 | 2420 |
| 763698 | N/A | N/A | 78306 | 78325 | TGAGAGGTGTTTGTTTTGAA | 15 | 2421 |
| 763699 | N/A | N/A | 78399 | 78418 | TGTTGGCAAGCTTGAAGGGA | 44 | 2422 |
| 763700 | N/A | N/A | 78495 | 78514 | AATTGAAGGGTTGTAACAGG | 29 | 2423 |
| 763701 | N/A | N/A | 78588 | 78607 | GCTGGAAAATTAGTCTGTAG | 75 | 2424 |
| 763702 | N/A | N/A | 78681 | 78700 | CATGGCATGGTCTATACATT | 62 | 2425 |
| 763703 | N/A | N/A | 78774 | 78793 | AGGTCTCATGGCTGGCAAGT | 27 | 2426 |
| 763704 | N/A | N/A | 78867 | 78886 | AAACACTTTATCAAATCTTA | 41 | 2427 |
| 763705 | N/A | N/A | 78960 | 78979 | ATCAGAACAAGTTAAACATT | 34 | 2428 |
| 763706 | N/A | N/A | 79053 | 79072 | TCTTTTATTCTTGTATCACT | 70 | 2429 |
| 763707 | N/A | N/A | 79146 | 79165 | TAGCCTTTTGATCTGTTTTT | 56 | 2430 |
| 763708 | N/A | N/A | 79239 | 79258 | TAAGAATTATGTTAAAACCA | 16 | 2431 |
| 763709 | N/A | N/A | 79332 | 79351 | CTTAAATTTTAACAATTAAA | 0 | 2432 |
| 763710 | N/A | N/A | 79425 | 79444 | AATTTACCCCCTAGTAGGCT | 57 | 2433 |
| 763711 | N/A | N/A | 79518 | 79537 | AGTAACATTTTGAAATGATG | 57 | 2434 |
| 763712 | N/A | N/A | 79611 | 79630 | CCTGTAGTTCAGTTTTACTG | 63 | 2435 |
| 763713 | N/A | N/A | 79704 | 79723 | AGATATGAAAATTTTCACTT | 25 | 2436 |
| 763714 | N/A | N/A | 79797 | 79816 | CTTTTAACTTTAGCTAAATA | 0 | 2437 |

TABLE 39-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763715 | N/A | N/A | 79890 | 79909 | AGGACCAAAGCTATGGTTAG | 52 | 2438 |
| 763716 | N/A | N/A | 79983 | 80002 | CAAACAAATAACAGCTTTCA | 58 | 2439 |
| 763717 | N/A | N/A | 80076 | 80095 | ATAACAAAATTCAGTGCAAC | 56 | 2440 |
| 763718 | N/A | N/A | 80169 | 80188 | ACATTTAAAGTTTTAACACT | 12 | 2441 |
| 763719 | N/A | N/A | 80262 | 80281 | GTTTTATAGTTGACAGATGA | 53 | 2442 |
| 763720 | N/A | N/A | 80355 | 80374 | TCTCTAAATTTGTTGATTTA | 26 | 2443 |
| 763721 | N/A | N/A | 80448 | 80467 | TGCAGGCACTCACAAACATT | 68 | 2444 |
| 763722 | N/A | N/A | 80555 | 80574 | ACACCTTTTCTCTTCTTTTT | 48 | 2445 |
| 763723 | N/A | N/A | 80648 | 80667 | ATCTACTGTTTGAAAGGGTG | 61 | 2446 |
| 763724 | N/A | N/A | 80741 | 80760 | ACATTGCTCAGAGTTCATGT | 44 | 2447 |
| 763725 | N/A | N/A | 80834 | 80853 | TAGGTACCATCAGAATTTCA | 57 | 2448 |
| 763726 | N/A | N/A | 80927 | 80946 | TCATTCTCTGCTACAATAAA | 43 | 2449 |
| 763727 | N/A | N/A | 80987 | 81006 | GAAATTTTCCAGCTAAAAAA | 19 | 2450 |
| 763728 | N/A | N/A | 80988 | 81007 | TGAAATTTTCCAGCTAAAAA | 0 | 2451 |
| 763729 | N/A | N/A | 80989 | 81008 | TTGAAATTTTCCAGCTAAAA | 47 | 2452 |
| 763730 | N/A | N/A | 80990 | 81009 | CTTGAAATTTTCCAGCTAAA | 51 | 2453 |
| 763731 | N/A | N/A | 80991 | 81010 | TCTTGAAATTTTCCAGCTAA | 47 | 2454 |
| 763732 | N/A | N/A | 80992 | 81011 | ATCTTGAAATTTTCCAGCTA | 45 | 2455 |
| 763733 | N/A | N/A | 80993 | 81012 | AATCTTGAAATTTTCCAGCT | 59 | 2456 |
| 763734 | N/A | N/A | 80994 | 81013 | AAATCTTGAAATTTTCCAGC | 60 | 2457 |
| 763735 | N/A | N/A | 80995 | 81014 | TAAATCTTGAAATTTTCCAG | 23 | 2458 |
| 763736 | N/A | N/A | 80996 | 81015 | ATAAATCTTGAAATTTTCCA | 24 | 2459 |
| 763737 | N/A | N/A | 80997 | 81016 | CATAAATCTTGAAATTTTCC | 40 | 2460 |
| 763738 | N/A | N/A | 81020 | 81039 | ATTTCTTTCTCAAGCCCAAA | 53 | 2461 |
| 763739 | N/A | N/A | 81113 | 81132 | TACATTCCTACTGTATTTAC | 38 | 2462 |
| 763740 | N/A | N/A | 81206 | 81225 | TGCTTTGATATGGCTTGGAG | 64 | 2463 |
| 763741 | N/A | N/A | 81299 | 81318 | TGGTATGAGTCACATAAGTA | 76 | 2464 |
| 763742 | N/A | N/A | 81392 | 81411 | CCTAGAAATTTTGCCTTTTC | 40 | 2465 |
| 763743 | N/A | N/A | 81485 | 81504 | CTGCAGGTTCTGGAGAGCTG | 56 | 2466 |
| 763744 | N/A | N/A | 81578 | 81597 | TGTTTACTGCCACTATTCAC | 53 | 2467 |
| 763745 | N/A | N/A | 81681 | 81700 | CTAACTGAACTTTTAAAAAT | 4 | 2468 |
| 763746 | N/A | N/A | 81774 | 81793 | AATACAATCTATCAGCATTA | 53 | 2469 |
| 763747 | N/A | N/A | 81868 | 81887 | AATTTTGGAGGAATTTATTT | 0 | 2470 |
| 763748 | N/A | N/A | 81961 | 81980 | TTGTGCTTCAATAATACCAA | 37 | 2471 |
| 763749 | N/A | N/A | 82112 | 82131 | TGGGTTTCATGGTGTTAGCT | 69 | 2472 |
| 763750 | N/A | N/A | 82237 | 82256 | GTAGGCTCAGTGCAAACTCT | 57 | 2473 |

TABLE 39-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763751 | N/A | N/A | 82330 | 82349 | AGTCTTTTTACATTATAATA | 28 | 2474 |
| 763752 | N/A | N/A | 82423 | 82442 | TAACAGATTTGTGGTGAAAA | 52 | 2475 |
| 763753 | N/A | N/A | 82516 | 82535 | AACCATAAGAGAGGACAAAC | 39 | 2476 |
| 763754 | N/A | N/A | 82609 | 82628 | AATGATCTTTAAAACATTCA | 9 | 2477 |
| 763755 | N/A | N/A | 82702 | 82721 | GAGGACAATAAAATGACCTT | 70 | 2478 |
| 763756 | N/A | N/A | 82810 | 82829 | CTCCTCTCAACTGCCAGCGC | 52 | 2479 |
| 763757 | N/A | N/A | 82903 | 82922 | TTTACTAAGTCATCTGTGAA | 19 | 2480 |

TABLE 40

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 75 | 33 |
| 741410 | N/A | N/A | 87946 | 87962 | GTAAGTTGTGACCATGC | 84 | 402 |
| 762837 | 238 | 257 | 4689 | 4708 | TGAATTCCTTTACACCACAC | 63 | 1639 |
| 763758 | N/A | N/A | 82996 | 83015 | CTTATGAGCTGTTTAGGAAG | 45 | 2481 |
| 763759 | N/A | N/A | 83089 | 83108 | TGTCAACTCTGCCAATGTGA | 56 | 2482 |
| 763760 | N/A | N/A | 83183 | 83202 | AATAAATGCTATGTAATTTA | 3 | 2483 |
| 763761 | N/A | N/A | 83276 | 83295 | GAAGGGTTGCTATGATAGTT | 56 | 2484 |
| 763762 | N/A | N/A | 83369 | 83388 | TGAATTCTAACCAAAAGCTT | 33 | 2485 |
| 763763 | N/A | N/A | 83462 | 83481 | GACAAATGTGTCACTTTTTA | 11 | 2486 |
| 763764 | N/A | N/A | 83555 | 83574 | AAATTCATGAGGAATGCAAT | 41 | 2487 |
| 763765 | N/A | N/A | 83648 | 83667 | CATACAATATTTTTGACAGA | 50 | 2488 |
| 763766 | N/A | N/A | 83741 | 83760 | GTGACGCACATTTACACCAG | 61 | 2489 |
| 763767 | N/A | N/A | 83834 | 83853 | AAAGATTTTTATCTTAGCCT | 42 | 2490 |
| 763768 | N/A | N/A | 83927 | 83946 | CCATTTACAAAGATGACCAG | 22 | 2491 |
| 763769 | N/A | N/A | 84020 | 84039 | TCAAAGTAGTGAATTACATC | 51 | 2492 |
| 763770 | N/A | N/A | 84113 | 84132 | TGTTTGGACTTATAAACTAT | 55 | 2493 |
| 763771 | N/A | N/A | 84206 | 84225 | TAATGGGCAAGCAAAAAATT | 0 | 2494 |
| 763772 | N/A | N/A | 84552 | 84571 | TCATGTTGCCTAGGCTAGAA | 58 | 2495 |
| 763773 | N/A | N/A | 84645 | 84664 | CTAGATAACATACAATATAA | 0 | 2496 |
| 763774 | N/A | N/A | 84752 | 84771 | GAGAAATTATTATATTTTAT | 0 | 2497 |
| 763775 | N/A | N/A | 84845 | 84864 | AGACTACAAAATTGCTAAAA | 32 | 2498 |
| 763776 | N/A | N/A | 84938 | 84957 | CAAAAGATTTTTATGGAGT | 3 | 2499 |
| 763777 | N/A | N/A | 85031 | 85050 | AATTTAAGTTTAAATATTCT | 0 | 2500 |
| 763778 | N/A | N/A | 85124 | 85143 | CCTCATTTTGCCAGTATTAA | 76 | 2501 |

TABLE 40-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763779 | N/A | N/A | 85217 | 85236 | ATGGGAAAATTGTGACTGTT | 59 | 2502 |
| 763780 | N/A | N/A | 85315 | 85334 | GCAAATATATGAATTTTTA | 12 | 2503 |
| 763781 | N/A | N/A | 85424 | 85443 | TCATTGGAAAATCTTGAACG | 61 | 2504 |
| 763782 | N/A | N/A | 85517 | 85536 | ATTTGTAGACCTATGTTGAA | 10 | 2505 |
| 763783 | N/A | N/A | 85610 | 85629 | GAATAATAAGATTCAGTCAT | 56 | 2506 |
| 763784 | N/A | N/A | 85703 | 85722 | GAAACCATTAAAATATTTAT | 0 | 2507 |
| 763785 | N/A | N/A | 85797 | 85816 | TCTAAGTTTTTATTAATTAA | 0 | 2508 |
| 763786 | N/A | N/A | 85891 | 85910 | ATGATTAGGATTTTTATTTC | 1 | 2509 |
| 763787 | N/A | N/A | 85984 | 86003 | TTTATATTTAAATCACACAA | 0 | 2510 |
| 763788 | N/A | N/A | 86077 | 86096 | AATTGCTGTTTTAATCATGA | 54 | 2511 |
| 763789 | N/A | N/A | 86170 | 86189 | CAGATTTATCTACTTGAAAC | 46 | 2512 |
| 763790 | N/A | N/A | 86263 | 86282 | GTAGAGTTTTTGGTCAGTGG | 63 | 2513 |
| 763791 | N/A | N/A | 86356 | 86375 | TTTTTGTTCTTGGGATGTTG | 53 | 2514 |
| 763792 | N/A | N/A | 86449 | 86468 | TAACTTTCAACCGTGAAAAA | 15 | 2515 |
| 763793 | N/A | N/A | 86542 | 86561 | GTCTGTTTTCTAACTAGCTT | 76 | 2516 |
| 763794 | N/A | N/A | 86635 | 86654 | GCACATTGTCAAATAAACAA | 61 | 2517 |
| 763795 | N/A | N/A | 86728 | 86747 | CAGGAATTATCCAAAGTCAC | 70 | 2518 |
| 763796 | N/A | N/A | 86821 | 86840 | ACCTGGGTTAAGTAAATGGC | 38 | 2519 |
| 763797 | N/A | N/A | 86914 | 86933 | CACTGGAGAGACTGTGAAGG | 53 | 2520 |
| 763798 | N/A | N/A | 87007 | 87026 | AGCAGCAGATTTCAAAAGGG | 69 | 2521 |
| 763799 | N/A | N/A | 87100 | 87119 | TTTTGATTGTGGTAATTGGA | 36 | 2522 |
| 763800 | N/A | N/A | 87193 | 87212 | TACAAGAGTGGAAATGGCTG | 27 | 2523 |
| 763801 | N/A | N/A | 87286 | 87305 | CCGTTACATGCTCTCTAATT | 46 | 2524 |
| 763802 | N/A | N/A | 87379 | 87398 | CTCCTGATCTCAATTGAAAT | 10 | 2525 |
| 763803 | N/A | N/A | 87472 | 87491 | AAGCCTTCATATACGAGTTT | 60 | 2526 |
| 763804 | N/A | N/A | 87565 | 87584 | TATCTCCAGCCTTCACCTCT | 13 | 2527 |
| 763805 | N/A | N/A | 87658 | 87677 | TCTCCTTCTTACAAAATCCA | 53 | 2528 |
| 763806 | N/A | N/A | 87759 | 87778 | GTTGTTCTTCTTCTTATTAT | 58 | 2529 |
| 763807 | N/A | N/A | 87854 | 87873 | GTTAAAATTTGAAATAATGA | 0 | 2530 |
| 763808 | N/A | N/A | 87940 | 87959 | AGTTGTGACCATGCAATAAA | 50 | 2531 |
| 763809 | N/A | N/A | 87941 | 87960 | AAGTTGTGACCATGCAATAA | 51 | 2532 |
| 763810 | N/A | N/A | 87942 | 87961 | TAAGTTGTGACCATGCAATA | 44 | 2533 |
| 763811 | N/A | N/A | 87943 | 87962 | GTAAGTTGTGACCATGCAAT | 65 | 2534 |
| 763812 | N/A | N/A | 87944 | 87963 | AGTAAGTTGTGACCATGCAA | 69 | 2535 |
| 763813 | N/A | N/A | 87945 | 87964 | TAGTAAGTTGTGACCATGCA | 68 | 2536 |
| 763814 | N/A | N/A | 87946 | 87965 | TTAGTAAGTTGTGACCATGC | 55 | 2537 |

TABLE 40-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763815 | N/A | N/A | 87947 | 87966 | ATTAGTAAGTTGTGACCATG | 44 | 2538 |
| 763816 | N/A | N/A | 87948 | 87967 | CATTAGTAAGTTGTGACCAT | 42 | 2539 |
| 763817 | N/A | N/A | 87949 | 87968 | CCATTAGTAAGTTGTGACCA | 71 | 2540 |
| 763818 | N/A | N/A | 87950 | 87969 | CCCATTAGTAAGTTGTGACC | 71 | 2541 |
| 763819 | N/A | N/A | 88040 | 88059 | GCTATCAAGACATTATGTAG | 58 | 2542 |
| 763820 | N/A | N/A | 88133 | 88152 | ATCTATGAAAGCAAATGTTT | 35 | 2543 |
| 763821 | N/A | N/A | 88227 | 88246 | CTTTTTTAAACAAAATACAG | 0 | 2544 |
| 763822 | N/A | N/A | 88320 | 88339 | ATGCTACAAGCAGGCACTTA | 22 | 2545 |
| 763823 | N/A | N/A | 88413 | 88432 | TCTGTTATCTTAAGAGGCTT | 76 | 2546 |
| 763824 | N/A | N/A | 88506 | 88525 | TGGACTTTATTGCTCAAAGC | 65 | 2547 |
| 763825 | N/A | N/A | 88599 | 88618 | CAGACAAAAACATCCGATAT | 28 | 2548 |
| 763826 | N/A | N/A | 88692 | 88711 | CCCTAGACAACTATCACCTG | 9 | 2549 |
| 763827 | N/A | N/A | 88785 | 88804 | TGGAAGCCCTGAGGAAGTGG | 59 | 2550 |
| 763828 | N/A | N/A | 88878 | 88897 | AACAGCAAGGACAATGTCTA | 53 | 2551 |
| 763829 | N/A | N/A | 88971 | 88990 | GCCATGTGTTATATACTTTG | 73 | 2552 |
| 763830 | N/A | N/A | 89075 | 89094 | ATTAGGTAGATTTTTTTTAA | 0 | 2553 |
| 763831 | N/A | N/A | 89169 | 89188 | ATGATGGTGAATAAATTAAA | 11 | 2554 |
| 763832 | N/A | N/A | 89262 | 89281 | AGAAAATGCTTTAAGCTCAT | 57 | 2555 |
| 763833 | N/A | N/A | 89355 | 89374 | AAAAGATAAATTGCTAGGTT | 16 | 2556 |
| 763834 | N/A | N/A | 89452 | 89471 | ACTAATTAATTAGTTGAATA | 8 | 2557 |

TABLE 41

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 67 | 33 |
| 741410 | N/A | N/A | 87946 | 87962 | GTAAGTTGTGACCATGC | 83 | 402 |
| 762837 | 238 | 257 | 4689 | 4708 | TGAATTCCTTTACACCACAC | 76 | 1639 |
| 763835 | N/A | N/A | 89545 | 89564 | TCAATTCTCTTTAGAATTTC | 27 | 2558 |
| 763836 | N/A | N/A | 89638 | 89657 | AGAGATTCATGCTCATTTAT | 45 | 2559 |
| 763837 | N/A | N/A | 89731 | 89750 | ATCTATCCACTCTCCTATAG | 0 | 2560 |
| 763838 | N/A | N/A | 89824 | 89843 | ACTTTTTATTAGAGCCCCC | 14 | 2561 |
| 763839 | N/A | N/A | 89917 | 89936 | GACTACATGTCCTTTAAATG | 64 | 2562 |
| 763840 | N/A | N/A | 90015 | 90034 | AAGACTGCAGGCTTGAGCCA | 23 | 2563 |
| 763841 | N/A | N/A | 90141 | 90160 | ATGCCACCACATCCCACTTT | 21 | 2564 |
| 763842 | N/A | N/A | 90312 | 90331 | TGTTATATTTTAAAAGTTTC | 0 | 2565 |

TABLE 41-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763843 | N/A<br>N/A | N/A<br>N/A | 90439<br>90405 | 90458<br>90424 | ATATACACAAAAGCAGATAT | 19 | 2566 |
| 763844 | N/A | N/A | 90500 | 90519 | AAATATATGTGTAAATACAC | 0 | 2567 |
| 763845 | N/A | N/A | 90593 | 90612 | CTCCCATTCTCTCTCTCTAC | 35 | 2568 |
| 763846 | N/A | N/A | 90686 | 90705 | CCCAGAAACTAACATCTTCT | 48 | 2569 |
| 763847 | N/A | N/A | 90779 | 90798 | CAGGAAAAGAATACTTTCT | 34 | 2570 |
| 763848 | N/A | N/A | 90945 | 90964 | TCCTGCCACCACACCCACTA | 11 | 2571 |
| 763849 | N/A | N/A | 91047 | 91066 | TAGCTATAGTGCAATGGCGC | 7 | 2572 |
| 763850 | N/A | N/A | 91140 | 91159 | TTTCATAACTGTATGATTTG | 33 | 2573 |
| 763851 | N/A | N/A | 91233 | 91252 | ACCATTAAAAGTTTAGTGGA | 43 | 2574 |
| 763852 | N/A | N/A | 91326 | 91345 | ATGTGCATGCCAGTGTGTTA | 34 | 2575 |
| 763853 | N/A | N/A | 91419 | 91438 | GATAAAGAAGGAATGCACAA | 34 | 2576 |
| 763854 | N/A | N/A | 91520 | 91539 | CTTACTTTCTTGCAAAAGGG | 43 | 2577 |
| 763855 | N/A | N/A | 91614 | 91633 | GAAAATAAAAAGGCAGCTTT | 13 | 2578 |
| 763856 | N/A | N/A | 91707 | 91726 | TAATAGTGAATGTTGTTTTA | 21 | 2579 |
| 763857 | N/A | N/A | 91800 | 91819 | CATGCATCTAAAGATAACTG | 33 | 2580 |
| 763858 | N/A | N/A | 91893 | 91912 | TCCTAGGCTTTGTCTCTTAA | 38 | 2581 |
| 763859 | N/A | N/A | 91986 | 92005 | TTTAAAACTTTATCTTCCTT | 35 | 2582 |
| 763860 | N/A | N/A | 92079 | 92098 | AGATACTGTTGCCCCAAGTA | 48 | 2583 |
| 763861 | N/A | N/A | 92172 | 92191 | TACTAAAAAAAACCACTAAC | 0 | 2584 |
| 763862 | N/A | N/A | 92265 | 92284 | CCACTGTCTAACAAATAATG | 32 | 2585 |
| 763863 | N/A | N/A | 92358 | 92377 | ATGATTGGTGTAAGCGAATG | 24 | 2586 |
| 763864 | N/A | N/A | 92451 | 92470 | ATTATCCTTCAACAGAGCTA | 21 | 2587 |
| 763865 | N/A | N/A | 92544 | 92563 | GCCCATCCTTAGATCTTAGT | 46 | 2588 |
| 763866 | N/A | N/A | 92642 | 92661 | CGAGTGACTCAGTTTCCTTA | 64 | 2589 |
| 763867 | N/A | N/A | 92735 | 92754 | CCTTCACTTTGGAGGATGCG | 37 | 2590 |
| 763868 | N/A | N/A | 92828 | 92847 | CCTAGAGGGTGCCTTCCCAG | 28 | 2591 |
| 763869 | N/A | N/A | 92921 | 92940 | ATATTTACACTGCTTCATAA | 3 | 2592 |
| 763870 | N/A | N/A | 93014 | 93033 | TTATGACCTGTAATGTACTT | 25 | 2593 |
| 763871 | N/A | N/A | 93151 | 93170 | CAAAAGACAAGCACACACAC | 0 | 2594 |
| 763872 | N/A | N/A | 93244 | 93263 | TAAGTATTTTTAGTACTTTA | 14 | 2595 |
| 763873 | N/A | N/A | 93337 | 93356 | GAGGGACTTTTGCAATTGTC | 15 | 2596 |
| 763874 | N/A | N/A | 93430 | 93449 | GAATCAAATAAGAGGTCAA | 35 | 2597 |
| 763875 | N/A | N/A | 93521 | 93540 | TTTTGAGTTCCAGGGATTCA | 54 | 2598 |
| 763876 | N/A | N/A | 93522 | 93541 | GTTTTGAGTTCCAGGGATTC | 70 | 2599 |
| 763877 | N/A | N/A | 93523 | 93542 | TGTTTTGAGTTCCAGGGATT | 74 | 2600 |
| 763878 | N/A | N/A | 93524 | 93543 | ATGTTTTGAGTTCCAGGGAT | 50 | 2601 |

TABLE 41-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763879 | N/A | N/A | 93525 | 93544 | AATGTTTTGAGTTCCAGGGA | 57 | 2602 |
| 763880 | N/A | N/A | 93526 | 93545 | CAATGTTTTGAGTTCCAGGG | 57 | 2603 |
| 763881 | N/A | N/A | 93527 | 93546 | GCAATGTTTTGAGTTCCAGG | 61 | 2604 |
| 763882 | N/A | N/A | 93528 | 93547 | AGCAATGTTTTGAGTTCCAG | 68 | 2605 |
| 763883 | N/A | N/A | 93529 | 93548 | CAGCAATGTTTTGAGTTCCA | 70 | 2606 |
| 763884 | N/A | N/A | 93530 | 93549 | TCAGCAATGTTTTGAGTTCC | 66 | 2607 |
| 763885 | N/A | N/A | 93531 | 93550 | TTCAGCAATGTTTTGAGTTC | 33 | 2608 |
| 763886 | N/A | N/A | 93621 | 93640 | GCATTTCTTAATTTTTTTAT | 6 | 2609 |
| 763887 | N/A | N/A | 93714 | 93733 | TTGTCTGCTACTATTTTTTC | 25 | 2610 |
| 763888 | N/A | N/A | 93807 | 93826 | TTTAATATTTATGAATGTGA | 15 | 2611 |
| 763889 | N/A | N/A | 93900 | 93919 | AAGCCTTTATTTTTTATTGC | 8 | 2612 |
| 763890 | N/A | N/A | 93993 | 94012 | ATGAGGGCAAGCTGGCTTTT | 40 | 2613 |
| 763891 | N/A | N/A | 94086 | 94105 | CAAGGAGATTGAGTTTACCA | 51 | 2614 |
| 763892 | N/A | N/A | 94179 | 94198 | CAAAGCATTCTTGCTTGCTC | 50 | 2615 |
| 763893 | N/A | N/A | 94272 | 94291 | TAATTTATGTCAGTCATTAA | 0 | 2616 |
| 763894 | N/A | N/A | 94365 | 94384 | GGCTGCCGAAAGCAGGAAAA | 32 | 2617 |
| 763895 | N/A | N/A | 94458 | 94477 | TTTAAATGTCACAGCTATTT | 15 | 2618 |
| 763896 | N/A | N/A | 94551 | 94570 | CTTCCCCTAAATCTCTCTGT | 20 | 2619 |
| 763897 | N/A | N/A | 94644 | 94663 | AGTTAACAAATTAATGAAAC | 10 | 2620 |
| 763898 | N/A | N/A | 94993 | 95012 | AACTTCAGTTTTGTGGCGGG | 15 | 2621 |
| 763899 | N/A | N/A | 95086 | 95105 | CCTGGAAAATGAGGACTTTC | 44 | 2622 |
| 763900 | N/A | N/A | 95179 | 95198 | ACTGATTAAGAAATGTGAGG | 31 | 2623 |
| 763901 | N/A | N/A | 95272 | 95291 | TGAAAGCCACCGTGATGAAC | 4 | 2624 |
| 763902 | N/A | N/A | 95365 | 95384 | AGATTAAAGCGATTCCTGCT | 12 | 2625 |
| 763903 | N/A | N/A | 95459 | 95478 | CTTAGTATCATCATCATCAC | 39 | 2626 |
| 763904 | N/A | N/A | 95552 | 95571 | CCCAGAAAATAAGCAGACTG | 45 | 2627 |
| 763905 | N/A | N/A | 95645 | 95664 | GCAAATACAATATTTGAAAG | 0 | 2628 |
| 763906 | N/A | N/A | 95738 | 95757 | GATCAGAATGACCAGTGCAC | 43 | 2629 |
| 763907 | N/A | N/A | 95831 | 95850 | TCAAACTATAATTTGGTGTC | 61 | 2630 |
| 763908 | N/A | N/A | 95924 | 95943 | TCTAGAGAATGATTCATCTT | 39 | 2631 |
| 763909 | N/A | N/A | 96017 | 96036 | TACCCTCTTGCTATACAAAC | 30 | 2632 |
| 763910 | N/A | N/A | 96110 | 96129 | GATGAAAATTGAAATTTGAT | 13 | 2633 |
| 763911 | N/A | N/A | 96203 | 96222 | TTAAAAATAACTGTATTTGG | 0 | 2634 |

TABLE 42

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 74 | 33 |
| 741410 | N/A | N/A | 87946 | 87962 | GTAAGTTGTGACCATGC | 80 | 402 |
| 762837 | 238 | 257 | 4689 | 4708 | TGAATTCCTTTACACCACAC | 67 | 1639 |
| 763912 | N/A | N/A | 96296 | 96315 | ATTAACTAAAAACCAAGTCT | 7 | 2635 |
| 763913 | N/A | N/A | 96391 | 96410 | CAAAGCTGCAGACCATTTTG | 25 | 2636 |
| 763914 | N/A | N/A | 96484 | 96503 | ACAGGCAAAGAATTTTTGAG | 35 | 2637 |
| 763915 | N/A | N/A | 96577 | 96596 | AAACAACTGCTGAGAAGCAG | 0 | 2638 |
| 763916 | N/A | N/A | 96670 | 96689 | TTTAATTGCTGTTGTGTGGT | 45 | 2639 |
| 763917 | N/A | N/A | 96763 | 96782 | TAAGACATAAATGTCAGAGG | 25 | 2640 |
| 763918 | N/A | N/A | 96858 | 96877 | TGAAGATGAAGAAAGGAAAG | 2 | 2641 |
| 763919 | N/A | N/A | 96951 | 96970 | GAGCCAATAACAGAGATGAT | 36 | 2642 |
| 763920 | N/A | N/A | 97044 | 97063 | AGACTGTTAATGTAGTAGGA | 29 | 2643 |
| 763921 | N/A | N/A | 97137 | 97156 | GGACAATTAATTTTGAGGGT | 48 | 2644 |
| 763922 | N/A | N/A | 97230 | 97249 | CTTCAGGAGATAAAGGAACC | 7 | 2645 |
| 763923 | N/A | N/A | 97323 | 97342 | TTATGCTTCAGGGATGCATA | 36 | 2646 |
| 763924 | N/A | N/A | 97416 | 97435 | TTTACTAAGTAATTGGTACT | 26 | 2647 |
| 763925 | N/A | N/A | 97509 | 97528 | AAGGCAGCAAAGAGGTAAAA | 2 | 2648 |
| 763926 | N/A | N/A | 97602 | 97621 | GGTAAGTCATCAGAGTTCAT | 27 | 2649 |
| 763927 | N/A | N/A | 97695 | 97714 | TTGAGTCTGAGATGCCTCCA | 34 | 2650 |
| 763928 | N/A | N/A | 97788 | 97807 | TTTGAGCTTGACCAACTAGG | 45 | 2651 |
| 763929 | N/A | N/A | 97881 | 97900 | GCAGTTACTGACTTGCTTGA | 38 | 2652 |
| 763930 | N/A | N/A | 97974 | 97993 | GCTGCAAGCACACCTGCCTT | 36 | 2653 |
| 763931 | N/A | N/A | 98067 | 98086 | AAGAGGAACGCAGAGCTCAG | 8 | 2654 |
| 763932 | N/A | N/A | 98160 | 98179 | GAGTATCATGATTTTCTTGC | 57 | 2655 |
| 763933 | N/A | N/A | 98253 | 98272 | CAAGCCTGCCAGTCTTTTGA | 43 | 2656 |
| 763934 | N/A | N/A | 98346 | 98365 | TATAGGTGCAAACTACAAGT | 35 | 2657 |
| 763935 | N/A | N/A | 98439 | 98458 | GGAATACAGCCAAAAACTTG | 13 | 2658 |
| 763936 | N/A | N/A | 98532 | 98551 | AGCTACATTCAAGTCTGCAA | 57 | 2659 |
| 763937 | N/A | N/A | 98803 | 98822 | CGAATGGGCGGATCACAAGG | 7 | 2660 |
| 763938 | N/A | N/A | 98896 | 98915 | AAGAATCGAAACTAAAAACC | 9 | 2661 |
| 763939 | N/A | N/A | 98989 | 99008 | AATGTATATCATATATTGTC | 57 | 2662 |
| 763940 | N/A | N/A | 99082 | 99101 | GACCCATGCACAGTCATAAT | 36 | 2663 |
| 763941 | N/A | N/A | 99175 | 99194 | CGTAAATGTTTCAACTGAAA | 45 | 2664 |
| 763942 | N/A | N/A | 99268 | 99287 | GTTGGAAGCTCAGGAGAAAA | 56 | 2665 |
| 763943 | N/A | N/A | 99361 | 99380 | TTGTTGAGGAACTGAAATTG | 20 | 2666 |
| 763944 | N/A | N/A | 99454 | 99473 | AGTGGGCTTGTGGTATTTGT | 7 | 2667 |
| 763945 | N/A | N/A | 99547 | 99566 | GCAAAGGGAGAACAAACAAA | 0 | 2668 |

TABLE 42-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763946 | N/A | N/A | 99641 | 99660 | CTGTATATAATTTTTTCAAC | 35 | 2669 |
| 763947 | N/A | N/A | 99734 | 99753 | ACTAAATGTTTATTTGCATT | 44 | 2670 |
| 763948 | N/A | N/A | 99827 | 99846 | GAATTTAAAGAGGAATAAAA | 0 | 2671 |
| 763949 | N/A | N/A | 99920 | 99939 | AATTTCATTATGATTATCGC | 64 | 2672 |
| 763950 | N/A | N/A | 100013 | 100032 | TCTTCAAACCTTTTGACCAA | 41 | 2673 |
| 763951 | N/A | N/A | 100111 | 100130 | GAAATAAATTGTTCATTTTG | 7 | 2674 |
| 763952 | N/A | N/A | 100205 | 100224 | GAAAAAATAGTTTATTATAA | 0 | 2675 |
| 763953 | N/A | N/A | 100298 | 100317 | TATATGATTTTTTGCAAGGG | 41 | 2676 |
| 763954 | N/A | N/A | 100394 | 100413 | GTTAAAGGAAATGTTTATAT | 12 | 2677 |
| 763955 | N/A | N/A | 100487 | 100506 | AAATTAATCCTTTCCAAATG | 0 | 2678 |
| 763956 | N/A | N/A | 100580 | 100599 | AATATTAGTTGTCAAATGTC | 42 | 2679 |
| 763957 | N/A | N/A | 100673 | 100692 | CTCTTTGAGGAAGTTACTAC | 23 | 2680 |
| 763958 | N/A | N/A | 100766 | 100785 | AATAACAATAACAGTTAATG | 0 | 2681 |
| 763959 | N/A | N/A | 100860 | 100879 | GATTATCAAGAAAGATAATG | 0 | 2682 |
| 763960 | N/A | N/A | 100953 | 100972 | GCTACTTTCTTTCAGTTACC | 49 | 2683 |
| 763961 | N/A | N/A | 101046 | 101065 | GCCAGAGGACCATAGTGGTT | 45 | 2684 |
| 763962 | N/A | N/A | 101143 | 101162 | TACTAAGTGAAGTTTGAGGG | 18 | 2685 |
| 763963 | N/A | N/A | 101236 | 101255 | AGAAAGGCTTTAAGATAGCT | 9 | 2686 |
| 763964 | N/A | N/A | 101329 | 101348 | AAGGATGGGCTCTGAAGCAG | 13 | 2687 |
| 763965 | N/A | N/A | 101422 | 101441 | CCCAGGAGTTTGCTCTCAAA | 36 | 2688 |
| 763966 | N/A | N/A | 101515 | 101534 | AGAGTCTGCTTTCATATTTT | 36 | 2689 |
| 763967 | N/A | N/A | 101914 | 101933 | TGGAGGCAGGTCTTTTTTTT | 32 | 2690 |
| 763968 | N/A | N/A | 102007 | 102026 | ACGATGTGAAGATGGGTCAA | 45 | 2691 |
| 763969 | N/A | N/A | 102100 | 102119 | TTAAACTATATTCAAATTTG | 0 | 2692 |
| 763970 | N/A | N/A | 102193 | 102212 | AATGCACAAAGGGAAATCTG | 38 | 2693 |
| 763971 | N/A | N/A | 102286 | 102305 | AATTAGCTGACTCACCTAAT | 4 | 2694 |
| 763972 | N/A | N/A | 102379 | 102398 | AGCAAAGAGGTAGTATGCTG | 61 | 2695 |
| 763973 | N/A | N/A | 102472 | 102491 | GTTTAAATACATTCAACCAT | 46 | 2696 |
| 763974 | N/A | N/A | 102565 | 102584 | GGTTTGGCAGTGGAGGAGAG | 28 | 2697 |
| 763975 | N/A | N/A | 102658 | 102677 | CCCTTCTAGCTGTTTCTTTA | 40 | 2698 |
| 763976 | N/A | N/A | 102831 | 102850 | TATAGAGATGAAGTTTCATT | 29 | 2699 |
| 763977 | N/A | N/A | 102982 | 103001 | CCCTATTGCCCAGGCTGTAA | 21 | 2700 |
| 763978 | N/A | N/A | 103075 | 103094 | CTTTAGAGAACCCAGTCTTA | 38 | 2701 |
| 763979 | N/A | N/A | 103175 | 103194 | ATAGTCACATTGGTGAACGC | 33 | 2702 |
| 763980 | N/A | N/A | 103268 | 103287 | TTGCTCTCCCTCAGTTATGT | 52 | 2703 |
| 763981 | N/A | N/A | 103361 | 103380 | TGCTATTATATATGCTAAGC | 54 | 2704 |

TABLE 42-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 763982 | N/A | N/A | 103454 | 103473 | CTGATGATCTCTGGTGCCAC | 35 | 2705 |
| 763983 | N/A | N/A | 103547 | 103566 | CTACTAACCTGTAAAAGACA | 1 | 2706 |
| 763984 | N/A | N/A | 103640 | 103659 | ACTTTACAACAAGATAAAAA | 0 | 2707 |
| 763985 | N/A | N/A | 103733 | 103752 | TCTGGTACAGTCCTACTACC | 61 | 2708 |
| 763986 | N/A | N/A | 103826 | 103845 | AATATAATTTATAGCATTAC | 0 | 2709 |
| 763987 | N/A | N/A | 103919 | 103938 | TGAGGCAATATGCAGACGAA | 51 | 2710 |
| 763988 | N/A | N/A | 104012 | 104031 | TTTAGAAATGCATCAAAGTG | 18 | 2711 |

TABLE 43

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 740410 | 240 | 256 | 4691 | 4707 | GAATTCCTTTACACCAC | 89 | 33 |
| 741410 | N/A | N/A | 87946 | 87962 | GTAAGTTGTGACCATGC | 90 | 402 |
| 762837 | 238 | 257 | 4689 | 4708 | TGAATTCCTTTACACCACAC | 79 | 1639 |
| 763989 | N/A | N/A | 104105 | 104124 | CAAACTTTAATTTTGGGAA | 31 | 2712 |
| 763990 | N/A | N/A | 104198 | 104217 | TGTATCCAATGCCCAAAGGA | 49 | 2713 |
| 763991 | N/A | N/A | 104291 | 104310 | CATTTATTGTTTACATACTC | 29 | 2714 |
| 763992 | N/A | N/A | 104384 | 104403 | GCAAAACAATATGCATATTT | 63 | 2715 |
| 763993 | N/A | N/A | 104477 | 104496 | GAGGTCTTGTTTTGGAAAGG | 54 | 2716 |
| 763994 | N/A | N/A | 104570 | 104589 | TGGATACTCTGATTTCTCTT | 76 | 2717 |
| 763995 | N/A | N/A | 104663 | 104682 | AGCAAAGGGCATCTGATTCA | 46 | 2718 |
| 763996 | N/A | N/A | 104756 | 104775 | ACCTTGTTAAAAAGCAAGGT | 2 | 2719 |
| 763997 | N/A | N/A | 104849 | 104868 | GGAGTGTGTACATAGTGTAG | 46 | 2720 |
| 763998 | N/A | N/A | 104942 | 104961 | AAAATGAAATCAAGCCCAGA | 23 | 2721 |
| 763999 | N/A | N/A | 105035 | 105054 | GAGATAGTAGCCAAAAAGAT | 22 | 2722 |
| 764000 | N/A | N/A | 105128 | 105147 | TTGTTTTGCTGCATTATTGA | 42 | 2723 |
| 764001 | N/A | N/A | 105221 | 105240 | CAACTTTCACAGCCTTAAAC | 38 | 2724 |
| 764002 | N/A | N/A | 105314 | 105333 | TTTGGAGCAATGTGATGTTT | 40 | 2725 |
| 764003 | N/A | N/A | 105407 | 105426 | GAGCTGCAGCAAGTTTTTTC | 56 | 2726 |
| 764004 | N/A | N/A | 105502 | 105521 | GCTGCTCTTTGAGAAAGTTC | 64 | 2727 |
| 764005 | N/A | N/A | 105595 | 105614 | AAGAAAAATTGAAATTCAAG | 9 | 2728 |
| 764006 | N/A | N/A | 105688 | 105707 | AAAATAGCAAGGTTTCATCA | 17 | 2729 |
| 764007 | N/A | N/A | 105781 | 105800 | TTAAAAAGATATGCTCATT | 12 | 2730 |
| 764008 | N/A | N/A | 105874 | 105893 | CACTGCCCGACATCACCAAT | 20 | 2731 |
| 764009 | N/A | N/A | 105967 | 105986 | AACCACACTCTTCTAGAATC | 41 | 2732 |

TABLE 43-continued

Percent reduction of human SNCA mRNA with 5-10-5 MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 764010 | N/A | N/A | 106060 | 106079 | TAAGGAAATTATCTTTATTC | 27 | 2733 |
| 764011 | N/A | N/A | 106153 | 106172 | TGTCTTTAGGAATACAACTA | 55 | 2734 |
| 764012 | N/A | N/A | 106246 | 106265 | GCTAATAGCTTATTGGGAAG | 47 | 2735 |
| 764013 | N/A | N/A | 106339 | 106358 | GGGTTGAATAGCTGATATAA | 65 | 2736 |
| 764014 | N/A | N/A | 106432 | 106451 | AGACTTAAAAGCTATATTAG | 6 | 2737 |
| 764015 | N/A | N/A | 106525 | 106544 | TCAGTTCAGTATCTTATATC | 68 | 2738 |
| 764016 | N/A | N/A | 106618 | 106637 | ACCTTTTATTCTCTCTCTAC | 60 | 2739 |
| 764017 | N/A | N/A | 106713 | 106732 | TAAAATAAATGAGAAAAACG | 2 | 2740 |
| 764018 | N/A | N/A | 106806 | 106825 | CCAATATAACAAATGTTAAA | 24 | 2741 |
| 764019 | N/A | N/A | 106899 | 106918 | GAGTATTCATGACTTGTTTT | 53 | 2742 |
| 764020 | N/A | N/A | 106999 | 107018 | TGTTATCTATAAAGAAATAT | 17 | 2743 |
| 764021 | N/A | N/A | 107092 | 107111 | AATATAACAACAAACACTTC | 2 | 2744 |
| 764022 | N/A | N/A | 107185 | 107204 | TATGTTTTTCTGAATATGTG | 36 | 2745 |
| 764023 | N/A | N/A | 107278 | 107297 | GCAATTTCAGGTGTCCTAGT | 79 | 2746 |
| 764024 | N/A | N/A | 107434 | 107453 | CCCACATAACTTTTATTACA | 42 | 2747 |
| 764025 | N/A | N/A | 107539 | 107558 | CGTGGTTTTGTTTTCCATGG | 70 | 2748 |
| 764026 | N/A | N/A | 107641 | 107660 | ATCTATCTAGGTTTGGGTGG | 57 | 2749 |
| 764027 | N/A | N/A | 107734 | 107753 | TTATTTCTTTAGGTGTGATG | 49 | 2750 |
| 764028 | N/A | N/A | 107827 | 107846 | ATTCTCATTGGGAACCCTAC | 40 | 2751 |
| 764029 | N/A | N/A | 107920 | 107939 | GTAAATTGCAACTAAAAGA | 8 | 2752 |
| 764030 | N/A | N/A | 108013 | 108032 | AAACATGTTCATTGCTTACA | 57 | 2753 |
| 764031 | N/A | N/A | 108271 | 108290 | GGTTCTCCTATAGTCCCAGC | 58 | 2754 |
| 764032 | N/A | N/A | 108364 | 108383 | ACATGATCGGTGAGGTCAGG | 40 | 2755 |
| 764033 | N/A | N/A | 108457 | 108476 | TCGACAATAGGGTTTACGAC | 56 | 2756 |
| 764034 | N/A | N/A | 108550 | 108569 | TTAAGTGGGCTATTGTTCAC | 39 | 2757 |
| 764035 | N/A | N/A | 108643 | 108662 | ACTATTGATGAAGTTAAGTG | 14 | 2758 |
| 764036 | N/A | N/A | 108736 | 108755 | TGCCATAGGACTTAATTCTT | 69 | 2759 |
| 764037 | N/A | N/A | 108857 | 108876 | TTGACTTGTTTGTATTAATC | 62 | 2760 |
| 764038 | N/A | N/A | 108970 | 108989 | CCTGCAGTAATGGAACAGCG | 67 | 2761 |
| 764039 | N/A | N/A | 109063 | 109082 | TGAACTTTGAAGGATGTACA | 40 | 2762 |
| 764040 | N/A | N/A | 109156 | 109175 | CTACCCTGTTTGTTGTTTGA | 15 | 2763 |
| 764041 | N/A | N/A | 109249 | 109268 | TTTTCCATGATTTTGAAACT | 30 | 2764 |
| 764042 | N/A | N/A | 109342 | 109361 | ACAACAGGGAGAAGGAAACG | 17 | 2765 |
| 764043 | N/A | N/A | 109435 | 109454 | ATGACAGAGCTTTTGTGATG | 35 | 2766 |
| 764044 | N/A | N/A | 109528 | 109547 | TTCACTTCTTGGTAGATACG | 45 | 2767 |
| 764045 | N/A | N/A | 109627 | 109646 | CTAAAAAAATCCAAATAAT | 14 | 2768 |

TABLE 43-continued

Percent reduction of human SNCA mRNA with 5-10-5
MOE gapmers with mixed internucleoside linkages

| Compound No | SEQ ID No: 1 start | SEQ ID No: 1 stop | SEQ ID No: 2 start | SEQ ID No: 2 stop | Sequence (5' to 3') | % Reduction | SEQ ID NO |
|---|---|---|---|---|---|---|---|
| 764046 | N/A | N/A | 109720 | 109739 | AGTAAGAAAAGGTCACACTA | 34 | 2769 |
| 764047 | N/A | N/A | 109813 | 109832 | ATTTTCAACAACATGTCTGA | 14 | 2770 |
| 764048 | N/A | N/A | 109906 | 109925 | AAAGGTAAGTGAAAATTCAA | 29 | 2771 |
| 764049 | N/A | N/A | 109999 | 110018 | CTCAGCCTGAAATGGTCATG | 39 | 2772 |
| 764050 | N/A | N/A | 110092 | 110111 | AGACTGAGACTATACATATT | 29 | 2773 |
| 764051 | N/A | N/A | 110185 | 110204 | AACTTTTATAACCACTTATA | 31 | 2774 |
| 764052 | N/A | N/A | 110278 | 110297 | AAAGGTAAAAAGTTTGGAAG | 6 | 2775 |
| 764053 | N/A | N/A | 110371 | 110390 | ATTATGTAACAACTACCTAT | 8 | 2776 |
| 764054 | N/A | N/A | 110624 | 110643 | GTTACAATGAAACCCCATCT | 29 | 2777 |
| 764055 | N/A | N/A | 110724 | 110743 | TTATTGCTGGGTGCAGTGGT | 24 | 2778 |
| 764056 | N/A | N/A | 110817 | 110836 | CCAAAGATATTTTCACAAG | 65 | 2779 |
| 764057 | N/A | N/A | 110910 | 110929 | AAACATTGCGGCAACATGGG | 22 | 2780 |
| 764058 | N/A | N/A | 111003 | 111022 | AAATCTTACATATAGGGATG | 39 | 2781 |
| 764059 | N/A | N/A | 111097 | 111116 | TCCTTCTTCATTCTAATATT | 7 | 2782 |

TABLE 44

Percent reduction of human SNCA mRNA with 5-10-5
MOE gapmers with mixed internucleoside linkages

| Compound No | SEQ ID No: 2 start | SEQ ID No: 2 stop | SEQ ID No: 5 start | SEQ ID No: 5 stop | Sequence (5' to 3') | % Reduction | SEQ ID NO |
|---|---|---|---|---|---|---|---|
| 740410 | 4691 | 4707 | N/A | N/A | GAATTCCTTTACACCAC | 89 | 33 |
| 741410 | 87946 | 87962 | N/A | N/A | GTAAGTTGTGACCATGC | 90 | 402 |
| 762837 | 4689 | 4708 | N/A | N/A | TGAATTCCTTTACACCACAC | 79 | 1639 |
| 764060 | N/A | N/A | 38 | 57 | CTTTACACCACACTCTTTCA | 23 | 2783 |
| 764061 | N/A | N/A | 39 | 58 | CCTTTACACCACACTCTTTC | 45 | 2784 |
| 764062 | N/A | N/A | 40 | 59 | TCCTTTACACCACACTCTTT | 56 | 2785 |
| 764063 | N/A | N/A | 41 | 60 | TTCCTTTACACCACACTCTT | 52 | 2786 |
| 764064 | N/A | N/A | 42 | 61 | ATTCCTTTACACCACACTCT | 70 | 2787 |
| 764065 | N/A | N/A | 43 | 62 | AATTCCTTTACACCACACTC | 67 | 2788 |

Example 6: Design of Gapmers with Mixed Internucleoside Linkages Complementary to Human SNCA Modified oligonucleotides complementary to a human SNCA nucleic acid were designed. The modified oligonucleotides in Table 45 are gapmers. The gapmers have a central gap segment that comprises 2'-deoxynucleosides and is flanked by wing segments on both the 5' end on the 3' end comprising 2'-MOE nucleosides and cEt nucleosides. All cytosine residues throughout each gapmer are 5-methyl cytosines. The internucleoside linkages are mixed phosphodiester internucleoside linkages and phosphorothioate internucleoside linkages. The sequence and chemical notation column specifies the sequence, including 5'-methy cytosines, sugar chemistry, and the internucleoside linkage chemistry, wherein subscript 'd' represents a 2'-deoxyribose sugar; subscript 'e' represents a 2'-MOE modified sugar; subscript 'k' represents a cEt modified sugar; subscript 'o' represents a phosphodiester internucleoside linkage; subscript 's' represents a phosphorothioate internucleoside linkage; and a 'm' superscript before the cytosine residue indicates a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the Tables below is complementary to human SNCA nucleic acid sequences SEQ ID NO: 2 or SEQ ID NO:5, as indicated. 'N/A' indicates that the modified oligonucleotide is not complementary to that particular nucleic acid with 100% complementarity.

TABLE 45

Modified oligonucleotides complementary to human SNCA mRNA

| Compound No | SEQ ID No: 2 start | SEQ ID No: 2 stop | SEQ ID No: 5 start | SEQ ID No: 5 stop | Sequence and chemical notation (5' to 3') | SEQ ID NO: |
|---|---|---|---|---|---|---|
| 788813 | N/A | N/A | 4686 | 4702 | $^mC_{es}{}^mC_{eo}T_{eo}T_{eo}T_{ds}A_{ds}{}^mC_{ds}A_{ds}{}^mC_{ds}{}^mC_{ds}A_{ds}{}^mC_{ds}A_{ds}{}^mC_{ko}T_{es}G_{es}G_e$ | 1038 |
| 788814 | 236 | 252 | 4687 | 4703 | $T_{es}{}^mC_{eo}{}^mC_{eo}T_{eo}T_{ds}A_{ds}T_{ds}A_{ds}{}^mC_{ds}A_{ds}{}^mC_{ds}{}^mC_{ds}A_{ds}{}^mC_{ds}A_{ko}{}^mC_{es}T_{es}G_e$ | 260 |
| 788815 | 237 | 253 | 4688 | 4704 | $T_{es}T_{eo}{}^mC_{eo}{}^mC_{eo}T_{ds}T_{ds}T_{ds}A_{ds}{}^mC_{ds}A_{ds}{}^mC_{ds}{}^mC_{ds}A_{ds}{}^mC_{ko}A_{es}{}^mC_{es}T_e$ | 335 |
| 788816 | 238 | 254 | 4689 | 4705 | $A_{es}T_{eo}T_{eo}{}^mC_{eo}{}^mC_{ds}T_{ds}T_{ds}T_{ds}A_{ds}{}^mC_{ds}A_{ds}{}^mC_{ds}{}^mC_{ds}A_{ko}{}^mC_{es}A_{es}{}^mC_e$ | 412 |
| 788817 | 239 | 255 | 4690 | 4706 | $A_{es}A_{eo}T_{eo}T_{eo}{}^mC_{ds}{}^mC_{ds}T_{ds}T_{ds}T_{ds}A_{ds}{}^mC_{ds}A_{ds}{}^mC_{ds}{}^mC_{ko}A_{es}{}^mC_{es}A_e$ | 577 |
| 788818 | 240 | 256 | 4691 | 4707 | $G_{es}A_{eo}A_{eo}T_{eo}T_{ds}{}^mC_{ds}{}^mC_{ds}T_{ds}T_{ds}T_{ds}A_{ds}{}^mC_{ds}A_{ds}{}^mC_{ko}{}^mC_{es}A_{es}{}^mC_e$ | 33 |
| 788819 | N/A | N/A | 4686 | 4702 | $^mC_{es}{}^mC_{eo}T_{eo}T_{es}T_{ds}A_{ds}{}^mC_{ds}A_{ds}{}^mC_{ds}{}^mC_{ds}A_{ds}{}^mC_{ds}A_{ds}{}^mC_{ko}T_{es}G_{es}G_e$ | 1038 |
| 788820 | 236 | 252 | 4687 | 4703 | $T_{es}{}^mC_{eo}{}^mC_{eo}T_{es}T_{ds}A_{ds}T_{ds}A_{ds}{}^mC_{ds}A_{ds}{}^mC_{ds}{}^mC_{ds}A_{ds}{}^mC_{ds}A_{ko}{}^mC_{es}T_{es}G_e$ | 260 |
| 788821 | 237 | 253 | 4688 | 4704 | $T_{es}T_{eo}{}^mC_{eo}{}^mC_{es}T_{ds}T_{ds}T_{ds}A_{ds}{}^mC_{ds}A_{ds}{}^mC_{ds}{}^mC_{ds}A_{ds}{}^mC_{ko}A_{es}{}^mC_{es}T_e$ | 335 |
| 788822 | 238 | 254 | 4689 | 4705 | $A_{es}T_{eo}T_{eo}{}^mC_{es}{}^mC_{ds}T_{ds}T_{ds}T_{ds}A_{ds}{}^mC_{ds}A_{ds}{}^mC_{ds}{}^mC_{ds}A_{ko}{}^mC_{es}A_{es}{}^mC_e$ | 412 |
| 788823 | 239 | 255 | 4690 | 4706 | $A_{es}A_{eo}T_{eo}T_{es}{}^mC_{ds}{}^mC_{ds}T_{ds}T_{ds}T_{ds}A_{ds}{}^mC_{ds}A_{ds}{}^mC_{ds}{}^mC_{ko}A_{es}{}^mC_{es}A_e$ | 577 |
| 788824 | 240 | 256 | 4691 | 4707 | $G_{es}A_{eo}A_{eo}T_{es}T_{ds}{}^mC_{ds}{}^mC_{ds}T_{ds}T_{ds}T_{ds}A_{ds}{}^mC_{ds}A_{ds}{}^mC_{ko}{}^mC_{es}A_{es}{}^mC_e$ | 33 |
| 788830 | 236 | 252 | 4687 | 4703 | $T_{es}{}^mC_{eo}{}^mC_{es}T_{es}T_{ds}A_{ds}T_{ds}A_{ds}{}^mC_{ds}A_{ds}{}^mC_{ds}{}^mC_{ds}A_{ds}{}^mC_{ds}A_{ko}{}^mC_{es}T_{es}G_e$ | 260 |
| 788831 | 237 | 253 | 4688 | 4704 | $T_{es}T_{eo}{}^mC_{es}{}^mC_{es}T_{ds}T_{ds}T_{ds}A_{ds}{}^mC_{ds}A_{ds}{}^mC_{ds}{}^mC_{ds}A_{ds}{}^mC_{ko}A_{es}{}^mC_{es}T_e$ | 335 |
| 788832 | 238 | 254 | 4689 | 4705 | $A_{es}T_{eo}T_{es}{}^mC_{es}{}^mC_{ds}T_{ds}T_{ds}T_{ds}A_{ds}{}^mC_{ds}A_{ds}{}^mC_{ds}{}^mC_{ds}A_{ko}{}^mC_{es}A_{es}{}^mC_e$ | 412 |
| 788833 | 239 | 255 | 4690 | 4706 | $A_{es}A_{eo}T_{es}T_{es}{}^mC_{ds}{}^mC_{ds}T_{ds}T_{ds}T_{ds}A_{ds}{}^mC_{ds}A_{ds}{}^mC_{ds}{}^mC_{ko}A_{es}{}^mC_{es}A_e$ | 577 |
| 788855 | N/A | N/A | 29458 | 29474 | $T_{es}T_{eo}T_{eo}G_{es}T_{ds}T_{ds}A_{ds}A_{ds}T_{ds}A_{ds}G_{ds}T_{ds}T_{ds}{}^mC_{ko}T_{ks}{}^mC_{es}T_e$ | 2789 |
| 788856 | N/A | N/A | 29459 | 29475 | $T_{es}T_{eo}T_{eo}T_{es}G_{ds}T_{ds}T_{ds}A_{ds}A_{ds}T_{ds}A_{ds}G_{ds}T_{ds}T_{ko}{}^mC_{ks}T_{es}{}^mC_e$ | 2790 |
| 788889 | N/A | N/A | 29458 | 29474 | $T_{es}T_{eo}T_{eo}G_{es}T_{ds}T_{ds}A_{ds}A_{ds}T_{ds}A_{ds}G_{ds}T_{ds}T_{ds}{}^mC_{ko}T_{es}{}^mC_{es}T_e$ | 2789 |
| 788890 | N/A | N/A | 29459 | 29475 | $T_{es}T_{eo}T_{eo}T_{es}G_{ds}T_{ds}T_{ds}A_{ds}A_{ds}T_{ds}A_{ds}G_{ds}T_{ds}T_{ko}{}^mC_{es}T_{es}{}^mC_e$ | 2790 |
| 789229 | N/A | N/A | 4686 | 4705 | $A_{es}T_{eo}T_{eo}{}^mC_{es}{}^mC_{es}T_{ds}T_{ds}T_{ds}A_{ds}{}^mC_{ds}A_{ds}{}^mC_{ds}{}^mC_{ds}A_{ds}{}^mC_{ds}A_{eo}{}^mC_{eo}T_{es}G_{es}G_e$ | 1682 |
| 789230 | 237 | 256 | 4688 | 4707 | $G_{es}A_{eo}A_{eo}T_{es}T_{es}{}^mC_{ds}{}^mC_{ds}T_{ds}T_{ds}T_{ds}A_{ds}{}^mC_{ds}A_{ds}{}^mC_{ds}{}^mC_{ds}A_{eo}{}^mC_{eo}A_{es}{}^mC_{es}T_e$ | 1638 |

TABLE 45-continued

Modified oligonucleotides complementary to human SNCA mRNA

| Compound No | SEQ ID No: 2 start | SEQ ID No: 2 stop | SEQ ID No: 5 start | SEQ ID No: 5 stop | Sequence and chemical notation (5' to 3') | SEQ ID NO: |
|---|---|---|---|---|---|---|
| 789231 | 238 | 257 | 4689 | 4708 | $T_{es}G_{eo}A_{eo}A_{es}T_{es}T_{ds}{}^mC_{ds}{}^mC_{ds}T_{ds}T_{ds}T_{ds}A_{ds}{}^mC_{ds}A_{ds}{}^mC_{ds}{}^mC_{eo}A_{eo}{}^mC_{es}A_{es}{}^mC_e$ | 1639 |
| 789232 | 239 | 258 | 4690 | 4709 | $A_{es}T_{eo}G_{es}A_{es}A_{es}T_{ds}T_{ds}{}^mC_{ds}{}^mC_{ds}T_{ds}T_{ds}T_{ds}A_{ds}{}^mC_{ds}A_{ds}{}^mC_{eo}{}^mC_{eo}A_{es}{}^mC_{es}A_e$ | 1640 |
| 789233 | 240 | 259 | 4691 | 4710 | $A_{es}A_{eo}T_{es}G_{es}A_{es}A_{ds}T_{ds}T_{ds}{}^mC_{ds}{}^mC_{ds}T_{ds}T_{ds}T_{ds}A_{ds}{}^mC_{ds}A_{eo}{}^mC_{eo}{}^mC_{es}A_{es}{}^mC_e$ | 1641 |
| 789234 | N/A | N/A | 29457 | 29476 | $T_{es}T_{eo}T_{eo}T_{es}T_{es}G_{ds}T_{ds}T_{ds}A_{ds}A_{ds}T_{ds}A_{ds}G_{ds}T_{ds}T_{ds}{}^mC_{eo}T_{eo}{}^mC_{es}T_{es}G_e$ | 1904 |
| 789235 | N/A | N/A | 4686 | 4705 | $A_{es}T_{eo}T_{es}{}^mC_{es}{}^mC_{es}T_{ds}T_{ds}T_{ds}A_{ds}{}^mC_{ds}A_{ds}{}^mC_{ds}{}^mC_{ds}A_{ds}{}^mC_{ds}A_{eo}{}^mC_{eo}T_{es}G_{es}G_e$ | 1682 |
| 789236 | 237 | 256 | 4688 | 4707 | $G_{es}A_{eo}A_{es}T_{es}T_{es}{}^mC_{ds}{}^mC_{ds}T_{ds}T_{ds}T_{ds}A_{ds}{}^mC_{ds}A_{ds}{}^mC_{ds}{}^mC_{ds}A_{eo}{}^mC_{eo}A_{es}{}^mC_{es}T_e$ | 1638 |
| 789237 | 238 | 257 | 4689 | 4708 | $T_{es}G_{eo}A_{es}A_{es}T_{es}T_{ds}{}^mC_{ds}{}^mC_{ds}T_{ds}T_{ds}T_{ds}A_{ds}{}^mC_{ds}A_{ds}{}^mC_{ds}{}^mC_{eo}A_{eo}{}^mC_{es}A_{es}{}^mC_e$ | 1639 |
| 789238 | 239 | 258 | 4690 | 4709 | $A_{es}T_{eo}G_{es}A_{es}A_{es}T_{ds}T_{ds}{}^mC_{ds}{}^mC_{ds}T_{ds}T_{ds}T_{ds}A_{ds}{}^mC_{ds}A_{ds}{}^mC_{eo}{}^mC_{eo}A_{es}{}^mC_{es}A_e$ | 1640 |
| 789239 | 240 | 259 | 4691 | 4710 | $A_{es}A_{eo}T_{es}G_{es}A_{es}A_{ds}T_{ds}T_{ds}{}^mC_{ds}{}^mC_{ds}T_{ds}T_{ds}T_{ds}A_{ds}{}^mC_{ds}A_{eo}{}^mC_{eo}{}^mC_{es}A_{es}{}^mC_e$ | 1641 |
| 789240 | N/A | N/A | 29457 | 29476 | $T_{es}T_{eo}T_{es}T_{es}G_{ds}T_{ds}T_{ds}A_{ds}A_{ds}T_{ds}A_{ds}G_{ds}T_{ds}T_{ds}{}^mC_{eo}T_{eo}{}^mC_{es}T_{es}G_e$ | 1904 |
| 789241 | N/A | N/A | 4686 | 4705 | $A_{es}T_{eo}T_{es}{}^mC_{es}{}^mC_{es}T_{ds}T_{ds}T_{ds}A_{ds}{}^mC_{ds}A_{ds}{}^mC_{ds}{}^mC_{ds}A_{ds}{}^mC_{ds}A_{eo}{}^mC_{eo}T_{es}G_{es}G_e$ | 1682 |
| 789242 | 237 | 256 | 4688 | 4707 | $G_{es}A_{eo}A_{es}T_{es}T_{es}{}^mC_{ds}{}^mC_{ds}T_{ds}T_{ds}T_{ds}A_{ds}{}^mC_{ds}A_{ds}{}^mC_{ds}{}^mC_{ds}A_{eo}{}^mC_{eo}A_{es}{}^mC_{es}T_e$ | 1638 |
| 789243 | 238 | 257 | 4689 | 4708 | $T_{es}G_{eo}A_{es}A_{es}T_{es}T_{ds}{}^mC_{ds}{}^mC_{ds}T_{ds}T_{ds}T_{ds}A_{ds}{}^mC_{ds}A_{ds}{}^mC_{ds}{}^mC_{es}A_{eo}{}^mC_{es}A_{es}{}^mC_e$ | 1639 |
| 789244 | 239 | 258 | 4690 | 4709 | $A_{es}T_{eo}G_{es}A_{es}A_{es}T_{ds}T_{ds}{}^mC_{ds}{}^mC_{ds}T_{ds}T_{ds}T_{ds}A_{ds}{}^mC_{ds}A_{ds}{}^mC_{es}{}^mC_{eo}A_{es}{}^mC_{es}A_e$ | 1640 |
| 789245 | 240 | 259 | 4691 | 4710 | $A_{es}A_{eo}T_{es}G_{es}A_{es}A_{ds}T_{ds}T_{ds}{}^mC_{ds}{}^mC_{ds}T_{ds}T_{ds}T_{ds}A_{ds}{}^mC_{ds}A_{es}{}^mC_{eo}{}^mC_{es}A_{es}{}^mC_e$ | 1641 |
| 789246 | N/A | N/A | 29457 | 29476 | $T_{es}T_{eo}T_{es}T_{es}T_{es}G_{ds}T_{ds}T_{ds}A_{ds}A_{ds}T_{ds}A_{ds}G_{ds}T_{ds}T_{ds}{}^mC_{es}T_{eo}{}^mC_{es}T_{es}G_e$ | 1904 |
| 806693 | N/A | N/A | 29458 | 29477 | $T_{es}T_{eo}T_{es}T_{es}T_{es}T_{ds}G_{ds}T_{ds}T_{ds}A_{ds}A_{ds}T_{ds}A_{ds}G_{ds}T_{ds}T_{eo}{}^mC_{eo}T_{es}{}^mC_{es}T_e$ | 2791 |
| 806694 | N/A | N/A | 29459 | 29478 | $T_{es}T_{eo}T_{es}T_{es}T_{es}T_{ds}T_{ds}G_{ds}T_{ds}T_{ds}A_{ds}A_{ds}T_{ds}A_{ds}G_{ds}T_{eo}T_{eo}{}^mC_{es}T_{es}{}^mC_e$ | 2792 |
| 806695 | N/A | N/A | 29460 | 29479 | $A_{es}T_{eo}T_{es}T_{es}T_{es}T_{ds}T_{ds}T_{ds}G_{ds}T_{ds}T_{ds}A_{ds}A_{ds}T_{ds}A_{ds}G_{eo}T_{eo}T_{es}{}^mC_{es}T_e$ | 2793 |
| 806696 | N/A | N/A | 29454 | 29473 | $T_{es}T_{eo}G_{es}T_{es}T_{es}A_{ds}A_{ds}T_{ds}A_{ds}G_{ds}T_{ds}T_{ds}{}^mC_{ds}T_{ds}{}^mC_{es}T_{es}G_{eo}T_{es}T_{es}T_e$ | 1901 |
| 806697 | N/A | N/A | 29455 | 29474 | $T_{es}T_{eo}T_{es}G_{es}T_{es}T_{ds}A_{ds}A_{ds}T_{ds}A_{ds}G_{ds}T_{ds}T_{ds}{}^mC_{ds}T_{ds}{}^mC_{es}T_{eo}G_{es}T_{es}T_e$ | 1902 |
| 806698 | N/A | N/A | 29456 | 29475 | $T_{es}T_{eo}T_{es}T_{es}G_{ds}T_{ds}T_{ds}A_{ds}A_{ds}T_{ds}A_{ds}G_{ds}T_{ds}T_{ds}{}^mC_{ds}T_{es}{}^mC_{eo}T_{es}G_{es}T_e$ | 1903 |
| 806699 | N/A | N/A | 29458 | 29477 | $T_{es}T_{eo}T_{es}T_{es}T_{es}T_{ds}G_{ds}T_{ds}T_{ds}A_{ds}A_{ds}T_{ds}A_{ds}G_{ds}T_{ds}T_{es}{}^mC_{eo}T_{es}{}^mC_{es}T_e$ | 2791 |
| 806700 | N/A | N/A | 29459 | 29478 | $T_{es}T_{eo}T_{es}T_{es}T_{es}T_{ds}T_{ds}G_{ds}T_{ds}T_{ds}A_{ds}A_{ds}T_{ds}A_{ds}G_{ds}T_{es}T_{eo}{}^mC_{es}T_{es}{}^mC_e$ | 2792 |
| 806701 | N/A | N/A | 29460 | 29479 | $A_{es}T_{eo}T_{es}T_{es}T_{es}T_{ds}T_{ds}T_{ds}G_{ds}T_{ds}T_{ds}A_{ds}A_{ds}T_{ds}A_{ds}G_{es}T_{eo}T_{es}{}^mC_{es}T_e$ | 2793 |

TABLE 45-continued

Modified oligonucleotides complementary to human SNCA mRNA

| Compound No | SEQ ID No: 2 start | SEQ ID No: 2 stop | SEQ ID No: 5 start | SEQ ID No: 5 stop | Sequence and chemical notation (5' to 3') | SEQ ID NO: |
|---|---|---|---|---|---|---|
| 806708 | N/A | N/A | 29454 | 29473 | $T_{es}T_{eo}G_{eo}T_{es}T_{es}A_{ds}A_{ds}T_{ds}A_{ds}G_{ds}T_{ds}T_{ds}{}^mC_{ds}T_{ds}{}^mC_{ds}T_{eo}G_{eo}T_{es}T_{es}T_e$ | 1901 |
| 806709 | N/A | N/A | 29455 | 29474 | $T_{es}T_{eo}T_{eo}G_{es}T_{es}T_{ds}A_{ds}A_{ds}T_{ds}A_{ds}G_{ds}T_{ds}T_{ds}{}^mC_{ds}T_{ds}{}^mC_{eo}T_{eo}G_{es}T_{es}T_e$ | 1902 |
| 806710 | N/A | N/A | 29456 | 29475 | $T_{es}T_{eo}T_{eo}T_{es}G_{es}T_{ds}T_{ds}A_{ds}A_{ds}T_{ds}A_{ds}G_{ds}T_{ds}T_{ds}{}^mC_{ds}T_{eo}{}^mC_{eo}T_{es}G_{es}T_e$ | 1903 |
| 806711 | N/A | N/A | 29458 | 29477 | $T_{es}T_{eo}T_{eo}T_{es}T_{es}T_{ds}G_{ds}T_{ds}T_{ds}A_{ds}A_{ds}T_{ds}A_{ds}G_{ds}T_{ds}T_{eo}{}^mC_{eo}T_{es}{}^mC_{es}T_e$ | 2791 |
| 806712 | N/A | N/A | 29459 | 29478 | $T_{es}T_{eo}T_{eo}T_{es}T_{es}T_{ds}T_{ds}G_{ds}T_{ds}T_{ds}A_{ds}A_{ds}T_{ds}A_{ds}G_{ds}T_{eo}T_{eo}{}^mC_{es}T_{es}{}^mC_e$ | 2792 |
| 806713 | N/A | N/A | 29460 | 29479 | $A_{es}T_{eo}T_{eo}T_{es}T_{es}T_{ds}T_{ds}T_{ds}G_{ds}T_{ds}T_{ds}A_{ds}A_{ds}T_{ds}A_{ds}G_{eo}T_{eo}T_{es}{}^mC_{es}T_e$ | 2793 |
| 806714 | N/A | N/A | 29454 | 29473 | $T_{es}T_{eo}G_{es}T_{es}T_{es}A_{ds}A_{ds}T_{ds}A_{ds}G_{ds}T_{ds}T_{ds}{}^mC_{ds}T_{ds}{}^mC_{ds}T_{eo}G_{eo}T_{es}T_{es}T_e$ | 1901 |
| 806715 | N/A | N/A | 29455 | 29474 | $T_{es}T_{eo}T_{es}G_{es}T_{es}T_{ds}A_{ds}A_{ds}T_{ds}A_{ds}G_{ds}T_{ds}T_{ds}{}^mC_{ds}T_{ds}{}^mC_{eo}T_{eo}G_{es}T_{es}T_e$ | 1902 |
| 806716 | N/A | N/A | 29456 | 29475 | $T_{es}T_{eo}T_{es}T_{es}G_{es}T_{ds}T_{ds}A_{ds}A_{ds}T_{ds}A_{ds}G_{ds}T_{ds}T_{ds}{}^mC_{ds}T_{eo}{}^mC_{eo}T_{es}G_{es}T_e$ | 1903 |
| 827592 | N/A | N/A | 19633 | 19652 | $A_{es}{}^mC_{eo}A_{eo}G_{es}A_{es}T_{ds}A_{ds}T_{ds}T_{ds}T_{ds}T_{ds}T_{ds}G_{ds}T_{ds}T_{ds}{}^mC_{eo}T_{eo}G_{es}{}^mC_{es}{}^mC_e$ | 1703 |
| 827599 | N/A | N/A | 19633 | 19652 | $A_{es}{}^mC_{eo}A_{es}G_{es}A_{es}T_{ds}A_{ds}T_{ds}T_{ds}T_{ds}T_{ds}T_{ds}G_{ds}T_{ds}T_{ds}{}^mC_{eo}T_{eo}G_{es}{}^mC_{es}{}^mC_e$ | 1703 |
| 827606 | N/A | N/A | 19633 | 19652 | $A_{es}{}^mC_{eo}A_{es}G_{es}A_{es}T_{ds}A_{ds}T_{ds}T_{ds}T_{ds}T_{ds}T_{ds}G_{ds}T_{ds}T_{ds}{}^mC_{es}T_{eo}G_{es}{}^mC_{es}{}^mC_e$ | 1703 |
| 827607 | N/A | N/A | 21224 | 21243 | $G_{es}T_{eo}T_{es}G_{es}T_{es}T_{ds}{}^mC_{ds}A_{ds}G_{ds}A_{ds}A_{ds}T_{ds}T_{ds}A_{ds}T_{ds}G_{eo}T_{eo}{}^mC_{es}A_{es}T_e$ | 1754 |
| 827611 | N/A | N/A | 23286 | 23305 | ${}^mC_{es}A_{eo}T_{es}A_{es}T_{es}T_{ds}G_{ds}T_{ds}T_{ds}{}^mC_{ds}T_{ds}{}^mC_{ds}A_{ds}G_{ds}A_{ds}G_{eo}A_{eo}{}^mC_{es}{}^mC_{es}A_e$ | 1804 |
| 827617 | N/A | N/A | 28456 | 28475 | ${}^mC_{es}A_{eo}G_{es}A_{es}{}^mC_{es}T_{ds}G_{ds}T_{ds}A_{ds}A_{ds}A_{ds}T_{ds}{}^mC_{ds}T_{ds}A_{ds}G_{ds}G_{eo}A_{eo}{}^mC_{es}{}^mC_{es}{}^mC_e$ | 1887 |
| 827630 | N/A | N/A | 50920 | 50939 | $G_{es}T_{eo}T_{es}T_{es}T_{es}{}^mC_{ds}A_{ds}T_{ds}{}^mC_{ds}A_{ds}A_{ds}A_{ds}T_{ds}A_{ds}T_{ds}{}^mC_{ds}T_{eo}G_{eo}{}^mC_{es}A_{es}A_e$ | 2193 |
| 827649 | N/A | N/A | 21224 | 21243 | $G_{es}T_{eo}T_{es}G_{es}T_{es}T_{ds}{}^mC_{ds}A_{ds}G_{ds}A_{ds}A_{ds}T_{ds}T_{ds}A_{ds}T_{ds}G_{es}T_{eo}{}^mC_{es}A_{es}T_e$ | 1754 |
| 827653 | N/A | N/A | 23286 | 23305 | ${}^mC_{es}A_{eo}T_{es}A_{es}T_{es}T_{ds}G_{ds}T_{ds}T_{ds}{}^mC_{ds}T_{ds}{}^mC_{ds}A_{ds}G_{ds}A_{ds}G_{es}A_{eo}{}^mC_{es}{}^mC_{es}A_e$ | 1804 |
| 827691 | N/A | N/A | 21224 | 21243 | $G_{es}T_{eo}T_{eo}G_{es}T_{es}T_{ds}{}^mC_{ds}A_{ds}G_{ds}A_{ds}A_{ds}T_{ds}T_{ds}A_{ds}T_{ds}G_{eo}T_{eo}{}^mC_{es}A_{es}T_e$ | 1754 |
| 827695 | N/A | N/A | 23286 | 23305 | ${}^mC_{es}A_{eo}T_{eo}A_{es}T_{es}T_{ds}G_{ds}T_{ds}T_{ds}{}^mC_{ds}T_{ds}{}^mC_{ds}A_{ds}G_{ds}A_{ds}G_{eo}A_{eo}{}^mC_{es}{}^mC_{es}A_e$ | 1804 |
| 827701 | N/A | N/A | 28456 | 28475 | ${}^mC_{es}A_{eo}G_{eo}A_{es}{}^mC_{es}T_{ds}G_{ds}T_{ds}A_{ds}A_{ds}A_{ds}T_{ds}{}^mC_{ds}T_{ds}A_{ds}G_{ds}G_{eo}A_{eo}{}^mC_{es}{}^mC_{es}{}^mC_e$ | 1887 |
| 827714 | N/A | N/A | 50920 | 50939 | $G_{es}T_{eo}T_{eo}T_{es}T_{es}{}^mC_{ds}A_{ds}T_{ds}{}^mC_{ds}A_{ds}A_{ds}A_{ds}T_{ds}A_{ds}T_{ds}{}^mC_{ds}T_{eo}G_{eo}{}^mC_{es}A_{es}A_e$ | 2193 |

Example 7: Effect of Modified Oligonucleotides on Human SNCA In Vitro, Multiple Doses Modified oligonucleotides selected from the examples above were tested at various doses in SH-SY5Y cells. Comparator oligonucleotide 387978 was also tested. Cells were plated at a density of 20,000 cells per well and transfected using electroporation with 0.55 μM, 1.67 μM, 5.00 μM and 15.00 μM concentrations of modified oligonucleotide, as specified in the tables below. After a treatment period of approximately 24 hours, total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA, relative to untreated control. A value of 0% reduction indicates that the compound had no effect or increased mRNA concentrations in the cell. As illustrated in the tables below, SNCA mRNA levels were reduced in a dose-dependent manner in modified oligonucleotide-treated cells. $IC_{50}$ was calculated using the "log(inhibitor) vs. response—variable slope (4 parameters)" formula using Prism6 software.

TABLE 46

Dose-dependent percent reduction of human SNCA mRNA by modified oligonucleotides

| Compound Number | SNCA inhibition (% reduction) | | | | $IC_{50}$ ($\mu M$) |
| --- | --- | --- | --- | --- | --- |
| | 0.55 $\mu M$ | 1.67 $\mu M$ | 5.00 $\mu M$ | 15.00 $\mu M$ | |
| 387978 | 20 | 44 | 50 | 75 | 3.49 |
| 709533 | 19 | 51 | 59 | 87 | 2.27 |
| 709551 | 20 | 41 | 61 | 75 | 2.97 |
| 709556 | 16 | 30 | 62 | 82 | 3.34 |
| 709654 | 16 | 47 | 64 | 83 | 2.42 |
| 709581 | 12 | 31 | 61 | 83 | 3.41 |
| 709582 | 10 | 34 | 57 | 76 | 3.86 |
| 709640 | 3 | 22 | 54 | 80 | 4.62 |
| 709875 | 22 | 45 | 58 | 82 | 2.60 |
| 709882 | 33 | 41 | 50 | 86 | 2.57 |
| 709893 | 43 | 70 | 87 | 92 | 0.72 |
| 709900 | 28 | 50 | 58 | 75 | 2.31 |
| 709919 | 26 | 55 | 52 | 88 | 2.07 |
| 709924 | 12 | 36 | 56 | 76 | 3.77 |
| 709936 | 16 | 39 | 60 | 80 | 3.06 |
| 709944 | 42 | 72 | 81 | 90 | 0.71 |
| 709949 | 23 | 35 | 55 | 84 | 3.16 |
| 709967 | 35 | 65 | 62 | 81 | 1.17 |
| 709979 | 30 | 56 | 67 | 76 | 1.62 |

TABLE 47

Dose-dependent percent reduction of human SNCA mRNA by modified oligonucleotides

| Compound Number | SNCA inhibition (% reduction) | | | | $IC_{50}$ ($\mu M$) |
| --- | --- | --- | --- | --- | --- |
| | 0.55 $\mu M$ | 1.67 $\mu M$ | 5.00 $\mu M$ | 15.00 $\mu M$ | |
| 387978 | 14 | 19 | 57 | 76 | 4.58 |
| 709543 | 15 | 37 | 61 | 75 | 3.35 |
| 709544 | 33 | 47 | 71 | 87 | 1.61 |
| 709550 | 33 | 51 | 53 | 78 | 2.12 |
| 709573 | 26 | 48 | 64 | 82 | 2.08 |
| 709579 | 0 | 29 | 67 | 90 | 3.19 |
| 709580 | 19 | 8 | 58 | 86 | 4.49 |
| 709856 | 0 | 21 | 48 | 62 | 7.15 |
| 709592 | 1 | 24 | 51 | 73 | 5.29 |
| 709597 | 7 | 40 | 62 | 86 | 2.96 |
| 709651 | 17 | 26 | 45 | 71 | 5.65 |
| 709873 | 7 | 24 | 74 | 73 | 3.40 |
| 709891 | 19 | 40 | 62 | 80 | 2.82 |
| 709892 | 19 | 33 | 67 | 77 | 3.01 |
| 709897 | 27 | 40 | 55 | 86 | 2.67 |
| 709898 | 32 | 64 | 87 | 90 | 1.04 |
| 709909 | 0 | 23 | 59 | 72 | 4.70 |
| 709953 | 0 | 34 | 55 | 75 | 4.29 |
| 709966 | 23 | 56 | 78 | 87 | 1.51 |

TABLE 48

Dose-dependent percent reduction of human SNCA mRNA by modified oligonucleotides

| Compound Number | SNCA inhibition (% reduction) | | | | $IC_{50}$ ($\mu M$) |
| --- | --- | --- | --- | --- | --- |
| | 0.55 $\mu M$ | 1.67 $\mu M$ | 5.00 $\mu M$ | 15.00 $\mu M$ | |
| 387978 | 6 | 42 | 65 | 72 | 3.23 |
| 709536 | 50 | 68 | 83 | 86 | <0.55 |
| 709548 | 18 | 37 | 59 | 76 | 3.33 |
| 709549 | 41 | 66 | 82 | 89 | 0.81 |
| 709555 | 20 | 45 | 53 | 58 | 4.93 |
| 709560 | 5 | 37 | 60 | 66 | 4.28 |
| 709572 | 43 | 54 | 64 | 79 | 1.12 |
| 709578 | 16 | 37 | 56 | 79 | 3.44 |
| 709591 | 0 | 23 | 50 | 86 | 4.64 |
| 709596 | 0 | 19 | 51 | 70 | 5.83 |
| 709632 | 14 | 39 | 65 | 77 | 2.97 |
| 709668 | 0 | 0 | 8 | 27 | 29.96 |
| 709788 | 0 | 12 | 40 | 72 | 7.11 |
| 709878 | 26 | 71 | 78 | 93 | 1.09 |
| 709879 | 17 | 50 | 84 | 93 | 1.66 |
| 709890 | 41 | 53 | 72 | 87 | 1.13 |
| 709915 | 37 | 64 | 65 | 86 | 1.07 |
| 709940 | 14 | 36 | 67 | 84 | 2.80 |
| 709977 | 37 | 34 | 49 | 68 | 4.04 |

TABLE 49

Dose-dependent percent reduction of human SNCA mRNA by modified oligonucleotides

| Compound Number | SNCA inhibition (% reduction) | | | | $IC_{50}$ ($\mu M$) |
| --- | --- | --- | --- | --- | --- |
| | 0.55 $\mu M$ | 1.67 $\mu M$ | 5.00 $\mu M$ | 15.00 $\mu M$ | |
| 387978 | 11 | 30 | 62 | 72 | 3.92 |
| 709534 | 23 | 48 | 67 | 81 | 2.11 |
| 709535 | 44 | 80 | 74 | 79 | <0.55 |
| 709547 | 37 | 55 | 61 | 83 | 1.42 |
| 709558 | 27 | 56 | 56 | 56 | 3.29 |
| 709563 | 12 | 49 | 64 | 77 | 2.61 |
| 709565 | 25 | 60 | 68 | 78 | 1.62 |
| 709571 | 9 | 47 | 59 | 69 | 3.45 |
| 709576 | 12 | 37 | 69 | 68 | 3.28 |
| 709588 | 9 | 53 | 84 | 84 | 1.73 |
| 709625 | 0 | 24 | 47 | 76 | 5.44 |
| 709727 | 0 | 34 | 49 | 71 | 5.14 |
| 709751 | 0 | 8 | 27 | 57 | 11.73 |
| 709877 | 27 | 52 | 75 | 88 | 1.56 |
| 709881 | 18 | 29 | 58 | 72 | 4.10 |
| 709883 | 21 | 56 | 76 | 83 | 1.63 |
| 709894 | 25 | 37 | 76 | 90 | 2.08 |
| 709895 | 24 | 49 | 77 | 91 | 1.67 |
| 709912 | 4 | 36 | 54 | 73 | 4.32 |

Example 8: Effect of Modified Oligonucleotides on Human SNCA In Vitro, Multiple Doses Modified oligonucleotides selected from the examples above were tested at various doses in SH-SY5Y cells. Cells were plated at a density of 20,000 cells per well and transfected using electroporation with 0.48 $\mu M$, 1.44 $\mu M$, 4.33 $\mu M$, and 13.00 $\mu M$ concentrations of modified oligonucleotide, as specified in the tables below. After a treatment period of approximately 24 hours, total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA, relative to untreated control. A value of 0% reduction indicates that the compound had no effect or increased mRNA concentrations in the cell. As illustrated in the tables below, SNCA mRNA levels were reduced in a dose-dependent manner in modified oligonucleotide-treated cells.

TABLE 50

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.48 μM | 1.44 μM | 4.33 μM | 13.00 μM | |
| 740363 | 7 | 37 | 64 | 89 | 2.53 |
| 740364 | 28 | 35 | 63 | 83 | 2.3 |
| 740406 | 45 | 66 | 85 | 83 | 0.59 |
| 740407 | 46 | 79 | 84 | 93 | 0.51 |
| 740408 | 68 | 81 | 93 | 95 | <0.48 |
| 740409 | 49 | 70 | 92 | 93 | 0.52 |
| 740410 | 43 | 70 | 80 | 90 | 0.62 |
| 740411 | 19 | 63 | 86 | 91 | 1.14 |
| 740412 | 31 | 68 | 75 | 93 | 0.92 |
| 740416 | 41 | 63 | 84 | 94 | 0.74 |
| 740422 | 51 | 69 | 86 | 86 | 0.43 |
| 740425 | 62 | 75 | 78 | 93 | n/a |
| 740427 | 45 | 75 | 87 | 63 | <0.48 |
| 740429 | 33 | 56 | 72 | 86 | 1.16 |
| 740430 | 42 | 70 | 90 | 95 | 0.65 |
| 740432 | 0 | 0 | 0 | 17 | >13 |
| 740438 | 32 | 54 | 67 | 89 | 1.29 |
| 740439 | 39 | 61 | 79 | 96 | 0.84 |
| 740440 | 36 | 55 | 79 | 94 | 1.01 |

TABLE 51

Dose-dependent percent reduction of human SNCA mRNA by modified oligonucleotides

| Compound Number | SNCA Inhibition (% reduction) | | | | IC$_{50}$ (μM) |
|---|---|---|---|---|---|
| | 0.48 μM | 1.44 μM | 4.33 μM | 13.00 μM | |
| 740410 | 43 | 59 | 76 | 68 | 0.68 |
| 740414 | 29 | 44 | 69 | 71 | 1.91 |
| 740431 | 51 | 63 | 68 | 72 | <0.48 |
| 740456 | 39 | 51 | 47 | 70 | 2.02 |
| 740482 | 30 | 44 | 63 | 70 | 2.14 |
| 740498 | 47 | 45 | 68 | 74 | 1.02 |
| 740500 | 46 | 53 | 79 | 78 | 0.74 |
| 740508 | 10 | 38 | 55 | 70 | 3.63 |
| 740509 | 44 | 67 | 80 | 85 | 0.6 |
| 740510 | 24 | 54 | 69 | 83 | 1.56 |
| 740513 | 19 | 35 | 66 | 44 | 6.31 |
| 740517 | 5 | 38 | 73 | 61 | 3.07 |
| 740527 | 0 | 47 | 65 | 80 | 2.43 |
| 740528 | 11 | 45 | 77 | 83 | 1.88 |
| 740533 | 12 | 29 | 76 | 81 | 2.43 |
| 740534 | 21 | 56 | 40 | 5 | n/a |
| 740535 | 7 | 37 | 24 | 62 | 9.22 |
| 740545 | 32 | 58 | 69 | 81 | 1.2 |
| 740612 | 0 | 16 | 69 | 65 | 4.02 |

TABLE 52

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.48 μM | 1.44 μM | 4.33 μM | 13.00 μM | |
| 740140 | 45 | 58 | 69 | 82 | 0.75 |
| 740585 | 19 | 46 | 66 | 62 | 2.70 |
| 740601 | 15 | 47 | 61 | 63 | 3.05 |
| 740604 | 16 | 34 | 45 | 62 | 5.64 |
| 740608 | 2 | 15 | 59 | 63 | 5.13 |
| 740610 | 8 | 43 | 58 | 56 | 4.49 |
| 740615 | 32 | 50 | 59 | 76 | 1.81 |
| 740625 | 7 | 33 | 49 | 78 | 3.88 |
| 740649 | 7 | 25 | 54 | 41 | 11.78 |
| 740650 | 25 | 34 | 54 | 66 | 3.80 |
| 740654 | 27 | 32 | 50 | 75 | 3.45 |
| 740668 | 36 | 41 | 53 | 44 | >13 |
| 740670 | 0 | 40 | 45 | 32 | >13 |
| 740692 | 21 | 28 | 52 | 65 | 4.64 |
| 740730 | 42 | 47 | 62 | 78 | 1.30 |
| 740783 | 36 | 48 | 48 | 74 | 2.23 |
| 740794 | 33 | 35 | 53 | 37 | >13 |
| 740801 | 10 | 38 | 58 | 67 | 3.62 |
| 740802 | 19 | 12 | 55 | 63 | 5.73 |

TABLE 53

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.48 μM | 1.44 μM | 4.33 μM | 13.00 μM | |
| 740140 | 41 | 52 | 71 | 68 | 1.04 |
| 740796 | 3 | 28 | 51 | 54 | 6.89 |
| 740808 | 9 | 32 | 47 | 73 | 4.40 |
| 740851 | 2 | 21 | 46 | 74 | 5.05 |
| 740893 | 4 | 24 | 63 | 72 | 3.71 |
| 740894 | 0 | 20 | 46 | 33 | >13 |
| 740904 | 6 | 19 | 51 | 72 | 4.81 |
| 740919 | 23 | 43 | 68 | 90 | 1.84 |
| 740922 | 0 | 23 | 49 | 63 | 5.89 |
| 740923 | 0 | 29 | 52 | 79 | 3.93 |
| 740927 | 8 | 29 | 58 | 82 | 3.30 |
| 740976 | 16 | 44 | 65 | 72 | 2.52 |
| 740997 | 0 | 26 | 61 | 74 | 3.69 |
| 741000 | 25 | 52 | 43 | 68 | 3.43 |
| 741001 | 34 | 52 | 65 | 78 | 1.41 |
| 741002 | 14 | 37 | 62 | 69 | 3.19 |
| 741005 | 6 | 19 | 45 | 65 | 6.14 |
| 741006 | 54 | 76 | 71 | 78 | <0.48 |
| 741008 | 42 | 54 | 72 | 80 | 0.92 |

TABLE 54

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.48 μM | 1.44 μM | 4.33 μM | 13.00 μM | |
| 740140 | 35 | 60 | 71 | 81 | 1.03 |
| 740939 | 13 | 28 | 60 | 80 | 3.21 |
| 740941 | 8 | 30 | 38 | 83 | 4.55 |
| 740972 | 0 | 29 | 64 | 73 | 3.43 |
| 741009 | 0 | 32 | 52 | 83 | 3.62 |
| 741321 | 59 | 69 | 79 | 89 | <0.48 |
| 741378 | 21 | 49 | 84 | 86 | 1.43 |
| 741410 | 57 | 79 | 85 | 92 | <0.48 |
| 741455 | 53 | 69 | 88 | 87 | <0.48 |
| 741472 | 11 | 40 | 61 | 60 | 3.83 |
| 741473 | 9 | 29 | 53 | 65 | 4.76 |
| 741477 | 32 | 32 | 50 | 49 | 10.65 |
| 741483 | 11 | 23 | 53 | 62 | 5.42 |

TABLE 54-continued

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.48 μM | 1.44 μM | 4.33 μM | 13.00 μM | |
| 741487 | 19 | 39 | 72 | 70 | 2.36 |
| 741502 | 14 | 26 | 51 | 61 | 5.58 |
| 741514 | 0 | 27 | 41 | 73 | 5.34 |
| 741516 | 8 | 13 | 63 | 70 | 4.29 |
| 741525 | 9 | 32 | 58 | 61 | 4.70 |
| 741540 | 0 | 25 | 41 | 26 | <0.48 |

Example 9: Effect of Modified Oligonucleotides on Human SNCA In Vitro, Multiple Doses Modified oligonucleotides selected from the examples above were tested at various doses in SH-SY5Y cells. Comparator oligonucleotide 397978 was also tested. Cells were plated at a density of 20,000 cells per well and transfected using electroporation with 0.11 μM, 0.33 μM, 1.00 μM, and 3.00 μM concentrations of modified oligonucleotide, as specified in the tables below. After a treatment period of approximately 24 hours, total RNA was isolated from the cells and SNCA mRNA levels were measured by quantitative real-time PCR. Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA, relative to untreated control. A value of 0% reduction indicates that the compound had no effect or increased mRNA concentrations in the cell. As illustrated in the tables below, SNCA mRNA levels were reduced in a dose-dependent manner in modified oligonucleotide-treated cells.

TABLE 55

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.11 μM | 0.33 μM | 1.00 μM | 3.00 μM | |
| 740140 | 16 | 43 | 62 | 90 | 0.51 |
| 741021 | 19 | 56 | 81 | 93 | 0.30 |
| 741022 | 28 | 62 | 83 | 87 | 0.24 |
| 741028 | 28 | 54 | 78 | 94 | 0.28 |
| 741029 | 36 | 57 | 87 | 83 | 0.22 |
| 741032 | 23 | 56 | 86 | 93 | 0.28 |
| 741037 | 26 | 64 | 88 | 89 | 0.23 |
| 741077 | 34 | 53 | 84 | 89 | 0.24 |
| 741122 | 30 | 69 | 88 | 87 | 0.20 |
| 741125 | 25 | 57 | 83 | 91 | 0.27 |
| 741169 | 34 | 66 | 94 | 96 | 0.19 |
| 741170 | 34 | 71 | 92 | 93 | 0.18 |
| 741189 | 35 | 56 | 81 | 95 | 0.23 |
| 741206 | 32 | 57 | 81 | 94 | 0.24 |
| 741207 | 26 | 63 | 91 | 96 | 0.23 |
| 741228 | 23 | 49 | 78 | 90 | 0.34 |
| 741229 | 10 | 58 | 81 | 95 | 0.31 |
| 741278 | 28 | 49 | 76 | 92 | 0.31 |
| 741379 | 22 | 70 | 86 | 93 | 0.22 |

TABLE 56

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.11 μM | 0.33 μM | 1.00 μM | 3.00 μM | |
| 740140 | 13 | 38 | 70 | 87 | 0.50 |
| 741016 | 30 | 42 | 74 | 91 | 0.36 |
| 741018 | 10 | 32 | 65 | 88 | 0.61 |
| 741019 | 14 | 20 | 56 | 86 | 0.82 |
| 741030 | 17 | 27 | 64 | 89 | 0.63 |
| 741034 | 12 | 28 | 47 | 80 | 0.93 |
| 741038 | 14 | 42 | 72 | 91 | 0.46 |
| 741039 | 63 | 42 | 70 | 93 | 0.11 |
| 741043 | 13 | 33 | 66 | 83 | 0.60 |
| 741047 | 29 | 45 | 72 | 94 | 0.35 |
| 741049 | 18 | 34 | 58 | 84 | 0.65 |
| 741073 | 4 | 46 | 75 | 93 | 0.43 |
| 741078 | 23 | 52 | 72 | 92 | 0.33 |
| 741080 | 15 | 37 | 66 | 78 | 0.59 |
| 741082 | 18 | 48 | 75 | 95 | 0.37 |
| 741083 | 17 | 36 | 72 | 82 | 0.51 |
| 741101 | 18 | 44 | 79 | 92 | 0.38 |
| 741111 | 0 | 29 | 68 | 88 | 0.64 |
| 741129 | 5 | 38 | 54 | 77 | 0.79 |

TABLE 57

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.11 μM | 0.33 μM | 1.00 μM | 3.00 μM | |
| 740140 | 39 | 34 | 69 | 81 | 0.39 |
| 741094 | 3 | 13 | 56 | 78 | 0.99 |
| 741110 | 5 | 26 | 47 | 66 | 1.26 |
| 741113 | 27 | 26 | 69 | 76 | 0.60 |
| 741167 | 16 | 37 | 70 | 79 | 0.54 |
| 741168 | 23 | 39 | 63 | 84 | 0.52 |
| 741178 | 29 | 34 | 58 | 77 | 0.62 |
| 741179 | 22 | 54 | 71 | 89 | 0.34 |
| 741188 | 0 | 25 | 70 | 77 | 0.70 |
| 741190 | 18 | 51 | 70 | 78 | 0.41 |
| 741191 | 23 | 37 | 63 | 82 | 0.55 |
| 741195 | 0 | 20 | 58 | 81 | 0.88 |
| 741197 | 20 | 34 | 69 | 76 | 0.58 |
| 741201 | 6 | 25 | 46 | 81 | 1.01 |
| 741205 | 14 | 34 | 66 | 87 | 0.57 |
| 741208 | 13 | 51 | 72 | 82 | 0.42 |
| 741227 | 8 | 30 | 61 | 78 | 0.74 |
| 741230 | 10 | 27 | 45 | 73 | 1.10 |
| 741231 | 0 | 20 | 33 | 82 | 1.31 |

TABLE 58

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.11 μM | 0.33 μM | 1.00 μM | 3.00 μM | |
| 387978 | 11 | 0 | 7 | 39 | >3.0 |
| 740140 | 26 | 35 | 52 | 80 | 0.67 |
| 740432 | 19 | 36 | 53 | 74 | 0.77 |
| 741187 | 18 | 30 | 60 | 78 | 0.72 |
| 741214 | 7 | 18 | 52 | 79 | 1.00 |
| 741220 | 16 | 35 | 49 | 73 | 0.91 |
| 741234 | 20 | 41 | 71 | 85 | 0.45 |
| 741241 | 15 | 25 | 53 | 78 | 0.88 |
| 741246 | 3 | 26 | 54 | 68 | 1.06 |
| 741280 | 21 | 44 | 62 | 78 | 0.52 |

TABLE 58-continued

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.11 µM | 0.33 µM | 1.00 µM | 3.00 µM | |
| 741301 | 22 | 46 | 66 | 84 | 0.44 |
| 741315 | 25 | 46 | 68 | 83 | 0.40 |
| 741320 | 17 | 36 | 65 | 85 | 0.55 |
| 741329 | 24 | 40 | 61 | 82 | 0.53 |
| 741330 | 13 | 36 | 69 | 85 | 0.55 |
| 741335 | 12 | 35 | 60 | 76 | 0.72 |
| 741368 | 18 | 46 | 72 | 87 | 0.42 |
| 741373 | 10 | 31 | 58 | 73 | 0.83 |
| 741393 | 17 | 37 | 67 | 82 | 0.54 |

Example 10: Effect of Modified Oligonucleotides on Human SNCA In Vitro, Multiple Doses Modified oligonucleotides selected from the examples above were tested at various doses in SH-SY5Y cells. Compound No. 387985, previously disclosed in WO 2012/068405 was also tested and is comparator oligonucleotide. Cells were plated at a density of 20,000 cells per well and transfected using electroporation with 0.44 µM, 1.33 µM, 4.00 µM, and 12.00 µM concentrations of modified oligonucleotide, as specified in the tables below. After a treatment period of approximately 24 hours, total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA, relative to untreated control. A value of 0% reduction indicates that the compound had no effect or increased mRNA concentrations in the cell. As illustrated in the tables below, SNCA mRNA levels were reduced in a dose-dependent manner in modified oligonucleotide-treated cells.

TABLE 59

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 42 | 76 | 86 | 93 | 0.56 |
| 741140 | 77 | 74 | 96 | 86 | <0.44 |
| 762851 | 24 | 45 | 76 | 93 | 1.45 |
| 762855 | 16 | 45 | 85 | 90 | 1.46 |
| 762858 | 25 | 55 | 84 | 96 | 1.11 |
| 762880 | 9 | 33 | 55 | 85 | 2.93 |
| 762882 | 75 | 92 | 94 | 90 | 0.07 |
| 762886 | 39 | 67 | 82 | 84 | 0.66 |
| 762891 | 25 | 61 | 88 | 93 | 0.97 |
| 762893 | 31 | 63 | 86 | 95 | 0.87 |
| 762899 | 42 | 74 | 88 | 82 | 0.53 |
| 762900 | 69 | 93 | 96 | 97 | <0.44 |
| 762901 | 63 | 86 | 90 | 93 | <0.44 |
| 762924 | 30 | 59 | 82 | 84 | 0.97 |
| 762926 | 40 | 63 | 80 | 92 | 0.72 |
| 762930 | 37 | 73 | 85 | 80 | 0.62 |
| 762932 | 42 | 72 | 94 | 93 | 0.58 |
| 762953 | 39 | 61 | 85 | 91 | 0.76 |
| 762969 | 60 | 72 | 86 | 92 | <0.44 |

TABLE 60

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 58 | 79 | 70 | 75 | <0.44 |
| 741140 | 84 | 93 | 89 | 79 | >12 |
| 762914 | 80 | 87 | 91 | 95 | <0.44 |
| 762952 | 42 | 74 | 85 | 94 | 0.57 |
| 762960 | 34 | 54 | 79 | 82 | 1.01 |
| 762962 | 52 | 81 | 84 | 94 | <0.44 |
| 762965 | 48 | 72 | 91 | 93 | 0.48 |
| 762987 | 37 | 69 | 86 | 75 | 0.65 |
| 763002 | 37 | 54 | 79 | 88 | 0.94 |
| 763019 | 30 | 51 | 77 | 91 | 1.19 |
| 763032 | 47 | 70 | 84 | 78 | <0.44 |
| 763033 | 68 | 84 | 89 | 86 | <0.44 |
| 763035 | 40 | 69 | 85 | 91 | 0.64 |
| 763040 | 36 | 67 | 85 | 94 | 0.73 |
| 763049 | 34 | 68 | 82 | 88 | 0.77 |
| 763050 | 54 | 87 | 87 | 84 | <0.44 |
| 763052 | 54 | 75 | 85 | 91 | <0.44 |
| 763059 | 4 | 67 | 83 | 89 | 1.08 |
| 763087 | 51 | 93 | 91 | 94 | <0.44 |

TABLE 61

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 48 | 60 | 61 | 75 | n/a |
| 741140 | 80 | 84 | 77 | 93 | n/a |
| 763065 | 22 | 55 | 73 | 89 | 1.32 |
| 763072 | 45 | 66 | 76 | 91 | 0.57 |
| 763075 | 39 | 58 | 86 | 89 | 0.78 |
| 763079 | 49 | 74 | 86 | 83 | <0.44 |
| 763081 | 39 | 69 | 70 | 83 | 0.68 |
| 763084 | 50 | 73 | 75 | 89 | <0.44 |
| 763085 | 57 | 81 | 88 | 83 | <0.44 |
| 763088 | 73 | 72 | 79 | 89 | <0.44 |
| 763102 | 20 | 55 | 77 | 68 | 1.51 |
| 763142 | 58 | 70 | 79 | 87 | <0.44 |
| 763150 | 44 | 60 | 74 | 84 | 0.68 |
| 763151 | 39 | 71 | 68 | 82 | 0.64 |
| 763166 | 52 | 77 | 75 | 84 | <0.44 |
| 763177 | 60 | 64 | 89 | 72 | <0.44 |
| 763182 | 22 | 57 | 67 | 76 | 1.49 |
| 763196 | 52 | 68 | 86 | 83 | <0.44 |
| 763207 | 49 | 73 | 79 | 82 | <0.44 |

TABLE 62

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 48 | 66 | 84 | 82 | 0.45 |
| 741140 | 77 | 88 | 89 | 97 | <0.44 |
| 763145 | 79 | 81 | 74 | 92 | <0.44 |
| 763185 | 31 | 64 | 79 | 86 | 0.90 |
| 763188 | 36 | 70 | 85 | 90 | 0.69 |
| 763216 | 41 | 72 | 68 | 94 | 0.61 |
| 763225 | 54 | 74 | 84 | 93 | <0.44 |
| 763228 | 18 | 53 | 79 | 93 | 1.32 |
| 763233 | 45 | 68 | 83 | 94 | 0.56 |
| 763249 | 25 | 48 | 65 | 89 | 1.56 |

TABLE 62-continued

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 763272 | 38 | 60 | 89 | 95 | 0.77 |
| 763281 | 58 | 74 | 92 | 96 | <0.44 |
| 763291 | 27 | 35 | 67 | 86 | 1.92 |
| 763299 | 52 | 71 | 83 | 87 | <0.44 |
| 763309 | 43 | 43 | 72 | 76 | 1.11 |
| 763312 | 45 | 68 | 82 | 94 | 0.56 |
| 763333 | 12 | 55 | 85 | 81 | 1.32 |
| 763341 | 34 | 61 | 67 | 89 | 0.96 |
| 763364 | 51 | 74 | 72 | 90 | <0.44 |

TABLE 63

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 27 | 47 | 55 | 55 | 3.65 |
| 741140 | 48 | 56 | 56 | 49 | <0.44 |
| 763295 | 22 | 51 | 64 | 71 | 1.88 |
| 763305 | 28 | 52 | 54 | 71 | 2.05 |
| 763348 | 27 | 40 | 51 | 68 | 3.12 |
| 763355 | 43 | 49 | 51 | 62 | 1.77 |
| 763359 | 35 | 57 | 61 | 68 | 1.32 |
| 763360 | 49 | 55 | 71 | 74 | 0.55 |
| 763370 | 18 | 54 | 61 | 75 | 1.93 |
| 763373 | 44 | 45 | 69 | 70 | 1.09 |
| 763384 | 23 | 52 | 40 | 69 | 3.43 |
| 763391 | 28 | 48 | 55 | 66 | 2.49 |
| 763393 | 49 | 36 | 50 | 71 | 1.96 |
| 763394 | 25 | 41 | 71 | 86 | 1.68 |
| 763418 | 0 | 31 | 57 | 41 | 9.00 |
| 763434 | 38 | 66 | 50 | 65 | 1.04 |
| 763440 | 25 | 46 | 49 | 51 | <0.44 |
| 763481 | 34 | 51 | 57 | 69 | 1.74 |
| 763491 | 32 | 47 | 54 | 64 | 2.53 |

TABLE 64

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 47 | 59 | 54 | 50 | <0.44 |
| 741140 | 62 | 58 | 74 | 68 | <0.44 |
| 763466 | 19 | 47 | 55 | 66 | 2.87 |
| 763485 | 34 | 49 | 71 | 70 | 1.33 |
| 763492 | 7 | 44 | 40 | 62 | 5.24 |
| 763501 | 25 | 36 | 59 | 62 | 3.35 |
| 763612 | 33 | 44 | 45 | 71 | 2.76 |
| 763627 | 39 | 62 | 60 | 68 | 0.91 |
| 763628 | 22 | 48 | 42 | 57 | <0.44 |
| 763629 | 31 | 48 | 53 | 76 | 2.00 |
| 763634 | 26 | 41 | 44 | 57 | 5.83 |
| 763640 | 12 | 44 | 31 | 74 | 4.70 |
| 763641 | 6 | 33 | 51 | 76 | 3.58 |
| 763643 | 16 | 32 | 49 | 57 | 5.74 |
| 763645 | 18 | 36 | 55 | 71 | 3.22 |
| 763650 | 45 | 61 | 46 | 65 | 0.83 |
| 763651 | 43 | 60 | 64 | 59 | 0.62 |
| 763671 | 17 | 47 | 43 | 59 | 5.08 |
| 763741 | 23 | 37 | 61 | 71 | 2.64 |

TABLE 65

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 42 | 61 | 84 | 75 | 0.65 |
| 741140 | 72 | 79 | 92 | 94 | <0.44 |
| 762837* | 20 | 37 | 62 | 81 | 2.4 |
| 763684 | 13 | 44 | 75 | 92 | 1.69 |
| 763685 | 27 | 64 | 83 | 90 | 0.95 |
| 763693 | 3 | 15 | 58 | 76 | 3.88 |
| 763701 | 1 | 38 | 74 | 77 | 2.26 |
| 763702 | 16 | 37 | 68 | 84 | 2.15 |
| 763706 | 12 | 48 | 57 | 86 | 2.17 |
| 763712 | 18 | 50 | 56 | 89 | 1.90 |
| 763721 | 1 | 37 | 61 | 60 | 3.90 |
| 763723 | 19 | 42 | 65 | 77 | 2.16 |
| 763734 | 0 | 22 | 56 | 77 | 3.78 |
| 763740 | 32 | 47 | 77 | 88 | 1.23 |
| 763749 | 24 | 61 | 81 | 71 | 1.16 |
| 763755 | 8 | 45 | 57 | 72 | 2.82 |
| 763778 | 25 | 59 | 78 | 76 | 1.18 |
| 763793 | 41 | 71 | 81 | 93 | 0.61 |
| 763823 | 23 | 60 | 82 | 71 | 1.17 |

*Values represent the average of three experiments

TABLE 66

Dose-dependent percent reduction of human SNCA mRNA by modified oligonucleotides in SH-SY5Y cells

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 50 | 59 | 68 | 93 | 0.58 |
| 741140 | 75 | 64 | 83 | 88 | n/a |
| 762837 | 12 | 37 | 64 | 82 | 2.43 |
| 762837 | 27 | 33 | 51 | 86 | 2.64 |
| 763795 | 17 | 42 | 62 | 79 | 2.26 |
| 763798 | 25 | 43 | 63 | 78 | 2.00 |
| 763817 | 10 | 38 | 57 | 88 | 2.55 |
| 763818 | 24 | 53 | 52 | 92 | 1.72 |
| 763829 | 41 | 68 | 66 | 94 | 0.68 |
| 763876 | 33 | 65 | 83 | 84 | 0.81 |
| 763877 | 25 | 49 | 47 | 83 | 2.23 |
| 763882 | 27 | 57 | 67 | 86 | 1.27 |
| 763883 | 44 | 63 | 71 | 92 | 0.67 |
| 763884 | 25 | 42 | 64 | 78 | 2.00 |
| 763936 | 19 | 31 | 56 | 80 | 2.92 |
| 763939 | 18 | 27 | 54 | 65 | 4.27 |
| 763949 | 12 | 28 | 58 | 67 | 3.83 |
| 763972 | 0 | 36 | 46 | 67 | 4.60 |
| 763985 | 6 | 28 | 60 | 65 | 3.86 |

TABLE 67

Dose-dependent percent reduction of human SNCA mRNA by modified oligonucleotides

| Compound Number | SNCA inhibition (% reduction) | | | | IC$_{50}$ (µM) |
|---|---|---|---|---|---|
| | 0.44 µM | 1.33 µM | 4.00 µM | 12.00 µM | |
| 740140 | 41 | 60 | 74 | 82 | 0.73 |
| 741140 | 79 | 89 | 91 | 87 | <0.44 |
| 763295 | 8 | 38 | 77 | 91 | 1.88 |
| 763305 | 19 | 52 | 75 | 89 | 1.41 |
| 763348 | 28 | 62 | 78 | 93 | 0.97 |
| 763355 | 25 | 61 | 86 | 85 | 0.99 |
| 763359 | 49 | 76 | 90 | 94 | 0.45 |
| 763360 | 60 | 86 | 94 | 94 | <0.44 |
| 763370 | 28 | 68 | 89 | 90 | 0.83 |

TABLE 67-continued

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.44 μM | 1.33 μM | 4.00 μM | 12.00 μM | |
| 763373 | 51 | 59 | 79 | 90 | 0.51 |
| 763384 | 37 | 67 | 85 | 92 | 0.70 |
| 763391 | 30 | 64 | 79 | 82 | 0.94 |
| 763393 | 35 | 76 | 84 | 93 | 0.67 |
| 763394 | 36 | 76 | 83 | 96 | 0.65 |
| 763418 | 0 | 26 | 54 | 81 | 3.52 |
| 763434 | 40 | 73 | 91 | 92 | 0.60 |
| 763440 | 15 | 51 | 74 | 83 | 1.57 |
| 763481 | 35 | 73 | 84 | 88 | 0.68 |
| 763491 | 31 | 53 | 80 | 83 | 1.11 |

TABLE 68

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.44 μM | 1.33 μM | 4.00 μM | 12.00 μM | |
| 740140 | 36 | 53 | 69 | 87 | 1.08 |
| 741140 | 60 | 70 | 87 | 88 | <0.44 |
| 763466 | 27 | 52 | 74 | 80 | 1.34 |
| 763485 | 36 | 66 | 80 | 87 | 0.75 |
| 763492 | 9 | 41 | 71 | 87 | 1.97 |
| 763501 | 24 | 48 | 71 | 79 | 1.58 |
| 763612 | 37 | 63 | 82 | 90 | 0.76 |
| 763627 | 41 | 63 | 84 | 82 | 0.66 |
| 763628 | 44 | 72 | 85 | 86 | 0.53 |
| 763629 | 29 | 59 | 80 | 85 | 1.02 |
| 763634 | 22 | 55 | 81 | 92 | 1.18 |
| 763640 | 34 | 48 | 80 | 88 | 1.13 |
| 763641 | 21 | 53 | 79 | 82 | 1.33 |
| 763643 | 35 | 53 | 82 | 82 | 0.97 |
| 763645 | 0 | 55 | 65 | 84 | 1.93 |
| 763650 | 46 | 71 | 81 | 92 | 0.51 |
| 763651 | 40 | 57 | 82 | 86 | 0.79 |
| 763671 | 0 | 31 | 54 | 76 | 3.55 |
| 763741 | 32 | 40 | 71 | 73 | 1.71 |

TABLE 69

Dose-dependent percent reduction of human SNCA mRNA by modified oligonucleotides

| Compound Number | SNCA inhibition (% reduction) | | | | IC$_{50}$ (μM) |
|---|---|---|---|---|---|
| | 0.44 μM | 1.33 μM | 4.00 μM | 12.00 μM | |
| 387985 | 0 | 22 | 48 | 67 | 5.00 |
| 789243 | 9 | 38 | 66 | 79 | 2.40 |
| 827599 | 52 | 71 | 86 | 91 | 0.40 |

Example 11: Effect of Modified Oligonucleotides on Human SNCA In Vitro, Multiple Doses Modified oligonucleotides selected from the examples above were tested at various doses in SH-SY5Y cells. Compound No. 387985, previously disclosed in WO 2012/068405 was also tested and is comparator oligonucleotide. Cells were plated at a density of 20,000 cells per well and transfected using electroporation with 0.032 μM, 0.160 μM, 0.800 μM, 4.000 μM, and 20.000 μM concentrations of modified oligonucleotide, as specified in the tables below. After a treatment period of approximately 24 hours, total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA, relative to untreated control. A value of 0% reduction indicates that the compound had no effect or increased mRNA concentrations in the cell. As illustrated in the tables below, SNCA mRNA levels were reduced in a dose-dependent manner in modified oligonucleotide-treated cells.

TABLE 70

Dose-dependent percent reduction of human SNCA mRNA by modified oligonucleotides

| Compound Number | SNCA inhibition (% reduction) | | | | | IC$_{50}$ (μM) |
|---|---|---|---|---|---|---|
| | 0.032 μM | 0.160 μM | 0.800 μM | 4.000 μM | 20.000 μM | |
| 762837 | 0 | 7 | 33 | 76.1 | 91 | 1.72 |
| 762901 | 8 | 33 | 73 | 91 | 93 | 0.32 |
| 762952 | 0 | 15 | 67 | 81 | 95 | 0.57 |
| 763002 | 0 | 8 | 47 | 75 | 94 | 1.10 |
| 763032 | 11 | 35 | 71 | 77 | 96 | 0.36 |
| 763085 | 0 | 31 | 63 | 83 | 94 | 0.47 |
| 763364 | 0 | 16 | 51 | 81 | 89 | 0.86 |
| 763391 | 0 | 14 | 48 | 71 | 91 | 1.10 |
| 788833 | 0 | 8 | 39 | 77 | 90 | 1.31 |
| 789239 | 0 | 0 | 14 | 61 | 87 | 3.02 |
| 789242 | 0 | 1 | 27 | 60 | 85 | 2.67 |
| 789243 | 0 | 1 | 27 | 64 | 90 | 2.25 |

TABLE 71

Dose-dependent percent reduction of human SNCA mRNA by modified oligonucleotides

| Compound Number | SNCA inhibition (% reduction) | | | | | IC$_{50}$ (μM) |
|---|---|---|---|---|---|---|
| | 0.032 μM | 0.160 μM | 0.800 μM | 4.000 μM | 20.000 μM | |
| 387985 | 0 | 0 | 13 | 54 | 77 | 4.20 |
| 789243 | 0 | 7 | 31 | 69 | 85 | 1.90 |
| 827599 | 10 | 34 | 65 | 84 | 91 | 0.40 |

Example 12: Effect of Modified Oligonucleotides on Human SNCA In Vitro, Multiple Doses Modified oligonucleotides selected from the examples above were tested at various doses in A431 cells. Cells were plated at a density of 5,000 cells per well and transfected by free uptake with 0.032 μM, 0.160 μM, 0.800 μM, 4.000 μM, and 20.000 μM concentrations of modified oligonucleotide, as specified in the tables below. After a treatment period of approximately 24 hours, total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA, relative to untreated control. A value of 0% reduction indicates that the compound had no effect or increased mRNA concentrations in the cell. As illustrated in the tables below, SNCA mRNA levels were reduced in a dose-dependent manner in modified oligonucleotide-treated cells.

TABLE 72

Dose-dependent percent reduction of human SNCA mRNA by modified oligonucleotides

| Compound Number | SNCA inhibition (% reduction) | | | | | IC$_{50}$ (µM) |
|---|---|---|---|---|---|---|
| | 0.032 µM | 0.160 µM | 0.800 µM | 4.000 µM | 20.000 µM | |
| 762837 | 0 | 6 | 7 | 33 | 51 | 16.95 |
| 762901 | 1 | 28 | 53 | 60 | 81 | 1.20 |
| 762952 | 16 | 38 | 59 | 81 | 93 | 0.41 |
| 763002 | 0 | 6 | 41 | 71 | 87 | 1.49 |
| 763032 | 12 | 60 | 89 | 96 | 97 | 0.13 |
| 763085 | 2 | 19 | 75 | 90 | 96 | 0.40 |
| 763364 | 38 | 57 | 77 | 93 | 97 | 0.09 |
| 763391 | 5 | 28 | 71 | 92 | 95 | 0.37 |
| 788833 | 8 | 23 | 53 | 71 | 93 | 0.82 |
| 789239 | 6 | 0 | 32 | 32 | 45 | 0.00 |
| 789242 | 0 | 0 | 4 | 32 | 66 | 9.78 |
| 789243 | 0 | 3 | 13 | 39 | 66 | 8.02 |

Example 13: Effect of Modified Oligonucleotides on Rhesus Monkey SNCA In Vitro, Multiple Doses Several of the modified oligonucleotides described hereinabove are complementary to rhesus monkey Human-monkey cross reactive modified oligonucleotides selected from the examples above were tested at various doses in LLC-MK2 monkey cells. Cells were plated at a density of 20,000 cells per well and transfected using electroporation with 6.9 nM, 20.5 nM, 61.8 nM, 185.2 nM, 500.0 nM, 1700.0 nM, 5000.0 nM, and 15,000.0 nM concentrations of modified oligonucleotide, as specified in the table below. After a treatment period of approximately 24 hours, total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA, relative to untreated control. The half maximal inhibitory concentration (IC$_{50}$) of each oligonucleotide is also presented in the table below. A value of 0% reduction indicates that the compound had no effect or increased mRNA concentrations in the cell. As illustrated in the tables below, SNCA mRNA levels were reduced in a dose-dependent manner in modified oligonucleotide-treated cells.

TABLE 73

Dose-dependent percent reduction of rhesus monkey SNCA mRNA by modified oligonucleotides

| Compound No. | SNCA Inhibition (% Reduction) | | | | | | | | IC$_{50}$ (µM) |
|---|---|---|---|---|---|---|---|---|---|
| | 6.9 nM | 20.5 nM | 61.8 nM | 185.2 nM | 500.0 nM | 1700.0 nM | 5000.0 nM | 15,000.0 nM | |
| 709534 | 0 | 0 | 0 | 0 | 8 | 46 | 66 | 79 | 2.8 |
| 709535 | 0 | 0 | 0 | 7 | 28 | 59 | 84 | 90 | 1.4 |
| 709536 | 0 | 0 | 0 | 16 | 44 | 66 | 78 | 90 | 1.1 |
| 709883 | 0 | 0 | 0 | 0 | 36 | 61 | 76 | 88 | 1.5 |
| 709967 | 0 | 0 | 0 | 0 | 8 | 35 | 73 | 90 | 2.5 |
| 741082* | 0 | 0 | 0 | 0 | 0 | 0 | 36 | 78 | 7.0 |

*one mismatch to rhesus monkey

Example 14: Effect of Modified Oligonucleotides on Monkey SNCA In Vitro, Multiple Doses Several of the modified oligonucleotides described hereinabove are complementary to rhesus monkeys. Human-monkey cross reactive modified oligonucleotides selected from the examples above were tested at various doses in LLC-MK2 monkey cells. Modified oligonucleotides with 1-3 mismatches to rhesus monkey sequence are marked in the table below. Cells were plated at a density of 20,000 cells per well and transfected using electroporation with 0.032 µM, 0.160 µM, 0.800 µM, 4.000 µM, and 20.000 µN concentrations of modified oligonucleotide, as specified in the table below. After a treatment period of approximately 24 hours, total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA, relative to untreated control. As illustrated in the tables below, SNCA mRNA levels were reduced in a dose-dependent manner in modified oligonucleotide-treated cells.

TABLE 74

Dose-dependent percent reduction of rhesus monkey SNCA mRNA by modified oligonucleotides

| Compound Number | SNCA inhibition (% reduction) | | | | | IC$_{50}$ (µM) |
|---|---|---|---|---|---|---|
| | 0.032 µM | 0.160 µM | 0.800 µM | 4.000 µM | 20.000 µM | |
| 762837 | 0 | 0 | 5 | 57 | 84 | 3.67 |
| 762901 | 0 | 18 | 47 | 88 | 98 | 0.80 |
| 762952** | 0 | 0 | 0 | 14 | 53 | 17.90 |
| 763002 | 12 | 0 | 36 | 85 | 93 | 1.23 |
| 763032 | 6 | 29 | 63 | 85 | 94 | 0.47 |
| 763085* | 0 | 0 | 28 | 60 | 81 | 2.75 |
| 763364* | 0 | 0 | 28 | 58 | 85 | 2.77 |
| 763391 | 0 | 3 | 50 | 65 | 87 | 1.46 |
| 788833 | 0 | 0 | 15 | 59 | 84 | 3.30 |
| 789239 | 0 | 0 | 3 | 45 | 78 | 5.61 |
| 789242 | 0 | 0 | 5 | 41 | 78 | 6.05 |
| 789243 | 0 | 0 | 19 | 56 | 85 | 3.28 |

*one mismatch to monkey;
**two mismatches to monkey

Example 15: Effect of Modified Oligonucleotides on Human SNCA in Human Neurons by Free Uptake, Single Dose Selected modified oligonucleotides complementary to human SNCA were tested for their effects on SCNA mRNA levels in human neurons in vitro by free uptake. Human IPS-cell derived neurons were plated at a density of 35,000 cells per well. After approximately 24 hours, 20 μM modified oligonucleotide was added and incubated with the cultured cells for 7 days. After 7 days, total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA relative to untreated control cells. As shown below, modified oligonucleotides complementary to human SNCA reduced the amount of human SNCA mRNA.

TABLE 75

Percent reduction of human SNCA mRNA in human neurons by free uptake

| Compound No | % Reduction |
|---|---|
| 709897 | 53 |
| 740425 | 58 |
| 741082 | 98 |
| 762836 | 80 |
| 762837 | 79 |
| 762838 | 75 |
| 762839 | 64 |
| 762840 | 54 |
| 762895 | 60 |
| 762896 | 63 |
| 762898 | 82 |
| 762899 | 86 |
| 762900 | 85 |
| 762901 | 41 |
| 762914 | 74 |
| 762948 | 33 |
| 762949 | 96 |
| 762951 | 45 |
| 762952 | 77 |
| 763001 | 84 |
| 763002 | 82 |
| 763003 | 86 |
| 763004 | 82 |
| 763032 | 88 |
| 763033 | 82 |
| 763035 | 68 |
| 763040 | 71 |
| 763050 | 78 |
| 763084 | 89 |
| 763085 | 95 |
| 763087 | 78 |
| 763102 | 66 |
| 763196 | 56 |
| 763207 | 90 |
| 763216 | 65 |
| 763233 | 68 |
| 763364 | 83 |
| 763391 | 95 |
| 763393 | 81 |
| 763813 | 57 |
| 763817 | 51 |
| 763818 | 61 |
| 788815 | 63 |
| 788816 | 67 |
| 788820 | 63 |
| 788821 | 69 |
| 788822 | 76 |
| 788823 | 81 |
| 788824 | 73 |
| 788830 | 64 |
| 788831 | 67 |
| 788832 | 73 |
| 788833 | 79 |
| 788855 | 83 |
| 788856 | 85 |
| 788889 | 70 |
| 788890 | 47 |
| 789235 | 36 |
| 789236 | 80 |
| 789237 | 61 |
| 789239 | 56 |
| 789240 | 44 |
| 789242 | 81 |
| 789243 | 77 |
| 789244 | 66 |
| 789245 | 59 |
| 789246 | 46 |

Example 16: Effect of Modified Oligonucleotides on Human SNCA in Human Neurons by Free Uptake, Multiple Dose Selected modified oligonucleotides complementary to human SNCA were tested for their effects on SCNA mRNA levels in human neurons in vitro by free uptake Human IPS-cell derived neurons were plated at a density of 35,000 cells per well and incubated with 247.00 nM, 740.70 nM, 2.22 μM, 6.66 μM, or 20.00 μM oligonucleotide. After a treatment period of 5 days total RNA was isolated from the cells and SNCA mRNA levels were measured by quantitative real-time PCR Human SNCA primer probe set RTS2621 (described hereinabove in Example 1) was used to measure mRNA levels. SNCA mRNA levels were adjusted according to total RNA content, as measured by RIBOGREEN®. Results are presented in the tables below as percent reduction of the amount of SNCA mRNA relative to untreated control cells. A value of 0% reduction indicates that the compound had no effect or increased mRNA concentrations in the cell. As shown below, modified oligonucleotides complementary to human SNCA reduced the amount of human SNCA mRNA.

TABLE 76

Dose-dependent percent reduction of human SNCA mRNA in human neurons by free uptake

| Compound Number | SNCA inhibition (% reduction) | | | | | $IC_{50}$ (μM) |
|---|---|---|---|---|---|---|
| | 0.247 μM | 0.741 μM | 2.220 μM | 6.660 μM | 20.000 μM | |
| 709534 | 0 | 0 | 0 | 3 | 11 | >20 |
| 709535 | 0 | 0 | 20 | 35 | 51 | 16.97 |
| 709536 | 0 | 12 | 21 | 55 | 68 | 7.01 |
| 709883 | 19 | 0 | 22 | 15 | 22 | >20 |
| 709967 | 0 | 0 | 0 | 0 | 42 | >20 |
| 741082 | 25 | 25 | 63 | 87 | 95 | 1.37 |

Example 17: Tolerability of Modified Oligonucleotides Complementary to Human SNCA in Mice, 700 µg Dose Modified oligonucleotides described above were tested in mice to assess the tolerability of the oligonucleotides. Compound No. 387985, previously disclosed in WO 2012/068405 was also tested and is comparator oligonucleotide. Wild type C57/B16 mice each received a single ICV dose of 700 µg of oligonucleotide listed in the table below. Each treatment group consisted of 4 mice. A group of four mice received PBS as a negative control. At 3 hours post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group. The results are presented in the table below.

TABLE 77

Tolerability scores in mice at 700 µg dose

| Compound No. | FOB 3 hour |
|---|---|
| PBS | 0.0 |
| 762836 | 0.0 |
| 762838 | 0.5 |
| 762839 | 0.8 |
| 762840 | 0.0 |
| 762880 | 5.8 |
| 762899 | 1.8 |
| 762900 | 1.8 |
| 762901 | 0.0 |
| 762932 | 4.5 |
| 762952 | 0.0 |
| 762953 | 2.0 |
| 763004 | 0.0 |
| 763052 | 6.5 |
| 763102 | 3.5 |
| 763391 | 0.0 |
| 763392 | 3.0 |
| 763393 | 4.0 |
| 763394 | 0.8 |
| 763811 | 7.0 |
| 763812 | 5.5 |
| 763813 | 3.8 |
| 763814 | 3.5 |
| 763815 | 6.8 |
| 763817 | 2.0 |
| 763818 | 3.8 |

TABLE 78

Tolerability scores in mice at 700 µg dose

| Compound No. | FOB 3 hour |
|---|---|
| 709897 | 0.0 |
| 709940 | 1.8 |
| 740416 | 1.3 |
| 741073 | 2.5 |
| 741168 | 5.8 |
| 741205 | 0.0 |
| 741229 | 1.0 |
| 741301 | 2.5 |
| 741330 | 3.3 |
| 762898 | 4.5 |
| 762949 | 3.8 |
| 762951 | 1.8 |
| 762955 | 2.3 |
| 763035 | 0.8 |
| 763040 | 2.8 |
| 763050 | 1.5 |
| 763079 | 6.5 |
| 763084 | 2.0 |
| 763085 | 0.8 |
| 763087 | 2.8 |
| 763088 | 4.5 |
| 763150 | 7.0 |
| 763151 | 6.8 |
| 763188 | 6.3 |
| 763196 | 2.0 |
| 763216 | 3.0 |
| 763225 | 6.8 |
| 763281 | 7.0 |
| 763299 | 5.0 |
| 763312 | 2.3 |
| 763359 | 7.0 |
| 763384 | 2.3 |
| 763481 | 5.3 |
| 763485 | 0.0 |
| 763650 | 6.8 |
| 762954 | 6.3 |

TABLE 79

Tolerability scores in mice at 700 µg dose

| Compound No. | FOB 3 hour |
|---|---|
| PBS | 0.0 |
| 709548 | 0.0 |
| 709632 | 6.3 |
| 740439 | 3.5 |
| 741018 | 6.8 |
| 741038 | 0.0 |
| 762895 | 3.0 |
| 762896 | 5.0 |
| 762897 | 6.0 |
| 762926 | 3.8 |
| 762946 | 2.0 |
| 762947 | 2.8 |
| 762948 | 1.3 |
| 762950 | 1.3 |
| 762956 | 6.0 |
| 763033 | 0.0 |

TABLE 80

Tolerability scores in mice at 700 µg dose

| Compound No. | FOB 3 hour |
|---|---|
| PBS | 0.0 |
| 788813 | 2.8 |
| 788814 | 0.8 |
| 788815 | 0.0 |
| 788816 | 0.0 |
| 788817 | 0.0 |
| 788818 | 0.0 |
| 788819 | 4.8 |
| 788820 | 2.3 |
| 789229 | 0.5 |
| 789230 | 0.0 |
| 789232 | 0.0 |
| 789233 | 0.0 |

TABLE 80-continued

Tolerability scores in mice at 700 µg dose

| Compound No. | FOB 3 hour |
|---|---|
| 789234 | 4.3 |
| 789235 | 4.3 |
| 789236 | 0.0 |
| 789237 | 0.0 |
| 789238 | 0.0 |
| 789239 | 0.0 |
| 789240 | 6.0 |
| 789241 | 5.0 |
| 789242 | 0.3 |
| 789243 | 0.3 |
| 789244 | 0.0 |
| 789245 | 0.0 |

TABLE 81

Tolerability scores in mice at 700 µg dose

| Compound No. | FOB 3 hr |
|---|---|
| PBS | 0.0 |
| 762837 | 0.0 |
| 762901 | 0.0 |
| 762952 | 0.3 |
| 763002 | 0.3 |
| 763032 | 5.0 |
| 763085 | 1.3 |
| 763364 | 1.3 |
| 763391 | 2.3 |
| 788833 | 0.0 |
| 789239 | 0.0 |
| 789242 | 0.0 |
| 789243 | 0.0 |

TABLE 82

Tolerability scores in mice at 700 µg dose

| Compound No. | FOB 3 hr |
|---|---|
| PBS | 0.0 |
| 387985 | 6.0 |
| 827592 | 0.0 |
| 827599 | 0.0 |
| 827606 | 0.0 |
| 827607 | 1.0 |
| 827611 | 0.5 |
| 827617 | 5.5 |
| 827630 | 0.0 |
| 827649 | 3.8 |
| 827653 | 3.3 |
| 827691 | 1.5 |
| 827695 | 0.0 |
| 827701 | 1.0 |
| 827714 | 0.0 |

Example 18: Tolerability of Modified Oligonucleotides Complementary to Human SNCA in Rats, 3 mg Dose Modified oligonucleotides described above were tested in rats to assess the tolerability of the oligonucleotides. Compound No. 387985, previously disclosed in WO 2012/068405 was also tested and is comparator oligonucleotide. Sprague Dawley rats each received a single intrathecal (IT) dose of 3 mg of oligonucleotide listed in the table below. Each treatment group consisted of 4 rats. A group of four rats received PBS as a negative control. At 3 hours post-injection, movement in 7 different parts of the body were evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a sub-score of 0 if the body part was moving or 1 if the body part was paralyzed. After each of the 7 body parts were evaluated, the sub-scores were summed for each rat and then averaged for each group. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Results are presented as the average score for each treatment group.

TABLE 83

Tolerability scores in rats at 3 mg dose

| Compound No. | FOB 3 hr |
|---|---|
| PBS | 0.0 |
| 762948 | 2.3 |
| 762949 | 2.0 |
| 762951 | 0.8 |
| 763001 | 1.3 |
| 763002 | 2.5 |
| 763003 | 2.5 |
| 763040 | 1.0 |
| 763050 | 3.0 |
| 763084 | 4.0 |
| 763085 | 2.0 |
| 763087 | 2.8 |
| 763196 | 3.0 |
| 763233 | 3.3 |
| 763391 | 0.0 |

TABLE 87

Tolerability scores in rats at 3 mg dose

| Compound No. | FOB 3 hr |
|---|---|
| PBS | 0.3 |
| 762946 | 1.5 |
| 762969 | 0.3 |
| 763394 | 3.5 |
| 763813 | 1.8 |
| 763817 | 4.5 |
| 763818 | 3.0 |
| 789235 | 3.3 |
| 789236 | 0.8 |
| 789237* | 2.0 |
| 789239 | 0.0 |
| 789242 | 1.0 |
| 789243 | 1.8 |
| 789244 | 0.8 |
| 789245 | 0.5 |

*789237 group had 5 rats

TABLE 85

Tolerability scores in rats at 3 mg dose

| Compound No. | FOB 3 hr |
|---|---|
| PBS | 0.0 |
| 762932 | 5.0 |
| 762962 | 6.0 |
| 763485 | 3.0 |
| 789231 | 2.5 |
| 806693 | 4.5 |
| 806694 | 3.0 |
| 806695 | 5.0 |
| 806697 | 1.3 |

TABLE 85-continued

Tolerability scores in rats at 3 mg dose

| Compound No. | FOB 3 hr |
|---|---|
| 806698 | 4.3 |
| 806700 | 5.3 |
| 806701 | 4.0 |
| 806714 | 3.5 |
| 806715 | 2.3 |
| 806716 | 3.5 |

TABLE 86

Tolerability scores in rats at 3 mg dose

| Compound No. | FOB 3 hr |
|---|---|
| PBS | 0.0 |
| 806708 | 2.8 |
| 806709 | 2.0 |
| 806710 | 3.3 |
| 806711 | 3.8 |
| 806712 | 3.5 |
| 806713 | 2.8 |

TABLE 87

Tolerability scores in rats at 3 mg dose

| Compound No. | FOB 3 hr |
|---|---|
| PBS | 0.0 |
| 762836 | 2.3 |
| 762837 | 1.0 |
| 762838 | 0.5 |
| 762839 | 0.0 |
| 762840 | 0.0 |
| 762895 | 3.5 |
| 762896 | 2.5 |
| 762899 | 2.8 |
| 763032 | 4.8 |
| 763364 | 3.3 |
| 788833 | 1.0 |
| 788890 | 3.0 |
| 763207 | 2.8 |
| 806716* | 3.0 |

*806716 group only contained 2 mice

TABLE 88

Tolerability scores in rats at 3 mg dose

| Compound No. | FOB 3 hr |
|---|---|
| PBS | 0.0 |
| 762837 | 1.0 |
| 762901 | 2.8 |
| 762952 | 4.0 |
| 763002 | 3.3 |
| 763032 | 4.5 |
| 763085 | 4.0 |
| 763364 | 4.0 |
| 763391 | 1.3 |
| 788833 | 0.8 |
| 789239 | 0.5 |
| 789242 | 3.0 |
| 789243 | 1.5 |

TABLE 89

Tolerability scores in rats at 3 mg dose

| Compound No. | FOB 3 hr |
|---|---|
| PBS | 0.25 |
| 387985 | 3.8 |
| 827592 | 3.5 |
| 827599 | 2.0 |
| 827606 | 4.0 |
| 827607 | 1.0 |
| 827611 | 2.5 |
| 827617 | 3.0 |
| 827630 | 1.0 |
| 827649 | 5.5 |
| 827653 | 2.4 |
| 827691 | 3.3 |
| 827695 | 1.8 |
| 827701 | 2.5 |
| 827714 | 0.3 |

Example 19: Potency of Modified Oligonucleotides Complementary to Human SNCA in Transgenic Mice Modified oligonucleotides described above were tested in the SNCA PAC transgenic mouse model which uses bacterial P1 artificial chromosome (PAC) containing the entire wild-type human SNCA gene.

Treatment

The SNCA PAC mice were divided into groups of 4-8 mice each. Two groups were tested with each compound. Groups were given a single ICV bolus of oligonucleotide at a dose of 10, 30, 100, 300, or 700 µg and sacrificed two weeks later. The PBS-injected group served as the control group to which oligonucleotide-treated groups were compared.

RNA Analysis

After two weeks, mice were sacrificed and RNA was extracted from cortical brain tissue for real-time PCR analysis of measurement of mRNA expression of SNCA using primer probe set hSNCA LTS00672 (forward sequence TGGCAGAAGCAGCAGGAAA, designated herein as SEQ ID NO: 14; reverse sequence TCCTTGGTTTTGGAGCC-TACA, designated herein as SEQ ID NO: 15; probe sequence 5'-FAM-CAAAAGAGGGTGTTCTC-3'MGB, designated herein as SEQ ID NO: 16.). Results are presented as percent change of mRNA, relative to PBS control, normalized with cyclophilin A.

As shown in the table below, treatment with modified oligonucleotides resulted in significant reduction of SNCA mRNA in comparison to the PBS control. Results are a combination of two individual studies Animals were removed from analysis using ROUT at 1% to remove outliers. 763085 had 3 animals removed with ROUT analysis and 1 animal did not survive surgery. 763364 had 2 animals removed with ROUT analysis. 763391 had one animal removed with a value of 253% of control and 3 animals did not survive surgery. 789243 had 1 animal removed with ROUT analysis. 827599 had 4 animals removed with ROUT analysis.

TABLE 90

Dose-dependent percent reduction of
human SNCA mRNA in transgenic mice

| Compound No. | Dose (µg) | Cortex % Reduction | ED50 (µg) |
|---|---|---|---|
| PBS | — | — | |
| 763085 | 10 | 0 | 35 |
| | 30 | 47 | |
| | 100 | 72 | |
| | 300 | 96 | |
| | 700 | 94 | |
| 763364 | 10 | 35 | 21 |
| | 30 | 55 | |
| | 100 | 87 | |
| | 300 | 90 | |
| | 700 | 97 | |
| 763391 | 10 | 17 | 19 |
| | 30 | 67 | |
| | 100 | 68 | |
| | 300 | 93 | |
| | 700 | 94 | |
| 789243 | 10 | 35 | 61 |
| | 30 | 20 | |
| | 100 | 60 | |
| | 300 | 85 | |
| | 700 | 92 | |
| 827599 | 10 | 1 | 56 |
| | 30 | 25 | |
| | 100 | 81 | |
| | 300 | 87 | |
| | 700 | 95 | |

Example 20: Potency of Modified Oligonucleotides Complementary to Human SNCA in Transgenic Mice Modified oligonucleotides described above were tested in the SNCA PAC transgenic mouse model which uses bacterial P1 artificial chromosome (PAC) containing the entire wild-type human SNCA gene.

Treatment

The SNCA PAC mice were divided into groups of 10 mice each. Two groups were tested with each compound. Groups were given a single ICV bolus of oligonucleotide at a dose of 10, 30, 100, 300, or 700 µg and sacrificed two weeks later. The PBS-injected group served as the control group to which oligonucleotide-treated groups were compared.

RNA Analysis

After two weeks, mice were sacrificed and RNA was extracted from cortical brain tissue for real-time PCR analysis of measurement of mRNA expression of SNCA using primer probe set hSNCA LTS00672 (forward sequence TGGCAGAAGCAGCAGGAAA, designated herein as SEQ ID NO: 14; reverse sequence TCCTTGGTTTTGGAGCC-TACA, designated herein as SEQ ID NO: 15; probe sequence 5'-FAM-CAAAAGAGGGTGTTCTC-3'MGB, designated herein as SEQ ID NO: 16.). Results are presented as percent change of mRNA, relative to PBS control, normalized with cyclophilin A.

As shown in the table below, treatment with modified oligonucleotides resulted in significant reduction of SNCA mRNA in comparison to the PBS control Animals were removed from analysis using ROUT at 1% to remove outliers. The values in the table below are the average of 10 animals for all groups except the 700 µg dose, which is the average of 7 animals

TABLE 91

Dose-dependent percent reduction of
human SNCA mRNA in transgenic mice

| Compound No. | PBS | Dose modified oligonucleotide | | | | | ED50 (µg) |
| | | 10 µg | 30 µg | 100 µg | 300 µg | 700 µg | |
|---|---|---|---|---|---|---|---|
| 763391 | 0 | 36 | 51 | 92 | 94 | 97 | 21 |

Example 21: Potency of Modified Oligonucleotides Targeting Human SNCA in Non-Human Primates, 2 Week Study Modified oligonucleotides described above were further evaluated for potency in non-human primates (NHP).

Treatment

Female cynomolgus monkeys were divided into groups of 4 NHP each. Groups received a single IT bolus of 35 mg of modified oligonucleotide 789243, 763391, 763364, 763085, or 827599. One group of NHP received a dose of artificial cerebrospinal fluid (aCSF). The aCSF-injected group served as the control group to which oligonucleotide-treated groups were compared. After two weeks, NHP were sacrificed and tissues were collected for analysis.

RNA Analysis

RNA was extracted from various neural tissues for real-time PCR analysis of mRNA expression of SNCA as in the previous example. Results are presented as percent change of mRNA, relative to aCSF control, normalized with NHP Cyclophylin A. As shown in the table below, treatment with modified oligonucleotides resulted in reduction of SNCA mRNA in comparison to the PBS control with some of the treatment groups. The lumbar cord is an average of 3 NHP for 763391 because one lumbar sample was only able to obtain cauda aquina, and thus not from the lumbar region.

TABLE 92

Reduction of human SNCA mRNA in Non-Human Primates

| | % Reduction | | | |
| Compound No | Lumbar Spinal Cord | Frontal Cortex | Thoracic cord | Temporal cortex |
|---|---|---|---|---|
| aCSF | 0 | 0 | 0 | 0 |
| 763085* | 22 | 9 | 9 | 5 |
| 763364* | 0 | 10 | 0 | 10 |
| 763391 | 85 | 50 | 59 | 45 |
| 789243 | 38 | 34 | 26 | 3 |
| 827599 | 51 | 29 | 32 | 28 |

*These two oligos each contain single mismatch to cynomolgus SNCA

Example 22: Potency of Modified Oligonucleotides Targeting Human SNCA in Non-Human Primates, 13 Week Study Modified oligonucleotides described above were further evaluated for potency and tolerability in non-human primates (NHP).

Treatment

Female cynomolgus monkeys were divided into groups of 4 NHP each. Groups received an IT bolus dose of 35 mg of Compund 763391 or Compund 827599 on day one, on day 14, and then monthly for a total of 5 doses. One group of NHP received doses of aCSF rather than oligonucleotide.

The aCSF-injected group served as the control group to which oligonucleotide-treated groups were compared. A week after the final dose, NHP were sacrificed and tissues were collected for analysis.

RNA Analysis

RNA was extracted from various neural tissues for real-time PCR analysis of mRNA expression of SNCA as in examples above. Results are presented as percent change of mRNA, relative to aCSF control, normalized with monkey Cyclophylin A.

As shown in the table below, treatment with modified oligonucleotides resulted in reduction of SNCA mRNA in comparison to the PBS control.

sequence of (from 5' to 3') TTTAATTACTTCCACCA (incorporated herein as SEQ ID NO:23), having a sugar motif of (from 5' to 3'): eeekddddddddkeeee; wherein 'd' represents a 2'-deoxyribose sugar; 'e' represents a 2'-MOE modified sugar; and 'k' represents a cEt modified sugar; and an internucleoside linkage motif of (from 5' to 3') sooossssssss-sooss; wherein 'o' represents a phosphodiester internucleoside linkage and 's' represents a phosphorothioate internucleoside linkage.

Experimental Protocol

Three groups of twelve mice wild-type B6C3F1 mice were treated according to the table below. 700 µg modified oligonucleotide or PBS was administered via ICV (intrac-

TABLE 93

Reduction of human SNCA mRNA in Non-Human Primates

| | % Reduction | | | | | | | | |
|---|---|---|---|---|---|---|---|---|---|
| Comp No | Cervical Spinal Cord | Thoracic Spinal Cord | Lumbar Spinal Cord | Motor Cortex | Frontal Cortex | Caudate | Amygdala | Pons | Midbrain (level of Substantia nigra) | Putamen |
| aCSF | 0 | 0 | 0 | 0 | 0 | 0 | 0 | 0 | 0 | 0 |
| 763391 | 96 | 96 | 97 | 98 | 98 | 57 | 98 | 77 | 83 | 9 |
| 827599 | 68 | 80 | 95 | 61 | 72 | 27 | 70 | 41 | 31 | 0 |

TABLE 94

Reduction of human SNCA mRNA in Cynomolgus Monkeys

| | % Reduction | | | | | | | | |
|---|---|---|---|---|---|---|---|---|---|
| Comp. No | Cerebellar Peduncle | Corpus Collosum | DCN | Ent Cortex | Hippo campus | Hypo | Insular Cortex | Medulla (rostral and dorsal) | Caudal Medulla | Central Gray |
| aCSF | 0 | 0 | 0 | 0 | 0 | 0 | 0 | 0 | 0 | 0 |
| 763391 | 90 | 91 | 47 | 97 | 90 | 78 | 97 | 74 | 90 | 68 |
| 827599 | 61 | 67 | 37 | 71 | 25 | 25 | 68 | 38 | 54 | 9 |

TABLE 95

Reduction of human SNCA mRNA in Cynomolgus Monkeys

| | % Reduction | | | | | | | | |
|---|---|---|---|---|---|---|---|---|---|
| Comp No | VPM/ VPL | Pulvinar | Occipital cortex | Cerebral cortex | Temporal Cortex | Dorsal Medial Thalamus | Globus Pallidus | VA/ VL | Rostral Ventral Medulla | Superior Colliculi |
| aCSF | 0 | 0 | 0 | 0 | 0 | 0 | 0 | 0 | 0 | 0 |
| 763391 | 63 | 96 | 96 | 58 | 97 | 12 | 56 | 45 | 84 | 68 |
| 827599 | 26 | 59 | 58 | 0 | 72 | 0 | 0 | 13 | 52 | 9 |

Example 23: Treatment of SNCA Pathology in Pre-Formed Fibril (PFF) Model in Wild-Type Mouse, Prophylactic Treatment Experimental Model The PFF (pre-formed fibril) model in mouse is an experimental model that has been used to investigate treatments for Parkinson's disease, as described in Luk, et. al., Science. 2012 Nov. 16; 338(6109):949-53. A single intrastriatal injection of pre-formed SNCA fibrils generates Lewy body pathology characteristic of Parkinson's disease.

Modified Oligonucleotide

Compound No: 678363 is a 4-8-5 MOE and cEt gapmer that is 100% complementary to mouse SNCA, having a erebroventricial) injection on day 0, and pre-formed fibrils were administered into the striatum on day 14. On day 56, a wirehang test was performed to measure motor function, and mice were sacrificed for mRNA and histological analysis. P-α-Syn aggregates in the substantia nigra were stained and quantified. Mouse SNCA mRNA was measured with RT-PCR as described above, using mouse primer probe set RTS2956 (forward sequence GTCATTGCACC-CAATCTCCTAAG, designated herein as SEQ ID NO: 17; reverse sequence GACTGGGCACATTGGAACTGA, designated herein as SEQ ID NO: 18; probe sequence CGGCTGCTCTTCCATGGCGTACAA, designated herein as SEQ ID: 19). SNCA mRNA levels were normalized to cyclophilin A and are presented as % of mRNA level in PBS-treated mice. As shown in the table below, modified oligonucleotide treated mice had reduced SNCA mRNA, fewer aggregates in substantia nigra and improved performance on the wirehang test as compared to PBS treated mice.

TABLE 96

Pre-formed fibril (PFF) model in wild-type mouse, prophylactic treatment

| Treatment group | Treatment Day 0 | Day 14 | SNCA mRNA Mid-brain | stri-atum | Avg. # aggregates in substantia nigra | Wirehang (seconds) |
|---|---|---|---|---|---|---|
| Naïve (Naïve) | PBS | none | 90 | 98 | 0 | 192 ± 82 |
| PBS + PFF (PBS) | PBS | PFF | 100 | 100 | 42 | 94 ± 69 |
| 678363 + PFF (Treatment) | 678363 | PFF | 51 | 47 | 0.64 | 154 ± 64 |

Example 24: Treatment of SNCA Pathology in Pre-Formed Fibril (PFF) Model in Mouse, Post-Symptomatic Treatment Experimental Protocol Three groups of twelve wild-type B6C3F1 mice were treated according to the table below. Pre-formed fibrils were administered into the striatum on day 0 and 700 µg modified oligonucleotide or PBS was administered via ICV (intracerebroventricial) injection on day 14. On day 56, a wirehang test was performed to measure motor function, and mice were sacrificed for mRNA and histological analysis. Phosphorylated-α-Syn aggregates in the substantia nigra were stained and quantified. Mouse SNCA mRNA was measured as in the previous example and normalized to PBS treated mice. As shown in the table below, modified oligonucleotide treated mice had reduced SNCA mRNA and fewer aggregates in substantia nigra and improved performance on the wirehang test as compared to PBS treated mice.

TABLE 97

Pre-formed fibril (PFF) model in wild-type mouse, post-symptomatic treatment

| Treatment group | Treatment Day 0 | Day 14 | SNCA mRNA Mid-brain | stri-atum | Avg. # p-αSyn aggregates in SN | Wirehang (s) |
|---|---|---|---|---|---|---|
| Naïve (Naïve) | PBS | none | 102 | 85 | 0 | 226 ± 88 |
| PFF + PBS (PBS) | PFF | PBS | 100 | 100 | 49.4 | 58 ± 63 |
| PFF + 678363 (Treatment) | PFF | 678363 | 32 | 32 | 1.9 | 132 ± 77 |

Example 25: Treatment of SNCA Pathology in Pre-Formed Fibril (PFF) Model in Mouse, Long-Term Prophylactic Treatment Experimental Protocol Three groups of twelve mice wild-type B6C3F1 mice were treated according to the table below. 700 µg modified oligonucleotide (control or treatment) or PBS was administered via ICV (intracerebroventricial) injection on day 0, pre-formed fibrils were administered into the striatum on day 14, and an additional 700 µg modified oligonucleotide or PBS was administered via ICV on day 90.

Control groups included a PBS-treated group and Compound No. 676630-treated group. Compound No: 676630 is a 5-10-5 MOE gapmer that is not complementary to mouse SNCA, having a sequence of (from 5' to 3') CCTATAGGACTATCCAGGAA (incorporated herein as SEQ ID NO: 2795) and having an internucleoside linkage motif of (from 5' to 3') sooossssssssssssoos, wherein 'o' represents a phosphodiester internucleoside linkage and 's' represents a phosphorothioate internucleoside linkage.

On day 180, mice were sacrificed for mRNA and histological analysis. Phosphorylated-α-Syn aggregates and neurtic pathology in the substantia nigra were stained and quantified for 6 mice in each group. Additionally, the number of TH (tyrosine hydroxylase)+cells in the substantia nigra pars compacta (SNpc), which is measure of death of dopaminergic neurons, were quantified for 6 mice in each group. Results are presented relative to the PBS-treated group. As shown in the table below, Compound No. 677363-treated mice had reduced SNCA mRNA, fewer aggregates in substantia nigra, and reduced neuritic pathology in substantia nigra as compared to PBS and 676630-treated mice.

TABLE 98

Pre-formed fibril (PFF) model in wild-type mouse, long-term prophylactic treatment

| Treatment group | Treatment Day 0 | Day 14 | Day 90 | SNCA mRNA Midbrain | striatum | Avg. # p-αSyn aggregates in SN | Avg. # neuritic pathology in SN | TH cells (% PBS) in SNpc |
|---|---|---|---|---|---|---|---|---|
| PFF + PBS | PBS | PFF | PBS | 100 | 100 | 271 | 1002 | 100 |
| 676630 (Control) | 676630 | PFF | 676630 | 95 | 107 | 160* | 580* | 99 |

TABLE 98-continued

Pre-formed fibril (PFF) model in wild-type mouse, long-term prophylactic treatment

| Treatment group | Treatment Day 0 | Treatment Day 14 | Treatment Day 90 | SNCA mRNA Midbrain | SNCA mRNA striatum | Avg. # p-αSyn aggregates in SN | Avg. # neuritic pathology in SN | TH cells (% PBS) in SNpc |
|---|---|---|---|---|---|---|---|---|
| 678363 (Treatment) | 678363 | PFF | 678363 | 59 | 70 | 0.7 | 51 | 139 |

*number represents the average from 4 mice.

Example 26: Tolerability of Modified Oligonucleotides Complementary to Human SNCA in Mice, 700 µg Dose Modified oligonucleotides described above were tested against Compound Nos. 1233344 and 1233345 (described herein below) to assess the tolerability of the oligonucleotides.

Compound No. 1233344 is a 15-mer gapmer, that is complementary to SNCA (wherein the 5'-most nucleoside to which the gapmer targets SEQ ID NO: 1 is at position 370), having a sequence of (from 5' to 3') CTACAT-AGAGAACAC (incorporated herein as SEQ m No. 2796), wherein each of the nucleosides 1-3, nucleoside 13 and nucleoside 14 (from 5' to 3') comprise an LNA sugar modification, and each of the nucleosides 442 and nucleoside 15 are deoxynucleosides, wherein the internucleoside linkages between the nucleosides are phosphorothioate internucleoside linkages, Compound. No. 1233344 is characterized by the following chemical notation: $C_{lnas}T_{lnas}A_{lnas}C_{ds}A_{ds}T_{ds}A_{ds}G_{ds}A_{ds}G_{ds}A_{ds}A_{ds}C_{lnas}C_{d}$ wherein, A=an adenine nucleobase.
C=a cytosine nucleobase.
G=a guanine nucleobase,
T=a thymine nucleobase,
d=a 2'-deoxyribose sugar,
s=a phosphorothioate internucleoside linkage, and
lna=an LNA modified sugar.

Compound No. 1233345 is a 15-mer gapmer, that is complementary to SNCA (wherein the 5'-most nucleoside to which the gapmer targets SEQ ID NO: 1 is at position 372), having a sequence of (from 5' to 3') GCCTACAT-AGAGAAC (incorporated herein as SEQ m No.: 2797), wherein each of the nucleosides 1-3, nucleoside 13 and nucleoside 14 (from 5' to 3') comprise an LNA sugar modification, and each of the nucleosides 442 and nucleoside 15 are deoxynucleosides, wherein the internucleoside linkages between the nucleosides are phosphorothioate internucleoside linkages. Compound. No, 1233345 is characterized by the following chemical notation: $G_{lnas}C_{lnas}C_{lnas}T_{ds}A_{ds}C_{ds}A_{ds}T_{ds}A_{ds}G_{ds}A_{ds}G_{ds}A_{lnas}A_{lnas}C_{d}$ wherein, A=an adenine nucleobase.
C=a cytosine nucleobase,
G=a guanine nucleobase,
T=a thymine nucleobase,
d a 2'-deoxyribose sugar,
s=a phosphorothioate internucleoside linkage, and
lna=an LNA modified sugar.

Treatment

Wildtype C57BL/6 mice each received a single ICV dose of 700 µg of modified oligonucleotide listed in the table below. Each treatment group consisted of 4 mice. A group of four mice received PBS as a negative control. At 3 hours post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching, (7) regular breathing. For each of the 7 criteria, a mouse was given a subscore of 0 if it met the criteria and 1 if it did not (the functional observational battery score or FOB). After all the 7 criteria were evaluated, the scores were summed for each mouse and averaged within each treatment group. The results are presented in the table below.

TABLE 99

Tolerability scores in mice at 700 µg dose

| Compound No. | FOB 3 hour |
|---|---|
| PBS | 0.0 |
| 763085 | 2.3 |
| 763364 | 2.8 |
| 763391 | 0.0 |
| 789243 | 1.0 |
| 827599 | 1.0 |
| 1233345 | 6.8 |
| 1233344 | 2.3 |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11230712B2). An electronic copy of the "Sequence Listing" will also be available from the USPTO upon request and payment of the fee set forth in 37 CFR 1.19(b)(3).

The invention claimed is:
1. A modified oligonucleotide according to the following chemical structure:
(SEQ ID NO: 1703)
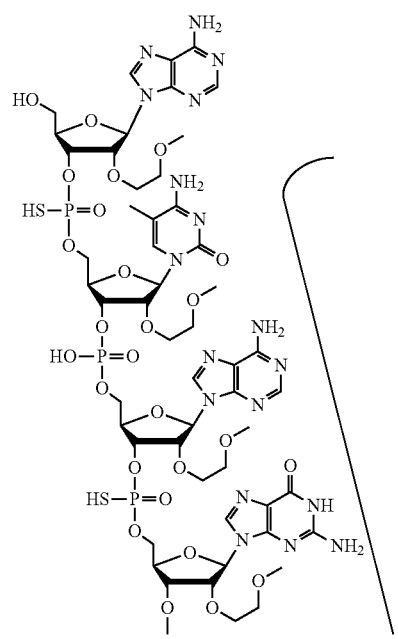
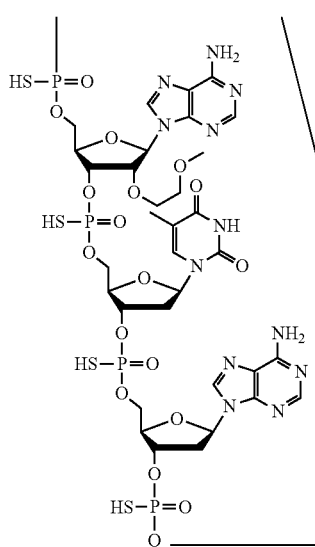
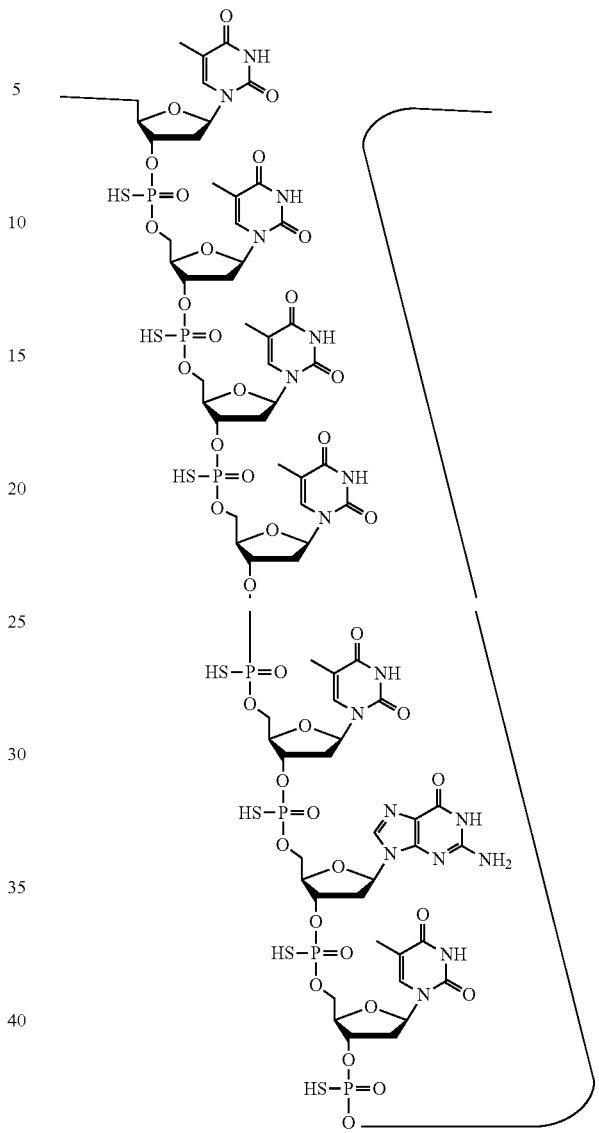

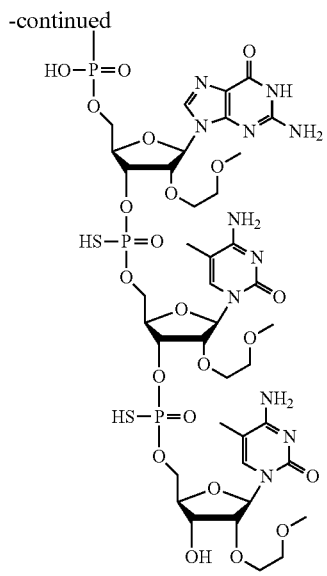

or a salt thereof.

2. The modified oligonucleotide of claim 1, which is the sodium salt or the potassium salt.

3. A population of modified oligonucleotides of claim 1, wherein all of the phosphorothioate internucleoside linkages of the modified oligonucleotide are stereorandom.

4. A pharmaceutical composition comprising the modified oligonucleotide of claim 1 and a pharmaceutically acceptable diluent.

5. The pharmaceutical composition of claim 4, wherein the pharmaceutically acceptable diluent is phosphate-buffered saline (PBS) or artificial cerebrospinal fluid (aCSF).

6. The pharmaceutical composition of claim 5, wherein the pharmaceutical composition consists essentially of the modified oligonucleotide and phosphate-buffered saline (PBS) or artificial cerebrospinal fluid (aCSF).

7. A method comprising administering to a subject the pharmaceutical composition of claim 4.

8. A method of treating a disease associated with SNCA comprising administering to a subject having or at risk for developing a disease associated with SNCA a therapeutically effective amount of a pharmaceutical composition of claim 4, thereby treating the disease associated with SNCA.

9. An oligomeric compound comprising a modified oligonucleotide according to the following chemical notation:

Aes mCeo Aes Ges Aes Tds Ads Tds Tds Tds Tds Tds Gds Tds Tds mCeo Teo Ges mCes mCe (SEQ ID NO: 1703); wherein, A=an adenine nucleobase,
$^m$C=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

10. A pharmaceutical composition comprising the oligomeric compound of claim 9 and a pharmaceutically acceptable diluent.

11. The pharmaceutical composition of claim 10, wherein the pharmaceutically acceptable diluent is phosphate-buffered saline (PBS) or artificial cerebrospinal fluid (aCSF).

12. The pharmaceutical composition of claim 11, wherein the pharmaceutical composition consists essentially of the oligomeric compound and phosphate-buffered saline (PBS) or artificial cerebrospinal fluid (aCSF).

13. A pharmaceutical composition comprising the population of modified oligonucleotides of claim 3 and a pharmaceutically acceptable diluent.

14. The pharmaceutical composition of claim 13, wherein the pharmaceutically acceptable diluent is phosphate-buffered saline (PBS) or artificial cerebrospinal fluid (aCSF).

15. The pharmaceutical composition of claim 14, wherein the pharmaceutical composition consists essentially of the population of modified oligonucleotides and phosphate-buffered saline (PBS) or artificial cerebrospinal fluid (aCSF).

16. The method of claim 8, wherein the disease associated with SNCA is a neurodegenerative disease.

17. The method of claim 16, wherein the neurodegenerative disease is Parkinson's disease, dementia with Lewy bodies, diffuse Lewy body disease, pure autonomic failure, multiple system atrophy, neuronopathic Gaucher's disease, or Alzheimer's disease.

18. The method of claim 17, wherein the administration improves motor function, reduces of alpha-synuclein aggregates, reduces neurodegeneration, and/or reduces dementia in the subject.

19. A method comprising administering to a subject the modified oligonucleotide of claim 1.

20. A method of treating a disease associated with SNCA comprising administering to a subject having or at risk for developing a disease associated with SNCA a therapeutically effective amount of the modified oligonucleotide of claim 1, thereby treating the disease associated with SNCA.

21. A method comprising administering to a subject the oligomeric compound of claim 9.

22. A method of treating a disease associated with SNCA comprising administering to a subject having or at risk for developing a disease associated with SNCA a therapeutically effective amount of the oligomeric compound of claim 9, thereby treating the disease associated with SNCA.

23. A method comprising administering to a subject the pharmaceutical composition of claim 10.

24. A method of treating a disease associated with SNCA comprising administering to a subject having or at risk for developing a disease associated with SNCA a therapeutically effective amount of the pharmaceutical composition of claim 10, thereby treating the disease associated with SNCA.

25. A method of treating a disease associated with SNCA comprising administering to a subject having or at risk for developing a disease associated with SNCA a therapeutically effective amount of the pharmaceutical composition of claim 13, thereby treating the disease associated with SNCA.

* * * * *

UNITED STATES PATENT AND TRADEMARK OFFICE
CERTIFICATE OF CORRECTION

PATENT NO. : 11,230,712 B2
APPLICATION NO. : 16/759698
DATED : January 25, 2022
INVENTOR(S) : Holly Kordasiewicz et al.

Page 1 of 1

It is certified that error appears in the above-identified patent and that said Letters Patent is hereby corrected as shown below:

In the Claims

Claim 1, Column 295, Line 8, to Column 297, Line 22, the structure should read as follows:

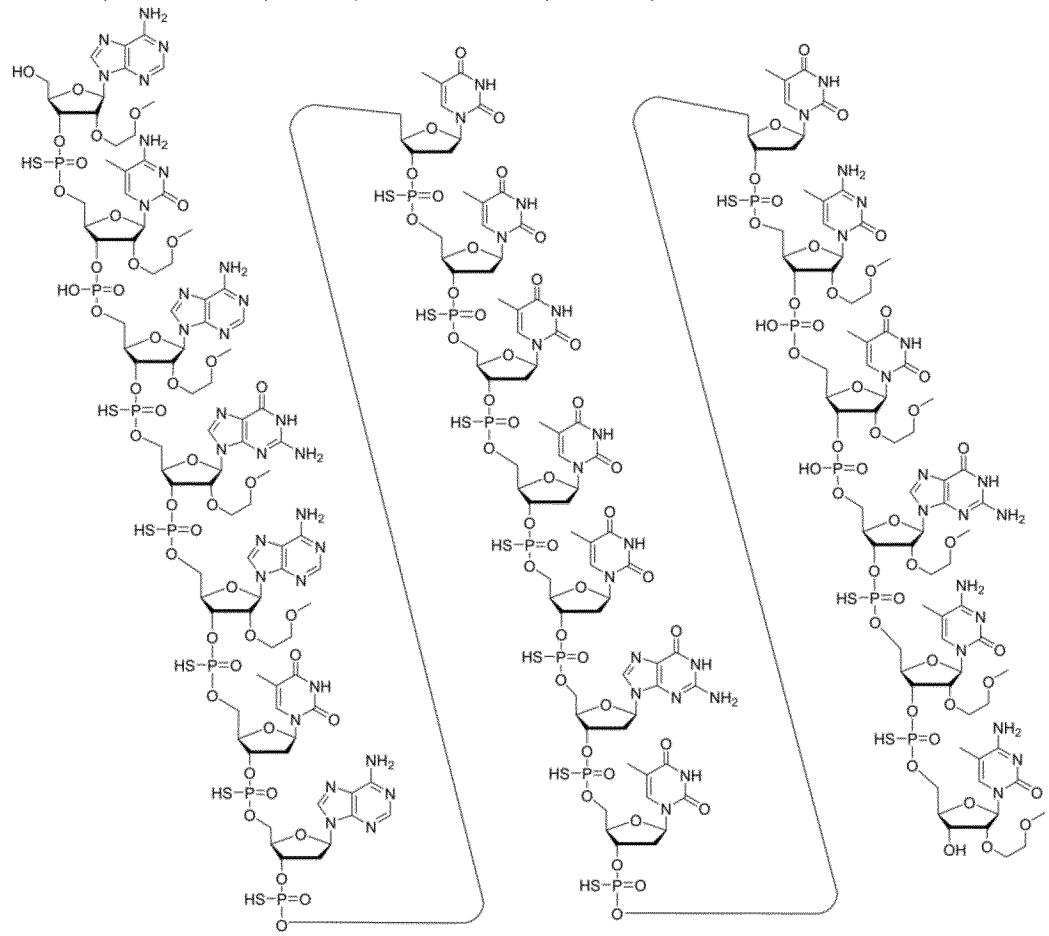

Signed and Sealed this
Eleventh Day of October, 2022

Katherine Kelly Vidal
*Director of the United States Patent and Trademark Office*